US012053495B2

(12) United States Patent
Caballero et al.

(10) Patent No.: US 12,053,495 B2
(45) Date of Patent: Aug. 6, 2024

(54) COMPOSITIONS AND METHODS FOR SUPPRESSING PATHOGENIC ORGANISMS

(71) Applicant: Vedanta Biosciences, Inc., Cambridge, MA (US)

(72) Inventors: Silvia Caballero, Cambridge, MA (US); Cintia Felix, Nashua, NH (US)

(73) Assignee: Vedanta Biosciences, Inc., Cambridge, MA (US)

( * ) Notice: Subject to any disclaimer, the term of this patent is extended or adjusted under 35 U.S.C. 154(b) by 197 days.

(21) Appl. No.: 16/771,075

(22) PCT Filed: Dec. 11, 2018

(86) PCT No.: PCT/US2018/065031
§ 371 (c)(1),
(2) Date: Jun. 9, 2020

(87) PCT Pub. No.: WO2019/118515
PCT Pub. Date: Jun. 20, 2019

(65) Prior Publication Data
US 2020/0405775 A1     Dec. 31, 2020

Related U.S. Application Data

(60) Provisional application No. 62/596,988, filed on Dec. 11, 2017, provisional application No. 62/616,394, filed on Jan. 11, 2018, provisional application No. 62/626,908, filed on Feb. 6, 2018, provisional application No. 62/643,554, filed on Mar. 15, 2018, provisional application No. 62/703,917, filed on Jul. 27, 2018, provisional application No. 62/769,461, filed on Nov. 19, 2018.

(51) Int. Cl.
| | | |
|---|---|---|
| *A61K 35/74* | (2015.01) | |
| *A61K 9/00* | (2006.01) | |
| *A61K 35/742* | (2015.01) | |
| *A61K 35/744* | (2015.01) | |
| *A61K 35/745* | (2015.01) | |
| *A61K 35/747* | (2015.01) | |
| *A61P 31/04* | (2006.01) | |

(52) U.S. Cl.
CPC ............ *A61K 35/74* (2013.01); *A61K 9/0031* (2013.01); *A61K 9/0053* (2013.01); *A61K 35/742* (2013.01); *A61K 35/744* (2013.01); *A61K 35/745* (2013.01); *A61K 35/747* (2013.01); *A61P 31/04* (2018.01)

(58) Field of Classification Search
None
See application file for complete search history.

(56) References Cited

U.S. PATENT DOCUMENTS

| | | |
|---|---|---|
| 2013/0266539 A1 | 10/2013 | Borody |
| 2016/0158295 A1 | 6/2016 | Afeyan et al. |
| 2016/0199424 A1 | 7/2016 | Berry et al. |
| 2016/0271188 A1* | 9/2016 | Berry ............... A61K 38/46 |
| 2017/0319633 A1 | 11/2017 | Allen-Vercoe et al. |
| 2019/0160114 A1 | 5/2019 | Madsen, II et al. |
| 2022/0409674 A1 | 12/2022 | Caballero et al. |

FOREIGN PATENT DOCUMENTS

| | | |
|---|---|---|
| CA | 3027917 A1 | 12/2017 |
| CN | 101198252 A | 6/2008 |
| CN | 109640688 A | 4/2019 |
| EP | 18889123.8 | 3/2022 |
| EP | 18889123.8 | 6/2022 |
| WO | WO 2007/075186 A2 | 7/2007 |
| WO | WO-2012142605 A1 * | 10/2012 ........... A23L 33/135 |
| WO | WO 2013/080561 A9 | 6/2013 |
| WO | WO 2014/182635 A1 | 11/2014 |
| WO | WO 2015/156419 A1 | 10/2015 |
| WO | WO 2016/209806 A1 | 12/2016 |
| WO | WO 2017/079450 A1 | 5/2017 |
| WO | WO 2017/160711 A1 | 9/2017 |
| WO | WO 2017/218680 A1 | 12/2017 |
| WO | WO 2018/136884 A1 | 7/2018 |
| WO | PCT/US2018/065031 | 2/2019 |
| WO | WO 2019/036510 A1 | 2/2019 |
| WO | PCT/US2018/065031 | 4/2019 |
| WO | WO 2019/094837 A1 | 5/2019 |
| WO | WO 2019/118515 A2 | 6/2019 |
| WO | PCT/US2018/065031 | 6/2020 |
| WO | PCT/US2020/045442 | 10/2020 |
| WO | PCT/US2020/045442 | 12/2020 |
| WO | WO 2021/016083 A1 | 1/2021 |
| WO | PCT/US2020/045442 | 2/2022 |
| WO | PCT/US2022/017043 | 5/2022 |

OTHER PUBLICATIONS

Chávarri, M., et al., "Probiotics", Chapter 23, IntechOpen: London, pp. 501-540 (Year: 2012).*
Wu, F., et al., "Phascolarctobacterium faecium abundant colonization in human gastrointestinal tract", Experimental and Therapeutic Medicine, vol. 14, pp. 3122-3126. (Year: 2017).*
Edgar, "Updating the 97% identity threshold for 16S ribosomal RNA OTUs", Bioinformatics, vol. 34(14), pp. 2371-2375. (Year: 2018).*
Genbank Accession No. AB215084 sequence. Bakir et al; May 27, 2005, pp. 1-2.

(Continued)

*Primary Examiner* — Michelle F. Paguio Frising
*Assistant Examiner* — Grant C Currens
(74) *Attorney, Agent, or Firm* — Wolf, Greenfield & Sacks, P.C.

(57) ABSTRACT

Provided herein are compositions and methods for the suppression of multi-drug resistant organisms. Provided herein are compositions and methods for treating diseases or disorders associated with bacterial colonization or treating diseases or disorders associated with an immune response induced by bacteria. Also provided herein are compositions and methods for suppressing colonization of the intestine of subject with oral microbiome bacteria.

12 Claims, 35 Drawing Sheets

Specification includes a Sequence Listing.

(56) References Cited

OTHER PUBLICATIONS

Genbank Accession No. LT223618 sequence. Urmite et al.; Feb. 6, 2013, pp. 1-2.
Ridaura et al., Gut Microbiota from Twins Discordant for Obesity Modulate Metabolism in Mice. Science. Sep. 6, 2013;341(6150):1241214. doi: 10.1126/science.1241214, pp. 1-13.
*U.S. Appl. No. 17/633,930, filed Feb. 8, 2022, Caballero.
Antunes et al., Antivirulence activity of the human gut metabolome. mBio. Jul. 29, 2014;5(4):e01183-14. doi: 10.1128/mBio.01183-14. 13 pages.
Atarashi et al., Ectopic colonization of oral bacteria in the intestine drives TH1 cell induction and inflammation. Science. Oct. 20, 2017;358(6361):359-365. doi: 10.1126/science.aan4526. Author Manuscript. 16 pages.
Atarashi et al., Treg induction by a rationally selected mixture of *Clostridia* strains from the human microbiota. Nature. Aug. 8, 2013;500(7461):232-6. doi: 10.1038/nature12331. Epub Jul. 10, 2013.
Caballero et al., Distinct but Spatially Overlapping Intestinal Niches for Vancomycin-Resistant Enterococcus faecium and Carbapenem-Resistant *Klebsiella pneumoniae*. PLoS Pathog. Sep. 3, 2015;11(9):e1005132. doi: 10.1371/journal.ppat.1005132. 20 pages.
Kulkarni et al., Roles of putative type II secretion and type IV pilus systems in the virulence of uropathogenic *Escherichia coli*. PLoS One. 2009;4(3):e4752. doi: 10.1371/journal.pone.0004752. Epub Mar. 9, 2009. 9 pages.
Morrison et al., Formation of short chain fatty acids by the gut microbiota and their impact on human metabolism. Gut Microbes. May 3, 2016;7(3):189-200. doi: 10.1080/19490976.2015.1134082. Epub Mar. 10, 2016.
Schirmer et al., Compositional and Temporal Changes in the Gut Microbiome of Pediatric Ulcerative Colitis Patients Are Linked to Disease Course. Cell Host Microbe. Oct. 10, 2018;24(4):600-610.e4 and Supplemental Information. doi: 10.1016/j.chom.2018.09.009. 20 pages.
Seekatz et al., Restoration of short chain fatty acid and bile acid metabolism following fecal microbiota transplantation in patients with recurrent *Clostridium difficile* infection. Anaerobe. Oct. 2018;53:64-73. doi: 10.1016/j.anaerobe.2018.04.001. Epub Apr. 12, 2018.
Stacy et al., Infection trains the host for microbiota-enhanced resistance to pathogens. Cell. Feb. 4, 2021;184(3):P615-627. doi: 10.1016/j.cell.2020.12.011. Epub Jan. 15, 2021.
Ubeda et al., Vancomycin-resistant Enterococcus domination of intestinal microbiota is enabled by antibiotic treatment in mice and precedes bloodstream invasion in humans. J Clin Invest. Dec. 2010; 120(12):4332-41. doi: 10.1172/JCI43918. Epub Nov. 22, 2010.
Yu et al., Effects of taurine on gut microbiota and metabolism in mice. Amino Acids. Jul. 2016;48(7):1601-17. doi: 10.1007/s00726-016-2219-y. Epub Mar. 30, 2016.
Xiao et al., Bacterial diversity and community structure of supragingival plaques in adults with dental health or caries revealed by 16S pyrosequencing. Frontiers in microbiology. Jul. 22, 2016;7:1145. 15 pages.
Wang et al., The value of serum PCT test in the treatment of gynecological infectious diseases. Chinese Journal of Public Health Engineering, China Sanitary Engineering. Apr. 20, 2017; 16(2): 215-216. DOI: 10.19937/j.issn. 1671-4199.2017.02.034.

* cited by examiner

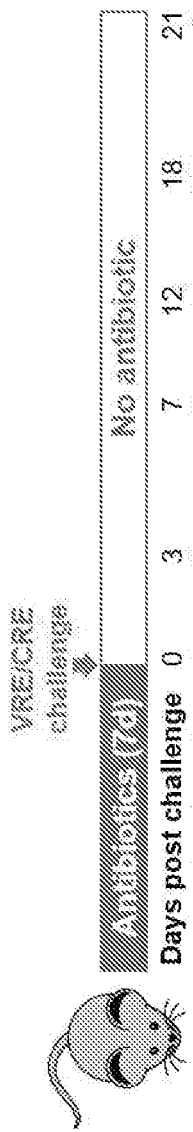
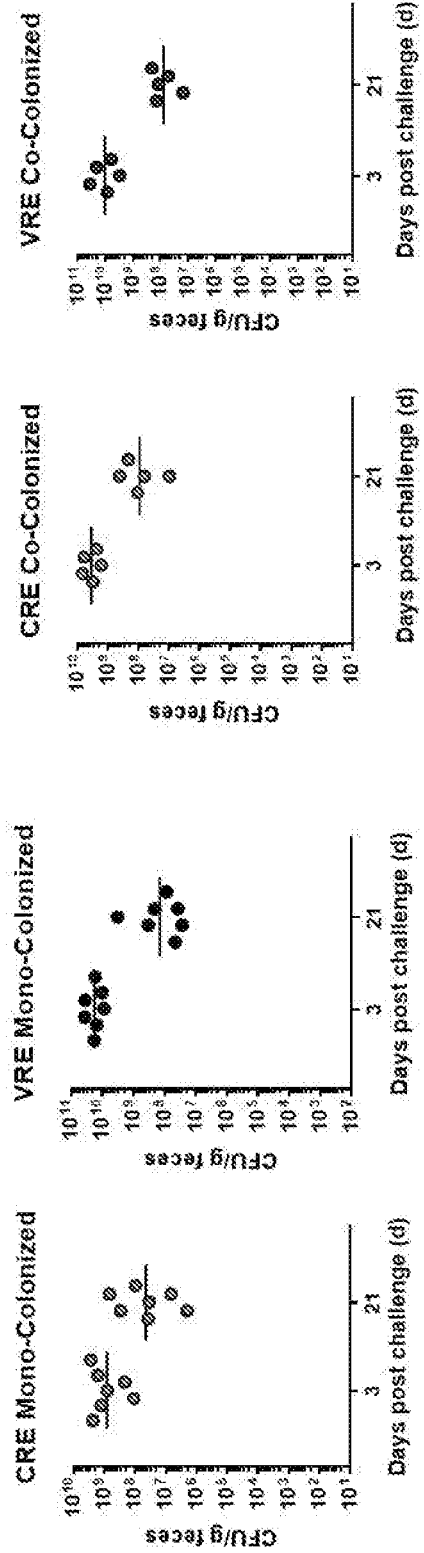
Fig. 1A
Fig. 1B
Fig. 1C
Fig. 1D
Fig. 1E

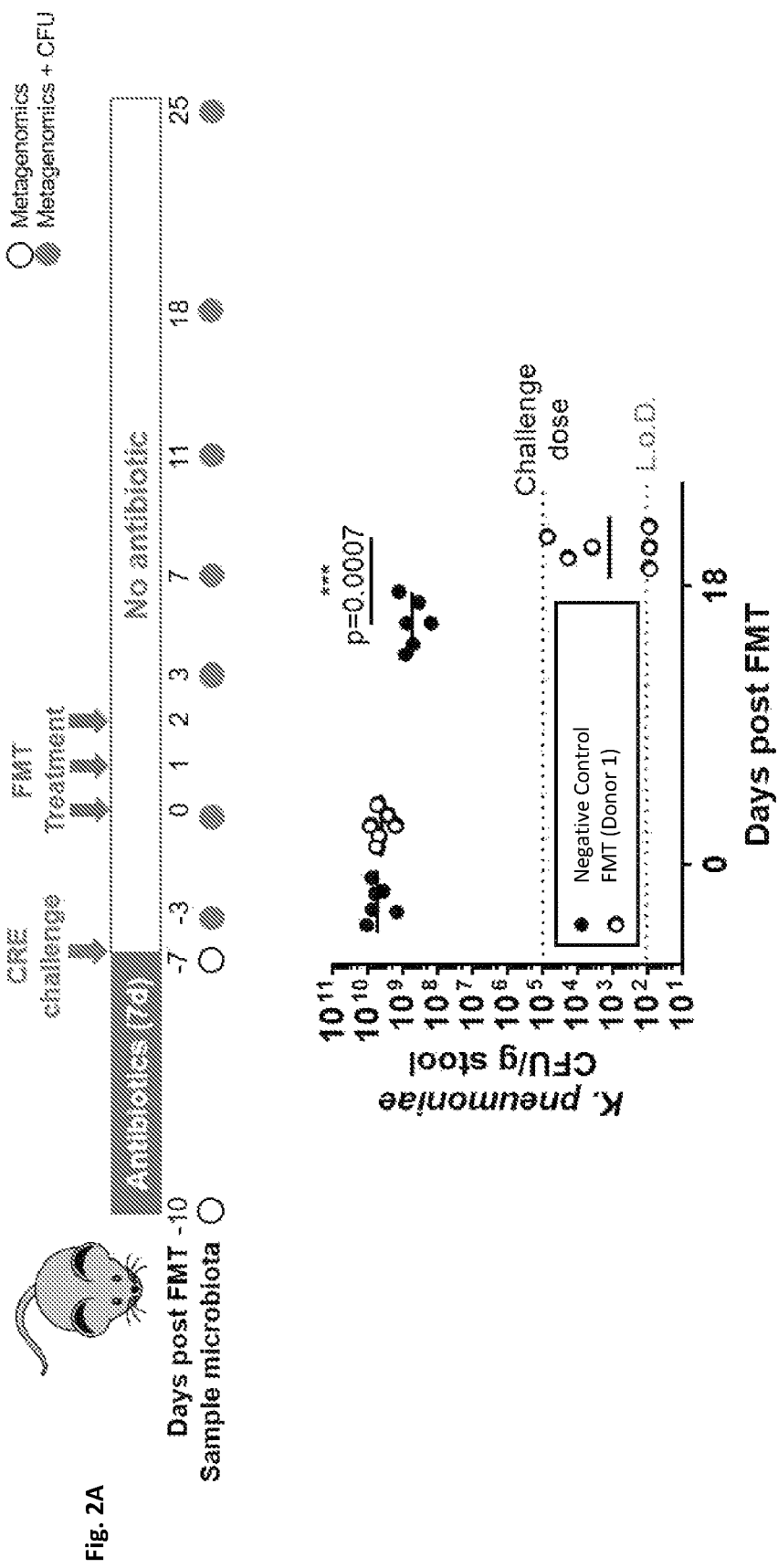

| Genus species | Strain No | SEQ ID NO | LBP 1 | LBP 2 | LBP 3 | LBP 4 | LBP 5 | LBP 6 | LBP 7 |
|---|---|---|---|---|---|---|---|---|---|
| Alistipes_putredinis | 26 | 1 | X | | | | | | |
| Bacteroides_uniformis | 27 | 2 | X | | | | | | |
| Bacteroides_vulgatus | 28 | 3 | X | X | X | X | X | X | X |
| Parabacteroides_merdae | 29 | 4 | X | X | X | X | | X | |
| Bifidobacterium_longum | 30 | 5 | X | X | X | X | | X | |
| Bifidobacterium_adolescentis | 31 | 6 | X | | X | | X | | X |
| Blautia_obeum | 32 | 7 | X | X | X | X | | X | X |
| Blautia_wexlerae | 33 | 8 | X | X | X | | | | X |
| Blautia_producta | 2 | 9 | | | | X | X | | |
| Clostridium_hathewayi | 20 | 10 | | | | X | X | | |
| Clostridium_bolteae | 34 | 11 | X | X | X | X | | | X |
| Parabacteroides_distasonis | 35 | 12 | X | | X | | X | X | X |
| Collinsella_aerofaciens | 36 | 13 | | X | | | | | X |
| Coprococcus_comes | 37 | 14 | X | X | | | | | |
| Dorea_longicatena | 38 | 15 | X | X | X | X | X | X | |
| Eubacterium_halli | 39 | 16 | X | X | X | X | X | X | X |
| Faecalibacterium_prausnitzii | 40 | 17 | X | X | X | X | X | X | |
| Parabacteroides_merdae | 41 | 18 | | X | | X | X | X | X |
| Parabacteroides_distasonis | 42 | 19 | X | | X | X | | X | |
| Prevotella_copri | 43 | 20 | X | X | X | X | X | | X |
| Roseburia_faecis | 44 | 21 | X | X | | X | | | |
| Ruminococcus_faecis | 45 | 22 | X | X | X | X | X | X | |

Fig. 4

| Strain |
|---|
| Bifidobacterium longum |
| Bifidobacterium adolescentis |
| Blautia wexlerae |
| Bacteroides vulgatus |
| Bacteroides uniformis |
| Collinsella aerofaciens |
| Faecalibacterium prausnitzii |
| Blautia obeum |
| Parabacteroides merdae |
| Parabacteroides distasonis |
| Roseburia faecis |
| Coprococcus comes |
| Dorea longicatena |
| Eubacterium hallii |

Fig. 7

| Level of Activity | 16 S rDNA SEQ ID NO | Strain | Classification |
|---|---|---|---|
| Strong | 23 | Strain 1 | Flavonifractor plautii |
| | 9 | Strain 2 | Blautia producta - 1 |
| | 24 | Strain 3 | Blautia producta - 2 |
| | 25 | Strain 4 | Blautia producta - 3 |
| | 26 | Strain 5 | Clostridium ramosum |
| | 27 | Strain 6 | Flavonifractor plautii |
| Medium | 28 | Strain 7 | Barnesiella |
| | 29 | Strain 8 | Clostridium symbiosum |
| Weak | | Strain 9 | Anaerotruncus colihominis |
| | | Strain 10 | Blautia producta - 4 |
| | | Strain 11 | Blautia producta - 5 |
| None | | Strain 12 | Clostridium innocuum |
| | | Strain 13 | Clostridium indolis |
| | | Strain 14 | Bacteroides ovatus |
| | | Strain 15 | Bacteroides cellulosilyticus |
| | | Strain 16 | Clostridium bolteae |
| | | Strain 17 | Drancourtella massiliensis |
| | | Strain 18 | Dorea longicatena |
| | | Strain 19 | Clostridium saccharogumia |
| | | Strain 20 | Clostridium hathewayi |
| | | Strain 21 | Clostridium MGL055 |
| | | Strain 22 | Clostridium asparagiforme |
| | | Strain 23 | Eubacterium fissicatena |
| | | Strain 24 | Clostridium scindens |
| | | Strain 25 | Lachnospiraceae bacterium |

Fig. 9

Species 1A = *Blautia producta* strain 2

Species 1B = *Blautia producta* strain 10

| Level of Activity | 16 S rDNA SEQ ID NO | Strain | Classification |
|---|---|---|---|
| Strong | 30 | Strain 23 | Eubacterium fissicatena |
| | 31 | Strain 25 | Lachnospiraceae bacterium |
| None | | Strain 3 | Blautia producta - 2 |
| | | Strain 4 | Blautia producta - 3 |
| | | Strain 5 | Clostridium ramosum |
| | | Strain 6 | Flavonifractor plautii |
| | | Strain 7 | Barnesiella |
| | | Strain 8 | Clostridium symbiosum |
| | | Strain 9 | Anaerotruncus colihominis |
| | | Strain 10 | Blautia producta - 4 |
| | | Strain 11 | Blautia producta - 5 |
| | | Strain 12 | Clostridium innocuum |
| | | Strain 13 | Clostridium indolis |
| | | Strain 14 | Bacteroides ovatus |
| | | Strain 15 | Bacteroides cellulosyliticus |
| | | Strain 16 | Clostridium bolteae |
| | | Strain 17 | Drancourtella massiliensis |
| | | Strain 18 | Dorea longicatena |
| | | Strain 1 | Flavonifractor plautii |
| | | Strain 19 | Clostridium saccharogumia |
| | | Strain 20 | Clostridium hathewayi |
| | | Strain 2 | Blautia producta |
| | | Strain 21 | Clostridium MGL055 |
| | | Strain 22 | Clostridium asparagiforme |
| | | Strain 24 | Clostridium scindens |

Fig. 17

Avg. CRE input: 300 CFU/ml

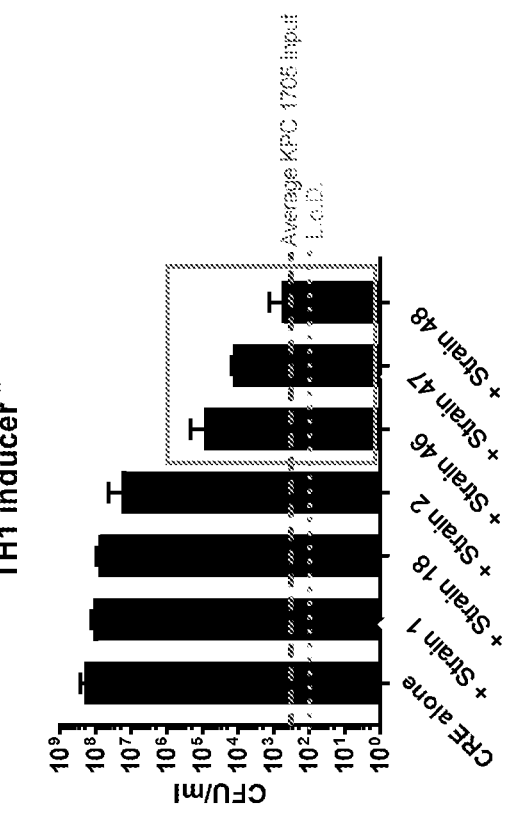
Fig. 25A *K. pneumoniae* ATCC BAA-2814 (KPC)
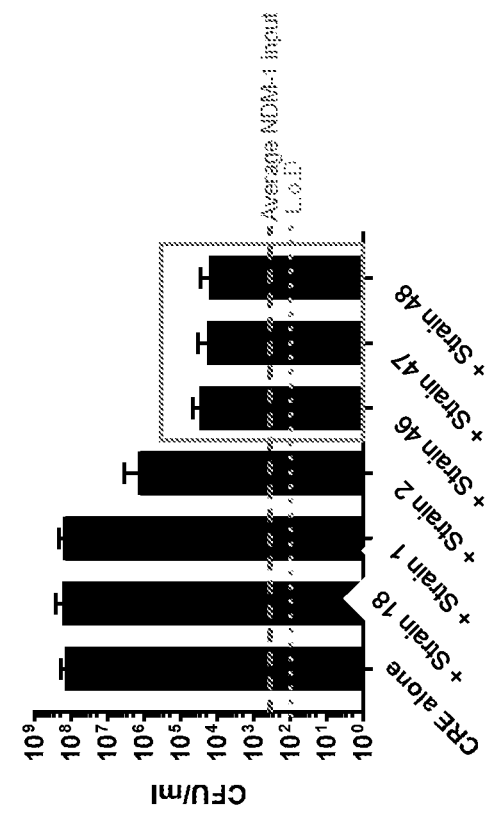
Fig. 25B *K. pneumoniae* ATCC BAA-1705 (KPC) TH1 inducer*
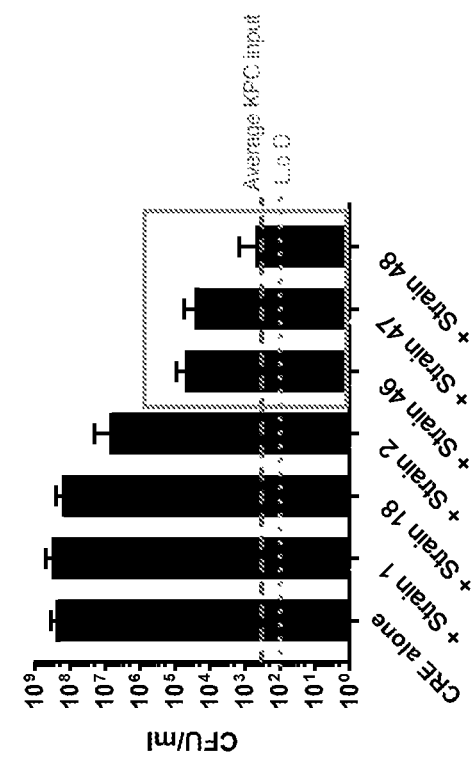
Fig. 25C *K. pneumoniae* ATCC BAA-2146 (NDM-1)

COMPOSITIONS AND METHODS FOR SUPPRESSING PATHOGENIC ORGANISMS

RELATED APPLICATIONS

This application is a national stage filing under 35 U.S.C. § 371 of international PCT application, PCT/US2018/065031, filed Dec. 11, 2018, which claims the benefit under 35 U.S.C. § 119(e) to U.S. provisional application No. 62/596,988, filed Dec. 11, 2017; U.S. provisional application No. 62/616,394, filed Jan. 11, 2018; U.S. provisional application No. 62/626,908, filed Feb. 6, 2018; U.S. provisional application No. 62/643,554, filed Mar. 15, 2018; U.S. provisional application No. 62/703,917, filed Jul. 27, 2018; and U.S. provisional application No. 62/769,461, filed Nov. 19, 2018. The entire contents of each of these referenced applications are incorporated by reference herein.

FIELD OF INVENTION

Provided herein are compositions and methods for suppressing multi-resistant organisms. Provided herein are compositions and methods for treating diseases or disorders associated with bacterial colonization or treating diseases or disorders associated with an immune response induced by bacteria. Also provided herein are compositions and methods for suppressing oral bacterial colonization of the intestine of subject.

BACKGROUND OF THE INVENTION

Multidrug resistant organisms (MDROs; "superbugs"), microorganisms that have developed resistance to one or more classes of antimicrobial agents, such as antibiotics, are emerging as serious global health threat. It is estimated that over 2 million people in the United States contract serious bacterial infections that are resistant to one or more antibiotics each year (CDC, Antibiotic Resistance Threats in the United States, 2013. Publication No. CS239559-B). Treatment options for subjects with MDROs are extremely limited; prevention of transmission is critical. The most important factor contributing to the generation and propagation of MDROs is the use and overuse/misuse of antibiotics and it is thought that the problem will increase in severity as further pathogenic organisms with antibiotic resistance arise (CDC, 2013; WHO 2017).

SUMMARY OF THE INVENTION

Provided herein are compositions and methods for suppressing multi-drug resistant organisms in a subject.

According to one aspect, compositions are provided that include two or more purified bacterial strains of species selected from the group consisting of *Alistipes putredinis, Bacteroides uniformis, Bacteroides vulgatus, Bifidobacterium longum, Bifidobacterium adolescentis, Blautia obeum, Blautia wexlerae, Blautia producta, Clostridium hathewayi, Clostridium bolteae, Collinsella aerofaciens, Coprococcus comes, Dorea longicatena, Eubacterium halli, Faecalibacterium prausnitzii, Parabacteroides merdae, Parabacteroides distasonis, Prevotella copri, Roseburia faecis,* and *Ruminococcus faecis.*

According to another aspect, compositions are provided that include two or more purified bacterial strains of species selected from the group consisting of *Alistipes putredinis, Bacteroides uniformis, Bacteroides vulgatus, Parabacteroides merdae, Bifidobacterium longum, Bifidobacterium adolescentis, Blautia obeum, Blautia wexlerae, Clostridium bolteae, Coprococcus comes, Dorea longicatena, Eubacterium halli, Faecalibacterium prausnitzii, Parabacteroides distasonis, Prevotella copri, Roseburia faecis,* and *Ruminococcus faecis.*

According to another aspect, compositions are provided that include two or more purified bacterial strains of species selected from the group consisting of *Alistipes putredinis, Bacteroides vulgatus, Bifidobacterium longum, Blautia obeum, Blautia wexlerae, Clostridium bolteae, Parabacteroides distasonis, Collinsella aerofaciens, Coprococcus comes, Dorea longicatena, Eubacterium halli, Faecalibacterium prausnitzii, Parabacteroides merdae, Prevotella copri, Roseburia faecis,* and *Ruminococcus faecis.*

According to another aspect, compositions are provided that include two or more purified bacterial strains of species selected from the group consisting of *Bacteroides uniformis, Bacteroides vulgatus, Parabacteroides merdae, Bifidobacterium longum, Bifidobacterium adolescentis, Blautia obeum, Blautia wexlerae, Clostridium bolteae, Dorea longicatena, Eubacterium halli, Faecalibacterium prausnitzii, Parabacteroides distasonis, Prevotella copri,* and *Ruminococcus faecis.*

According to another aspect, compositions are provided that include two or more purified bacterial strains of species selected from the group consisting of *Bacteroides vulgatus, Parabacteroides merdae, Bifidobacterium longum, Blautia obeum, Blautia producta, Clostridium hathewayi, Clostridium bolteae, Dorea longicatena, Eubacterium halli, Faecalibacterium prausnitzii, Parabacteroides distasonis, Prevotella copri,* and *Ruminococcus faecis.*

According to another aspect, compositions are provided that include two or more purified bacterial strains of species selected from the group consisting of *Bacteroides uniformis, Bacteroides vulgatus, Bifidobacterium adolescentis, Blautia producta, Clostridium hathewayi, Clostridium innocuum, Dorea longicatena, Eubacterium halli, Faecalibacterium prausnitzii, Parabacteroides merdae, Prevotella copri,* and *Ruminococcus faecis.*

According to another aspect, compositions are provided that include two or more purified bacterial strains of species selected from the group consisting of *Bacteroides vulgatus, Parabacteroides merdae, Bifidobacterium longum, Blautia obeum, Dorea longicatena, Eubacterium halli, Faecalibacterium prausnitzii, Parabacteroides distasonis,* and *Ruminococcus faecis.*

According to another aspect, compositions are provided that include two or more purified bacterial strains of species selected from the group consisting of *Bacteroides vulgatus, Bifidobacterium adolescentis, Blautia obeum, Blautia wexlerae, Clostridium bolteae, Parabacteroides distasonis, Collinsella aerofaciens, Eubacterium halli, Parabacteroides merdae,* and *Prevotella copri.*

According to another aspect, compositions are provided that include two or more purified bacterial strains of species selected from the group consisting of *Flavonifractor plautii, Blautia producta, Clostridium ramosum, Barnesiella* spp, *Clostridium symbiosum, Anaerotruncus colihominis, Clostridium innocuum, Clostridium indolis, Bacteroides ovatus, Bacteroides cellulosyliticus, Eubacterium fissicatena, Lachnospiraceae bacterium, Escherichia coli, Lactococcus lactis, Lactobacillus ruminis, Lactobacillus animalis,* or *Lactobacillus rhamnosus.*

According to another aspect, compositions are provided that include two or more purified bacterial strains of species selected from the group consisting of *Escherichia coli,*

*Lactococcus lactus, Lactobacillus ruminis, Lactobacillus animalis*, or *Lactobacillus rhamnosus*.

According to another aspect, compositions are provided that include two or more purified bacterial strains of species selected from the group consisting of *Flavonifractor plautii, Blautia producta, Clostridium ramosum, Barnesiella* spp, *Clostridium symbiosum, Anaerotruncus colihominis, Clostridium innocuum, Clostridium indolis, Bacteroides ovatus*, or *Bacteroides cellulosyliticus*.

According to another aspect, compositions are provided that include two or more purified bacterial strains of species selected from the group consisting of *Eubacterium fissicatena, Lachnospiraceae bacterium, Escherichia coli, Lactococcus lactus, Lactobacillus ruminis, Lactobacillus animalis*, or *Lactobacillus rhamnosus*.

According to another aspect, compositions are provided that include two or more purified bacterial strains, wherein the two or more purified bacterial strains comprise 16S rDNA sequences having at least 97% sequence identity with nucleic acid sequences selected from the group consisting of SEQ ID NOs: 1-22.

According to another aspect, compositions are provided that include two or more purified bacterial strains, wherein the two or more purified bacterial strains comprise 16S rDNA sequences having at least 97% sequence identity with nucleic acid sequences selected from the group consisting of SEQ ID NOs:1-8, 11, 12, 14-17, and 19-22.

According to another aspect, compositions are provided that include two or more purified bacterial strains, wherein the two or more purified bacterial strains comprise 16S rDNA sequences having at least 97% sequence identity with nucleic acid sequences selected from the group consisting of SEQ ID NOs: 1, 3-5, 7, 8, 11, 13-18, and 20-22.

According to another aspect, compositions are provided that include two or more purified bacterial strains, wherein the two or more purified bacterial strains comprise 16S rDNA sequences having at least 97% sequence identity with nucleic acid sequences selected from the group consisting of SEQ ID NOs: 2-8, 11, 12, 15-17, 19, 20, and 22.

According to another aspect, compositions are provided that include two or more purified bacterial strains, wherein the two or more purified bacterial strains comprise 16S rDNA sequences having at least 97% sequence identity with nucleic acid sequences selected from the group consisting of SEQ ID NOs: 3-5, 7, 9-11, 15-17, 19, 20, and 22.

According to another aspect, compositions are provided that include two or more purified bacterial strains, wherein the two or more purified bacterial strains comprise 16S rDNA sequences having at least 97% sequence identity with nucleic acid sequences selected from the group consisting of SEQ ID NOs: 2, 3, 6, 9, 10, 12, 15-18, 20, and 22.

According to another aspect, compositions are provided that include two or more purified bacterial strains, wherein the two or more purified bacterial strains comprise 16S rDNA sequences having at least 97% sequence identity with nucleic acid sequences selected from the group consisting of SEQ ID NOs: 3-5, 7, 12, 15-17, 19, and 22

According to another aspect, compositions are provided that include two or more purified bacterial strains, wherein the two or more purified bacterial strains comprise 16S rDNA sequences having at least 97% sequence identity with nucleic acid sequences selected from the group consisting of SEQ ID NOs: 3, 6-8, 11-13, 16, 18, and 20.

According to another aspect, compositions are provided that include two or more purified bacterial strains of species selected from the group consisting of *Bifidobacterium longum, Bifidobacterium adolescentis, Blautia wexlerae, Bacteroides vulgatus, Bacteroides uniformis, Collinsella aerofaciens, Faecalibacterium prausnitzii, Blautia obeum, Parabacteroides merdae, Parabacteroides distasonis, Roseburia faecis, Coprococcus comes, Dorea longicatena*, and *Eubacterium hallii*.

According to another aspect, compositions are provided that include one or more purified bacterial strains of species selected from the group consisting of *Flavonifractor plautii, Blautia producta, Clostridium ramosum, Barnesiella* spp, *Clostridium symbiosum, Anaerotruncus colihominis, Clostridium innocuum, Clostridium indolis, Bacteroides ovatus, Bacteroides cellulosyliticus, Eubacterium fissicatena*, and *Lachnospiraceae bacterium*.

According to another aspect, compositions are provided that include one or more purified bacterial strains of species selected from the group consisting of *Flavonifractor plautii, Blautia producta, Clostridium ramosum, Barnesiella* spp, and *Clostridium symbiosum*.

According to another aspect, compositions are provided that consist of one or more purified bacterial strains of species selected from the group consisting of *Flavonifractor plautii, Blautia producta, Clostridium ramosum, Barnesiella* spp, *Clostridium symbiosum, Anaerotruncus colihominis, Clostridium innocuum, Clostridium indolis, Bacteroides ovatus, Bacteroides cellulosyliticus, Eubacterium fissicatena*, and *Lachnospiraceae bacterium*.

According to another aspect, compositions are provided that consist of one or more purified bacterial strains of species selected from the group consisting of *Flavonifractor plautii, Blautia producta*, and *Clostridium ramosum*.

According to another aspect, compositions are provided that comprise two or more purified bacterial strains of species selected from the group consisting of *Bacteroides caccae, Bacteroides intestinalis (Bacteroides cellulosyticus), Bacteroides faecis, Bacteroides ovatus, Bacteroides thetaiotaomicron, Bacteroides uniformis, Bacteroides vulgatus, Bifidobacterium adolescentis, Bifidobacterium longum, Bifidobacterium pseudocatenulatum, Clostridiales bacterium* VE202-06 (*Blautia producta, Blautia coccoides*), *Clostridium citroniae, Clostridium* sp. C105KSO14 (*Clostridium clostridioforme*), *Clostridiales bacterium* VE202-21 (*Eubacterium contortum, Clostridium innocuum*), *Erysipelotrichaceae bacterium* 6_1_45 (*Clostridium innocuum*), *Paeniclostridium sordellii, Coprococcus comes, Dorea longicatena, Erysipelatoclostridium ramosum, Eubacterium rectale, Odoribacter* sp. UNK.MGS-12, *Bacteroides* sp. 1_1_14 (*Parabacteroides merdae*), *Bacteroides* sp. UNK.MGS-14 (*Parabacteroides merdae*), *Bacteroides xylanisolvens, Blautia obeum, Alistipes putredinis, Collinsella aerofaciens, Eubacterium hallii, Alistipes shahii, Anaerostipes caccae, Phascolarctobacterium faecis, Agathobaculum, Bacteroides* sp. 2_1_56FAA (*Bacteroides. fragilis*), *Fusobacterium mortiferum, Paraclostridium bifermentans*, and *Escherichia* sp. 3_2_53FAA.

According to another aspect, compositions are provided that comprise two or more purified bacterial strains, wherein the two or more purified bacterial strains comprise 16S rDNA sequences having at least 97% sequence identity with nucleic acid sequences selected from the group consisting of SEQ ID NOs: 42-77.

According to another aspect, compositions are provided that comprise two or more purified bacterial strains of species selected from the group consisting of *Bacteroides caccae, Bacteroides intestinalis (Bacteroides cellulosyticus), Bacteroides faecis, Bacteroides ovatus, Bacteroides thetaiotaomicron, Bacteroides uniformis, Bacteroides vulgatus, Clostridiales bacterium* VE202-06 (*Blautia producta, *Blautia coccoides*), *Clostridium citroniae*, *Clostridium* sp. C105KSO14 (*Clostridium clostridioforme*), *Clostridiales bacterium* VE202-21 (*Eubacterium contortum*, *Clostridium innocuum*), *Erysipelotrichaceae bacterium* 6_1_45 (*Clostridium innocuum*), *Coprococcus comes*, *Dorea longicatena*, *Erysipelatoclostridium ramosum*, *Eubacterium rectale*, *Bacteroides xylanisolvens*, *Blautia obeum*, *Alistipes putredinis*, *Eubacterium hallii*, *Alistipes shahii*, *Fusobacterium mortiferum*, and *Escherichia* sp. 3_2_53FAA According to another aspect, compositions are provided that comprise two or more purified bacterial strains comprise 16S rDNA sequences having at least 97% sequence identity with nucleic acid sequences selected from the group consisting of 42-48, 52-56, 58-61, 65-67, 69, 70, 75, and 77.

According to another aspect, compositions are provided that include at least the 5, 10, 20, 23, or 36 most abundant bacterial strains present in a spore forming fraction of a fecal sample obtained from a subject. According to another aspect, compositions are provided that include at least the 5, 10, 20, 23, or 36 most abundant bacterial species present in a spore forming fraction of a fecal sample obtained from a subject.

According to another aspect, compositions are provided that include at least the 5, 10, 20, 23, or 36 most abundant bacterial strains present in a non-spore forming fraction of a fecal sample obtained from a subject. According to another aspect, compositions are provided that include at least the 5, 10, 20, 23, or 36 most abundant bacterial species present in a non-spore forming fraction of a fecal sample obtained from a subject.

According to another aspect, compositions are provided that include at least 5, 10, 20, 23, or 36 bacterial strains present in a spore forming fraction of a fecal sample obtained from a subject, wherein the bacterial species suppress the replication, survival, and/or colonization of one or more pathogenic organisms. According to another aspect, compositions are provided that include at least 5, 10, 20, 23, or 36 bacterial species present in a spore forming fraction of a fecal sample obtained from a subject, wherein the bacterial species suppress the replication, survival, and/or colonization of one or more pathogenic organisms.

According to another aspect, compositions are provided that include at least 5, 10, 20, 23, or 36 bacterial strains present in a non-spore forming fraction of a fecal sample obtained from a subject, wherein the bacterial species suppress the replication, survival, and/or colonization of one or more pathogenic organisms. According to another aspect, compositions are provided that include at least 5, 10, 20, 23, or 36 bacterial species present in a non-spore forming fraction of a fecal sample obtained from a subject, wherein the bacterial species suppress the replication, survival, and/or colonization of one or more pathogenic organisms.

In some embodiments, the foregoing compositions include bacterial strains that originate from more than one human donor.

In some embodiments, the foregoing compositions include at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, or at least 22 purified bacterial strains.

In some embodiments, the foregoing compositions suppress the replication, survival, and/or colonization of one or more pathogenic organisms. In some embodiments, the pathogenic organism is susceptible to antibiotics. In some embodiments, the pathogenic organism is resistant to antibiotics. In some embodiments, the pathogenic organism is a multi-drug resistant organism. In some embodiments, the multi-drug resistant organism is Vancomycin Resistant *Enterococci* (VRE), Carbapenem Resistant *Enterobacteriaceae* (CRE), *Neisseria gonorrheae*, Multidrug Resistant *Acinetobacter*, *Campylobacter*, Extended spectrum beta-lactamase (ESBL) producing *Enterobacteriaceae*, Multi-drug Resistant *Pseudomonas aeruginosa*, *Salmonella*, Drug resistant non-typhoid *Salmonella*, Drug resistant *Salmonella Typhi*, Drug resistant *Shigella*, Methicillin Resistant *Staphylococcus aureus*, Drug resistant *Streptococcus pneumoniae*, Drug resistant Tuberculosis, Vancomycin resistant *Staphylococcus aureus*, Erythromycin Resistant Group A *Streptococcus*, or Clindamycin resistant Group B *Streptococcus*. In some embodiments, the pathogenic organism is an oral microbiome bacteria.

In some embodiments, the foregoing compositions suppress the replication, survival, and/or colonization of the intestine by one or more bacteria associated with induction of a Th1 immune response.

In some embodiments, the foregoing compositions suppress the replication, survival, and/or colonization of the intestine by one or more oral microbiome bacteria.

In some embodiments, in the foregoing compositions the bacterial strains are lyophilized. In some embodiments, in the foregoing compositions the bacterial strains are spray-dried.

According to another aspect, pharmaceutical compositions are provided that include any of the foregoing compositions and further include a pharmaceutically acceptable excipient. In some embodiments, the pharmaceutical composition is formulated for oral delivery. In some embodiments, the pharmaceutical composition is formulated for rectal delivery. In some embodiments, any of the foregoing pharmaceutical compositions is formulated for delivery to the intestine. In some embodiments, any of the foregoing pharmaceutical compositions is formulated for delivery to the colon.

According to another aspect, food products are provided that include any of the foregoing compositions and a nutrient.

According to another aspect, methods of suppressing a pathogenic organism in a subject are provided. The methods include administering to the subject a therapeutically effective amount of any of the foregoing compositions, pharmaceutical compositions or food products. In some embodiments, the pathogenic organism is susceptible to antibiotics. In some embodiments, the pathogenic organism is resistant to antibiotics. In some embodiments, the pathogenic organism is *Clostridium difficile*. In some embodiments, the pathogenic organism is a multi-drug resistant organism.

In some embodiments, of the foregoing methods of suppressing a pathogenic organism the pathogenic organism is an oral microbiome bacteria. In some embodiments, the oral microbiome bacteria is pathogenic when it is present in the intestine.

In some embodiments of the foregoing methods of suppressing a pathogenic organism, the pathogenic organism is *Klebsiella pneumoniae*. In some embodiments, the *Klebsiella pneumoniae* is multi-drug resistant. In some embodiments, the multi-drug resistant *Klebsiella pneumoniae* is carbapenem-resistant *Klebsiella pneumoniae*. In some embodiments, the *Klebsiella pneumoniae* induces a Th1 response. In some embodiments, the *Klebsiella pneumoniae* is strain BAA-2552, strain KP-1, strain 700721, strain 13882, strain 34E1, strain BAA-1705, strain 700603, or strain Kp-2H7. In some embodiments, the *Klebsiella pneumoniae* is strain Kp-2H7.

In some embodiments of the foregoing methods of suppressing a pathogenic organism, the subject is human. In some embodiments of the foregoing methods of suppressing a pathogenic organism, the composition is administered to the subject more than once. In some embodiments of the foregoing methods of suppressing a pathogenic organism, the composition is administered to the subject by oral administration. In some embodiments of the foregoing methods of suppressing a pathogenic organism, the composition is administered to the subject by rectal administration. In some embodiments of the foregoing methods of suppressing a pathogenic organism, the administering suppresses the replication, survival, and/or colonization of the pathogenic organism.

In some embodiments of the foregoing methods of suppressing a pathogenic organism, the pathogenic organism is Vancomycin Resistant *Enterococci* (VRE), Carbapenem Resistant *Enterobacteriaceae* (CRE), *Neisseria gonorrheae*, Multidrug Resistant *Acinetobacter, Campylobacter*, Extended spectrum beta-lactamase (ESBL) producing *Enterobacteriaceae*, Multidrug Resistant *Pseudomonas aeruginosa, Salmonella*, Drug resistant non-typhoid *Salmonella*, Drug resistant *Salmonella Typhi*, Drug resistant *Shigella*, Methicillin Resistant *Staphylococcus aureus*, Drug resistant *Streptococcus pneumoniae*, Drug resistant Tuberculosis, Vancomycin resistant *Staphylococcus aureus*, Erythromycin Resistant Group A *Streptococcus*, or Clindamycin resistant Group B *Streptococcus*.

In some embodiments of the foregoing methods of suppressing a pathogenic organism, the methods also include administering one or more additional compositions comprising bacteria.

According to another aspect, methods of treating a disease or disorder associated with bacterial colonization in a subject are provided. The methods include administering to the subject a therapeutically effective amount of any of the foregoing compositions, pharmaceutical compositions or food products. In some embodiments, the disease or disorder is associated with a Th1 immune response.

In some embodiments of the foregoing methods of treating a disease or disorder associated with bacterial colonization, the bacterial colonization induces a Th1 immune response in the subject.

In some embodiments of the foregoing methods of treating a disease or disorder associated with bacterial colonization, the disease or disorder is an autoimmune disease or an inflammatory bowel disorder. In some embodiments, the inflammatory bowel disorder is ulcerative colitis or Crohn's disease.

In some embodiments of the foregoing methods of treating a disease or disorder associated with bacterial colonization, the disease or disorder is non-alcoholic steatohepatitis (NASH), primary sclerosing cholangitis (PSC), non-alcoholic fatty liver disease (NAFLD), gastroesophageal reflux disease (GERD), or alcoholism.

In some embodiments of the foregoing methods of treating a disease or disorder associated with bacterial colonization, the subject has a disease or disorder associated with use of a proton pump inhibitor.

In some embodiments of the foregoing methods of treating a disease or disorder associated with bacterial colonization, the subject is human. In some embodiments of the foregoing methods of treating a disease or disorder associated with bacterial colonization, the composition is administered to the subject more than once. In some embodiments of the foregoing methods of treating a disease or disorder associated with bacterial colonization, the composition is administered to the subject by oral administration. In some embodiments of the foregoing methods of treating a disease or disorder associated with bacterial colonization, the composition is administered to the subject by rectal administration. In some embodiments of the foregoing methods of treating a disease or disorder associated with bacterial colonization, the administering suppresses the replication, survival, and/or colonization of the bacteria.

In some embodiments of the foregoing methods of treating a disease or disorder associated with bacterial colonization, the bacteria is Vancomycin Resistant *Enterococci* (VRE), Carbapenem Resistant *Enterobacteriaceae* (CRE), *Neisseria gonorrheae*, Multidrug Resistant *Acinetobacter, Campylobacter*, Extended spectrum beta-lactamase (ESBL) producing *Enterobacteriaceae*, Multidrug Resistant *Pseudomonas aeruginosa, Salmonella*, Drug resistant non-typhoid *Salmonella*, Drug resistant *Salmonella Typhi*, Drug resistant *Shigella*, Methicillin Resistant *Staphylococcus aureus*, Drug resistant *Streptococcus pneumoniae*, Drug resistant Tuberculosis, Vancomycin resistant *Staphylococcus aureus*, Erythromycin Resistant Group A *Streptococcus*, Clindamycin resistant Group B *Streptococcus, Clostridium difficile*, multi-drug resistant *Klebsiella pneumoniae*, carbapenem-resistant *Klebsiella pneumoniae, Klebsiella pneumoniae* strain BAA-2552, *Klebsiella pneumoniae* strain KP-1, *Klebsiella pneumoniae* strain 700721, *Klebsiella pneumoniae* strain 13882, *Klebsiella pneumoniae* strain 34E1, *Klebsiella pneumoniae* strain BAA-1705, *Klebsiella pneumoniae* strain 700603, or *Klebsiella pneumoniae* strain Kp-2H7.

In some embodiments of the foregoing methods of treating a disease or disorder associated with bacterial colonization, the methods also include administering one or more additional compositions comprising bacteria.

According to another aspect, methods of treating a disease or disorder associated with an immune response induced by bacteria in a subject are provided. The methods include administering to the subject a therapeutically effective amount of any of the foregoing compositions, pharmaceutical compositions or food products.

In some embodiments of the foregoing methods of treating a disease or disorder associated with an immune response induced by bacteria, the subject is human.

In some embodiments of the foregoing methods of treating a disease or disorder associated with an immune response induced by bacteria, the composition is administered to the subject more than once. In some embodiments of the foregoing methods of treating a disease or disorder associated with an immune response induced by bacteria, the composition is administered to the subject by oral administration. In some embodiments of the foregoing methods of treating a disease or disorder associated with an immune response induced by bacteria, the composition is administered to the subject by rectal administration. In some embodiments of the foregoing methods of treating a disease or disorder associated with an immune response induced by bacteria, the administering suppresses the replication, survival, and/or colonization of the bacteria.

In some embodiments of the foregoing methods of treating a disease or disorder associated with an immune response induced by bacteria, the bacteria is Vancomycin Resistant *Enterococci* (VRE), Carbapenem Resistant *Enterobacteriaceae* (CRE), *Neisseria gonorrheae*, Multidrug Resistant *Acinetobacter, Campylobacter*, Extended spectrum beta-lactamase (ESBL) producing *Enterobacteriaceae*, Multidrug Resistant *Pseudomonas aeruginosa*, *Salmonella*, Drug resistant non-typhoid *Salmonella*, Drug resistant *Salmonella Typhi*, Drug resistant *Shigella*, Methicillin Resistant *Staphylococcus aureus*, Drug resistant *Streptococcus pneumoniae*, Drug resistant Tuberculosis, Vancomycin resistant *Staphylococcus aureus*, Erythromycin Resistant Group A *Streptococcus*, Clindamycin resistant Group B *Streptococcus, Clostridium difficile*, multi-drug resistant *Klebsiella pneumoniae*, carbapenem-resistant *Klebsiella pneumoniae, Klebsiella pneumoniae* strain BAA-2552, *Klebsiella pneumoniae* strain KP-1, *Klebsiella pneumoniae* strain 700721, *Klebsiella pneumoniae* strain 13882, *Klebsiella pneumoniae* strain 34E1, *Klebsiella pneumoniae* strain BAA-1705, *Klebsiella pneumoniae* strain 700603, or *Klebsiella pneumoniae* strain Kp-2H7.

In some embodiments of the foregoing methods of treating a disease or disorder associated with an immune response induced by bacteria, the methods also include administering one or more additional compositions comprising bacteria.

According to another aspect, methods of suppressing colonization of the intestine of a subject with oral microbiome bacteria are provided. The methods include administering to the subject a therapeutically effective amount of any of the foregoing compositions, pharmaceutical compositions or food products.

In some embodiments of the foregoing methods of suppressing colonization of the intestine of a subject with oral microbiome bacteria, the subject is human.

In some embodiments of the foregoing methods of suppressing colonization of the intestine of a subject with oral microbiome bacteria, the composition is administered to the subject more than once.

In some embodiments of the foregoing methods of suppressing colonization of the intestine of a subject with oral microbiome bacteria, the composition is administered to the subject by oral administration.

In some embodiments of the foregoing methods of suppressing colonization of the intestine of a subject with oral microbiome bacteria, the composition is administered to the subject by rectal administration.

In some embodiments of the foregoing methods of suppressing colonization of the intestine of a subject with oral microbiome bacteria, the administering suppresses the replication, survival, and/or colonization of the bacteria.

In some embodiments of the foregoing methods of suppressing colonization of the intestine of a subject with oral microbiome bacteria, the oral microbiome bacteria is Carbapenem Resistant *Enterobacteriaceae* (CRE), Multidrug Resistant *Acinetobacter, Campylobacter*, Extended spectrum beta-lactamase (ESBL) producing *Enterobacteriaceae*, Multidrug Resistant *Pseudomonas aeruginosa*, *Salmonella*, Drug resistant non-typhoid *Salmonella*, Drug resistant *Salmonella Typhi*, Drug resistant *Shigella*, Methicillin Resistant *Staphylococcus aureus*, Drug resistant *Streptococcus pneumoniae*, Drug resistant Tuberculosis, Vancomycin resistant *Staphylococcus aureus*, Erythromycin Resistant Group A *Streptococcus*, Clindamycin resistant Group B *Streptococcus*, multi-drug resistant *Klebsiella pneumoniae*, carbapenem-resistant *Klebsiella pneumoniae, Klebsiella pneumoniae* strain BAA-2552, *Klebsiella pneumoniae* strain KP-1, *Klebsiella pneumoniae* strain 700721, *Klebsiella pneumoniae* strain 13882, *Klebsiella pneumoniae* strain 34E1, *Klebsiella pneumoniae* strain BAA-1705, *Klebsiella pneumoniae* strain 700603, or *Klebsiella pneumoniae* strain Kp-2H7.

In some embodiments of the foregoing methods of suppressing colonization of the intestine of a subject with oral microbiome bacteria, the methods also include administering one or more additional compositions comprising bacteria.

Each of the limitations of the invention can encompass various embodiments of the invention. It is, therefore, anticipated that each of the limitations of the invention involving any one element or combinations of elements can be included in each aspect of the invention.

This invention is not limited in its application to the details of construction and the arrangement of components set forth in the following description or illustrated in the drawings. The invention is capable of other embodiments and of being practiced or of being carried out in various ways.

BRIEF DESCRIPTION OF THE DRAWINGS

The accompanying drawings are not intended to be drawn to scale. The figures are illustrative only and are not required for enablement of the disclosure. For purposes of clarity, not every component may be labeled in every drawing. In the drawings:

FIGS. 1A-1E show a mouse model of mono- and co-colonization of VRE and CRE. FIG. 1A presents the timeline of the mouse model of colonization. FIG. 1B shows CFU levels of CRE in CRE mono-colonized mice. FIG. 1C shows CFU levels of VRE in VRE mono-colonized mice. FIG. 1D shows CFU levels of CRE in CRE and VRE co-colonized mice. FIG. 1E shows CFU levels of VRE in CRE and VRE co-colonized mice.

FIGS. 2A and 2B show FMT samples from a donor reduce the CRE burden in colonized mice. FIG. 2A presents the experimental timeline. FIG. 2B shows *K. pneumoniae* CFU levels in mice at day 18 post fecal matter treatment (FMT).

FIG. 3A presents the experimental timeline. FIG. 3B shows *K. pneumoniae* CFU levels in mice at day 18 following the first fecal matter/stool fraction treatment. Stool fractions were enriched in non-spore forming ("NSP") or spore-forming ("SP") bacteria.

FIG. 4 is a table showing the bacterial strains present in each of live bacterial products (LBP) 1-7 tested.

FIG. 5A shows *K. pneumoniae* CFU levels on day 0 ("D0") prior to administration of the indicated LBP or FMT. FIG. 5B shows *K. pneumoniae* CFU levels on day 4 ("D4") following administration of the indicated LBP or FMT. FIG. 5C shows *K. pneumoniae* CFU levels on day 7 ("D7") following administration of the indicated LBP or FMT. FIG. 5D shows *K. pneumoniae* CFU levels on day 12 ("D12") following administration of the indicated LBP or FMT.

FIG. 7 is a table presenting bacterial strains identified in stool samples from donors and present in the live bacteria products shown in FIG. 4.

FIG. 9 is a table presenting results from a soft agar overlay assay demonstrated in FIG. 8. Bacterial strains having strong, medium, weak, or no detectable antagonistic activity towards CRE are shown.

FIG. 12A presents the experimental timeline. FIG. 12B shows VRE CFU levels in mice at the days 25-28 post fecal matter treatment.

FIG. 13A presents the experimental time line. FIG. 13B shows VRE CFU levels in mice at day 25 following the three doses of the fecal matter/stool fraction treatment. Stool fractions were enriched in non-spore forming ("NSP") or spore-forming ("SP") bacteria.

FIG. 17 is a table presenting results from a soft agar overlay assay depicted in FIG. 16. Bacterial strains having strong or no antagonistic activity towards VRE are shown.

FIG. 23A presents the experimental timeline. FIG. 23B shows *K. pneumoniae* CFU levels in mice at the indicated time points.

FIGS. 25A-25C show the ability of the indicated bacterial strains to suppress growth of different CRE strains. FIG. 25A shows inhibition of *K. pneumoniae* strain ATCC BAA-2814 (KPC). FIG. 25B shows inhibition of *K. pneumoniae* strain ATCC BAA-1705 (KPC). FIG. 25C shows inhibition of *K. pneumoniae* strain ATCC BAA-2146 (NDM-1). L.o.D. is Limit of Detection.

FIG. 26A shows inhibition of CRE by, from left-to-right for each time point: control (PBS), single doses of FMT from donors D1 (also referred to as "donor 3"), D2 (also referred to as "donor 1"), D11 (also referred to as "donor 2"), and D14 (also referred to as "donor 4"). Results are shown at 0 and 16 days post-treatment. FIG. 26B shows inhibition of CRE by, from left-to-right for each time point: single dose of FMT from donor D14 and triple dose of FMT from donor D14. Results are shown at 0 and 16 days post-treatment. FIG. 26C shows inhibition of CRE by, from left-to-right: control (PBS), single dose of FMT from donor D11, triple dose of FMT from donor D11, single dose of FMT from donor D14, triple dose of FMT from donor D14, single dose of FMT from donor D2, and triple dose of FMT from donor D2. Results are shown at 10 days post-treatment. L.o.D. is Limit of Detection.

DETAILED DESCRIPTION OF THE INVENTION

Figures 3A, 3B:
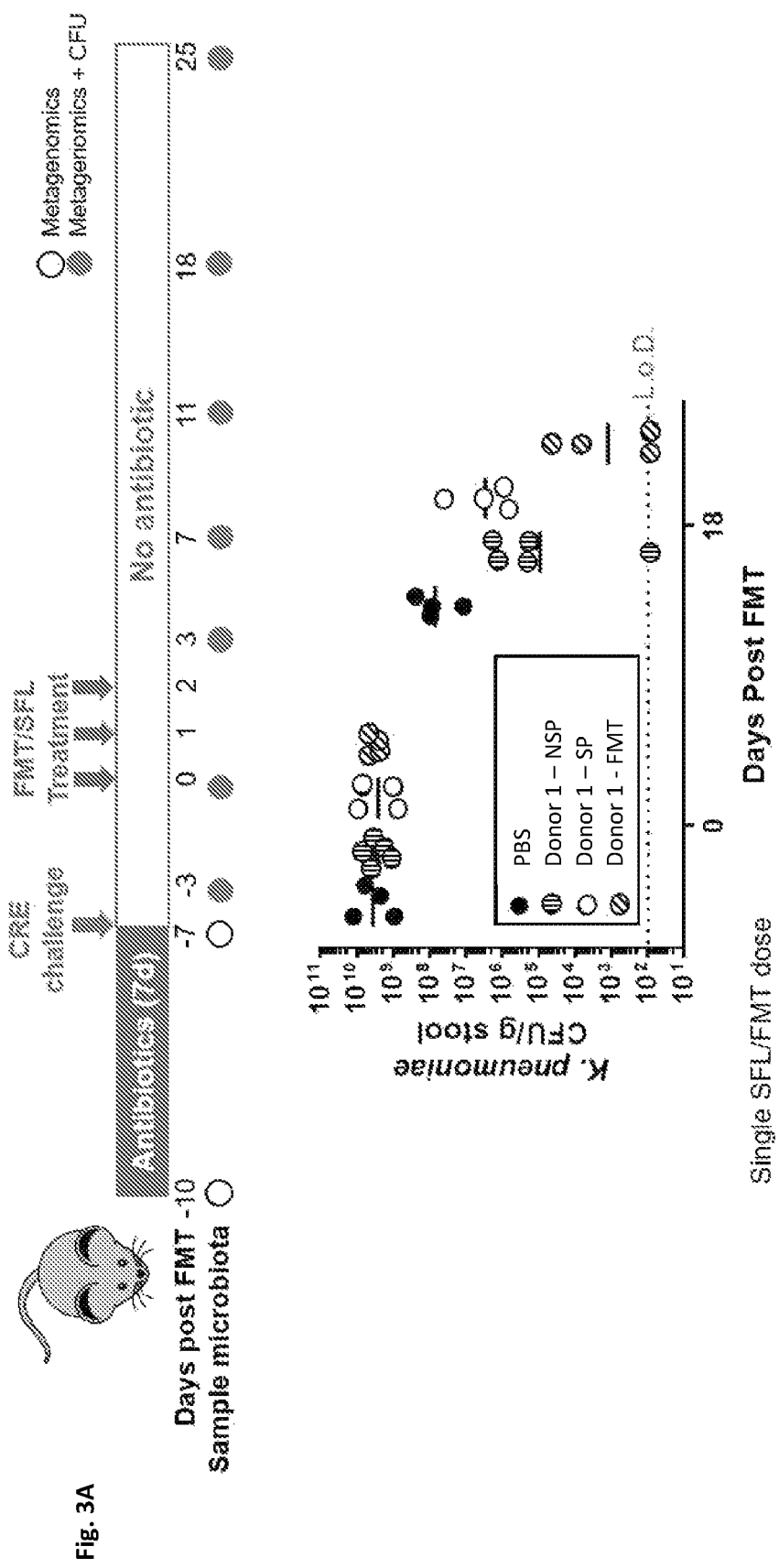
FIGS. 3A and 3B show stool fractions from a donor reduce the CRE burden in colonized mice.
Figure 5B:
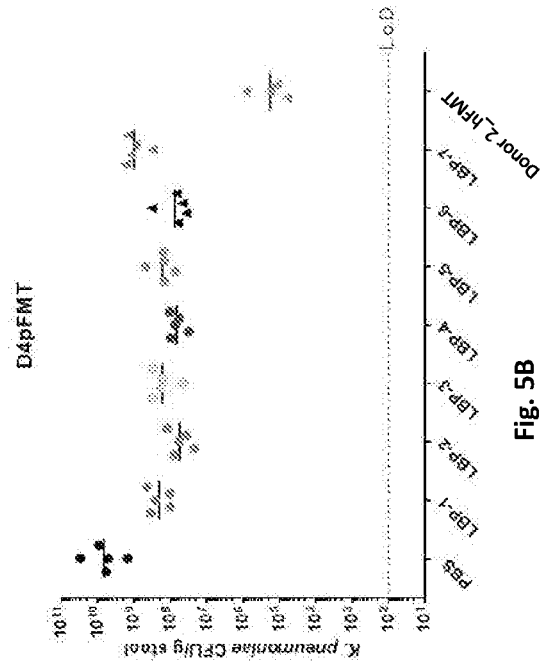
FIGS. 5A-5D show the *K. pneumoniae* CFU levels in mice feces following administration of the indicated LBP or FMT.
Figure 5D:
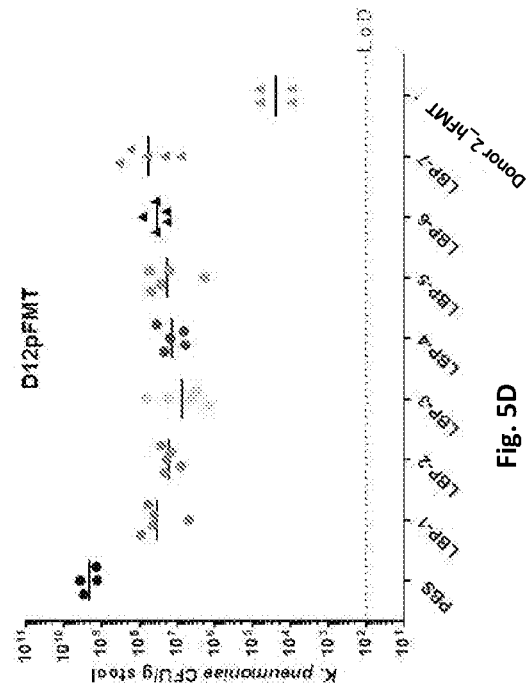
Figure 5A:
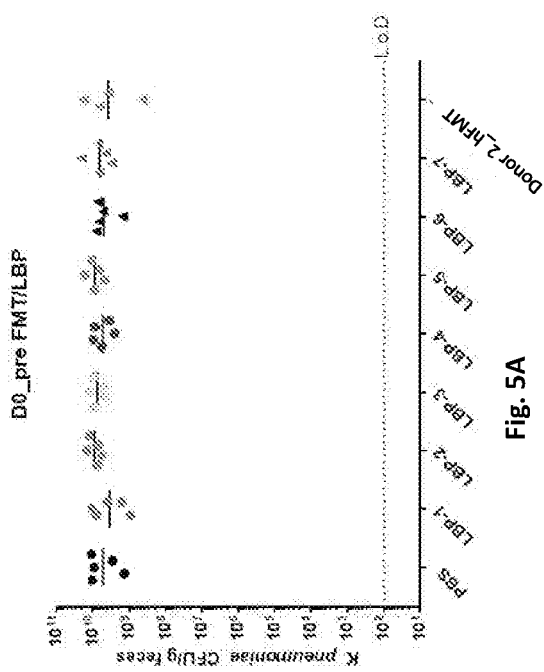
Figure 5C:
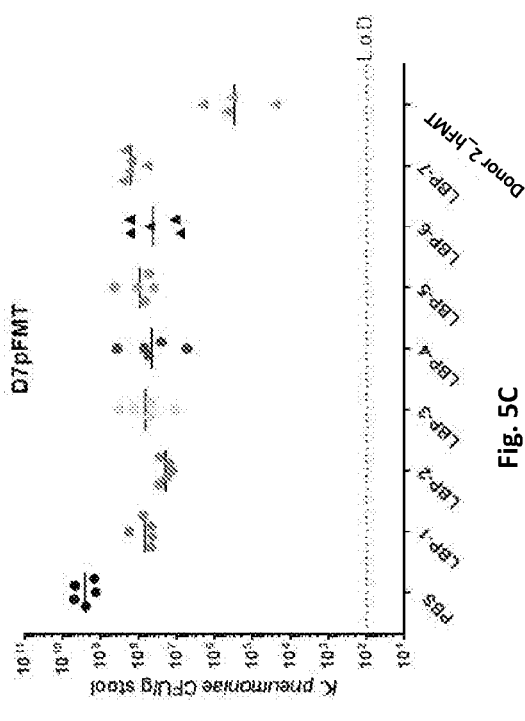

Suppressing or preventing undesired bacteria in a subject or suppressing or preventing colonization of bacteria in a particular region of the body can be challenging. Bacterial colonization may induce immune responses (local or systemic) in the subject, which may lead to serious disease. In particular, for multi-drug resistant organisms elimination with many conventional therapeutics, such as antibiotics, may not be possible due to resistance or tolerance of the therapeutic. Additionally, it has been recently appreciated that intestinal colonization by bacteria of the oral microbiome may influence the immune environment of the intestine, such as induce Th1-dominated immune responses and lead to chronic inflammation and inflammatory conditions (see, e.g., Atarashi et al. *Science* (2017) 358 (359-365)). Normal bacterial colonization of different regions of the body, such as the oral cavity, may provide a reservoir of bacteria that can migrate and colonize other regions, such as the intestines.

Provided herein are compositions and methods for suppressing colonization by multi-drug resistant organisms. Also provided herein are compositions and methods for suppressing colonization of the intestine of subject with bacteria of the oral microbiome. Provided herein are compositions and methods for treating diseases or disorders associated with bacterial colonization or treating diseases or disorders associated with an immune response induced by bacteria.

In some embodiments, the one or more of the bacterial strains of the compositions provided herein colonize or recolonize the intestinal tract or parts of the intestinal tract (e.g., the colon or the cecum) of the subject. Such colonization or recolonization may also be referred to as grafting. In some embodiments, the one or more of the bacterial strains of the compositions recolonize the intestinal tract (e.g., the colon or the cecum) of the subject, for example after another organism or population of organisms has been partially or completely removed. In some embodiments, one or more of the bacterial strains of the compositions recolonize the intestinal track (e.g., the colon or the cecum) after one or more multi-drug resistant organism or other organism (e.g., bacteria that induce an immune response) has been removed. In some embodiments, the recolonization of the intestinal tract or parts thereof by the bacterial strains of the compositions described herein prevents or suppresses colonization by undesired organisms (e.g., multi-drug resistant organisms, oral microbiome bacteria, bacteria that induce immune responses, pathobionts).

In some embodiments, the one or more of the bacterial strains of the compositions can "outgrow" a pathogen or undesired bacteria, such as a multi-drug resistant organism, oral microbiome bacteria, bacteria that induce immune responses. Thus, in some embodiments, if a pathogen or undesired bacteria (e.g., a multi-drug resistant organism, oral microbiome bacteria, bacteria that induce immune responses) and one or more bacteria of compositions provided herein are both present in the intestinal tract (e.g., the colon or the cecum), the one or more bacteria of compositions provided herein grow faster (e.g., have a shorter doubling time) than the pathogen, thereby preventing the pathogen from accumulating in the intestinal tract (e.g., the colon or the cecum). In some embodiments, the faster growth results because the one or more bacteria of the compositions provided herein are better at grafting in the intestinal tract (e.g., the colon or the cecum). In some embodiments, the faster growth results because the one or more bacteria of the compositions provided herein are better at metabolizing nutrients present in the intestinal tract (e.g., the colon or the cecum). In some embodiments, the compositions of bacterial strains provided herein prevent or inhibit replication of the pathogen. In some embodiments, the compositions of bacterial strains provided herein induce death of (kill) the pathogen. In some embodiments, the bacterial strains of the compositions provided herein can treat pathogenic infections, because of the synergy between the bacterial strains.

In some embodiments, the bacterial compositions described herein prevent recolonization by a pathogen or undesired bacteria (e.g., a multi-drug resistant organism, oral microbiome bacteria, bacteria that induce immune responses, pathobionts). For example, in some embodiments, the pathogen or undesired bacteria has been reduced or eliminated from the subject, for example, using a first therapeutic agent, and the bacterial compositions described herein are administered to prevent recolonization of the subject. In some embodiments, the bacterial compositions described herein reduce or eliminate a pathogen or undesired bacteria from the subject and prevent recolonization of the subject.

In some embodiments, the combination of bacterial strains of the compositions provided herein is superior in the use of nutrients when compared to the pathogen or undesired bacteria, thereby suppressing the growth of the pathogen or undesired bacteria. In some embodiments, the combination of bacterial strains of the compositions provided herein is superior in grafting when compared to the pathogen or undesired bacteria, thereby suppressing the growth of the pathogen or undesired bacteria. In some embodiments, the combination of bacterial strains of the compositions provided herein is superior in the use of nutrients and in grafting when compared to the pathogen or undesired bacteria, thereby suppressing the growth of the pathogen or undesired bacteria. In some embodiments, the combination of bacterial strains of the compositions provided herein inhibits the growth, survival, and/or colonization of the pathogen or undesired bacteria.

In some embodiments, the combination of bacterial strains of the compositions provided herein has antagonizing or inhibitory activity towards the pathogen or undesired bacteria, thereby inhibiting the growth, survival, and/or colonization of the pathogen or undesired bacteria. In some embodiments, at least one bacterial strain of the compositions provided herein has antagonizing or inhibitory activity towards the pathogen or undesired bacteria, thereby inhibiting the growth, survival, and/or colonization of the pathogen or undesired bacteria.

In some embodiments, the synergistic effect is provided by the capacity of the combination to colonize specific niches in the intestinal tract (e.g., the colon or the cecum). In some embodiments, the synergistic effect is provided by the capacity of the combination to metabolize specific nutrients. In some embodiments, the synergistic effect is provided by the capacity of the combination to provide specific metabolites to the environment.

The bacterial strains used in the compositions provided herein generally are isolated from the microbiome of healthy individuals. In some embodiments, the compositions include strains originating from a single individual. In some embodiments, the compositions include strains originating from multiple individuals. In some embodiments, the bacterial strains are obtained from multiple individuals, isolated and grown up individually. The bacterial compositions that are grown up individually may subsequently be combined to provide the compositions of the disclosure. It should be appreciated that the origin of the bacterial strains of the compositions provided herein is not limited to the human microbiome from a healthy individual. In some embodiments, the bacterial strains originate from a human with a microbiome in dysbiosis. In some embodiments, the bacteria originate from a spore-forming fraction of the microbiome. In some embodiments, the bacteria originate from a non-spore-forming fraction of the microbiome. In some embodiments, the bacterial strains originate from non-human animals or the environment (e.g., soil or surface water). In some embodiments, the combinations of bacterial strains provided herein originate from multiple sources (e.g., human and non-human animals).

In some embodiments, the bacteria of the compositions provided herein are anaerobic bacteria. In some embodiments, the bacteria of the compositions provided herein are obligate anaerobic bacteria. In some embodiments, the bacteria of the compositions provided herein are clostridia. Clostridia may be classified into phylogenetic clusters with other closely related strains and species. (See e.g., Rajilic-Stojanovic, M., and de Vos, W. M. *FEMS Microbiol Rev* 38, (2014) 996-1047). In general, clostridia are classified as belonging to a specific cluster based on their 16S rRNA (or 16S rDNA) nucleic acid sequence. Methods for determining the identity of specific bacterial species based on their 16S rRNA (or 16S rDNA) nucleic acid sequence are well known in the art (See e.g., Jumpstart Consortium Human Microbiome Project Data Generation Working, G. *PLoS One* (2012) 7, e39315).

In some embodiments, the bacteria of the compositions provided herein are *Bacteroides*.

In one aspect, the disclosure provides composition comprising one or more bacterial strains comprising a 16S rDNA sequence with nucleic acid sequences selected from the group consisting of SEQ ID NOs: 1-22 or any of the other 16S sequences provided herein. In one aspect, the disclosure provides composition comprising two or more bacterial strains comprising a 16S rDNA sequence with nucleic acid sequences selected from the group consisting of SEQ ID NOs: 1-22 or any of the other 16S sequences provided herein. It should be appreciated that SEQ ID NOs: 1-22 or any of the other 16S sequences provided herein may include both full length and partial 16S rDNA sequences.

In one aspect, the disclosure provides compositions comprising two or more bacterial strains comprising 16S rDNA sequences selected from the group consisting of SEQ ID NOs: 1-22. In one aspect, the disclosure provides compositions comprising as active ingredients two or more bacterial strains comprising 16S rDNA sequences selected from the group consisting of SEQ ID NOs: 1-22. It should be appreciated that for all compositions provided herein, in some embodiments, the bacterial strain or bacterial strains are the active ingredient(s) of the composition.

It should be appreciated that for all compositions provided herein, in some embodiments, the bacterial strains are purified. Thus, for example the disclosure provides purified bacterial strains comprising 16S rDNA sequences with nucleic acid sequences selected from the group consisting of SEQ ID NOs: 1-22. In addition, for example, the disclosure provides compositions comprising purified bacterial strains comprising a 16S rDNA sequence with a nucleic acid sequence selected from the group consisting of SEQ ID NOs: 1-22. The bacterial strains disclosed herein originally may have been obtained and purified from the microbiota of one or more human individuals or obtained from sources other than the human microbiota, including soil and non-human microbiota. As provided herein, in some embodiments, bacteria isolated from the human microbiota, non-human microbiota, soil, or any alternative source are purified prior to use in the compositions and methods provided herein.

In one aspect, the disclosure provides compositions comprising one or more purified bacterial strains wherein the one or more purified bacterial strains comprise 16S rDNA sequences having at least 97% sequence identity with nucleic acid sequences selected from the group consisting of SEQ ID NOs: 1-22. In one aspect, the disclosure provides compositions comprising two or more purified bacterial strains wherein the two or more purified bacterial strains comprise 16S rDNA sequences having at least 97% sequence identity with nucleic acid sequences selected from the group consisting of SEQ ID NOs: 1-22. As discussed above, in some embodiments, the bacterial strains are the active ingredient of the composition. Thus, in some embodiments, the disclosure provides compositions comprising as an active ingredient two or more purified bacterial strains wherein the two or more purified bacterial strains comprise 16S rDNA sequences having at least 97% sequence identity with nucleic acid sequences selected from the group consisting of SEQ ID NOs: 1-22.

In one aspect, the disclosure provides bacterial strains and combinations of bacterial strains that have a high percent of sequence identity or have a high percent of homology with bacterial strains comprising 16S rDNA sequences selected from the group consisting of SEQ ID NOs: 1-22. As discussed previously, in some embodiments, the bacterial strains are purified. The bacterial strains disclosed herein that have a 16S rDNA sequence with a nucleic acid sequence selected from the group consisting of SEQ ID NOs: 1-22 have a high percent of sequence identity or homology (e.g., greater than 90%) with 16S rDNA sequences of bacterial strains that have been described in various databases (See e.g., the National Center for Biotechnology Information). FIG. 4 and Tables 1-4 provide the closest known species by sequence identity when the 16S rDNA sequences comprising SEQ ID NOs: 1-22 are compared to 16S rDNA sequences of bacterial species available in public databases. By way of example, the bacterial strain comprising a 16S rDNA sequence with SEQ ID NO: 1 (also referred to herein as "Strain 26") disclosed herein has the highest sequence identity with a bacterial strain of the species *Alistipes putredinis*. While the bacterial strain with 16S rDNA sequence of SEQ ID NO: 1 has sequence identity with other published bacterial strains as well, the highest sequence identity is with a bacterial strain of the species *Alistipes putredinis*. It should be appreciated that multiple bacterial strains disclosed herein may have the highest sequence identity with the same species (e.g., both SEQ ID NO: 4 and SEQ ID NO: 18 have the highest sequence identity with a 16S rDNA sequence of a strain of the species *Parabacteroides merdae*; and both SEQ ID NO: 12 and SEQ ID NO: 19 have the highest sequence identity with a 16S rDNA sequence of a strain of the species *Parabacteroides distasonis*).

It should further be appreciated that the bacterial strains disclosed herein that have a 16S rDNA sequence with a nucleic acid sequence selected from the group consisting of SEQ ID NO: 1-22 may have a high level of sequence identity or homology to other strains based on their whole genome sequence or subset of their whole genome sequence.

TABLE A

| Genus species | Strain No | 16 S rDNA SEQ ID NO |
|---|---|---|
| Alistipes_putredinis | 26 | 1 |
| Bacteroides_uniformis | 27 | 2 |
| Bacteroides_vulgatus | 28 | 3 |
| Parabacteroides_merdae | 29 | 4 |
| Bifidobacterium_longum | 30 | 5 |
| Bifidobacterium_adolescentis | 31 | 6 |
| Blautia_obeum | 32 | 7 |
| Blautia_wexlerae | 33 | 8 |
| Blautia_producta | 2 | 9 |
| Clostridium_hathewayi | 20 | 10 |
| Clostridium_bolteae | 34 | 11 |
| Parabacteroides_distasonis | 35 | 12 |
| Collinsella_aerofaciens | 36 | 13 |
| Coprococcus comes | 37 | 14 |
| Dorea longicatena | 38 | 15 |
| Eubacterium_halli | 39 | 16 |
| Faecalibacterium_prausnitzii | 40 | 17 |
| Parabacteroides_merdae | 41 | 18 |
| Parabacteroides_distasonis | 42 | 19 |
| Prevotella_copri | 43 | 20 |
| Roseburia_faecis | 44 | 21 |
| Ruminococcus_faecis | 45 | 22 |

In one aspect, the disclosure provides compositions comprising one or more bacterial species selected from the group consisting of *Alistipes putredinis, Bacteroides uniformis, Bacteroides vulgatus, Barnesiella intestinihominis, Bifidobacterium longum, Bifidobacterium adolescentis, Blautia obeum, Blautia wexlerae, Blautia producta, Clostridium hathewayi, Clostridium bolteae, Clostridium innocuum, Collinsella aerofaciens, Coprococcus comes, Dorea longicatena, Eubacterium halli, Faecalibacterium prausnitzii, Parabacteroides merdae, Parabacteroides distasonis, Prevotella copri, Roseburia faecis*, and *Ruminococcus*.

In one aspect, the disclosure provides composition comprising one or more bacterial strains selected from the group consisting of strains 26-45 (See, FIG. 4 and Table A).

In one aspect, the disclosure provides compositions comprising two or more bacterial species selected from the group consisting of *Alistipes putredinis, Bacteroides uniformis, Bacteroides vulgatus, Barnesiella intestinihominis, Bifidobacterium longum, Bifidobacterium adolescentis, Blautia obeum, Blautia wexlerae, Blautia producta, Clostridium hathewayi, Clostridium bolteae, Clostridium innocuum, Collinsella aerofaciens, Coprococcus comes, Dorea longicatena, Eubacterium halli, Faecalibacterium prausnitzii, Parabacteroides merdae, Parabacteroides distasonis, Prevotella copri, Roseburia faecis*, and *Ruminococcus faecis*. *Clostridium hathewayi* also can be referred to herein as *Hungatella effluvia*.

It should be appreciated that the compositions may contain multiple strains of a particular bacterial species. For example, in some embodiments, the composition may comprise two strains of *Parabacteroides distasonis* and/or two strains of *Parabacteroides merdae*.

The disclosure also encompasses compositions comprising bacterial strains having close sequence identity or homology to and/or fall within the species of *Alistipes putredinis, Bacteroides uniformis, Bacteroides vulgatus, Barnesiella intestinihominis, Bifidobacterium longum, Bifidobacterium adolescentis, Blautia obeum, Blautia wexlerae, Blautia producta, Clostridium hathewayi, Clostridium bolteae, Clostridium innocuum, Collinsella aerofaciens, Coprococcus comes, Dorea longicatena, Eubacterium halli, Faecalibacterium prausnitzii, Parabacteroides merdae, Parabacteroides distasonis, Prevotella copri, Roseburia faecis*, and *Ruminococcus faecis*. In some embodiments, the compositions include two or more bacterial strains comprising 16S rDNA sequences having at least 97% sequence identity or homology with the nucleic acid sequences selected from the group consisting of SEQ ID NOs: 1-22.

In some embodiments, the compositions disclosed herein comprise two or more bacterial strains. In some embodiments, the compositions described herein comprise at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, or at least 20, at least 21, at least 22, at least 23, at least 24, at least 25, at least 26, at least 27, at least 28, at least 29, at least 30, at least 31, at least 32, at least 33, at least 34, at least 35, at least 36 or more bacterial strains (e.g., purified bacterial strains).

In some embodiments, the composition suppresses the replication, survival, and/or colonization of one or more pathogenic organism. In some instances, the pathogenic organism is susceptible to antibiotics, while in other instances, the pathogenic organism is resistant to antibiotics. In some embodiments, the pathogenic organism is a multi-drug resistant organism, which are described elsewhere herein. In some embodiments, the pathogenic organism is an oral microbiome bacteria. It should be noted that oral microbiome bacteria are not necessarily pathogenic, but may become so when located elsewhere, such as in the gastrointestinal tract. The amount of suppression of replication, survival, and/or colonization of the one or more pathogenic organism can be measured or identified using standard assays known in the art, some of which are further described and exemplified herein.

In some embodiments, the pathogenic organism is *Clostridium difficile*.

In some embodiments, the pathogenic organism is *Klebsiella pneumoniae*. In some embodiments, the *Klebsiella pneumoniae* is multi-drug resistant. In some embodiments, the multi-drug resistant *Klebsiella pneumoniae* is carbapenem-resistant *Klebsiella pneumoniae*. In some embodiments, the *Klebsiella* organism induces a Th1 response. In some embodiments, the *Klebsiella pneumoniae* is multi-drug resistant and induces a Th1 response. In some embodiments, the *Klebsiella pneumoniae* is one or more of those described in Atarashi et al. Science 358, 359-365 (2017), such as strain BAA-2552, strain KP-1, strain 700721, strain 13882, strain 34E1, strain BAA-1705, strain 700603, and/or strain Kp-2H7. In one particular embodiment, the *Klebsiella pneumoniae* is strain Kp-2H7.

In some embodiments, the pathogenic organism is a pathobiont, i.e., a potentially pathogenic organism which, under normal circumstances, lives as a symbiont.

It should be appreciated that the terms "bacteria" and "bacterial strains" as used herein are interchangeable. The compositions described herein containing multiple purified bacterial strains may also be referred to as "live bacterial products."

In one aspect, the disclosure provides live bacterial product 1 (LBP 1) (see, e.g., FIG. 4, Table 1). As shown in FIG. 4 and Table 1, live bacterial product 1 contains bacterial strains that comprise 16S rDNA sequences with nucleic acid sequences SEQ ID NOs: 1-8, 11, 12, 14-17, and 19-22. In some embodiments, the compositions comprise at least two (e.g., 2, 3, 4, 5, or more) bacterial strains that comprise 16S rDNA sequences with nucleic acid sequences SEQ ID NO: 1-8, 11, 12, 14-17, and 19-22. In some embodiments, the composition comprises 18 purified bacterial strains, wherein the bacterial strains comprise 16S rDNA sequences with nucleic acid sequences SEQ ID NOs: 1-8, 11, 12, 14-17, and 19-22. In some embodiments, the composition consists of 18 purified bacterial strains, wherein the bacterial strains comprise 16S rDNA sequences with nucleic acid sequences SEQ ID NOs: 1-8, 11, 12, 14-17, and 19-22. In some embodiments, the composition essentially consists of 18 purified bacterial strains, wherein the bacterial strains comprise 16S rDNA sequences with nucleic acid sequences SEQ ID NOs: 1-8, 11, 12, 14-17, and 19-22. As used herein, "essentially consists of" (and like phrases) refers to a composition that includes no additional bacterial strains.

In some embodiments, the disclosure provides compositions with bacterial strains that comprise 16S rDNA sequences having at least 97% sequence identity with nucleic acid sequences selected from the group consisting of SEQ ID NOs: 1-8, 11, 12, 14-17, and 19-22. In some embodiments, the disclosure provides compositions comprising two or more (e.g., 2, 3, 4, 5, or more) purified bacterial strains that comprise 16S rDNA sequences having at least 97% sequence identity with nucleic acid sequences selected from the group consisting of SEQ ID NOs: 1-8, 11, 12, 14-17, and 19-22. In some embodiments, the compositions comprise 18 purified bacterial strains, wherein the bacterial strains comprise 16S rDNA sequences having at least 97% sequence identity with nucleic acid sequences SEQ ID NOs: 1-8, 11, 12, 14-17, and 19-22. In some embodiments, the compositions consist of 18 purified bacterial strains, wherein the bacterial strains comprise 16S rDNA sequences having at least 97% sequence identity with nucleic acid sequences SEQ ID NOs: 1-8, 11, 12, 14-17, and 19-22. In some embodiments, the compositions essentially consist of 18 purified bacterial strains, wherein the bacterial strains comprise 16S rDNA sequences having at least 97% sequence identity with nucleic acid sequences SEQ ID NOs: 1-8, 11, 12, 14-17, and 19-22.

The bacterial strains in live bacterial product 1 are related to the following species: *Alistipes putredinis*, *Bacteroides uniformis*, *Bacteroides vulgatus*, *Barnesiella intestinihominis*, *Parabacteroides merdae*, *Bifidobacterium longum*, *Bifidobacterium adolescentis*, *Blautia obeum*, *Blautia wexlerae*, *Clostridium bolteae*, *Clostridium innocuum*, *Coprococcus comes*, *Dorea longicatena*, *Eubacterium halli*, *Faecalibacterium prausnitzii*, *Parabacteroides distasonis*, *Prevotella copri*, *Roseburia faecis*, and *Ruminococcus faecis* (see, e.g., Table 1). It should be appreciated that multiple bacterial strains of the compositions described herein can have the same related bacterial species. For example, the bacterial strains having 16S rDNA sequences with nucleic acid sequences SEQ ID NO: 12 and SEQ ID NO: 19 both have *Parabacteroides distasonis* as the related species. In some embodiments, the compositions comprise two or more (e.g., 2, 3, 4, 5, or more) bacterial species selected from the group consisting of *Alistipes putredinis*, *Bacteroides uniformis*, *Bacteroides vulgatus*, *Barnesiella intestinihominis*, *Parabacteroides merdae*, *Bifidobacterium longum*, *Bifidobacterium adolescentis*, *Blautia obeum*, *Blautia wexlerae*, *Clostridium bolteae*, *Clostridium innocuum*, *Coprococcus comes*, *Dorea longicatena*, *Eubacterium halli*, *Faecalibacterium prausnitzii*, *Parabacteroides distasonis*, *Prevotella copri*, *Roseburia faecis*, and *Ruminococcus faecis*. In some embodiments, the compositions comprise 18 bacterial species: *Alistipes putredinis*, *Bacteroides uniformis*, *Bacteroides vulgatus*, *Barnesiella intestinihominis*, *Parabacteroides merdae*, *Bifidobacterium longum*, *Bifidobacterium adolescentis*, *Blautia obeum*, *Blautia wexlerae*, *Clostridium bolteae*, *Clostridium innocuum*, *Coprococcus comes*, *Dorea longicatena*, *Eubacterium halli*, *Faecalibacterium prausnitzii*, *Parabacteroides distasonis*, *Prevotella copri*, *Roseburia faecis*, and *Ruminococcus faecis*. In some embodiments, the compositions consist of 18 bacterial species: *Alistipes putredinis*, *Bacteroides uniformis*, *Bacteroides vulgatus*, *Barnesiella intestinihominis*, *Parabacteroides merdae*, *Bifidobacterium longum*, *Bifidobacterium adolescentis*, *Blautia obeum*, *Blautia wexlerae*, *Clostridium bolteae*, *Clostridium innocuum*, *Coprococcus comes*, *Dorea longicatena*, *Eubacterium halli*, *Faecalibacterium prausnitzii*, *Parabacteroides distasonis*, *Prevotella copri*, *Roseburia faecis*, and *Ruminococcus faecis*. In some embodiments, the compositions essentially consist of 18 bacterial species: *Alistipes putredinis*, *Bacteroides uniformis*, *Bacteroides vulgatus*, *Barnesiella intestinihominis*, *Parabacteroides merdae*, *Bifidobacterium longum*, *Bifidobacterium adolescentis*, *Blautia obeum*, *Blautia wexlerae*, *Clostridium bolteae*, *Clostridium innocuum*, *Coprococcus comes*, *Dorea longicatena*, *Eubacterium halli*, *Faecalibacterium prausnitzii*, *Parabacteroides distasonis*, *Prevotella copri*, *Roseburia faecis*, and *Ruminococcus faecis*.

In one aspect, the disclosure provides composition comprising one or more bacterial strains selected from the group consisting of strains 26-33, 34, 35, 37-40 and 42-45 (See Table 1).

TABLE 1

Live bacterial product 1

| Genus species | Strain No. | 16S rDNA SEQ ID NO |
|---|---|---|
| Alistipes_putredinis | Strain 26 | 1 |
| Bacteroides_uniformis | Strain 27 | 2 |
| Bacteroides_vulgatus | Strain 28 | 3 |
| Parabacteroides merdae | Strain 29 | 4 |
| Bifidobacterium_longum | Strain 30 | 5 |
| Bifidobacterium_adolescentis | Strain 31 | 6 |
| Blautia_obeum | Strain 32 | 7 |
| Blautia_wexlerae | Strain 33 | 8 |
| Clostridium_bolteae | Strain 34 | 11 |
| Parabacteroides distasonis | Strain 35 | 12 |
| Coprococcus comes | Strain 37 | 14 |
| Dorea longicatena | Strain 38 | 15 |
| Eubacterium_halli | Strain 39 | 16 |
| Faecalibacterium_prausnitzii | Strain 40 | 17 |
| Parabacteroides_distasonis | Strain 42 | 19 |
| Prevotella_copri | Strain 43 | 20 |
| Roseburia_faecis | Strain 44 | 21 |
| Ruminococcus_faecis | Strain 45 | 22 |

In one aspect, the disclosure provides live bacterial product 2 (LBP 2) (see, e.g., FIG. 4, Table 2). As shown in FIG. 4 and Table 2, live bacterial product 2 contains bacterial strains that comprise 16S rDNA sequences with nucleic acid sequences SEQ ID NOs: 1, 3-5, 7, 8, 11, 13-18, and 20-22. In some embodiments, the compositions comprise at least two (e.g., 2, 3, 4, 5, or more) bacterial strains that comprise 16S rDNA sequences with nucleic acid sequences SEQ ID NOs: 1, 3-5, 7, 8, 11, 13-18, and 20-22. In some embodiments, the composition comprises 16 purified bacterial strains, wherein the bacterial strains comprise 16S rDNA sequences with nucleic acid sequences SEQ ID NOs: 1, 3-5, 7, 8, 11, 13-18, and 20-22. In some embodiments, the composition consists of 16 purified bacterial strains, wherein the bacterial strains comprise 16S rDNA sequences with nucleic acid sequences SEQ ID NOs: 1, 3-5, 7, 8, 11, 13-18, and 20-22. In some embodiments, the composition essentially consists of 16 purified bacterial strains, wherein the bacterial strains comprise 16S rDNA sequences with nucleic acid sequences SEQ ID NOs: 1, 3-5, 7, 8, 11, 13-18, and 20-22. As used herein, "essentially consists of" (and like phrases) refers to a composition that includes no additional bacterial strains.

In some embodiments, the disclosure provides compositions with bacterial strains that comprise 16S rDNA sequences having at least 97% sequence identity with nucleic acid sequences selected from the group consisting of SEQ ID NOs: 1, 3-5, 7, 8, 11, 13-18, and 20-22. In some embodiments, the disclosure provides compositions comprising two or more (e.g., 2, 3, 4, 5, or more) purified bacterial strains that comprise 16S rDNA sequences having at least 97% sequence identity with nucleic acid sequences selected from the group consisting of SEQ ID NOs: 1, 3-5, 7, 8, 11, 13-18, and 20-22. In some embodiments, the compositions comprise 16 purified bacterial strains, wherein the bacterial strains comprise 16S rDNA sequences having at least 97% sequence identity with nucleic acid sequences SEQ ID NOs: 1, 3-5, 7, 8, 11, 13-18, and 20-22. In some embodiments, the compositions consist of 16 purified bacterial strains, wherein the bacterial strains comprise 16S rDNA sequences having at least 97% sequence identity with nucleic acid sequences SEQ ID NOs: 1, 3-5, 7, 8, 11, 13-18, and 20-22. In some embodiments, the compositions essentially consist of 16 purified bacterial strains, wherein the bacterial strains comprise 16S rDNA sequences having at least 97% sequence identity with nucleic acid sequences SEQ ID NOs: 1, 3-5, 7, 8, 11, 13-18, and 20-22.

The bacterial strains in live bacterial product 2 are related to the following species: Alistipes putredinis, Bacteroides vulgatus, Barnesiella intestinihominis, Bifidobacterium longum, Blautia obeum, Blautia wexlerae, Clostridium bolteae, Parabacteroides distasonis, Collinsella aerofaciens, Coprococcus comes, Dorea longicatena, Eubacterium halli, Faecalibacterium prausnitzii, Parabacteroides merdae, Prevotella copri, Roseburia faecis, and Ruminococcus faecis (see, e.g., Table 2). It should be appreciated that multiple bacterial strains of the compositions described herein can have the same related bacterial species. For example, the bacterial strains having 16S rDNA sequences with nucleic acid sequences SEQ ID NO: 4 and SEQ ID NO: 18 both have Parabacteroides merdae as the related species. In some embodiments, the compositions comprise two or more (e.g., 2, 3, 4, 5, or more) bacterial species selected from the group consisting of Alistipes putredinis, Bacteroides vulgatus, Barnesiella intestinihominis, Bifidobacterium longum, Blautia obeum, Blautia wexlerae, Clostridium bolteae, Parabacteroides distasonis, Collinsella aerofaciens, Coprococcus comes, Dorea longicatena, Eubacterium halli, Faecalibacterium prausnitzii, Parabacteroides merdae, Prevotella copri, Roseburia faecis, and Ruminococcus faecis. In some embodiments, the compositions comprise 16 bacterial species: Alistipes putredinis, Bacteroides vulgatus, Barnesiella intestinihominis, Bifidobacterium longum, Blautia obeum, Blautia wexlerae, Clostridium bolteae, Parabacteroides distasonis, Collinsella aerofaciens, Coprococcus comes, Dorea longicatena, Eubacterium halli, Faecalibacterium prausnitzii, Parabacteroides merdae, Prevotella copri, Roseburia faecis, and Ruminococcus faecis. In some embodiments, the compositions consist of 16 bacterial species: Alistipes putredinis, Bacteroides vulgatus, Barnesiella intestinihominis, Bifidobacterium longum, Blautia obeum, Blautia wexlerae, Clostridium bolteae, Parabacteroides distasonis, Collinsella aerofaciens, Coprococcus comes, Dorea longicatena, Eubacterium halli, Faecalibacterium prausnitzii, Parabacteroides merdae, Prevotella copri, Roseburia faecis, and Ruminococcus faecis. In some embodiments, the compositions essentially consist 16 bacterial species: Alistipes putredinis, Bacteroides vulgatus, Barnesiella intestinihominis, Bifidobacterium longum, Blautia obeum, Blautia wexlerae, Clostridium bolteae, Parabacteroides distasonis, Collinsella aerofaciens, Coprococcus comes, Dorea longicatena, Eubacterium halli, Faecalibacterium prausnitzii, Parabacteroides merdae, Prevotella copri, Roseburia faecis, and Ruminococcus faecis.

In one aspect, the disclosure provides compositions comprising one or more bacterial strains selected from the group consisting of strains 26, 28-30, 32, 33, 34, 36-41 and 43-45 (See Table 2).

TABLE 2

Live bacterial product 2

| Genus species | Strain No. | 16S rDNA SEQ ID NO: |
|---|---|---|
| Alistipes_putredinis | Strain 26 | 1 |
| Bacteroides_vulgatus | Strain 28 | 3 |
| Parabacteroides merdae | Strain 29 | 4 |
| Bifidobacterium_longum | Strain 30 | 5 |

TABLE 2-continued

Live bacterial product 2

| Genus species | Strain No. | 16S rDNA SEQ ID NO: |
|---|---|---|
| *Blautia_obeum* | Strain 32 | 7 |
| *Blautia_wexlerae* | Strain 33 | 8 |
| *Clostridium_bolteae* | Strain 34 | 11 |
| *Collinsella_aerofaciens* | Strain 36 | 13 |
| *Coprococcus comes* | Strain 37 | 14 |
| *Dorea longicatena* | Strain 38 | 15 |
| *Eubacterium_halli* | Strain 39 | 16 |
| *Faecalibacterium_prausnitzii* | Strain 40 | 17 |
| *Parabacteroides_merdae* | Strain 41 | 18 |
| *Prevotella_copri* | Strain 43 | 20 |
| *Roseburia_faecis* | Strain 44 | 21 |
| *Ruminococcus_faecis* | Strain 45 | 22 |

In one aspect, the disclosure provides live bacterial product 3 (LBP 3) (see, e.g., FIG. 4, Table 3). As shown in FIG. 4 and Table 3, live bacterial product 3 contains bacterial strains that comprise 16S rDNA sequences with nucleic acid sequences SEQ ID NOs: 2-8, 11, 12, 15-17, 19, 20, and 22. In some embodiments, the compositions comprise at least two (e.g., 2, 3, 4, 5, or more) bacterial strains that comprise 16S rDNA sequences with nucleic acid sequences SEQ ID NOs: 2-8, 11, 12, 15-17, 19, 20, and 22. In some embodiments, the composition comprises 15 purified bacterial strains, wherein the bacterial strains comprise 16S rDNA sequences with nucleic acid sequences SEQ ID NOs: 2-8, 11, 12, 15-17, 19, 20, and 22. In some embodiments, the composition consists of 15 purified bacterial strains, wherein the bacterial strains comprise 16S rDNA sequences with nucleic acid sequences SEQ ID NOs: 2-8, 11, 12, 15-17, 19, 20, and 22. In some embodiments, the composition essentially consists of 15 purified bacterial strains, wherein the bacterial strains comprise 16S rDNA sequences with nucleic acid sequences SEQ ID NOs: 2-8, 11, 12, 15-17, 19, 20, and 22.

In some embodiments, the disclosure provides compositions with bacterial strains that comprise 16S rDNA sequences having at least 97% sequence identity with nucleic acid sequences selected from the group consisting of SEQ ID NOs: 2-8, 11, 12, 15-17, 19, 20, and 22. In some embodiments, the disclosure provides compositions comprising two or more (e.g., 2, 3, 4, 5, or more) purified bacterial strains that comprise 16S rDNA sequences having at least 97% sequence identity with nucleic acid sequences selected from the group consisting of SEQ ID NOs: 2-8, 11, 12, 15-17, 19, 20, and 22. In some embodiments, the compositions comprise 15 purified bacterial strains, wherein the bacterial strains comprise 16S rDNA sequences having at least 97% sequence identity with nucleic acid sequences SEQ ID NOs: 2-8, 11, 12, 15-17, 19, 20, and 22. In some embodiments, the compositions consist of 15 purified bacterial strains, wherein the bacterial strains comprise 16S rDNA sequences having at least 97% sequence identity with nucleic acid sequences SEQ ID NOs: 2-8, 11, 12, 15-17, 19, 20, and 22. In some embodiments, the compositions essentially consist of 15 purified bacterial strains, wherein the bacterial strains comprise 16S rDNA sequences having at least 97% sequence identity with nucleic acid sequences SEQ ID NOs: 2-8, 11, 12, 15-17, 19, 20, and 22.

The bacterial strains in live bacterial product 3 are related to the following species: *Bacteroides uniformis, Bacteroides vulgatus, Barnesiella intestinihominis, Parabacteroides merdae, Bifidobacterium longum, Bifidobacterium adolescentis, Blautia obeum, Blautia wexlerae, Clostridium bolteae, Clostridium innocuum, Dorea longicatena, Eubacterium halli, Faecalibacterium prausnitzii, Parabacteroides distasonis, Prevotella copri*, and *Ruminococcus faecis* (see, e.g., Table 3). It should be appreciated that multiple bacterial strains of the compositions described herein can have the same related bacterial species. For example, the bacterial strains having 16S rDNA sequences with nucleic acid sequences SEQ ID NO: 12 and SEQ ID NO: 119 both have *Parabacteroides distasonis* as the related species. In some embodiments, the compositions comprise two or more (e.g., 2, 3, 4, 5, or more) bacterial species selected from the group consisting of *Bacteroides uniformis, Bacteroides vulgatus, Barnesiella intestinihominis, Parabacteroides merdae, Bifidobacterium longum, Bifidobacterium adolescentis, Blautia obeum, Blautia wexlerae, Clostridium bolteae, Clostridium innocuum, Dorea longicatena, Eubacterium halli, Faecalibacterium prausnitzii, Parabacteroides distasonis, Prevotella copri*, and *Ruminococcus faecis*. In some embodiments, the compositions comprise 15 bacterial species: *Bacteroides uniformis, Bacteroides vulgatus, Barnesiella intestinihominis, Parabacteroides merdae, Bifidobacterium longum, Bifidobacterium adolescentis, Blautia obeum, Blautia wexlerae, Clostridium bolteae, Clostridium innocuum, Dorea longicatena, Eubacterium halli, Faecalibacterium prausnitzii, Parabacteroides distasonis, Prevotella copri*, and *Ruminococcus faecis*. In some embodiments, the compositions consist of 15 bacterial species: *Bacteroides uniformis, Bacteroides vulgatus, Barnesiella intestinihominis, Parabacteroides merdae, Bifidobacterium longum, Bifidobacterium adolescentis, Blautia obeum, Blautia wexlerae, Clostridium bolteae, Clostridium innocuum, Dorea longicatena, Eubacterium halli, Faecalibacterium prausnitzii, Parabacteroides distasonis, Prevotella copri*, and *Ruminococcus faecis*. In some embodiments, the compositions essentially consist 15 bacterial species: *Bacteroides uniformis, Bacteroides vulgatus, Barnesiella intestinihominis, Parabacteroides merdae, Bifidobacterium longum, Bifidobacterium adolescentis, Blautia obeum, Blautia wexlerae, Clostridium bolteae, Clostridium innocuum, Dorea longicatena, Eubacterium halli, Faecalibacterium prausnitzii, Parabacteroides distasonis, Prevotella copri*, and *Ruminococcus faecis*.

In one aspect, the disclosure provides composition comprising one or more bacterial strains selected from the group consisting of strains 27-33, 34, 35, 38-40, 42, 43, and 45 (See Table 3).

TABLE 3

Live bacterial product 3

| Genus species | Strain No. | 16S rDNA SEQ ID NO |
|---|---|---|
| *Bacteroides_uniformis* | Strain 27 | 2 |
| *Bacteroides_vulgatus* | Strain 28 | 3 |
| *Parabacteroides merdae* | Strain 29 | 4 |
| *Bifidobacterium_longum* | Strain 30 | 5 |
| *Bifidobacterium_adolescentis* | Strain 31 | 6 |
| *Blautia_obeum* | Strain 32 | 7 |
| *Blautia_wexlerae* | Strain 33 | 8 |
| *Clostridium_bolteae* | Strain 34 | 11 |
| *Parabacteroides distasonis* | Strain 35 | 12 |
| *Dorea longicatena* | Strain 38 | 15 |
| *Eubacterium_halli* | Strain 39 | 16 |
| *Faecalibacterium_prausnitzii* | Strain 40 | 17 |
| *Parabacteroides_distasonis* | Strain 42 | 19 |

TABLE 3-continued

Live bacterial product 3

| Genus species | Strain No. | 16S rDNA SEQ ID NO |
|---|---|---|
| Prevotella_copri | Strain 43 | 20 |
| Ruminococcus_faecis | Strain 45 | 22 |

In one aspect, the disclosure provides live bacterial product 4 (LBP 4) (see, e.g., FIG. 4, Table 4). As shown in FIG. 4 and Table 4, live bacterial product 4 contains bacterial strains that comprise 16S rDNA sequences with nucleic acid sequences SEQ ID NOs: 3-5, 7, 9-11, 15-17, 19, 20, and 22. In some embodiments, the compositions comprise at least two (e.g., 2, 3, 4, 5, or more) bacterial strains that comprise 16S rDNA sequences with nucleic acid sequences SEQ ID NOs: 3-5, 7, 9-11, 15-17, 19, 20, and 22. In some embodiments, the composition comprises 13 purified bacterial strains, wherein the bacterial strains comprise 16S rDNA sequences with nucleic acid sequences SEQ ID NOs: 3-5, 7, 9-11, 15-17, 19, 20, and 22. In some embodiments, the composition consists of 13 purified bacterial strains, wherein the bacterial strains comprise 16S rDNA sequences with nucleic acid sequences SEQ ID NOs: 3-5, 7, 9-11, 15-17, 19, 20, and 22. In some embodiments, the composition essentially consists of 13 purified bacterial strains, wherein the bacterial strains comprise 16S rDNA sequences with nucleic acid sequences SEQ ID NOs: 3-5, 7, 9-11, 15-17, 19, 20, and 22.

In some embodiments, the disclosure provides compositions with bacterial strains that comprise 16S rDNA sequences having at least 97% sequence identity with nucleic acid sequences selected from the group consisting of SEQ ID NOs: 3-5, 7, 9-11, 15-17, 19, 20, and 22. In some embodiments, the disclosure provides compositions comprising two or more (e.g., 2, 3, 4, 5, or more) purified bacterial strains that comprise 16S rDNA sequences having at least 97% sequence identity with nucleic acid sequences selected from the group consisting of SEQ ID NOs: 3-5, 7, 9-11, 15-17, 19, 20, and 22. In some embodiments, the compositions comprise 13 purified bacterial strains, wherein the bacterial strains comprise 16S rDNA sequences having at least 97% sequence identity with nucleic acid sequences SEQ ID NOs: 3-5, 7, 9-11, 15-17, 19, 20, and 22. In some embodiments, the compositions consist of 13 purified bacterial strains, wherein the bacterial strains comprise 16S rDNA sequences having at least 97% sequence identity with nucleic acid sequences SEQ ID NOs: 3-5, 7, 9-11, 15-17, 19, 20, and 22. In some embodiments, the compositions essentially consist of 13 purified bacterial strains, wherein the bacterial strains comprise 16S rDNA sequences having at least 97% sequence identity with nucleic acid sequences SEQ ID NOs: 3-5, 7, 9-11, 15-17, 19, 20, and 22.

The bacterial strains in live bacterial product 4 are related to the following species: *Bacteroides vulgatus, Barnesiella intestinihominis, Parabacteroides merdae, Bifidobacterium longum, Blautia obeum, Blautia producta, Clostridium hathewayi, Clostridium bolteae, Dorea longicatena, Eubacterium halli, Faecalibacterium prausnitzii, Parabacteroides distasonis, Prevotella copri*, and *Ruminococcus faecis* (see, e.g., Table 4). In some embodiments, the compositions comprise two or more (e.g., 2, 3, 4, 5, or more) bacterial species selected from the group consisting of *Bacteroides vulgatus, Barnesiella intestinihominis, Parabacteroides merdae, Bifidobacterium longum, Blautia obeum, Blautia producta, Clostridium hathewayi, Clostridium bolteae, Dorea longicatena, Eubacterium halli, Faecalibacterium prausnitzii, Parabacteroides distasonis, Prevotella copri*, and *Ruminococcus faecis*. In some embodiments, the compositions comprise 13 bacterial species: *Bacteroides vulgatus, Barnesiella intestinihominis, Parabacteroides merdae, Bifidobacterium longum, Blautia obeum, Blautia producta, Clostridium hathewayi, Clostridium bolteae, Dorea longicatena, Eubacterium halli, Faecalibacterium prausnitzii, Parabacteroides distasonis, Prevotella copri*, and *Ruminococcus faecis*. In some embodiments, the compositions consist of 13 bacterial species: *Bacteroides vulgatus, Barnesiella intestinihominis, Parabacteroides merdae, Bifidobacterium longum, Blautia obeum, Blautia producta, Clostridium hathewayi, Clostridium bolteae, Dorea longicatena, Eubacterium halli, Faecalibacterium prausnitzii, Parabacteroides distasonis, Prevotella copri*, and *Ruminococcus faecis*. In some embodiments, the compositions essentially consist 13 bacterial species: *Bacteroides vulgatus, Barnesiella intestinihominis, Parabacteroides merdae, Bifidobacterium longum, Blautia obeum, Blautia producta, Clostridium hathewayi, Clostridium bolteae, Dorea longicatena, Eubacterium halli, Faecalibacterium prausnitzii, Parabacteroides distasonis, Prevotella copri*, and *Ruminococcus faecis*.

In one aspect, the disclosure provides composition comprising one or more bacterial strains selected from the group consisting of strains 28-30, 32, 2, 20, 34, 38-40, 42, 43, and 45 (See Table 4).

TABLE 4

Live bacterial product 4

| Genus species | Strain No. | 16S rDNA SEQ ID NO |
|---|---|---|
| Bacteroides_vulgatus | Strain 28 | 3 |
| Parabacteroides merdae | Strain 29 | 4 |
| Bifidobacterium_longum | Strain 30 | 5 |
| Blautia_obeum | Strain 32 | 7 |
| Blautia_producta | Strain 2 | 9 |
| Clostridium_hathewayi | Strain 20 | 10 |
| Clostridium_bolteae | Strain 34 | 11 |
| Dorea longicatena | Strain 38 | 15 |
| Eubacterium_halli | Strain 39 | 16 |
| Faecalibacterium_prausnitzii | Strain 40 | 17 |
| Parabacteroides_distasonis | Strain 42 | 19 |
| Prevotella_copri | Strain 43 | 20 |
| Ruminococcus_faecis | Strain 45 | 22 |

In one aspect, the disclosure provides live bacterial product 5 (LBP 5) (see, e.g., FIG. 4, Table 5). As shown in FIG. 4 and Table 5, live bacterial product 5 contains bacterial strains that comprise 16S rDNA sequences with nucleic acid sequences SEQ ID NOs: 2, 3, 6, 9, 10, 12, 15-18, 20, and 22. In some embodiments, the compositions comprise at least two (e.g., 2, 3, 4, 5, or more) bacterial strains that comprise 16S rDNA sequences with nucleic acid sequences SEQ ID NOs: 2, 3, 6, 9, 10, 12, 15-18, 20, and 22. In some embodiments, the composition comprises 12 purified bacterial strains, wherein the bacterial strains comprise 16S rDNA sequences with nucleic acid sequences SEQ ID NOs: 2, 3, 6, 9, 10, 12, 15-18, 20, and 22. In some embodiments, the composition consists of 12 purified bacterial strains, wherein the bacterial strains comprise 16S rDNA sequences with nucleic acid sequences SEQ ID NOs: 2, 3, 6, 9, 10, 12, 15-18, 20, and 22. In some embodiments, the composition essentially consists of 12 purified bacterial strains, wherein the bacterial strains comprise 16S rDNA sequences with nucleic acid sequences SEQ ID NOs: 2, 3, 6, 9, 10, 12, 15-18, 20, and 22.

In some embodiments, the disclosure provides compositions with bacterial strains that comprise 16S rDNA sequences having at least 97% sequence identity with nucleic acid sequences selected from the group consisting of SEQ ID NOs: 2, 3, 6, 9, 10, 12, 15-18, 20, and 22. In some embodiments, the disclosure provides compositions comprising two or more (e.g., 2, 3, 4, 5, or more) purified bacterial strains that comprise 16S rDNA sequences having at least 97% sequence identity with nucleic acid sequences selected from the group consisting of SEQ ID NOs: 2, 3, 6, 9, 10, 12, 15-18, 20, and 22. In some embodiments, the compositions comprise 12 purified bacterial strains, wherein the bacterial strains comprise 16S rDNA sequences having at least 97% sequence identity with nucleic acid sequences SEQ ID NOs: 2, 3, 6, 9, 10, 12, 15-18, 20, and 22. In some embodiments, the compositions consist of 12 purified bacterial strains, wherein the bacterial strains comprise 16S rDNA sequences having at least 97% sequence identity with nucleic acid sequences SEQ ID NOs: 2, 3, 6, 9, 10, 12, 15-18, 20, and 22. In some embodiments, the compositions essentially consist of 12 purified bacterial strains, wherein the bacterial strains comprise 16S rDNA sequences having at least 97% sequence identity with nucleic acid sequences SEQ ID NOs: 2, 3, 6, 9, 10, 12, 15-18, 20, and 22.

The bacterial strains in live bacterial product 5 are related to the following species: *Bacteroides uniformis, Bacteroides vulgatus, Bifidobacterium adolescentis, Blautia producta, Clostridium hathewayi, Clostridium innocuum, Dorea longicatena, Eubacterium halli, Faecalibacterium prausnitzii, Parabacteroides merdae, Prevotella copri,* and *Ruminococcus faecis* (see, e.g., Table 5). In some embodiments, the compositions comprise two or more (e.g., 2, 3, 4, 5, or more) bacterial species selected from the group consisting of *Bacteroides uniformis, Bacteroides vulgatus, Bifidobacterium adolescentis, Blautia producta, Clostridium hathewayi, Clostridium innocuum, Dorea longicatena, Eubacterium halli, Faecalibacterium prausnitzii, Parabacteroides merdae, Prevotella copri,* and *Ruminococcus faecis*. In some embodiments, the compositions comprise 12 bacterial species: *Bacteroides uniformis, Bacteroides vulgatus, Bifidobacterium adolescentis, Blautia producta, Clostridium hathewayi, Clostridium innocuum, Dorea longicatena, Eubacterium halli, Faecalibacterium prausnitzii, Parabacteroides merdae, Prevotella copri,* and *Ruminococcus faecis*. In some embodiments, the compositions consist of 12 bacterial species: *Bacteroides uniformis, Bacteroides vulgatus, Bifidobacterium adolescentis, Blautia producta, Clostridium hathewayi, Clostridium innocuum, Dorea longicatena, Eubacterium halli, Faecalibacterium prausnitzii, Parabacteroides merdae, Prevotella copri,* and *Ruminococcus faecis*. In some embodiments, the compositions essentially consist of 12 bacterial species: *Bacteroides uniformis, Bacteroides vulgatus, Bifidobacterium adolescentis, Blautia producta, Clostridium hathewayi, Clostridium innocuum, Dorea longicatena, Eubacterium halli, Faecalibacterium prausnitzii, Parabacteroides merdae, Prevotella copri,* and *Ruminococcus faecis*.

In one aspect, the disclosure provides compositions comprising one or more bacterial strains selected from the group consisting of strains 27, 28, 31, 2, 20, 35, 38-41, 43, and 45 (See, Table 5).

TABLE 5

Live bacterial product 5

| Genus species | Strain No | 16S rDNA SEQ ID NO |
|---|---|---|
| Bacteroides_uniformis | Strain 27 | 2 |
| Bacteroides_vulgatus | Strain 28 | 3 |
| Bifidobacterium_adolescentis | Strain 31 | 6 |
| Blautia_producta | Strain 2 | 9 |
| Clostridium_hathewayi | Strain 20 | 10 |
| Parabacteroides distasonis | Strain 35 | 12 |
| Dorea longicatena | Strain 38 | 15 |
| Eubacterium_halli | Strain 39 | 16 |
| Faecalibacterium_prausnitzii | Strain 40 | 17 |
| Parabacteroides_merdae | Strain 41 | 18 |
| Prevotella_copri | Strain 43 | 20 |
| Ruminococcus_faecis | Strain 45 | 22 |

In one aspect, the disclosure provides live bacterial product 6 (LBP 6) (see, e.g., FIG. 4, Table 6). As shown in FIG. 4 and Table 6, live bacterial product 6 contains bacterial strains that comprise 16S rDNA sequences with nucleic acid sequences SEQ ID NOs: 3-5, 7, 12, 15-17, 19, and 22. In some embodiments, the compositions comprise at least two (e.g., 2, 3, 4, 5, or more) bacterial strains that comprise 16S rDNA sequences with nucleic acid sequences SEQ ID NOs: 3-5, 7, 12, 15-17, 19, and 22. In some embodiments, the composition comprises 10 purified bacterial strains, wherein the bacterial strains comprise 16S rDNA sequences with nucleic acid sequences SEQ ID NOs: 3-5, 7, 12, 15-17, 19, and 22. In some embodiments, the composition consists of 10 purified bacterial strains, wherein the bacterial strains comprise 16S rDNA sequences with nucleic acid sequences SEQ ID NOs: 3-5, 7, 12, 15-17, 19, and 22. In some embodiments, the composition essentially consists of 10 purified bacterial strains, wherein the bacterial strains comprise 16S rDNA sequences with nucleic acid sequences SEQ ID NOs: 3-5, 7, 12, 15-17, 19, and 22.

In some embodiments, the disclosure provides compositions with bacterial strains that comprise 16S rDNA sequences having at least 97% sequence identity with nucleic acid sequences selected from the group consisting of SEQ ID NOs: 3-5, 7, 12, 15-17, 19, and 22. In some embodiments, the disclosure provides compositions comprising two or more (e.g., 2, 3, 4, 5, or more) purified bacterial strains that comprise 16S rDNA sequences having at least 97% sequence identity with nucleic acid sequences selected from the group consisting of SEQ ID NOs: 3-5, 7, 12, 15-17, 19, and 22. In some embodiments, the compositions comprise 10 purified bacterial strains, wherein the bacterial strains comprise 16S rDNA sequences having at least 97% sequence identity with nucleic acid sequences SEQ ID NOs: 3-5, 7, 12, 15-17, 19, and 22. In some embodiments, the compositions consist of 10 purified bacterial strains, wherein the bacterial strains comprise 16S rDNA sequences having at least 97% sequence identity with nucleic acid sequences SEQ ID NOs: 3-5, 7, 12, 15-17, 19, and 22. In some embodiments, the compositions essentially consist of 10 purified bacterial strains, wherein the bacterial strains comprise 16S rDNA sequences having at least 97% sequence identity with nucleic acid sequences SEQ ID NOs: 3-5, 7, 12, 15-17, 19, and 22.

The bacterial strains in live bacterial product 6 are related to the following species: *Bacteroides vulgatus, Barnesiella intestinihominis, Parabacteroides merdae, Bifidobacterium longum, Blautia obeum, Clostridium innocuum, Dorea longicatena, Eubacterium halli, Faecalibacterium prausnitzii,*

*Parabacteroides distasonis*, and *Ruminococcus faecis* (see, e.g., Table 6). It should be appreciated that multiple bacterial strains of the compositions described herein can have the same related bacterial species. For example, the bacterial strains having 16S rDNA sequences with nucleic acid sequences SEQ ID NO: 12 and SEQ ID NO: 119 both have *Parabacteroides distasonis* as the related species. In some embodiments, the compositions comprise two or more (e.g., 2, 3, 4, 5, or more) bacterial species selected from the group consisting of *Bacteroides vulgatus, Barnesiella intestinihominis, Parabacteroides merdae, Bifidobacterium longum, Blautia obeum, Clostridium innocuum, Dorea longicatena, Eubacterium halli, Faecalibacterium prausnitzii, Parabacteroides distasonis,* and *Ruminococcus faecis.* In some embodiments, the compositions comprise 10 bacterial species: *Bacteroides vulgatus, Barnesiella intestinihominis, Parabacteroides merdae, Bifidobacterium longum, Blautia obeum, Clostridium innocuum, Dorea longicatena, Eubacterium halli, Faecalibacterium prausnitzii, Parabacteroides distasonis,* and *Ruminococcus faecis.* In some embodiments, the compositions consist of 10 bacterial species: *Bacteroides vulgatus, Barnesiella intestinihominis, Parabacteroides merdae, Bifidobacterium longum, Blautia obeum, Clostridium innocuum, Dorea longicatena, Eubacterium halli, Faecalibacterium prausnitzii, Parabacteroides distasonis,* and *Ruminococcus faecis.* In some embodiments, the compositions essentially consist 10 bacterial species: *Bacteroides vulgatus, Barnesiella intestinihominis, Parabacteroides merdae, Bifidobacterium longum, Blautia obeum, Clostridium innocuum, Dorea longicatena, Eubacterium halli, Faecalibacterium prausnitzii, Parabacteroides distasonis,* and *Ruminococcus faecis.*

In one aspect, the disclosure provides compositions comprising one or more bacterial strains selected from the group consisting of strains 28-30, 32, 35, 38-40, 42 and 45 (See Table 6).

TABLE 6

Live bacterial product 6

| Genus species | Strain No. | 16S rDNA SEQ ID NO |
|---|---|---|
| *Bacteroides_vulgatus* | Strain 28 | 3 |
| *Parabacteroides merdae* | Strain 29 | 4 |
| *Bifidobacterium_longum* | Strain 30 | 5 |
| *Blautia_obeum* | Strain 32 | 7 |
| *Parabacteroides distasonis* | Strain 35 | 12 |
| *Dorea longicatena* | Strain 38 | 15 |
| *Eubacterium_halli* | Strain 39 | 16 |
| *Faecalibacterium_prausnitzii* | Strain 40 | 17 |
| *Parabacteroides_distasonis* | Strain 42 | 19 |
| *Ruminococcus_faecis* | Strain 45 | 22 |

In one aspect, the disclosure provides live bacterial product 7 (LBP 7) (see, e.g., FIG. 4, Table 7). As shown in FIG. 4 and Table 7, live bacterial product 7 contains bacterial strains that comprise 16S rDNA sequences with nucleic acid sequences SEQ ID NOs: 3, 6-8, 11-13, 16, 18, and 20. In some embodiments, the compositions comprise at least two (e.g., 2, 3, 4, 5, or more) bacterial strains that comprise 16S rDNA sequences with nucleic acid sequences SEQ ID NOs: 3, 6-8, 11-13, 16, 18, and 20. In some embodiments, the composition comprises 10 purified bacterial strains, wherein the bacterial strains comprise 16S rDNA sequences with nucleic acid sequences SEQ ID NOs: 3, 6-8, 11-13, 16, 18, and 20. In some embodiments, the composition consists of 10 purified bacterial strains, wherein the bacterial strains comprise 16S rDNA sequences with nucleic acid sequences SEQ ID NOs: 3, 6-8, 11-13, 16, 18, and 20. In some embodiments, the composition essentially consists of 10 purified bacterial strains, wherein the bacterial strains comprise 16S rDNA sequences with nucleic acid sequences SEQ ID NOs: 3, 6-8, 11-13, 16, 18, and 20.

In some embodiments, the disclosure provides compositions with bacterial strains that comprise 16S rDNA sequences having at least 97% sequence identity with nucleic acid sequences selected from the group consisting of SEQ ID NOs: 3, 6-8, 11-13, 16, 18, and 20. In some embodiments, the disclosure provides compositions comprising two or more (e.g., 2, 3, 4, 5, or more) purified bacterial strains that comprise 16S rDNA sequences having at least 97% sequence identity with nucleic acid sequences selected from the group consisting of SEQ ID NOs: 3, 6-8, 11-13, 16, 18, and 20. In some embodiments, the compositions comprise 10 purified bacterial strains, wherein the bacterial strains comprise 16S rDNA sequences having at least 97% sequence identity with nucleic acid sequences SEQ ID NOs: 3, 6-8, 11-13, 16, 18, and 20. In some embodiments, the compositions consist of 10 purified bacterial strains, wherein the bacterial strains comprise 16S rDNA sequences having at least 97% sequence identity with nucleic acid sequences SEQ ID NOs: 3, 6-8, 11-13, 16, 18, and 20. In some embodiments, the compositions essentially consist of 10 purified bacterial strains, wherein the bacterial strains comprise 16S rDNA sequences having at least 97% sequence identity with nucleic acid sequences SEQ ID NOs: 3, 6-8, 11-13, 16, 18, and 20.

The bacterial strains in live bacterial product 7 are related to the following species: *Bacteroides vulgatus, Bifidobacterium adolescentis, Blautia obeum, Blautia wexlerae, Clostridium bolteae, Clostridium innocuum, Parabacteroides distasonis, Collinsella aerofaciens, Eubacterium halli, Parabacteroides merdae,* and *Prevotella copri* (see, e.g., Table 7). In some embodiments, the compositions comprise two or more (e.g., 2, 3, 4, 5, or more) bacterial species selected from the group consisting of *Bacteroides vulgatus, Bifidobacterium adolescentis, Blautia obeum, Blautia wexlerae, Clostridium bolteae, Clostridium innocuum, Parabacteroides distasonis, Collinsella aerofaciens, Eubacterium halli, Parabacteroides merdae,* and *Prevotella copri.* In some embodiments, the compositions comprise 10 bacterial species: *Bacteroides vulgatus, Bifidobacterium adolescentis, Blautia obeum, Blautia wexlerae, Clostridium bolteae, Clostridium innocuum, Parabacteroides distasonis, Collinsella aerofaciens, Eubacterium halli, Parabacteroides merdae,* and *Prevotella copri.* In some embodiments, the compositions consist of 10 bacterial species: *Bacteroides vulgatus, Bifidobacterium adolescentis, Blautia obeum, Blautia wexlerae, Clostridium bolteae, Clostridium innocuum, Parabacteroides distasonis, Collinsella aerofaciens, Eubacterium halli, Parabacteroides merdae,* and *Prevotella copri.* In some embodiments, the compositions essentially consist 10 bacterial species: *Bacteroides vulgatus, Bifidobacterium adolescentis, Blautia obeum, Blautia wexlerae, Clostridium bolteae, Clostridium innocuum, Parabacteroides distasonis, Collinsella aerofaciens, Eubacterium halli, Parabacteroides merdae,* and *Prevotella copri.*

In one aspect, the disclosure provides compositions comprising one or more bacterial strains selected from the group consisting of strains 28, 31-33, 34-36, 39, 41 and 43 (See Table 7).

TABLE 7

Live bacterial product 7

| Genus species | Strain No. | 16S rDNA SEQ ID NO |
|---|---|---|
| Bacteroides_vulgatus | Strain 28 | 3 |
| Bifidobacterium_adolescentis | Strain 31 | 6 |
| Blautia_obeum | Strain 32 | 7 |
| Blautia_wexlerae | Strain 33 | 8 |
| Clostridium_bolteae | Strain 34 | 11 |
| Parabacteroides distasonis | Strain 35 | 12 |
| Collinsella_aerofaciens | Strain 36 | 13 |
| Eubacterium_halli | Strain 39 | 16 |
| Parabacteroides_merdae | Strain 41 | 18 |
| Prevotella_copri | Strain 43 | 20 |

In one aspect, the composition comprises bacterial strains of species identified in stool samples from donors and also present in the live bacteria products (e.g., LBP 1-7) provided herein. In one aspect, the composition comprises one or more bacterial strains, wherein the bacterial strains are related to the following species: Bifidobacterium longum, Bifidobacterium adolescentis, Blautia wexlerae, Bacteroides vulgatus, Bacteroides uniformis, Collinsella aerofaciens, Faecalibacterium prausnitzii, Blautia obeum, Parabacteroides merdae, Parabacteroides distasonis, Roseburia faecis, Coprococcus comes, Dorea longicatena, and Eubacterium hallii (see, e.g., FIG. 7). In some embodiments, the composition comprises at least two bacterial strains, wherein the bacterial strains are related to the following species: Bifidobacterium longum, Bifidobacterium adolescentis, Blautia wexlerae, Bacteroides vulgatus, Bacteroides uniformis, Collinsella aerofaciens, Faecalibacterium prausnitzii, Blautia obeum, Parabacteroides merdae, Parabacteroides distasonis, Roseburia faecis, Coprococcus comes, Dorea longicatena, and Eubacterium hallii (see, e.g., FIG. 7). In some embodiments, the compositions comprise two or more (e.g., 2, 3, 4, 5, or more) bacterial species selected from the group consisting of Bifidobacterium longum, Bifidobacterium adolescentis, Blautia wexlerae, Bacteroides vulgatus, Bacteroides uniformis, Collinsella aerofaciens, Faecalibacterium prausnitzii, Blautia obeum, Parabacteroides merdae, Parabacteroides distasonis, Roseburia faecis, Coprococcus comes, Dorea longicatena, and Eubacterium hallii. In some embodiments, the compositions consist of two or more (e.g., 2, 3, 4, 5, or more) bacterial species selected from the group consisting of Bifidobacterium longum, Bifidobacterium adolescentis, Blautia wexlerae, Bacteroides vulgatus, Bacteroides uniformis, Collinsella aerofaciens, Faecalibacterium prausnitzii, Blautia obeum, Parabacteroides merdae, Parabacteroides distasonis, Roseburia faecis, Coprococcus comes, Dorea longicatena, and Eubacterium hallii. In some embodiments, the compositions essentially consist of two or more (e.g., 2, 3, 4, 5, or more) bacterial species selected from the group consisting of Bifidobacterium longum, Bifidobacterium adolescentis, Blautia wexlerae, Bacteroides vulgatus, Bacteroides uniformis, Collinsella aerofaciens, Faecalibacterium prausnitzii, Blautia obeum, Parabacteroides merdae, Parabacteroides distasonis, Roseburia faecis, Coprococcus comes, Dorea longicatena, and Eubacterium hallii.

In some embodiments, bacterial strains that are considered pathogen-antagonistic bacterial strains may be selected and included in any of the bacterial compositions described herein. Pathogen-antagonistic strains may be identified by any method known in the art. For example, in some embodiments, bacterial strains are evaluated for pathogen-antagonizing activity using assays, such as a soft agar overlay assay, as described in the Examples. Briefly, a soft agar overlay assay involves growing bacterial isolates (test strains) and spotting them onto agar plates (for example, tryptone soy agar, TSA). A second layer of soft agar (e.g., 0.7% w/v agar) is seeded with an inoculum of the target strain. The plate is incubated, and a zone of inhibition of bacterial growth is indicative of suppression (antagonizing activity) of the target strain. Inhibitory cultures may be subjected to 16S rRNA gene sequencing for strain identification. Alternatively, or in addition, growth competition assays may be used to evaluated pathogen-antagonistic activity of bacterial strains. Briefly, growth competition assays (or fitness assays or competition assays) involve co-culturing two or more candidate bacterial strains. The co-cultured strains are allowed to compete for limited resources and then plating diluted samples on selective growth media to determine relative fitness (see, e.g., Lenski et al., Proc. Natl. Sci. USA 91:6808-6814 (1994)).

In some embodiments, the compositions described herein comprise one or more (e.g., 1, 2, 3, 4, 5, or more) purified bacterial strain that has been identified as a pathogen-antagonizing strain. In some embodiments, the compositions described herein comprise one or more (e.g., 1, 2, 3, 4, 5, or more) purified bacterial strain that has been identified as have antagonistic or inhibitory activity towards Carbapenem Resistant Enterobacteriaceae (CRE). In some embodiments, the compositions described herein comprise one or more (e.g., 1, 2, 3, 4, 5, or more) purified bacterial strain that has been identified as have antagonistic or inhibitory activity towards Vancomycin Resistant Enterococci (VRE). In some embodiments, the compositions described herein comprise one or more (e.g., 1, 2, 3, 4, 5 or more) purified bacterial strain selected from the group consisting of the following species Flavonifractor plautii, Blautia producta, Clostridium ramosum, Barnesiella spp, Clostridium symbiosum, Anaerotruncus colihominis, Clostridium innocuum, Clostridium indolis, Bacteroides ovatus, Bacteroides cellulosyliticus, Eubacterium fissicatena, and Lachnospiraceae bacterium. In some embodiments, the compositions described herein consists of one or more (e.g., 1, 2, 3, 4, 5 or more) purified bacterial strain selected from the group consisting of the following species Flavonifractor plautii, Blautia producta, Clostridium ramosum, Barnesiella spp, Clostridium symbiosum, Anaerotruncus colihominis, Clostridium innocuum, Clostridium indolis, Bacteroides ovatus, Bacteroides cellulosyliticus, Eubacterium fissicatena, and Lachnospiraceae bacterium. In some embodiments, the "Barnesiella spp" is referred to as a "Parabacteroides spp".

In some embodiments, the compositions described herein comprise one or more (e.g., 1, 2, 3, 4, 5, or more) purified bacterial strain that has been identified as a pathogen-antagonizing strain. In some embodiments, the compositions described herein comprise one or more (e.g., 1, 2, 3, 4, 5, or more) purified bacterial strain listed in Tables B, C, D and E (See also FIGS. 9, 17, 19, 20, and 22.

TABLE B

Strains antagonistic to CRE as identified by soft agar assay

| Strain | Classification | 16 S rDNA SEQ ID NO |
|---|---|---|
| Strain 1 | Flavonifractor plautii | 23 |
| Strain 2 | Blautia producta - 1 | 9 |
| Strain 3 | Blautia producta -2 | 24 |
| Strain 4 | Blautia producta - 3 | 25 |
| Strain 5 | Clostridium ramosum | 26 |

TABLE B-continued

Strains antagonistic to CRE as identified by soft agar assay

| Strain | Classification | 16 S rDNA SEQ ID NO |
|---|---|---|
| Strain 6 | *Flavonifractor plautii* | 27 |
| Strain 7 | *Barnesiella* | 28 |
| Strain 8 | *Clostridium symbiosum* | 29 |

TABLE C

Strains antagonistic to VRE as identified by soft agar assay

| Strain | Classification | 16S rDNA SEQ ID NO |
|---|---|---|
| Strain 23 | *Eubacterium fissicatena* | 30 |
| Strain 25 | Lachnospiraceae bacterium | 31 |

TABLE D

Strains antagonistic to CRE as identified by broth competition assay

| Strain ID | Closest relative | 16S rDNA SEQ ID NO |
|---|---|---|
| Strain 1 | *Flavonifractor plautii* | 23 |
| Strain 18 | *Dorea longicatena* | 32 |
| Strain 10 | *Blautia producta* | 33 |
| Strain 2 | *Blautia producta* | 9 |
| Strain 46 | *Escherichia coli* | 34 |
| Strain 47 | *Lactococcus lactis* | 35 |
| Strain 48 | *Lactobacillus ruminis* | 36 |

TABLE E

Strains antagonistic to CRE as identified by broth competition assay

| Strain ID | Closest relative | 16 S rDNA SEQ ID NO |
|---|---|---|
| Strain 47 | *Lactococcus lactis* | 35 |
| Strain 18 | *Dorea longicatena* | 32 |
| Strain 48 | *Lactobacillus ruminis* | 36 |
| Strain 49 | *Lactobacillus ruminis* | 37 |
| Strain 50 | *Lactobacillus animalis* | 38 |
| Strain 51 | *Lactobacillus rhamnosus* | 39 |
| Strain 52 | *Lactobacillus rhamnosus* | 40 |
| Strain 53 | *Lactobacillus rhamnosus* | 41 |

In some embodiments, the compositions described herein comprise one or more (e.g., 1, 2, 3, 4, 5, or more) purified bacterial strain that has been identified as a pathogen-antagonizing strain. In some embodiments, the compositions described herein comprise one or more (e.g., 1, 2, 3, 4, 5, or more) purified bacterial strain that has been identified as have antagonistic or inhibitory activity towards Carbapenem Resistant *Enterobacteriaceae* (CRE). In some embodiments, the compositions described herein comprise one or more (e.g., 1, 2, 3, 4, 5 or more) purified bacterial strain that has been identified as have antagonistic or inhibitory activity towards Vancomycin Resistant *Enterococci* (VRE). In some embodiments, the compositions described herein comprise one or more (e.g., 1, 2, 3, 4, 5 or more) purified bacterial strain selected from the group consisting of the following species *Flavonifractor plautii, Blautia producta, Clostridium ramosum, Barnesiella* spp, *Clostridium symbiosum, Anaerotruncus colihominis, Clostridium innocuum, Clostridium indolis, Bacteroides ovatus, Bacteroides cellulosyliticus, Eubacterium fissicatena, Lachnospiraceae bacterium, Escherichia coli, Lactococcus lactis, Lactobacillus ruminis, Lactobacillus animalis,* or *Lactobacillus rhamnosus*. In some embodiments, the compositions described herein consists of one or more (e.g., 1, 2, 3, 4, 5 or more) purified bacterial strain selected from the group consisting of the following species *Flavonifractor plautii, Blautia producta, Clostridium ramosum, Barnesiella* spp, *Clostridium symbiosum, Anaerotruncus colihominis, Clostridium innocuum, Clostridium indolis, Bacteroides ovatus, Bacteroides cellulosyliticus, Eubacterium fissicatena, Lachnospiraceae bacterium, Escherichia coli, Lactococcus lactis, Lactobacillus ruminis, Lactobacillus animalis,* or *Lactobacillus rhamnosus*.

In one aspect, the disclosure provides composition comprising one or more bacterial strains selected from the group consisting of strains 1-8, 23, 25, 18, 10, and 46-53 (See Tables B-E).

In some embodiments, the compositions described herein comprise one or more (e.g., 1, 2, 3, 4, 5, or more) purified bacterial strain that has been identified as a pathogen-antagonizing strain. In some embodiments, the compositions described herein comprise one or more (e.g., 1, 2, 3, 4, 5, or more) purified bacterial strain that has been identified as have antagonistic or inhibitory activity towards Carbapenem Resistant *Enterobacteriaceae* (CRE). In some embodiments, the compositions described herein comprise one or more (e.g., 1, 2, 3, 4, 5, or more) purified bacterial strain that has been identified as have antagonistic or inhibitory activity towards Vancomycin Resistant *Enterococci* (VRE). In some embodiments, the compositions described herein comprise one or more (e.g., 1, 2, 3, 4, 5 or more) purified bacterial strain selected from the group consisting of the following species *Escherichia coli, Lactococcus lactus, Lactobacillus ruminis, Lactobacillus, animalis,* or *Lactobacillus rhamnosus*. In some embodiments, the compositions described herein consists of one or more (e.g., 1, 2, 3, 4, 5 or more) purified bacterial strain selected from the group consisting of the following species *Escherichia coli, Lactococcus lactus, Lactobacillus ruminis, Lactobacillus animalis,* or *Lactobacillus rhamnosus*.

In one aspect, the disclosure provides composition comprising one or more bacterial strains selected from the group consisting of strains 46-53 (See Tables D-E).

In some embodiments, the compositions described herein comprise one or more (e.g., 1, 2, 3, 4, 5, or more) purified bacterial strain that has been identified as a pathogen-antagonizing strain. In some embodiments, the compositions described herein comprise one or more (e.g., 1, 2, 3, 4, 5, or more) purified bacterial strain that has been identified as have antagonistic or inhibitory activity towards Vancomycin Resistant *Enterococci* (VRE). In some embodiments, the compositions that have antagonistic or inhibitory activity towards Vancomycin Resistant *Enterococci* (VRE) described herein comprise one or two purified bacterial strains selected from the group consisting of the following species: *Eubacterium fissicatena* and *Lachnospiraceae bacterium*. In some embodiments, the compositions that have antagonistic or inhibitory activity towards Vancomycin Resistant *Enterococci* (VRE) described herein consist of one or two purified bacterial strains selected from the group consisting of the following species: *Eubacterium fissicatena* and *Lachnospiraceae bacterium*.

In one aspect, the disclosure provides composition comprising one or more bacterial strains selected from the group consisting of strains 23 and 25 (See Table C).

In some embodiments, the compositions described herein comprise one or more (e.g., 1, 2, 3, 4, 5, or more) purified bacterial strain that has been identified as a pathogen-antagonizing strain. In some embodiments, the compositions described herein comprise one or more (e.g., 1, 2, 3, 4, 5, or more) purified bacterial strain that has been identified as have antagonistic or inhibitory activity towards Carbapenem Resistant *Enterobacteriaceae* (CRE). In some embodiments, the compositions described herein that have antagonistic or inhibitory activity towards Carbapenem Resistant *Enterobacteriaceae* (CRE) comprise one or more (e.g., 1, 2, 3, 4, 5 or more) purified bacterial strain selected from the group consisting of the following species *Flavonifractor plautii, Blautia producta, Clostridium ramosum, Barnesiella* spp, *Clostridium symbiosum, Anaerotruncus colihominis, Clostridium innocuum, Clostridium indolis, Bacteroides ovatus, Bacteroides cellulosyliticus, Escherichia coli, Lactococcus lactus, Lactobacillus ruminis, Lactobacillus animalis*, and *Lactobacillus rhamnosus*. In some embodiments, the compositions described herein comprise one or more (e.g., 1, 2, 3, 4, 5, or more) purified bacterial strain that has been identified as having antagonistic or inhibitory activity towards Carbapenem Resistant *Enterobacteriaceae* (CRE). In some embodiments, the compositions described herein that have antagonistic or inhibitory activity towards Carbapenem Resistant *Enterobacteriaceae* (CRE) consist of one or more (e.g., 1, 2, 3, 4, 5 or more) purified bacterial strain selected from the group consisting of the following species: *Escherichia coli, Lactococcus lactus, Lactobacillus ruminis, Lactobacillus animalis*, and *Lactobacillus rhamnosus*.

In one aspect, the disclosure provides composition comprising one or more bacterial strains selected from the group consisting of strains 1, 2, 18, 10, and 46-53 (See Tables B and D-E). In one aspect, the disclosure provides compositions comprising bacterial strains that comprise 16S rDNA sequences with nucleic acid sequences SEQ ID NOs: 1-41. In some embodiments, the compositions comprise at least two (e.g., 2, 3, 4, 5, or more) bacterial strains that comprise 16S rDNA sequences with nucleic acid sequences SEQ ID NOs: 1-41. In some embodiments, the composition comprises 16 purified bacterial strains, wherein the bacterial strains comprise 16S rDNA sequences with nucleic acid sequences SEQ ID NOs: 1-41. In some embodiments, the composition consists of 16 purified bacterial strains, wherein the bacterial strains comprise 16S rDNA sequences with nucleic acid sequences SEQ ID NOs: 1-41. In some embodiments, the composition essentially consists of 16 purified bacterial strains, wherein the bacterial strains comprise 16S rDNA sequences with nucleic acid sequences SEQ ID NOs: 1-41. As used herein, "essentially consists of" (and like phrases) refers to a composition that includes no additional bacterial strains.

In some embodiments, the disclosure provides compositions with bacterial strains that comprise 16S rDNA sequences having at least 97% sequence identity with nucleic acid sequences selected from the group consisting of SEQ ID NOs: 1-41. In some embodiments, the disclosure provides compositions comprising two or more (e.g., 2, 3, 4, 5, or more) purified bacterial strains that comprise 16S rDNA sequences having at least 97% sequence identity with nucleic acid sequences selected from the group consisting of SEQ ID NOs: 1-41. In some embodiments, the compositions comprise 16 purified bacterial strains, wherein the bacterial strains comprise 16S rDNA sequences having at least 97% sequence identity with nucleic acid sequences SEQ ID NOs: 1-41. In some embodiments, the compositions consist of 16 purified bacterial strains, wherein the bacterial strains comprise 16S rDNA sequences having at least 97% sequence identity with nucleic acid sequences SEQ ID NOs: 1-41. In some embodiments, the compositions essentially consist of 16 purified bacterial strains, wherein the bacterial strains comprise 16S rDNA sequences having at least 97% sequence identity with nucleic acid sequences SEQ ID NOs: 1-41.

In one aspect, the disclosure provides compositions comprising bacterial strains that comprise 16S rDNA sequences with nucleic acid sequences SEQ ID NOs: 9, 23, and 24-41. In some embodiments, the compositions comprise at least two (e.g., 2, 3, 4, 5, or more) bacterial strains that comprise 16S rDNA sequences with nucleic acid sequences SEQ ID NOs: 9, 23, and 24-41. In some embodiments, the composition comprises 16 purified bacterial strains, wherein the bacterial strains comprise 16S rDNA sequences with nucleic acid sequences SEQ ID NOs: 9, 23, and 24-41. In some embodiments, the composition consists of 16 purified bacterial strains, wherein the bacterial strains comprise 16S rDNA sequences with nucleic acid sequences SEQ ID NOs: 9, 23, and 24-41. In some embodiments, the composition essentially consists of 16 purified bacterial strains, wherein the bacterial strains comprise 16S rDNA sequences with nucleic acid sequences SEQ ID NOs: 9, 23, and 24-41. As used herein, "essentially consists of" (and like phrases) refers to a composition that includes no additional bacterial strains.

In some embodiments, the disclosure provides compositions with bacterial strains that comprise 16S rDNA sequences having at least 97% sequence identity with nucleic acid sequences selected from the group consisting of SEQ ID NOs: 9, 23, and 24-41. In some embodiments, the disclosure provides compositions comprising two or more (e.g., 2, 3, 4, 5, or more) purified bacterial strains that comprise 16S rDNA sequences having at least 97% sequence identity with nucleic acid sequences selected from the group consisting of SEQ ID NOs: 9, 23, and 24-41. In some embodiments, the compositions comprise 16 purified bacterial strains, wherein the bacterial strains comprise 16S rDNA sequences having at least 97% sequence identity with nucleic acid sequences SEQ ID NOs: 9, 23, and 24-41. In some embodiments, the compositions consist of 16 purified bacterial strains, wherein the bacterial strains comprise 16S rDNA sequences having at least 97% sequence identity with nucleic acid sequences SEQ ID NOs: 9, 23, and 24-41. In some embodiments, the compositions essentially consist of 16 purified bacterial strains, wherein the bacterial strains comprise 16S rDNA sequences having at least 97% sequence identity with nucleic acid sequences SEQ ID NOs: 9, 23, and 24-41.

In some embodiments, the compositions comprise two or more (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36 or more) bacterial species selected from the group consisting of *Bacteroides caccae, Bacteroides intestinalis (Bacteroides cellulosyticus), Bacteroides faecis, Bacteroides ovatus, Bacteroides thetaiotaomicron, Bacteroides uniformis, Bacteroides vulgatus, Bifidobacterium adolescentis, Bifidobacterium longum, Bifidobacterium pseudocatenulatum, Clostridiales bacterium* VE202-06 (*Blautia coccoides, Blautia producta*), *Clostridium citroniae, Clostridium* sp. C105KSO14 (*Clostridium clostridioforme*), Clostridiales bacterium VE202-21 (*Eubacterium contortum, Clostridium innocuum*), Erysipelotrichaceae bacterium 6_1_45 (*Clostridium innocuum*), *Paeniclostridium sordellii, Coprococcus comes, Dorea longicatena, Erysipelatoclostridium ramosum, Eubacterium* rectale, *Odoribacter* sp. UNKMGS-12, *Bacteroides* sp. 1_1_14 (*Parabacteroides merdae*), *Bacteroides* sp. UNK.MGS-14 (*Parabacteroides merdae*), *Bacteroides xylanisolvens, Blautia obeum, Alistipes putredinis, Collinsella aerofaciens, Eubacterium hallii, Alistipes shahii, Anaerostipes caccae, Phascolarctobacterium faecis, Agathobaculum, Bacteroides* sp. 2_1_56FAA (*Bacteroides. fragilis*), *Fusobacterium mortiferum, Paraclostridium bifermentans*, and *Escherichia* sp. 3_2_53E4A.

In some embodiments, the compositions comprise 36 bacterial species: *Bacteroides caccae, Bacteroides intestinalis* (*Bacteroides cellulosyticus*), *Bacteroides faecis, Bacteroides ovatus, Bacteroides thetaiotaomicron, Bacteroides uniformis, Bacteroides vulgatus, Bifidobacterium adolescentis, Bifidobacterium longum, Bifidobacterium pseudocatenulatum*, Clostridiales bacterium VE202-06 (*Blautia coccoides, Blautia producta*), *Clostridium citroniae, Clostridium* sp. C105KSO14 (*Clostridium clostridioforme*), Clostridiales bacterium VE202-21 (*Eubacterium contortum, Clostridium innocuum*), Erysipelotrichaceae bacterium 6_1_45 (*Clostridium innocuum*), *Paeniclostridium sordellii, Coprococcus comes, Dorea longicatena, Erysipelatoclostridium ramosum, Eubacterium* rectale, *Odoribacter* sp. UNKMGS-12, *Bacteroides* sp. 1_1_14 (*Parabacteroides merdae*), *Bacteroides* sp. UNKMGS-14 (*Parabacteroides merdae*), *Bacteroides xylanisolvens, Blautia obeum, Alistipes putredinis, Collinsella aerofaciens, Eubacterium hallii, Alistipes shahii, Anaerostipes caccae, Phascolarctobacterium faecis, Agathobaculum, Bacteroides* sp. 2_1_56FAA (*Bacteroides. fragilis*), *Fusobacterium mortiferum, Paraclostridium bifermentans*, and *Escherichia* sp. 3_2_53E4A. In some embodiments, the compositions consist of 36 bacterial species: *Bacteroides caccae, Bacteroides intestinalis* (*Bacteroides cellulosyticus*), *Bacteroides faecis, Bacteroides ovatus, Bacteroides thetaiotaomicron, Bacteroides uniformis, Bacteroides vulgatus, Bifidobacterium adolescentis, Bifidobacterium longum, Bifidobacterium pseudocatenulatum*, Clostridiales bacterium VE202-06 (*Blautia coccoides, Blautia producta*), *Clostridium citroniae, Clostridium* sp. C105KSO14 (*Clostridium clostridioforme*), Clostridiales bacterium VE202-21 (*Eubacterium contortum, Clostridium innocuum*), Erysipelotrichaceae bacterium 6_1_45 (*Clostridium innocuum*), *Paeniclostridium sordellii, Coprococcus comes, Dorea longicatena, Erysipelatoclostridium ramosum, Eubacterium* rectale, *Odoribacter* sp. UNKMGS-12, *Bacteroides* sp. 1_1_14 (*Parabacteroides merdae*), *Bacteroides* sp. UNKMGS-14 (*Parabacteroides merdae*), *Bacteroides xylanisolvens, Blautia obeum, Alistipes putredinis, Collinsella aerofaciens, Eubacterium hallii, Alistipes shahii, Anaerostipes caccae, Phascolarctobacterium faecis, Agathobaculum, Bacteroides* sp. 2_1_56FAA (*Bacteroides. fragilis*), *Fusobacterium mortiferum, Paraclostridium bifermentans*, and *Escherichia* sp. 3_2_53FAA. In some embodiments, the compositions essentially consist of 36 bacterial species: *Bacteroides caccae, Bacteroides intestinalis* (*Bacteroides cellulosyticus*), *Bacteroides faecis, Bacteroides ovatus, Bacteroides thetaiotaomicron, Bacteroides uniformis, Bacteroides vulgatus, Bifidobacterium adolescentis, Bifidobacterium longum, Bifidobacterium pseudocatenulatum*, Clostridiales bacterium VE202-06 (*Blautia coccoides, Blautia producta*), *Clostridium citroniae, Clostridium* sp. C105KSO14 (*Clostridium clostridioforme*), Clostridiales bacterium VE202-21 (*Eubacterium contortum, Clostridium innocuum*), Erysipelotrichaceae bacterium 6_1_45 (*Clostridium innocuum*), *Paeniclostridium sordellii, Coprococcus comes, Dorea longicatena, Erysipelatoclostridium ramosum, Eubacterium* rectale, *Odoribacter* sp. UNKMGS-12, *Bacteroides* sp. 1_1_14 (*Parabacteroides merdae*), *Bacteroides* sp. UNKMGS-14 (*Parabacteroides merdae*), *Bacteroides xylanisolvens, Blautia obeum, Alistipes putredinis, Collinsella aerofaciens, Eubacterium hallii, Alistipes shahii, Anaerostipes caccae, Phascolarctobacterium faecis, Agathobaculum, Bacteroides* sp. 2_1_56FAA (*Bacteroides. fragilis*), *Fusobacterium mortiferum, Paraclostridium bifermentans*, and *Escherichia* sp. 3_2_53FAA.

In one aspect, the disclosure provides compositions comprising bacterial strains that comprise 16S rDNA sequences with nucleic acid sequences selected from the group consisting of SEQ ID NOs: 42-77. In some embodiments, the compositions comprise at least two (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36 or more) bacterial strains that comprise 16S rDNA sequences with nucleic acid sequences selected from the group consisting of SEQ ID NOs: 42-77. In some embodiments, the composition comprises 36 purified bacterial strains, wherein the bacterial strains comprise 16S rDNA sequences with nucleic acid sequences SEQ ID NOs: 42-77. In some embodiments, the composition consists of 36 purified bacterial strains, wherein the bacterial strains comprise 16S rDNA sequences with nucleic acid sequences SEQ ID NOs: 42-77. In some embodiments, the composition essentially consists of 36 purified bacterial strains, wherein the bacterial strains comprise 16S rDNA sequences with nucleic acid sequences SEQ ID NOs: 42-77. As used herein, "essentially consists of" (and like phrases) refers to a composition that includes no additional bacterial strains.

In some embodiments, the disclosure provides compositions with bacterial strains that comprise 16S rDNA sequences having at least 97% sequence identity with nucleic acid sequences selected from the group consisting of SEQ ID NOs: 42-77. In some embodiments, the disclosure provides compositions comprising two or more (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36 or more) purified bacterial strains that comprise 16S rDNA sequences having at least 97% sequence identity with nucleic acid sequences selected from the group consisting of SEQ ID NOs: 42-77. In some embodiments, the compositions comprise 36 purified bacterial strains, wherein the bacterial strains comprise 16S rDNA sequences having at least 97% sequence identity with nucleic acid sequences SEQ ID NOs: 42-77. In some embodiments, the compositions consist of 36 purified bacterial strains, wherein the bacterial strains comprise 16S rDNA sequences having at least 97% sequence identity with nucleic acid sequences SEQ ID NOs: 42-77. In some embodiments, the compositions essentially consist of 36 purified bacterial strains, wherein the bacterial strains comprise 16S rDNA sequences having at least 97% sequence identity with nucleic acid sequences SEQ ID NOs: 42-77. As used herein, "essentially consists of" (and like phrases) refers to a composition that includes no additional bacterial strains.

In some embodiments, the compositions comprise 23 bacterial species: *Bacteroides caccae, Bacteroides intestinalis* (*Bacteroides cellulosyticus*), *Bacteroides faecis, Bacteroides ovatus, Bacteroides thetaiotaomicron, Bacteroides uniformis, Bacteroides vulgatus*, Clostridiales bacterium VE202-06 (*Blautia coccoides, Blautia producta*), *Clostridium citroniae, Clostridium* sp. C105KSO14

(*Clostridium clostridioforme*), *Clostridiales bacterium* VE202-21 (*Eubacterium contortum, Clostridium innocuum*), *Erysipelotrichaceae bacterium* 6_1_45 (*Clostridium innocuum*), *Coprococcus comes, Dorea longicatena, Erysipelatoclostridium ramosum, Eubacterium rectale, Bacteroides* xylanisolvens, *Blautia obeum, Alistipes putredinis, Eubacterium hallii, Alistipes shahii, Fusobacterium mortiferum,* and *Escherichia* sp. 3_2_53E4A. In some embodiments, the compositions consist of 23 bacterial species: *Bacteroides caccae, Bacteroides intestinalis* (*Bacteroides cellulosyticus*), *Bacteroides faecis, Bacteroides ovatus, Bacteroides thetaiotaomicron, Bacteroides uniformis, Bacteroides vulgatus, Clostridiales bacterium* VE202-06 (*Blautia coccoides, Blautia producta*), *Clostridium citroniae, Clostridium* sp. C105KSO14 (*Clostridium clostridioforme*), *Clostridiales bacterium* VE202-21 (*Eubacterium contortum, Clostridium innocuum*), *Erysipelotrichaceae bacterium* 6_1_45 (*Clostridium innocuum*), *Coprococcus comes, Dorea longicatena, Erysipelatoclostridium ramosum, Eubacterium rectale, Bacteroides* xylanisolvens, *Blautia obeum, Alistipes putredinis, Eubacterium hallii, Alistipes shahii, Fusobacterium mortiferum,* and *Escherichia* sp. 3_2_53E4A. In some embodiments, the compositions essentially consist 23 bacterial species: *Bacteroides caccae, Bacteroides intestinalis* (*Bacteroides cellulosyticus*), *Bacteroides faecis, Bacteroides ovatus, Bacteroides thetaiotaomicron, Bacteroides uniformis, Bacteroides vulgatus, Clostridiales bacterium* VE202-06 (*Blautia coccoides, Blautia producta*), *Clostridium citroniae, Clostridium* sp. C105KSO14 (*Clostridium clostridioforme*), *Clostridiales bacterium* VE202-21 (*Eubacterium contortum, Clostridium innocuum*), *Erysipelotrichaceae bacterium* 6_1_45 (*Clostridium innocuum*), *Coprococcus comes, Dorea longicatena, Erysipelatoclostridium ramosum, Eubacterium rectale, Bacteroides* xylanisolvens, *Blautia obeum, Alistipes putredinis, Eubacterium hallii, Alistipes shahii, Fusobacterium mortiferum,* and *Escherichia* sp. 3_2_53E4A.

In one aspect, the disclosure provides compositions comprising bacterial strains that comprise 16S rDNA sequences with nucleic acid sequences selected from the group consisting of SEQ ID NOs: 42-48, 52-56, 58-61, 65-67, 69, 70, 75, and 77. In some embodiments, the compositions comprise at least two (e.g., 2, 3, 4, 5, 6, 7, 8, 9, 10, 11, 12, 13, 14, 15, 16, 17, 18, 19, 20, 21, 22, 23 or more) bacterial strains that comprise 16S rDNA sequences with nucleic acid sequences selected from the group consisting of SEQ ID NOs: 42-48, 52-56, 58-61, 65-67, 69, 70, 75, and 77. In some embodiments, the composition comprises 23 purified bacterial strains, wherein the bacterial strains comprise 16S rDNA sequences with nucleic acid sequences SEQ ID NOs: 42-48, 52-56, 58-61, 65-67, 69, 70, 75, and 77. In some embodiments, the composition consists of 23 purified bacterial strains, wherein the bacterial strains comprise 16S rDNA sequences with nucleic acid sequences SEQ ID NOs: 42-48, 52-56, 58-61, 65-67, 69, 70, 75, and 77. In some embodiments, the composition essentially consists of 23 purified bacterial strains, wherein the bacterial strains comprise 16S rDNA sequences with nucleic acid sequences SEQ ID NOs: 42-48, 52-56, 58-61, 65-67, 69, 70, 75, and 77. As used herein, "essentially consists of" (and like phrases) refers to a composition that includes no additional bacterial strains.

In some embodiments, the disclosure provides compositions with bacterial strains that comprise 16S rDNA sequences having at least 97% sequence identity with nucleic acid sequences selected from the group consisting of SEQ ID NOs: 42-48, 52-56, 58-61, 65-67, 69, 70, 75, and 77. In some embodiments, the disclosure provides compositions comprising two or more (e.g., 2, 3, 4, 5, 6, 7, 8, 9, 10, 11, 12, 13, 14, 15, 16, 17, 18, 19, 20, 21, 22, 23 or more) purified bacterial strains that comprise 16S rDNA sequences having at least 97% sequence identity with nucleic acid sequences selected from the group consisting of SEQ ID NOs: 42-48, 52-56, 58-61, 65-67, 69, 70, 75, and 77. In some embodiments, the compositions comprise 23 purified bacterial strains, wherein the bacterial strains comprise 16S rDNA sequences having at least 97% sequence identity with nucleic acid sequences SEQ ID NOs: 42-48, 52-56, 58-61, 65-67, 69, 70, 75, and 77. In some embodiments, the compositions consist of 23 purified bacterial strains, wherein the bacterial strains comprise 16S rDNA sequences having at least 97% sequence identity with nucleic acid sequences SEQ ID NOs: 42-48, 52-56, 58-61, 65-67, 69, 70, 75, and 77. In some embodiments, the compositions essentially consist of 23 purified bacterial strains, wherein the bacterial strains comprise 16S rDNA sequences having at least 97% sequence identity with nucleic acid sequences SEQ ID NOs: 42-48, 52-56, 58-61, 65-67, 69, 70, 75, and 77.

In some embodiments, the composition comprises at least the 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36 or more most abundant bacterial strains present in a spore forming fraction of a fecal sample obtained from a subject. In some embodiments, the composition comprises at least the 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36 or more most abundant bacterial species present in a spore forming fraction of a fecal sample obtained from a subject.

In some embodiments, the composition comprises at least the 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36 or more most abundant bacterial strains present in a non-spore forming fraction of a fecal sample obtained from a subject. In some embodiments, the composition comprises at least the 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36 or more most abundant bacterial species present in a non-spore forming fraction of a fecal sample obtained from a subject.

In some embodiments, the composition comprises at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36 or more bacterial strains present in a spore forming fraction of a fecal sample obtained from a subject, wherein the bacterial species suppress the replication, survival, and/or colonization of one or more pathogenic organisms. In some embodiments, the composition comprises at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36 or more bacterial species present in a spore forming fraction of a fecal sample obtained from a subject, wherein the bacterial species suppress the replication, survival, and/or colonization of one or more pathogenic organisms.

In some embodiments, the composition comprises at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36 or more bacterial strains present in a non-spore forming fraction of a fecal sample obtained from a subject, wherein the bacterial species suppress the replication, survival, and/or colonization of one or more pathogenic organisms. In some embodiments, the composition comprises 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36 or more bacterial species present in a non-spore forming fraction of a fecal sample obtained from a subject, wherein the bacterial species suppress the replication, survival, and/or colonization of one or more pathogenic organisms.

As will be appreciated by one of skill in the art, any one or more bacterial strain identified as having pathogen-antagonizing activity may be included in any of the compositions described herein.

In some embodiments, bacterial strains found to be present in a sample obtained from a donor may be identified and selected to be included in any of the bacterial compositions described herein. In some embodiments, a fecal sample or stool fraction thereof is analyzed to determine the bacterial composition of the sample or fraction thereof and identify the most abundant bacterial strains. For example, as described in Example 2, nucleic acids obtained from a fecal sample or stool fraction (e.g., a spore forming fraction or a non-spore forming fraction) may be sequenced to identify the bacterial strains present in the fecal sample or stool fraction. The relative abundance of the bacterial strains may be determined using nucleic acid sequencing data, for example by determining the number of reads associated with a bacterial strain relative to the number of reads of a control or the total number of reads in the sequencing reaction. The bacterial strains in the sample may be ranked based on the relative abundance in the sample. Tables 8-11 show the most abundant bacterial species identified in spore forming fractions (Tables 8 and 10) and non-spore forming fractions (Tables 9 and 11) obtained from two example donors. Any one or more of the bacterial strains identified in a fecal sample or stool fraction from a donor may be selected and included in a bacterial composition as described herein.

In one aspect, the compositions comprise a fraction of a fecal sample. In some embodiments, the compositions comprise a non-spore forming fraction of a fecal sample. In some embodiments, the compositions comprise a spore forming fraction of a fecal sample.

In some embodiments, the compositions comprise the most abundant bacterial species present in a fecal sample or stool sample from a donor. In some embodiments, the compositions comprise the 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36 or more of the most abundant bacterial species present in a fecal sample or stool sample obtained from a donor or a fecal sample or stool sample obtained from more than one donor. In some embodiments, the compositions comprise the 5 most abundant bacterial species present in a fecal sample or stool sample obtained from a donor or a fecal sample or stool sample obtained from more than one donor. In some embodiments, the compositions comprise the 10 most abundant bacterial species present in a fecal sample or stool sample obtained from a donor or a fecal sample or stool sample obtained from more than one donor. In some embodiments, the compositions comprise the 15 most abundant bacterial species present in a fecal sample or stool sample obtained from a donor or a fecal sample or stool sample obtained from more than one donor. In some embodiments, the compositions comprise the 20 most abundant bacterial species present in a fecal sample or stool sample obtained from a donor or a fecal sample or stool sample obtained from more than one donor. In some embodiments, the compositions comprise the 23 most abundant bacterial species present in a fecal sample or stool sample obtained from a donor or a fecal sample or stool sample obtained from more than one donor. In some embodiments, the compositions comprise the 36 most abundant bacterial species present in a fecal sample or stool sample obtained from a donor or a fecal sample or stool sample obtained from more than one donor.

In some embodiments, the compositions comprise the 5 most abundant bacterial species presented in any of Tables 8-12. In some embodiments, the compositions comprise the 10 most abundant bacterial species presented in any of Tables 8-12. In some embodiments, the compositions comprise the 15 most abundant bacterial species presented in any of Tables 8-12. In some embodiments, the compositions comprise the 20 most abundant bacterial species presented in any of Tables 8-12. In some embodiments, the compositions comprise the 23 most abundant bacterial species presented in any of Tables 8-12. In some embodiments, the compositions comprise the 36 most abundant bacterial species presented in any of Tables 8-12.

In some embodiments, the compositions comprise one or more bacterial strains identified in the non-spore and/or spore forming fractions (Tables 8-12) and are found in any of the live bacterial products presented herein (Tables 1-7). In some embodiments, the compositions comprise one or more bacterial strains from species selected from the group consisting of *Bifidobacterium longum*, *Bifidobacterium adolescentis*, *Blautia* wexlerae, *Bacteroides vulgatus*, *Bacteroides uniformis*, *Collinsella aerofaciens*, *Faecalibacterium prausnitzii*, *Blautia obeum*, *Parabacteroides merdae*, *Parabacteroides distasonis*, *Roseburia faecis*, *Coprococcus comes*, *Dorea longicatena*, and *Eubacterium hallii* (see also FIG. 7).

Aspects of the disclosure relate to bacterial strains with 16S rDNA sequences that have sequence identity to a nucleic acid sequence of any one of the sequences of the bacterial strains or species described herein. The terms "identical," or percent "identity," in the context of two or more nucleic acids or amino acid sequences, refer to two or more sequences or subsequences that are the same. Two sequences are "substantially identical" if two sequences have a specified percentage of amino acid residues or nucleotides that are the same (e.g., at least 80%, 85%, 90%, 95%, 96%, 97%, 98%, 99%, 99.5%, 99.6%, 99.7%, 99.8% or 99.9% sequence identity) over a specified region of a nucleic acid or amino acid sequence or over the entire sequence, when compared and aligned for maximum correspondence over a comparison window, or designated region as measured using one of the following sequence comparison algorithms or by manual alignment and visual inspection. Optionally, the identity exists over a region that is at least about 50 nucleotides in length, or more preferably over a region that is 100 to 500 or 1000 or more nucleotides in length. In some embodiments, the identity exists over the length the 16S rRNA or 16S rDNA sequence.

In some embodiments, the bacterial strain has at least 60%, at least 70%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or up to 100% sequence identity relative to any of the strains or bacterial species described herein over a specified region or over the entire sequence. It would be appreciated by one of skill in the art that the term "sequence identity" or "percent sequence identity," in the context of two or more nucleic acid sequences or amino acid sequences, refers to a measure of similarity between two or more sequences or portion(s) thereof.

In some embodiments, the composition includes two or more (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36 or more) bacterial strains, wherein the two or more bacterial strains contain 16S rDNA sequences having at least 97% sequence identity with nucleic acid sequences selected from SEQ ID NOs: 1-22.

In some embodiments, the composition includes two or more (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36 or more) bacterial strains, wherein the two or more bacterial strains contain 16S rDNA sequences having at least 97% sequence identity with nucleic acid sequences selected from SEQ ID NOs: 42-77.

In some embodiments, the composition includes two or more (e.g., 2, 3, 4, 5, 6, 7, 8, 9, 10, 11, 12, 13, 14, 15, 16, 17, 18, 19, 20, 21, 22, 23, or more) bacterial strains, wherein the two or more bacterial strains contain 16S rDNA sequences having at least 97% sequence identity with nucleic acid sequences selected from SEQ ID NOs: 42-48, 52-56, 58-61, 65-67, 69, 70, 75, 77.

Additionally, or alternatively, two or more sequences may be assessed for the alignment between the sequences. The terms "alignment" or percent "alignment" in the context of two or more nucleic acids or amino acid sequences, refer to two or more sequences or subsequences that are the same. Two sequences are "substantially aligned" if two sequences have a specified percentage of amino acid residues or nucleotides that are the same (e.g., at least 80%, 85%, 90%, 95%, 96%, 97%, 98%, 99%, 99.5%, 99.6%, 99.7%, 99.8% or 99.9% identical) over a specified region or over the entire sequence, when compared and aligned for maximum correspondence over a comparison window, or designated region as measured using one of the following sequence comparison algorithms or by manual alignment and visual inspection. Optionally, the alignment exists over a region that is at least about 50 nucleotides in length, or more preferably over a region that is 100 to 500 or 1000 or more nucleotides in length. In some embodiments, the identity exists over the length the 16S rRNA or 16S rDNA sequence.

For sequence comparison, typically one sequence acts as a reference sequence, to which test sequences are compared. Methods of alignment of sequences for comparison are well known in the art. See, e.g., by the local homology algorithm of Smith and Waterman (1970) *Adv. Appl. Math.* 2:482c, by the homology alignment algorithm of Needleman and Wunsch, *J. Mol. Biol.* 48:443, 1970, by the search for similarity method of Pearson and Lipman. *Proc. Natl. Acad. Sci. USA* 85:2444, 1988, by computerized implementations of these algorithms (GAP, BESTFIT, FASTA, and TFASTA in the Wisconsin Genetics Software Package, Genetics Computer Group. Madison. WI), or by manual alignment and visual inspection (see. e.g., Brent et al., *Current Protocols in Molecular Biology*, John Wiley & Sons, Inc. (Ringbou ed., 2003)). Two examples of algorithms that are suitable for determining percent sequence identity and sequence similarity are the BLAST and BLAST 2.0 algorithms, which are described in Altschul et al., *Nuc. Acids Res.* 25:3389-3402, 1977; and Altschul et al., *J. Mol. Biol.* 215:403-410, 1990, respectively.

In one aspect, the 16S rDNA sequences of purified bacterial strains were compared to 16S rDNA sequences of known bacterial species/strains in a bacterial genome database to identify the closest known related bacterial species to the bacterial strains disclosed herein. It should be appreciated that multiple bacterial strains of the compositions disclosed herein may have the same closest related bacterial species.

In some embodiments, the compositions described herein comprise spore forming and non-spore forming bacterial strains. In some embodiments, the compositions described herein comprise spore forming bacterial strains. In some embodiments, the compositions described herein comprise only spore forming bacterial strains. In some embodiments, the compositions described herein comprise only non-spore forming bacterial strains. The spore-forming bacteria can be in spore form (i.e., as spores) or in vegetative form (i.e., as vegetative cells). In spore form, bacteria are generally more resistant to environmental conditions, such as heat, acid, radiation, oxygen, chemicals, and antibiotics. In contrast, in the vegetative state or actively growing state, bacteria are more susceptible to such environmental conditions, compared to in the spore form. In general, bacterial spores are able to germinate from the spore form into a vegetative/actively growing state, under appropriate conditions. For instance, bacteria in spore form may germinate when they are introduced in the intestine.

In some embodiments, at least one (e.g., 1, 2, 3, 4, 5, or more) of the bacterial strains in the composition is a spore former. In some embodiments, at least one (e.g., 1, 2, 3, 4, 5, or more) of the bacterial strains in the composition is in spore form. In some embodiments, at least one (e.g., 1, 2, 3, 4, 5, or more) of the bacterial strains in the composition is a non-spore former. In some embodiments, at least one (e.g., 1, 2, 3, 4, 5, or more) of the bacterial strains in the composition is in vegetative form. As discussed above, spore forming bacteria can also be in vegetative form. In some embodiments, at least one (e.g., 1, 2, 3, 4, 5, or more) of the bacterial strains in the composition is in spore form and at least one (e.g., 1, 2, 3, 4, 5, or more) of the bacterial strains in the composition is in vegetative form. In some embodiments, at least one bacterial strain that is considered able to form spores (i.e., a spore-former) but is present in the composition in vegetative form. In some embodiments, at least one bacterial strain that is considered able to form spores is present in the composition both in spore form and in vegetative form.

In some embodiments, the compositions comprise bacterial strains that are spore forming bacterial strains. In some embodiments, the compositions comprise bacterial strains that are non-spore forming bacterial strains. In some embodiments, the compositions comprise bacterial strains that are spore forming bacterial strains and bacterial strains that are non-spore forming bacterial strains. In some embodiments, the compositions comprise a mixture of bacterial strains wherein at least 10% of the bacterial strains are spore forming bacterial strains, at least 20% of the bacterial strains are spore forming bacterial strains, at least 30% of the bacterial strains are spore forming bacterial strains, at least 40% of the bacterial strains are spore forming bacterial strains, at least 50% of the bacterial strains are spore forming bacterial strains, at least 60% of the bacterial strains are spore forming bacterial strains, at least 70% of the bacterial strains are spore forming bacterial strains, at least 80% of the bacterial strains are spore forming bacterial strains, at least 90% of the bacterial strains are spore forming bacterial strains bacteria or up to 100% spore forming bacterial strains. Whether a bacterial strain is a spore forming strain can be determined for instance by evaluating the genome of the bacterial strain for the presence of sporulation genes. However, it should be appreciated that not all bacteria that are predicted to encode spore forming genes can be made to sporulate. In addition, whether a bacterial strain is a spore forming strain can be determined by exposing the bacterial strain to stress conditions, e.g., heat or exposure to chemicals (e.g., ethanol or chloroform), that are known to induce sporulation.

It should be appreciated that spore forming bacteria can be in spore form or in vegetative form. In some embodiments of the compositions provided herein, the spore forming bacteria are in spore form. In some embodiments, the spore forming bacteria are in vegetative form. In some embodiments, the spore forming bacteria are both present in spore form and in vegetative form. In some embodiments, compositions comprise spore forming bacteria and at least 10% of the spore forming bacteria are in spore format, at least 20% of the spore forming bacteria are in spore format, at least 30% of the spore forming bacteria are in spore format, at least 40% of the spore forming bacteria are in spore format, at least 50% of the spore forming bacteria are in spore format, at least 60% of the spore forming bacteria are in spore format, at least 70% of the spore forming bacteria are in spore format, at least 80% of the spore forming bacteria are in spore format, at least 90% of the spore forming bacteria are in spore format, or up to 100% of the spore forming bacteria are in spore format.

It is envisioned that the bacterial strains of the compositions provided herein are alive and will be alive when they reach the target area (e.g., the intestines). Bacterial spores are considered to be alive in this regards. In some embodiments, bacteria that are administered as spores may germinate in the target area (e.g., the intestines). It should further be appreciated that not all of the bacteria are alive and the compositions can include a percentage (e.g., by weight) that is not alive. In addition, in some embodiments, the compositions include bacterial strains that are not alive when administered or at the time when the composition reaches the target area (e.g., the intestines). It is envisioned that non-living bacteria may still be useful by providing some nutrients and metabolites for the other bacterial strains in the composition.

Methods of inducing sporulation of spore-forming bacterial strains are well known in the art (See e.g., Paredes-Sabja et al., *Trends Microbiol*. (2011) 19(2):85-94). Generally, bacterial strains that are spore-formers can be made to go into spore form by stressing the bacterial strains. Non-limiting examples of stresses that can induce sporulation are an increase in temperature, change in the nutrients available and/or exposure to chemicals (e.g., ethanol or chloroform). It should be noted that bacteria that are non-spore formers, for instance because they are missing sporulation genes, cannot be made to sporulate by stress. To prepare compositions in which all the bacterial strains are in the spore form, the composition or bacterial cultures used to prepare the composition may be subjected to treatment to kill any bacteria not in spore form (e.g., in vegetative form), for example by exposing the composition to heat and are chemically breaking down the non-spore bacteria. The bacteria in spore format can subsequently be separated from the non-spore bacteria for instance by filtration.

The amount of spores can be quantified using techniques know in the art. These techniques include phase contrast microscopy for enumerating spores using a hemocytometer. In addition, the viability of spores can be determined by plating the spores and growing the spores. For instance, spores can be plated in appropriate media and incubated in the anaerobic chamber for a period of time (e.g., 48-96 hrs.). Viability can subsequently be determined by quantifying the colony forming units which correspond to spores that germinated. For instance, spores can be plated on TCCFA plates (Taurocholate, cycloserine, cefoxintin, fructose agar plates), in which taurocholate helps the spores to germinate. In addition, spores can be quantified using the dipicolinic assay (DPA assay). DPA is an agent that allows for spore selection and is a clear indicator of endospores. When complexed with terbium, bright green luminescence is observed.

In some embodiments, the compositions comprise bacterial strains that are non-spore forming bacterial strains. In some embodiments, the compositions comprise bacterial strains that are spore forming bacterial strains and bacterial strains that are non-spore forming bacterial strains. In some embodiments, the compositions comprise a mixture of bacterial strains wherein at least 10% of the bacterial strains are non-spore forming bacterial strains, at least 20% of the bacterial strains are non-spore forming bacterial strains, at least 30% of the bacterial strains are non-spore forming bacterial strains, at least 40% of the bacterial strains are non-spore forming bacterial strains, at least 50% of the bacterial strains are non-spore forming bacterial strains, at least 60% of the bacterial strains are non-spore forming bacterial strains, at least 70% of the bacterial strains are non-spore forming bacterial strains, at least 80% of the bacterial strains are non-spore forming bacterial strains, at least 90% of the bacterial strains are non-spore forming bacterial strains bacteria, or up to 100% non-spore forming bacterial strains.

In any of the compositions provided herein, the bacterial strains may be purified. In any of the compositions provided herein, the bacterial strains may be isolated. Any of the bacterial strains described herein may be isolated and/or purified, for example, from a source such as a culture or a microbiota sample (e.g., fecal matter). The bacterial strains used in the compositions provided herein generally are isolated from the microbiome of healthy individuals. However, bacterial strains can also be isolated from individuals that are considered not to be healthy. In some embodiments, the compositions include strains originating from multiple individuals.

As used herein, the term "isolated" refers to a bacteria or bacterial strain that has been separated from one or more undesired component, such as another *bacterium* or bacterial strain, one or more component of a growth medium, and/or one or more component of a sample, such as a fecal sample. In some embodiments, the bacteria are substantially isolated from a source such that other components of the source are not detected.

As also used herein, the term "purified" refers to a bacterial strain or composition comprising such that has been separated from one or more components, such as contaminants. In some embodiments, the bacterial strain is substantially free of contaminants. In some embodiments, one or more bacterial strains of a composition may be independently purified from one or more other bacteria produced and/or present in a culture or a sample containing the bacterial strain. In some embodiments, a bacterial strain is isolated or purified from a sample and then cultured under the appropriate conditions for bacterial replication, e.g., under anaerobic culture conditions. The bacteria that is grown under appropriate conditions for bacterial replication can subsequently be isolated/purified from the culture in which it is grown.

In some embodiments, the bacterial strains of the compositions provided herein are obligate anaerobes. In some embodiments, the bacterial strains of the compositions provided herein are facultative anaerobes.

Aspects of the present disclosure are related to methods for suppressing multi-drug resistant organisms in a subject. Aspects of the present disclosure are related to methods of suppressing or preventing colonization of the intestine with oral microbiome bacteria. Aspects of the present disclosure are related to methods for treating a disease or disorder associated with bacterial colonization in a subject. Aspects of the present disclosure are related to method for treating a disease or disorder associate with an immune response induced by bacteria in a subject. The methods described herein involve administering to a subject a therapeutically effective amount of any of the compositions described herein. As used herein, a "subject," "individual," and "patient" are used interchangeably, and refer to a vertebrate, preferably a mammal such as a human. Mammals include, but are not limited to, human primates, non-human primates or murine, bovine, equine, canine or feline species. In some embodiments, the subject is a human.

In some embodiments, the methods described herein are for suppressing undesired bacteria. As used herein, the term "suppressing" refers to any form of inhibiting an undesired bacteria. In some embodiments, the methods described herein reduce/inhibit or prevent the colonization, replication, proliferation, and/or survival of the undesired bacteria (e.g., multi-drug resistant organisms, oral microbiome bacteria). In some embodiments, the methods described herein directly or indirectly induce death of the undesired bacteria (e.g., multi-drug resistant organisms, oral microbiome bacteria).

In some embodiments, administration of the compositions described herein reduces/inhibits or prevents the colonization, re-colonization, replication, proliferation, and/or survival of multi-drug resistant organisms. In some embodiments, administration of the compositions described herein allows for colonization of the gastrointestinal tract of the subject by the bacterial strain(s) of the compositions thereby preventing colonization by multi-drug resistant organisms.

In some embodiments, the subject is a carrier of a multi-drug resistant organism and is suffering from the effects of the infection. In some embodiments the subject is an asymptomatic carrier of a multi-drug resistant organism. In some embodiments, the subject has experienced recurrent or chronic colonization with a multi-drug resistant organism. In some embodiments, the subject is suffering from a first occurrence of a particular multi-drug resistant organism. In some embodiments, the subject is at risk of colonization with a multi-drug resistant organism, such as prior antibiotic use. In some embodiments, the subject has a risk factor associated with colonization with a multidrug resistant organism. In some embodiments, the subject has had a previous infection or colonization with a multi-drug resistant organism. In some embodiments, the subject has been treated with antibiotics which resulted in the recurrence of the multi-drug resistant organism.

In some embodiments, the subject is to undergo a procedure that puts the subject at a higher risk of colonization and the compositions are administered prophylactically. In some embodiments, the subject has a disease or disorder associated with use of a proton pump inhibitor, which may increase the likelihood of an oral *bacterium* migrating to the intestine. In some embodiments, the compositions provided herein are administered to a subject to lower the risk of becoming colonized with a multidrug resistant organism. In some embodiments, the bacterial compositions provided herein administered to a subject that is receiving a proton pump inhibitor.

Individuals may be at risk of acquiring a multi-drug resistant organism if they have recently received antimicrobials, are in an immunosuppressed state (e.g., on chemotherapy, have a malignancy, undergoing or received a transplant), have a chronic disease or inflammatory condition (such as diabetes, renal disease, etc.), are older, are undergoing hemodialysis, surgery or other invasive procedures, have indwelling device(s), and/or are living in a long-term care facility or are hospitalized. In some embodiments, the subject is colonized with a multi-drug resistant organism. Skin and mucosal colonization are common (Cassone et al., Curr Geriatr Rep. 2015; 4(1): 87-89), but multi-drug resistant organisms may also colonize the gastrointestinal (GI) tract and oral cavity, causing inflammation (Atarashi et al., *Science* (2017)). Colonization can lead to significant infections, such as in the skin, lungs, urinary tract, or bloodstream, which may result in serious complications, including death (CDC, 2013). In some instances, multi-drug resistant organisms may be ingested, leading to consequences throughout the digestive system. In some embodiments, a multi-drug resistant organism may colonize the oral cavity.

In some embodiments, the multi-drug resistant organism is Vancomycin Resistant *Enterococci* (VRE), Carbapenem Resistant *Enterobacteriaceae* (CRE), *Neisseria gonorrheae*, Multidrug Resistant *Acinetobacter*, *Campylobacter*, Extended spectrum beta-lactamase (ESBL) producing *Enterobacteriaceae*, Multidrug Resistant *Pseudomonas aeruginosa*, *Salmonella*, Drug resistant non-typhoid *Salmonella*, Drug resistant *Salmonella Typhi*, Drug resistant *Shigella*, Methicillin Resistant *Staphylococcus aureus*, Drug resistant *Streptococcus pneumoniae*, Drug resistant Tuberculosis, Vancomycin resistant *Staphylococcus aureus*, Erythromycin Resistant Group A *Streptococcus*, or Clindamycin resistant Group B *Streptococcus*. In some embodiments, the multi-drug resistant organism is Vancomycin Resistant *Enterococci* (VRE). In some embodiments, the multi-drug resistant organism is Carbapenem Resistant *Enterobacteriaceae* (CRE).

In some embodiments, administration of the compositions described herein reduces/inhibits or prevents intestinal colonization with oral microbiome bacteria. In some embodiments, administration of the compositions described herein reduces/inhibits or prevents the colonization, replication, proliferation, and/or survival of oral microbiome bacteria in the intestinal tract of the subject. In some embodiments, administration of the compositions described herein allows for colonization of the gastrointestinal tract of the subject by the bacterial strain(s) of the compositions thereby preventing colonization by oral microbiome bacteria.

In some embodiments, the subject is a carrier of an oral *bacterium* and is suffering from the effects of the infection. In some embodiments the subject is an asymptomatic carrier of an oral *bacterium*. In some embodiments, the subject has experienced recurrent or chronic colonization with an oral *bacterium*. In some embodiments, the subject is at risk of colonization with an oral *bacterium*. In some embodiments, the subject has a risk factor associated with colonization with an oral *bacterium*. In some embodiments, the subject is taking a proton pump inhibitor. In some embodiments, the subject has had a previous infection or colonization with an oral *bacterium*.

In some embodiments, the subject is to undergo a procedure that puts the subject at a higher risk of colonization and the compositions are administered prophylactically. In some embodiments, the compositions provided herein are administered to a subject to lower the risk of becoming colonized with an oral *bacterium*.

Over 700 bacterial species or phylotypes have been found in the oral cavity; however, over 50% have not yet been cultivated. A number of phyla have been identified in the oral microbiome *Actinobacteria, Arachnia, Bacteroidetes,*

*Bifidobacterium, Chlamydiae, Chloroflexi, Eubacterium, Euryarchaeota, Fusobacterium, Firmicutes, Fusobacteria, Lactobacillus, Leptotrichia, Peptococcus, Peptostreptococcus, Propionibacterium, Proteobacteria, Selenomonas, Spirochaetes, SRL Synergistetes, Tenericutes, Treponema,* TM7, and *Veillonella* (Dewhirst et al., J of Bacteriology, 2010, 192(19): 5002-5010). Examples of oral microbiome bacteria include, without limitation, *Streptococcus sanguis, Streptococcus salivarius, Streptococcus mitis, Streptococcus mutans, Treponema denticola, Eikenella corrodens, Streptococcus gordonii, Streptococcus oxalis, Acinomyces maeslundii,* and *Bacteroides melaningenicus*. A list of example species found in the human oral cavity can be found on the Human Oral Microbiome Database (homd.org). In some embodiments, the oral microbiome bacteria may be pathogenic. In some embodiments, the oral microbiome bacteria may be pathogenic if the bacteria gain access to another site of the body. In some embodiments, the oral microbiome bacteria are not pathogenic.

In some embodiments, administration of the compositions described herein reduces/inhibits or prevents intestinal colonization with oral microbiome bacteria. In some embodiments, the oral microbiome bacteria is *Fusobacterium nucleatum* (See e.g., Yoneda et al. *J Gastrointest Dig Syst* (2016) 6:2). In some embodiments, the oral microbiome bacteria is *Campylobacter* concisus (See e.g., Yoneda et al. *J Gastrointest Dig Syst* (2016) 6:2). In some embodiments, the oral microbiome bacteria is *Streptococcus mutans* (See e.g., Yoneda et al. *J Gastrointest Dig Syst* (2016) 6:2). Additional oral microbiome bacteria are described in Table S1A of Atarashi et al. (Atarashi et al., *Science* 358, 359-365 (2017)), such as *Rothia mucilaginosa, Neisseria subflava, Granulicatella para-adiacens, Streptococcus salivarius, Streptococcus mitis, Fusobacterium* sp. 1_1_41FAA, *Streptococcus oralis, Streptococcus salivarius, Neisseria subflava, Prevotella scopos, Veillonella parvula, Streptococcus* sp. M143, *Haemophilus parainfluenzae, Prevotella* sp. CD3_34, *Neisseria macacae, Prevotella histicola, Prevotella pallens, Streptococcus infantis, Streptococcus parasanguinis, Porphyromonas* CW034, *Streptococcus* sp. oral strain T1-E5, *Gemella* sp. 933-88, *Veillonella parvula,* and *Prevotella* sp. C561.

In some embodiments, intestinal colonization with an oral microbiome *bacterium* induces a Th1 immune response in the subject. Examples of oral microbiome bacteria that may induce Th1 immune responses have been isolated, showing significant similarity (≥96.3%) to the following species: *Mogibacterium* sp. CM96, *Peptostreptococcus stomatis, Bifidobacterium* sp. Group 111-3, *Slackia exigua, Veillonella denticariosi, Atopobium parvulum, Veillonella* sp. 2011_oral_VSA_A3, *Campylobacter concisus, Actinomyces odontolyticus, Solobacterium moorei, Enterococcus faecium, Bifidobacterium dentium, Veillonella parvela, Fusobacterium* sp. 3_1_33, *Klebsiella aeromobilis,* and *Klebsiella pneumoniae* (see, e.g., Atarashi et al., *Science* (2017) 358: 359-365, Schirmer et al., *Cell Host and Microbe* (2018) 24: 600-610).

In some embodiments, the *bacterium* that induces a Th1 immune response (e.g., IBD) in a subject is a pathobiont. "Pathobiont" refers to a potentially pathological (disease-causing) organism which, under normal circumstances, lives as a symbiont. Examples of pathibionts are a *bacterium* that is associated with chronic inflammatory conditions (e.g., IBD). Non-limiting examples of pathobionts include *Shigella* spp., *Campylobacter* spp., *Cryptosporidium* spp., *Salmonella* spp., *Escherichia coli* strains (e.g., Enteropathogenic *E. coli,* Enteroaggregative *E. coli,* Enterotoxigenic *E. coli*), *Veillonella dispar, Aggregatibacter segnis, Campylobacter, Lachnospiraceae, Veillonella parvula, Haemophilus parainfluenzae, Megasphaera, Escherichia coli, Enterobacteriaceae* spp., *Enterococcus* spp., *Fusobacterium* spp., *Gemella* spp., *Veillonella* spp., *Pasteurella* spp., *Neisseria* spp., *Haemophilus* spp., *Campylobacter* spp., and *Bifidobacterium* spp.

In some embodiments, the methods may involve determining whether an oral *bacterium* is present in the subject. In some embodiments, the methods may involve determining whether an oral *bacterium* colonizes the oral cavity of the subject. In some embodiments, a subject may be at risk of intestinal colonization if the oral *bacterium* is present in the oral cavity of the subject. In some embodiments, the methods involve administering the combinations described herein to the subject, if an oral *bacterium* is detected in the oral cavity of the subject.

In some embodiments, the methods may involve determining whether an oral *bacterium* is present in the intestine of the subject. In some embodiments, the methods involve administering the combinations described herein to the subject, if an oral *bacterium* is detected in the intestine of the subject.

In some embodiments, the methods are for treating a disease or disorder associated with bacterial colonization in a subject. In some embodiments, the methods are for treating a disease or disorder associated with an immune response induced by bacteria in a subject. In some embodiments, the methods are for treating a disease or disorder associated with an undesired immune response induced by bacteria in a subject.

In some embodiments, the methods may involve determining whether the subject is colonized with a bacteria. In some embodiments, the methods may involve determining whether the subject has or is experiencing an immune response induced by bacterial colonization. In some embodiments, a subject may be at risk of an immune response induced by bacterial colonization if the subject is colonized by the bacteria. In some embodiments, the methods involve administering the combinations described herein to the subject, if the subject is determined to be colonized by the bacteria. In some embodiments, the methods involve administering the combinations described herein to the subject, if the subject is determined to be experiencing or have experienced an immune response induced by bacterial colonization.

In some embodiments, the immune response induced by bacterial colonization is an Th1 immune response. As will be evident to one of skill in the art, Th1 immune responses are mediated the Th1 population of CD4+ cells. Th1 cells produce IFN-γ and other pro-inflammatory factors. The differentiation of CD4+ cells to Th1 cells is promoted by the presence of IL-2 and/or IL-12 and activation of the transcription factors STAT4 and T-bet. In some embodiments, the immune responses induced by bacterial colonization are Th1 pro-inflammatory responses. Any direct or indirect measure of Th1 immune response, such as the amount of IFN-γ or the number of Th1 cells, may be used to assess the level or extent of the immune response in a sample from a subject.

In some embodiments, the compositions provided herein are administered to a subject if the subject has an autoimmune disease. Examples of autoimmune diseases include, without limitation, inflammatory bowel disease (IBD), ulcerative colitis, Crohn's disease, sprue, autoimmune arthritis, rheumatoid arthritis, graft versus host disease, Type I diabetes, multiple sclerosis, osteoarthritis, juvenile chronic arthritis, Lyme arthritis, psoriatic arthritis, reactive arthritis, spondyloarthropathy, systemic lupus erythematosus, insulin dependent diabetes mellitus, thyroiditis, asthma, psoriasis, dermatitis scleroderma, atopic dermatitis, sarcoidosis, atherosclerosis, disseminated intravascular coagulation, Kawasaki's disease, Grave's disease, nephrotic syndrome, chronic fatigue syndrome, Wegener's granulomatosis, Henoch-Schoenlejn *purpurea*, microscopic vasculitis of the kidneys, chronic active hepatitis, uveitis, cachexia, acute transverse myelitis, Huntington's chorea, Parkinson's disease, Alzheimer's disease, stroke, primary biliary cirrhosis, hemolytic anemia, polyglandular deficiency type I syndrome and polyglandular deficiency type II syndrome, Schmidt's syndrome, adult (acute) respiratory distress syndrome, alopecia, alopecia areata, seronegative arthopathy, arthropathy, Reiter's disease, psoriatic arthropathy, *chlamydia, yersinia* and *salmonella* associated arthropathy, spondyloarhopathy, atheromatous disease/arteriosclerosis, pemphigus vulgaris, pemphigus *foliaceus*, pemphigoid, linear IgA disease, autoimmune haemolytic anaemia, Coombs positive haemolytic anaemia, acquired pernicious anaemia, juvenile pernicious anaemia, myalgic encephalitis/Royal Free Disease, chronic mucocutaneous candidiasis, giant cell arteritis, primary sclerosing hepatitis, cryptogenic autoimmune hepatitis, Acquired Immunodeficiency Disease Syndrome, Acquired Immunodeficiency Related Diseases, common varied immunodeficiency (common variable hypogammaglobulinaemia), dilated cardiomyopathy, fibrotic lung disease, cryptogenic fibrosing alveolitis, postinflammatory interstitial lung disease, interstitial pneumonitis, connective tissue disease associated interstitial lung disease, mixed connective tissue disease associated lung disease, systemic sclerosis associated interstitial lung disease, rheumatoid arthritis associated interstitial lung disease, systemic lupus erythematosus associated lung disease, dermatomyositis/polymyositis associated lung disease, Sjogren's disease associated lung disease, ankylosing spondylitis associated lung disease, vasculitic diffuse lung disease, haemosiderosis associated lung disease, drug-induced interstitial lung disease, radiation fibrosis, bronchiolitis obliterans, chronic eosinophilic pneumonia, lymphocytic infiltrative lung disease, postinfectious interstitial lung disease, gouty arthritis, autoimmune hepatitis, type-1 autoimmune hepatitis (classical autoimmune or lupoid hepatitis), autoimmune mediated hypoglycemia, type B insulin resistance with acanthosis nigricans, hypoparathyroidism, acute immune disease associated with organ transplantation, chronic immune disease associated with organ transplantation, osteoarthrosis, primary sclerosing cholangitis, idiopathic leucopenia, autoimmune neutropenia, renal disease NOS, glomerulonephritides, microscopic vasulitis of the kidneys, discoid lupus, erythematosus, male infertility idiopathic or NOS, sperm autoimmunity, insulin-dependent diabetes mellitus, sympathetic ophthalmia, pulmonary hypertension secondary to connective tissue disease, Goodpasture's syndrome, pulmonary manifestation of polyarteritis *nodosa*, acute rheumatic fever, rheumatoid spondylitis, Still's disease, systemic sclerosis, Takayasu's disease/arteritis, autoimmune thrombocytopenia, idiopathic thrombocytopenia, autoimmune thyroid disease, hyperthyroidism, goitrous autoimmune hypothyroidism (Hashimoto's disease), atrophic autoimmune hypothyroidism, primary myxoedema, phacogenic uveitis, primary vasculitis, vitiligo, eosinophilic esophagitis, hypereosinophilic syndrome, eosinophilic gastroenteritis cutaneous lupus erythematosus, eosinophilic esophagitis, hypereosinophilic syndrome, and eosinophilic gastroenteritis, and diarrhea. In some embodiments, the autoimmune disease is inflammatory bowel disease (IBD).

In some embodiments, the autoimmune disease is ulcerative colitis. In some embodiments, the autoimmune disease is Crohn's disease.

In some embodiments, the compositions provided herein are administered to a subject if the subject has non-alcoholic steatohepatitis (NASH), primary sclerosing cholangitis (PSC), non-alcoholic fatty liver disease (NAFLD), gastroesophageal reflux disease (GERD), or alcoholism.

In some embodiments, the compositions provided herein are administered to a subject if an immune response associated with bacterial colonization has been detected in the subject. In some embodiments, the methods involve determining whether the subject has an immune response induced by or associated with colonization with an undesired organism.

In some embodiments, the compositions provided herein are administered to a subject if the subject has a dysbiosis (e.g., has as microbiome associated with a disease state). In some embodiments, treatment with the compositions provided herein results in the change in the microbiome of the subject. In some embodiments, treatment with the compositions provided herein removes the dysbiosis in the subject resulting in a healthy microbiome. In some embodiments, treatment with the compositions provided herein removes the dysbiosis in the subject resulting in microbiome refractory or less susceptible to infection by a pathogen.

Any of the compositions described herein may be administered to a subject in a therapeutically effective amount or a dose of a therapeutically effective amount to treat or prevent a disease or disorder, for example associated with colonization with bacteria or an immune response associated with colonization with bacteria. The terms "treat" or "treatment" refer to reducing or alleviating one or more of the symptoms associated with colonization with bacteria or an immune response associated with colonization with bacteria. In some embodiments, any of the compositions described herein may be administered to a subject to prevent a disease or disorder. In some embodiments, any of the compositions described herein may be administered to a subject to prevent a Th1 related disease or disorder. In some embodiments, any of the compositions described herein may be administered to a subject to prevent IBD. The terms "prevent" or "prevention" encompass prophylactic administration and may reduce the incidence or likelihood of colonization with bacteria or an immune response associated with colonization with bacteria. For instance, in some embodiments, administration of the compositions provided herein result in a healthy microbiome that is refractory to pathogenic infection, thereby preventing the pathogenic infection or re-colonization with the pathogenic organism.

As used herein, a "therapeutically effective amount" may be used interchangeably with the term "effective amount." A therapeutically effective amount or an effective amount of composition, such as a pharmaceutical composition, is any amount that results in a desired response or outcome in a subject, such as those described herein, including but not limited to reducing or preventing colonization with bacteria or an immune response associated with colonization with bacteria.

It should be appreciated that the term effective amount may be expressed in number of bacteria or bacterial spores to be administered. It should further be appreciated that the bacteria can multiply once administered. Thus, administration of even a relatively small amount of bacteria may have therapeutic effects.

In some embodiments, the therapeutically effective amount of any of the compositions described herein is an amount sufficient to enhance survival of the subject, reduce or prevent bacterial colonization of the subject, and/or reduce or inhibit toxin production by the pathogenic infection. In some embodiments, colonization may be assessed by detecting and/or quantifying the bacteria in a sample from the subject, such as a fecal sample. In some embodiments, the therapeutically effective amount is an amount sufficient to reduce the colonization bacteria (e.g., multi-drug resistant organism, oral microbiome bacteria) in a fecal sample from the subject by at least 1.5-fold, 2-fold, 3-fold, 4-fold, 5-fold, 6-fold, 7-fold, 8-fold, 9-fold, 10-fold, 20-fold, 30-fold, 40-fold, 50-fold, 100-fold, 1000-fold, 104-fold, 105-fold or more, as compared to the bacterial burden in a subject that has not received any of the compositions described herein, or as compared to a fecal sample from the same subject that was collected prior to administration of any of the compositions.

In some embodiments, the compositions provided herein reduce an immune response associated with bacterial colonization or induced by bacterial colonization. In some embodiments, the therapeutically effective amount is an amount sufficient to reduce an immune response associated with bacterial colonization or induced by bacterial colonization by at least 1.5-fold, 2-fold, 3-fold, 4-fold, 5-fold, 6-fold, 7-fold, 8-fold, 9-fold, 10-fold, 20-fold, 30-fold, 40-fold, 50-fold, 100-fold, 150-fold, 200-fold, 500-fold or more, as compared to the immune response associated with bacterial colonization or induced by bacterial colonization prior to administration of any of the compositions.

In some embodiments, the therapeutically effective amount is an amount sufficient to recolonize or repopulate the gastrointestinal tract of the subject with non-pathogenic bacteria. In some embodiments, the therapeutically effective amount is an amount sufficient to graft one or more of the bacterial strains of the composition in the gastrointestinal tract of the subject. In some embodiments, a fecal sample is obtained from the subject to assess the bacterial burden of undesired bacteria (e.g., multi-drug resistant organisms, oral microbiome bacteria) and/or evaluate the efficacy of administration of the bacterial compositions described herein. In some embodiments, the microbiota of the subject (e.g., the identity and abundance of strains and/or species of the microbiota) may be assessed to determine a disease state of the subject and/or assess progress of the treatment. In some embodiments, the microbiota of the subject having a pathogenic infection is compared to the microbiota of a healthy subject, such as a subject that is not experiencing or has not experienced the pathogenic infection. In some embodiments, the microbiota of the subject having a pathogenic infection is compared to the microbiota of the same subject from a fecal sample obtained from the subject prior to the pathogenic infection.

In some embodiments, administration of the compositions provided herein results in a healthy microbiome that reduces or prevents colonization of the subject by any undesired organism. In some embodiments, administration of the compositions provided herein results in a healthy microbiome that reduces or prevents intestinal colonization of the subject by any undesired organism (e.g., multi-drug resistant organisms, oral microbiome bacteria). In some embodiments, administration of the compositions provided herein results in a healthy microbiome that reduces an immune response associated with bacterial colonization, such as colonization with undesired bacteria. In some embodiments, administration of the compositions provided herein results in a healthy microbiome that reduces a Th1 immune response in the subject.

Any of the compositions described herein may be administered in combination with one or more additional compositions that can suppress a Th1 response and/or induces the accumulation and/or proliferation of regulatory T cells, and/or Th17 cells. In some embodiments, any of the compositions described herein may be administered in combination with a composition that induces the proliferation and/or accumulation of regulatory T cells.

In some embodiments, any of the compositions described herein may be administered in combination with VE-202, a T-reg inducing composition of 17 bacterial strains, described for instance in Atarashi et al., *Nature* (2013) 500: 232-236. The 17 bacterial strains of VE-202 are represented by the following species: *Clostridium saccharogumia, Flavonifractor plautii, Clostridium hathewayi, Blautia coccoides, Clostridium bolteae* ATCC BAA-613, cf. *Clostridium* sp. MLG055, *Clostridium indolis, Anaerotruncus colihominis, Ruminococcus* sp. IDB, *Clostridium asparagiforme* DSM 15981, *Clostridium symbiosum, Clostridium ramosum, Eubacterium contortum, Lachnospiraceae bacterium* 5_1_57FAA, *Lachnospiraceae bacterium* 3_1_57FAA_CT1, *Clostridiales bacterium* 1_7_47FAA, and *Lachnospiraceae bacterium* A4. It should be appreciated that subsets of the VE-202 bacteria can also induce Treg cells. Examples of subsets of VE202 that induce Treg cells are found for instance in Atarashi et al., *Nature* (2013) 500: 232-236 and corresponding Supplemental Information. In some embodiments, any of the compositions described herein may be administered in combination with any of the bacterial compositions as described in PCT Publication WO 2016/209806.

As used herein, the phrase "induces proliferation and/or accumulation of regulatory T cells" refers to an effect of inducing the differentiation of immature T cells into regulatory T cells, which differentiation leads to the proliferation and/or the accumulation of regulatory T cells. Further, the meaning of "induces proliferation and/or accumulation of regulatory T cells" includes in vivo effects, in vitro effects, and/or ex vivo effects. In some embodiments, the proliferation and/or accumulation of regulatory T cells may be assessed by detecting and/or quantifying the number of cells that express markers of regulatory T cells (e.g., Foxp3 and CD4), for example by flow cytometry. In some embodiments, the proliferation and/or accumulation of regulatory T cells may be assessed by determining the activity of the regulatory T cells, such as the production of cytokines (e.g., IL-10).

In some embodiments, any of the compositions described herein may be administered in combination with a composition that induces the accumulation and/or proliferation of Th17 cells, see e.g., compositions disclosed in PCT Publication WO 2015/156419.

In some embodiments, suppressing live bacterial product also repopulates the microbiota of the subject.

Any of the compositions described herein, including the pharmaceutical compositions and food products comprising the compositions, may contain bacterial strains in any form, for example in an aqueous form, such as a solution or a suspension, embedded in a semi-solid form, in a powdered form or freeze dried form. In some embodiments, the composition or the bacterial strains of the composition are lyophilized. In some embodiments, a subset of the bacterial strains in a composition is lyophilized. Methods of lyophilizing compositions, specifically compositions comprising bacteria, are well known in the art. See, e.g., U.S. Pat. Nos. 3,261,761; 4,205,132; PCT Publications WO 2014/029578 and WO 2012/098358, herein incorporated by reference in their entirety. The bacteria may be lyophilized as a combination and/or the bacteria may be lyophilized separately and combined prior to administration. A bacterial strain may be combined with a pharmaceutical excipient prior to combining it with the other bacterial strain or multiple lyophilized bacteria may be combined while in lyophilized form and the mixture of bacteria, once combined may be subsequently be combined with a pharmaceutical excipient. In some embodiments, the bacterial strain is a lyophilized cake. In some embodiments, the compositions comprising the one or more bacterial strains are a lyophilized cake.

In some embodiments, one or more of the bacterial strains of the compositions, including pharmaceutical compositions and food products, has been spray-dried. In some embodiments, a subset of the bacterial strains is spray-dried. The process of spray-drying refers to production of dry powder from a liquid comprising bacterial compositions (See, e.g., Ledet, et al., Spray Draying of Pharmaceuticals in "*Lyophilized Biologics and Vaccines*" pages 273-294, Springer). In general, the process involves rapidly drying the bacterial compositions with a hot gas. A bacterial strain may be combined with a pharmaceutical excipient prior to combining it with the other bacterial strains or multiple spray-dried bacterial strains may be combined while in spray-dried form and the mixture of bacterial strains, once combined, may be subsequently combined with a pharmaceutical excipient.

The bacterial strains of the composition can be manufactured using fermentation techniques well known in the art. In some embodiments, the active ingredients are manufactured using anaerobic fermenters, which can support the rapid growth of anaerobic bacterial species. The anaerobic fermenters may be, for example, stirred tank reactors or disposable wave bioreactors. Culture media such as BL media and EG media, or similar versions of these media devoid of animal components, can be used to support the growth of the bacterial species. The bacterial product can be purified and concentrated from the fermentation broth by traditional techniques, such as centrifugation and filtration, and can optionally be dried and lyophilized by techniques well known in the art.

In some embodiments, the composition of bacterial strains may be formulated for administration as a pharmaceutical composition. The term "pharmaceutical composition" as used herein means a product that results from the mixing or combining of at least one active ingredient, such as any two or more purified bacterial strains described herein, and one or more inactive ingredients, which may include one or more pharmaceutically acceptable excipient.

An "acceptable" excipient refers to an excipient that must be compatible with the active ingredient and not deleterious to the subject to which it is administered. In some embodiments, the pharmaceutically acceptable excipient is selected based on the intended route of administration of the composition, for example a composition for oral or nasal administration may comprise a different pharmaceutically acceptable excipient than a composition for rectal administration. Examples of excipients include sterile water, physiological saline, solvent, a base material, an emulsifier, a suspending agent, a surfactant, a stabilizer, a flavoring agent, an aromatic, an excipient, a vehicle, a preservative, a binder, a diluent, a tonicity adjusting agent, a soothing agent, a bulking agent, a disintegrating agent, a buffer agent, a coating agent, a lubricant, a colorant, a sweetener, a thickening agent, and a solubilizer.

Pharmaceutical compositions disclosed herein can be prepared in accordance with methods well known and routinely practiced in the art (see e.g., Remington: The Science and Practice of Pharmacy, Mack Publishing Co. 20th ed. 2000). The pharmaceutical compositions described herein may further comprise any carriers or stabilizers in the form of a lyophilized formulation or an aqueous solution. Acceptable excipients, carriers, or stabilizers may include, for example, buffers, antioxidants, preservatives, polymers, chelating reagents, and/or surfactants. Pharmaceutical compositions are preferably manufactured under GMP conditions. The pharmaceutical compositions can be used orally, nasally or parenterally, for instance, in the form of capsules, tablets, pills, sachets, liquids, powders, granules, fine granules, film-coated preparations, pellets, troches, sublingual preparations, chewables, buccal preparations, pastes, syrups, suspensions, elixirs, emulsions, liniments, ointments, plasters, cataplasms, transdermal absorption systems, lotions, inhalations, aerosols, injections, suppositories, and the like. In some embodiments, the pharmaceutical compositions can be used by injection, such as by intravenous, intramuscular, subcutaneous, or intradermal administration.

In some embodiments, the compositions comprising bacterial strains are formulated for delivery to the intestines (e.g., the small intestine and/or the colon). In some embodiments, the compositions comprising bacterial strains are formulated with an enteric coating that increases the survival of the bacteria through the harsh environment in the stomach. The enteric coating is one which resists the action of gastric juices in the stomach so that the bacteria of the composition therein will pass through the stomach and into the intestines. The enteric coating may readily dissolve when in contact with intestinal fluids, so that the bacteria enclosed in the coating will be released in the intestinal tract. Enteric coatings may consist of polymer and copolymers well known in the art, such as commercially available EUDRAGIT (Evonik Industries). (See e.g., Zhang, *AAPS PharmSci Tech* (2016) 17(1): 56-67).

The compositions comprising bacterial strains may also be formulated for rectal delivery to the intestine (e.g., the colon). Thus, in some embodiments, compositions comprising bacterial strains may be formulated for delivery by suppository, colonoscopy, endoscopy, sigmoidoscopy or enema. A pharmaceutical preparation or formulation and particularly a pharmaceutical preparation for oral administration, may include an additional component that enables efficient delivery of the compositions of the disclosure to the intestine (e.g., the colon). A variety of pharmaceutical preparations that allow for the delivery of the compositions to the intestine (e.g., the colon) can be used. Examples thereof include pH sensitive compositions, more specifically, buffered sachet formulations or enteric polymers that release their contents when the pH becomes alkaline after the enteric polymers pass through the stomach. When a pH sensitive composition is used for formulating the pharmaceutical preparation, the pH sensitive composition is preferably a polymer whose pH threshold of the decomposition of the composition is between about 6.8 and about 7.5. Such a numeric value range is a range in which the pH shifts toward the alkaline side at a distal portion of the stomach, and hence is a suitable range for use in the delivery to the colon. It should further be appreciated that each part of the intestine (e.g., the duodenum, jejunum, ileum, cecum, colon and rectum), has different biochemical and chemical environment. For instance, parts of the intestines have different pHs, allowing for targeted delivery by compositions that have a specific pH sensitivity. Thus, the compositions provided herein may be formulated for delivery to the intestine or specific parts of the intestine (e.g., the duodenum, jejunum, ileum, cecum, colon and rectum) by providing formulations with the appropriate pH sensitivity. (See e.g., Villena et al., Int J Pharm 2015, 487 (1-2): 314-9).

Another embodiment of a pharmaceutical preparation useful for delivery of the compositions to the intestine (e.g., the colon) is one that ensures the delivery to the colon by delaying the release of the contents (e.g., the bacterial strains) by approximately 3 to 5 hours, which corresponds to the small intestinal transit time. In one embodiment of a pharmaceutical preparation for delayed release, a hydrogel is used as a shell. The hydrogel is hydrated and swells upon contact with gastrointestinal fluid, with the result that the contents are effectively released (released predominantly in the colon). Delayed release dosage units include drug-containing compositions having a material which coats or selectively coats a drug or active ingredient to be administered. Examples of such a selective coating material include in vivo degradable polymers, gradually hydrolyzable polymers, gradually water-soluble polymers, and/or enzyme degradable polymers. A wide variety of coating materials for efficiently delaying the release is available and includes, for example, cellulose-based polymers such as hydroxypropyl cellulose, acrylic acid polymers and copolymers such as methacrylic acid polymers and copolymers, and vinyl polymers and copolymers such as polyvinylpyrrolidone.

Additional examples of pharmaceutical compositions that allow for the delivery to the intestine (e.g., the colon) include bioadhesive compositions which specifically adhere to the colonic mucosal membrane (for example, a polymer described in the specification of U.S. Pat. No. 6,368,586) and compositions into which a protease inhibitor is incorporated for protecting particularly a biopharmaceutical preparation in the gastrointestinal tracts from decomposition due to an activity of a protease.

Another example of a system enabling the delivery to the intestine (e.g., the colon) is a system of delivering a composition to the colon by pressure change in such a way that the contents are released by utilizing pressure change caused by generation of gas in bacterial fermentation at a distal portion of the stomach. Such a system is not particularly limited, and a more specific example thereof is a capsule which has contents dispersed in a suppository base and which is coated with a hydrophobic polymer (for example, ethyl cellulose).

A further example of a system enabling the delivery of a composition to the intestine (e.g., the colon), is a composition that includes a coating that can be removed by an enzyme present in the gut (e.g., the colon), such as, for example, a carbohydrate hydrolase or a carbohydrate reductase. Such a system is not particularly limited, and more specific examples thereof include systems which use food components such as non-starch polysaccharides, amylose, xanthan gum, and azopolymers.

The compositions provided herein can also be delivered to specific target areas, such as the intestine, by delivery through an orifice (e.g., a nasal tube) or through surgery. In addition, the compositions provided herein that are formulated for delivery to a specific area (e.g., the cecum or the colon), may be administered by a tube (e.g., directly into the small intestine). Combining mechanical delivery methods such as tubes with chemical delivery methods such as pH specific coatings, allow for the delivery of the compositions provided herein to a desired target area (e.g., the cecum or the colon).

The compositions comprising bacterial strains are formulated into pharmaceutically acceptable dosage forms by conventional methods known to those of skill in the art. Dosage regimens are adjusted to provide the optimum desired response (e.g., the prophylactic or therapeutic effect). In some embodiments, the dosage form of the composition is a tablet, pill, capsule, powder, granules, solution, or suppository. In some embodiments, the pharmaceutical composition is formulated for oral administration. In some embodiments, the pharmaceutical composition is formulated such that the bacteria of the composition, or a portion thereof, remain viable after passage through the stomach of the subject. In some embodiments, the pharmaceutical composition is formulated for rectal administration, e.g. as a suppository. In some embodiments, the pharmaceutical composition is formulated for delivery to the intestine or a specific area of the intestine (e.g., the colon) by providing an appropriate coating (e.g., a pH specific coating, a coating that can be degraded by target area specific enzymes, or a coating that can bind to receptors that are present in a target area).

Dosages of the active ingredients in the pharmaceutical compositions disclosed herein can be varied so as to obtain an amount of the active ingredient which is effective to achieve the desired pharmaceutical response for a particular subject, composition, and mode of administration, without being toxic or having an adverse effect on the subject. The selected dosage level depends upon a variety of factors including the activity of the particular compositions employed, the route of administration, the time of administration, the duration of the treatment, other drugs, compounds and/or materials used in combination with the particular compositions employed, the age, sex, weight, condition, general health and prior medical history of the subject being treated, and like factors.

A physician, veterinarian or other trained practitioner, can start doses of the pharmaceutical composition at levels lower than that required to achieve the desired therapeutic effect and gradually increase the dosage until the desired effect is achieved. In general, effective doses of the compositions, for the prophylactic or therapeutic treatment of groups of people as described herein vary depending upon many different factors, including routes of administration, physiological state of the subject, whether the subject is human or an animal, other medications administered, and the therapeutic effect desired. Dosages need to be titrated to optimize safety and efficacy. In some embodiments, the dosing regimen entails oral administration of a dose of any of the compositions described herein. In some embodiments, the dosing regimen entails oral administration of multiple doses of any of the compositions described herein. In some embodiments, the composition is administered orally the subject once, twice, 3 times, 4 times, 5 times, 6 times, 7 times, 8 times, 9 times, or at least 10 times. In some embodiments, any of the compositions described herein are administered the subject in multiple doses at a regular interval, such as every 2 weeks, every month, every 2 months, every 3 months, every 4 months, every 5 months, every 6 months, or more.

The compositions, including the pharmaceutical compositions disclosed herein, include compositions that contain selected bacterial strains. The amount of bacteria, including the amount of bacteria of each of the bacterial strains, in the compositions, including pharmaceutical compositions, may be expressed in weight, number of bacteria and/or CFUs (colony forming units). In some embodiments, the compositions, including pharmaceutical compositions, comprise about 10, about $10^2$, about $10^3$, about $10^4$, about $10^5$, about $10^6$, about $10^7$, about $10^8$, about $10^9$, about $10^{10}$, about $10^{11}$, about $10^{12}$, about $10^{13}$ or more of each of the bacterial strains per dosage amount. In some embodiments, the compositions, including pharmaceutical compositions, comprise about 10, about $10^2$, about $10^3$, about $10^4$, about $10^5$, about $10^6$, about $10^7$, about $10^8$, about $10^9$, about $10^{10}$, about $10^{11}$, about $10^{12}$, about $10^{13}$ or more total bacteria per dosage amount. It should further be appreciated that bacteria of each of the bacterial strains may be present in different amounts. Thus, for instance, as a non-limiting example, composition may include $10^3$ of bacteria A, $10^4$ of bacteria B and $10^6$ of bacteria C. In some embodiments, compositions, including pharmaceutical composition, comprise about 10, about $10^2$, about $10^3$, about $10^4$, about $10^5$, about $10^6$, about $10^7$, about $10^8$, about $10^9$, about $10^{10}$, about $10^{11}$, about $10^{12}$, about $10^{13}$ or more CFUs of each of the bacterial strains per dosage amount. In some embodiments, compositions, including pharmaceutical compositions, comprise about $10^1$, about $10^2$, about $10^3$, about $10^4$, about $10^5$, about $10^6$, about $10^7$, about $10^8$, about $10^9$, about $10^{10}$, about $10^{11}$, about $10^{12}$, about $10^{13}$ or more CFUs in total for all of the bacterial strains combined per dosage amount. As discussed above, bacteria of each of the bacterial strains may be present in different amounts. In some embodiments, the compositions, including pharmaceutical compositions, contain about $10^{-7}$, about $10^{-6}$, about $10^{-5}$, about $10^{-4}$, about $10^{-3}$, about $10^{-2}$, about $10^{-1}$ or more grams of bacteria of each of the bacterial strains in the composition per dosage amount. In some embodiments, the compositions, including pharmaceutical compositions, contain about $10^{-7}$, about $10^{-6}$, about $10^{-5}$, about $10^{-4}$, about $10^{-3}$, about $10^{-2}$, about $10^{-1}$ or more grams of bacteria in total for all of the bacterial strains combined per dosage amount. In some embodiments, the dosage amount is one administration device (e.g., one table, pill or capsule). In some embodiment, the dosage amount is the amount that is administered in a particular period (e.g., one day or one week).

In some embodiments, the compositions, including pharmaceutical compositions, contain between 10 and $10^{13}$, between $10^2$ and $10^{13}$, between $10^3$ and $10^{13}$, between $10^4$ and $10^{13}$, between $10^5$ and $10^{13}$, between $10^6$ and $10^{13}$, between $10^7$ and $10^{13}$, between $10^8$ and $10^{13}$, between $10^9$ and $10^{13}$, between $10^{10}$ and $10^{13}$, between $10^{11}$ and $10^{13}$, between $10^{12}$ and $10^{13}$, between 10 and $10^{12}$, between $10^2$ and $10^{12}$, between $10^3$ and $10^{12}$, between $10^4$ and $10^{12}$, between $10^5$ and $10^{12}$, between $10^6$ and $10^{12}$, between $10^7$ and $10^{12}$, between $10^8$ and $10^{12}$, between $10^9$ and $10^{12}$, between $10^{10}$ and $10^{12}$, between $10^{11}$ and $10^{12}$, between 10 and $10^{11}$, between $10^2$ and $10^{11}$, between $10^3$ and $10^{13}$, between $10^4$ and $10^{13}$, between $10^5$ and $10^{13}$, between $10^6$ and $10^{13}$, between $10^7$ and $10^{11}$, between $10^8$ and $10^{11}$, between $10^9$ and $10^{11}$, between $10^{10}$ and $10^{11}$, between 10 and $10^{10}$, between $10^2$ and $10^{10}$, between $10^3$ and $10^{10}$, between $10^4$ and $10^{10}$, between $10^5$ and $10^{10}$, between $10^6$ and $10^{10}$, between $10^7$ and $10^{10}$, between $10^8$ and $10^{10}$, between $10^9$ and $10^{10}$, between 10 and $10^9$, between $10^2$ and $10^9$, between $10^3$ and $10^9$, between $10^4$ and $10^9$, between $10^5$ and $10^9$, between $10^6$ and $10^9$, between $10^7$ and $10^9$, between $10^8$ and $10^9$, between 10 and $10^8$, between $10^2$ and $10^8$, between $10^3$ and $10^8$, between $10^4$ and $10^8$, between $10^5$ and $10^8$, between $10^6$ and $10^8$, between $10^7$ and $10^8$, between 10 and $10^7$, between $10^2$ and $10^7$, between $10^3$ and $10^7$, between $10^4$ and $10^7$, between $10^5$ and $10^7$, between $10^6$ and $10^7$, between 10 and $10^6$, between $10^2$ and $10^6$, between $10^3$ and $10^6$, between $10^4$ and $10^6$, between $10^5$ and $10^6$, between 10 and $10^5$, between $10^2$ and $10^5$, between $10^3$ and $10^5$, between $10^4$ and $10^5$, between 10 and $10^4$, between $10^2$ and $10^4$, between $10^3$ and $10^4$, between 10 and $10^3$, between $10^2$ and $10^3$, or between 10 and $10^2$ of each of the bacterial strains per dosage amount. In some embodiments, the compositions, including pharmaceutical compositions, contain between 10 and $10^{13}$, between $10^2$ and $10^{13}$, between $10^3$ and $10^{13}$, between $10^4$ and $10^{13}$, between $10^5$ and $10^{13}$, between $10^6$ and $10^{13}$, between $10^7$ and $10^{13}$, between $10^8$ and $10^{13}$, between $10^9$ and $10^{13}$, between $10^{10}$ and $10^{13}$, between $10^{11}$ and $10^{13}$, between $10^{12}$ and $10^{13}$, between 10 and $10^{12}$, between $10^2$ and $10^{12}$, between $10^3$ and $10^{12}$, between $10^4$ and $10^{12}$, between $10^5$ and $10^{12}$, between $10^6$ and $10^{12}$, between $10^7$ and $10^{12}$, between $10^8$ and $10^{12}$, between $10^9$ and $10^{12}$, between $10^{10}$ and $10^{12}$, between $10^{11}$ and $10^{12}$, between 10 and $10^{11}$, between $10^2$ and $10^{11}$, between $10^3$ and $10^{11}$, between 10 and $10^{10}$, between $10^2$ and $10^{10}$, or between 10 and $10^2$ total bacteria per dosage amount.

In some embodiments, the compositions, including pharmaceutical compositions, contain between 10 and $10^{13}$, between $10^2$ and $10^{13}$, between $10^3$ and $10^{13}$, between $10^4$ and $10^{13}$, between $10^5$ and $10^{13}$, between $10^6$ and $10^{13}$, between $10^7$ and $10^{13}$, between $10^8$ and $10^{13}$, between $10^9$ and $10^{13}$, between $10^{10}$ and $10^{13}$, between $10^{11}$ and $10^{13}$, between $10^{12}$ and $10^{13}$, between 10 and $10^{12}$, between $10^2$ and $10^{12}$, between $10^3$ and $10^{12}$, between $10^4$ and $10^{12}$, between $10^5$ and $10^{12}$, between $10^6$ and $10^{12}$, between $10^7$ and $10^{12}$, between $10^8$ and $10^{12}$, between $10^9$ and $10^{12}$, between $10^{10}$ and $10^{12}$, between $10^{11}$ and $10^{12}$, between 10 and $10^{11}$, between $10^2$ and $10^{11}$, between $10^3$ and $10^{13}$, between $10^4$ and $10^{13}$, between $10^5$ and $10^{13}$ between $10^6$ and $10^{13}$, between $10^7$ and $10^{11}$ between $10^8$ and $10^{11}$, between $10^9$ and $10^{11}$ between $10^{10}$ and $10^{11}$, between 10 and $10^{10}$ between $10^2$ and $10^{10}$, between $10^3$ and $10^{10}$ between $10^4$ and $10^{10}$, between $10^5$ and $10^{10}$ between $10^6$ and $10^{10}$, between $10^7$ and $10^{10}$ between $10^8$ and $10^{10}$, between $10^9$ and $10^{10}$, between 10 and $10^9$, between $10^2$ and $10^9$, between $10^3$ and $10^9$, between $10^4$ and $10^9$, between $10^5$ and $10^9$, between $10^6$ and $10^9$, between $10^7$ and $10^9$, between $10^8$ and $10^9$, between 10 and $10^8$, between $10^2$ and $10^8$, between $10^3$ and $10^8$, between $10^4$ and $10^8$, between $10^5$ and $10^8$, between $10^6$ and $10^8$, between $10^7$ and $10^8$, between 10 and $10^7$, between $10^2$ and $10^7$, between $10^3$ and $10^7$, between $10^4$ and $10^7$, between $10^5$ and $10^7$, between $10^6$ and $10^7$, between 10 and $10^6$, between $10^2$ and $10^6$, between $10^3$ and $10^6$, between $10^4$ and $10^6$, between $10^5$ and $10^6$, between 10 and $10^5$, between $10^2$ and $10^5$, between $10^3$ and $10^5$, between $10^4$ and $10^5$, between 10 and $10^4$, between $10^2$ and $10^4$, between $10^3$ and $10^4$, between 10 and $10^3$, or between 10 and $10^2$ CFUs of each of the bacterial strains per dosage amount. In some embodiments, the compositions, including pharmaceutical compositions contain between 10 and $10^{13}$, between $10^2$ and $10^{13}$, between $10^3$ and $10^{13}$, between $10^4$ and $10^{13}$, between $10^5$ and $10^{13}$, between $10^6$ and $10^{13}$, between $10^7$ and $10^{13}$, between $10^8$ and $10^{13}$, between $10^9$ and $10^{13}$, between $10^{10}$ and $10^{13}$, between $10^{11}$ and $10^{13}$, between $10^{12}$ and $10^{13}$, between 10 and $10^{12}$, between $10^2$ and $10^{12}$, between $10^3$ and $10^{12}$, between $10^4$ and $10^{12}$, between $10^5$ and $10^{12}$, between $10^6$ and $10^{12}$, between $10^7$ and $10^{12}$, between $10^8$ and $10^{12}$, between $10^9$ and $10^{12}$, between $10^{10}$ and $10^{12}$, between $10^{11}$ and $10^{12}$, between 10 and $10^{11}$, between $10^2$ and $10^{11}$, between $10^3$ and $10^{13}$, between $10^4$ and $10^{13}$, between $10^5$ and $10^{13}$, between $10^6$ and $10^{13}$, between $10^7$ and $10^{11}$, between $10^8$ and $10^{11}$, between $10^9$ and $10^{11}$, between $10^{10}$ and $10^{11}$, between 10 and $10^{10}$, between $10^2$ and $10^{10}$, between $10^3$ and $10^{10}$, between $10^4$ and $10^{10}$, between $10^5$ and $10^{10}$, between $10^6$ and $10^{10}$, between $10^7$ and $10^{10}$, between $10^8$ and $10^{10}$, between $10^9$ and $10^{10}$, between 10 and $10^9$, between $10^2$ and $10^9$, between $10^3$ and $10^9$, between $10^4$ and $10^9$, between $10^5$ and $10^9$, between $10^6$ and $10^9$, between $10^7$ and $10^9$, between $10^8$ and $10^9$, between 10 and $10^8$, between $10^2$ and $10^8$, between $10^3$ and $10^8$, between $10^4$ and $10^8$, between $10^5$ and $10^8$, between $10^6$ and $10^8$, between $10^7$ and $10^8$, between 10 and $10^7$, between $10^2$ and $10^7$, between $10^3$ and $10^7$, between $10^4$ and $10^7$, between $10^5$ and $10^7$, between $10^6$ and $10^7$, between 10 and $10^6$, between $10^2$ and $10^6$, between $10^3$ and $10^6$, between $10^4$ and $10^6$, between $10^5$ and $10^6$, between 10 and $10^5$, between $10^2$ and $10^5$, between $10^3$ and $10^5$, between $10^4$ and $10^5$, between 10 and $10^4$, between $10^2$ and $10^4$, between $10^3$ and $10^4$, between 10 and $10^3$, between $10^2$ and $10^3$, or between 10 and $10^2$ total CFUs per dosage amount.

In some embodiments, the compositions, including pharmaceutical compositions, contain between $10^{-7}$ and $10^{-1}$, between $10^{-6}$ and $10^{-1}$, between $10^{-5}$ and $10^{-1}$, between $10^{-4}$ and $10^{-1}$, between $10^{-3}$ and $10^{-1}$, between $10^{-2}$ and $10^{-1}$, between $10^{-7}$ and $10^{-2}$, between $10^{-6}$ and $10^{-2}$, between $10^{-5}$ and $10^{-2}$, between $10^{-4}$ and $10^{-2}$, between $10^{-3}$ and $10^{-2}$, between $10^{-7}$ and $10^{-3}$, between $10^{-2}$ and $10^{-3}$, between $10^{-5}$ and $10^{-3}$, between $10^{-4}$ and $10^{-3}$, between $10^{-7}$ and $10^{-5}$, between $10^{-6}$ and $10^{-4}$, between $10^{-5}$ and $10^{-4}$, between $10^{-7}$ and $10^{-5}$ between $10^{-6}$ and $10^{-5}$, or between $10^{-7}$ and $10^{-6}$ grams of bacteria of each of the bacterial strains in the composition per dosage amount. In some embodiments, the compositions, including pharmaceutical compositions, disclosed herein contain between $10^{-7}$ and $10^{-1}$, between $10^{-6}$ and $10^{-1}$, between $10^{-5}$ and $10^{-1}$, between $10^{-4}$ and $10^{-1}$, between $10^{-3}$ and $10^{-1}$, between $10^{-2}$ and $10^{-1}$, between $10^{-7}$ and $10^{-2}$, between $10^{-6}$ and $10^{-2}$, between $10^{-5}$ and $10^{-2}$, between $10^{-4}$ and $10^{-2}$, between $10^{-3}$ and $10^{-3}$, between $10^{-7}$ and $10^{-3}$, between $10^{-6}$ and $10^{-3}$, between $10^{-5}$ and $10^{-3}$, between $10^{-4}$ and $10^{-3}$, between $10^{-7}$ and $10^{-4}$, between $10^{-6}$ and $10^{-4}$, between $10^{-5}$ and $10^{-4}$, between $10^{-7}$ and $10^{-5}$ between $10^{-6}$ and $10^{-5}$, or between $10^{-7}$ and $10^{-6}$ grams of all of the bacteria combined (total) per dosage amount.

Aspects of the present disclosure also provide food products comprising any of the compositions described herein and a nutrient. Also with the scope of the present disclosure are food products comprising any of the bacterial strains described herein and a nutrient. Food products are, in general, intended for the consumption of a human or an animal. Any of the bacterial strains described herein may be formulated as a food product. In some embodiments, the bacterial strains are formulated as a food product in spore form. In some embodiments, the bacterial strains are formulated as a food product in vegetative form. In some embodiments, the food product comprises both vegetative bacteria and bacteria in spore form. The compositions disclosed herein can be used in a food or beverage, such as a health food or beverage, a food or beverage for infants, a food or beverage for pregnant women, athletes, senior citizens or other specified group, a functional food, a beverage, a food or beverage for specified health use, a dietary supplement, a food or beverage for patients, or an animal feed.

Non-limiting examples of the foods and beverages include various beverages such as juices, refreshing beverages, tea beverages, drink preparations, jelly beverages, and functional beverages; alcoholic beverages such as beers; carbohydrate-containing foods such as rice food products, noodles, breads, and pastas; paste products such as fish hams, sausages, paste products of seafood; retort pouch products such as curries, food dressed with a thick starchy sauces, soups; dairy products such as milk, dairy beverages, ice creams, cheeses, and yogurts; fermented products such as fermented soybean pastes, yogurts, fermented beverages, and pickles; bean products; various confectionery products such as Western confectionery products including biscuits, cookies, and the like, Japanese confectionery products including steamed bean-jam buns, soft adzuki-bean jellies, and the like, candies, chewing gums, gummies, cold desserts including jellies, cream caramels, and frozen desserts; instant foods such as instant soups and instant soy-bean soups; microwavable foods; and the like. Further, the examples also include health foods and beverages prepared in the forms of powders, granules, tablets, capsules, liquids, pastes, and jellies.

Food products containing bacterial strains described herein may be produced using methods known in the art and may contain the same amount of bacteria (e.g., by weight, amount or CFU) as the pharmaceutical compositions provided herein. Selection of an appropriate amount of bacteria in the food product may depend on various factors, including for example, the serving size of the food product, the frequency of consumption of the food product, the specific bacterial strains contained in the food product, the amount of water in the food product, and/or additional conditions for survival of the bacteria in the food product.

Examples of food products which may be formulated to contain any of the bacterial strains described herein include, without limitation, a beverage, a drink, a bar, a snack, a dairy product, a confectionery product, a cereal product, a ready-to-eat product, a nutritional formula, such as a nutritional supplementary formulation, a food or beverage additive.

The nucleic acid sequences of the 16S rDNA, or portion thereof, for the bacterial strains described herein are provided below:

>SEQ ID NO 22: Ruminococcus_faecis; Strain 45
GCGNTCGGTCACCTTCGGCAGCTCCCTCCTTACGGTTGGGTCACTGACTTCGGGCGTTACTGACTCCCATGGTGTG

ACGGGCGGTGTGTACAAGACCCGGGAACGTATTCACCGCGACATTCTGATTCGCGATTACTAGCGATTCCAGCTTC

ATGTAGTCGAGTTGCAGACTACAATCCGAACTGAGACGTTATTTTTGGGATTTGCTCGACCTCGCGGTTCTGCCTC

CCTTTGTTTACGCCATTGTAGCACGTGTGTAGCCCTGCTCATAAGGGGCATGATGATTTGACGTCATCCCCACCTT

-continued

```
CCTCCAGGTTATCCCTGGCAGTCTCTCTAGAGTGCCCGGCCAAACCGCTGGCTACTAAAGATAGGGGTTGCGCTCG
TTGCGGGACTTAACCCAACATCTCACGACACGAGCTGACGACAACCATGCACCACCTGTCATCCCTGTCCCGAAGG
AAAGGCAACATTACTTGCCGGTCAGGGAGATGTCAAGAGCAGGTAAGGTTCTTCGCGTTGCTTCGAATTAAACCAC
ATGCTCCACCGCTTGTGCGGGTCCCCGTCAATTCCTTTGAGTTTCATTCTTGCGAACGTACTCCCCAGGTGGACTA
CTTATTGCGTTTGCTGCGGCACCGAACAGCTTTGCTGCCCGACACCTAGTAGTCATCGTTTACGGCGTGGACTACC
AGGGTATCTAATCCTGTTTGCTCCCCACGCTTTCGAGCCTCAACGTCAGTTACCGTCCAGTAAGCCGCCTTCGCCA
CTGGTGTTCCTCCTAATATCTACGCATTTCACCGCTACACTAGGAATTCCGCTTACCTCTCCGGTACTCTAGATTG
ACAGTTTCCAATGCAGTCCCGGGGTTGAGCCCCGGGTTTTCACATCAGACTTGCCACTCCGTCTACGCTCCCTTTA
CACCCAGTAAATCCGGATAACGCTTGCACCATACGTATTACCGCGGCTGCTGGCACGTATTTAGCCTGTGCTTCTA
GTCAGGTACCGTCATTTTCTTCCCTGCTGATAGAGCTTTACATACCGAATACTTCATCCCCTCCCGCG
```

>SEQ ID NO 6: Bifidobacterium_adolescentis; Strain 31
```
GAATTCGAGTCTCACCTTAGACGGCTCCCCCCAAAAGGTTGGGCCACCGGCTTCGGGTGCTACCCACTTTCATGAC
TTGACGGGCGGTGTGTACAAGGCCCGGGAACGCATTCACCGCGGCGTTGCTGATCCGCGATTACTAGCGACTCCGC
CTTCATGGAGTCGGGTTGCAGACTCCAATCCGAACTGAGACCGGTTTTAAGGGATCCGCTCCACCTCGCGGTGTCG
CATCCCGTTGTACCGGCCATTGTAGCATGCGTGAAGCCCTGGACGTAAGGGGCATGATGATCTGACGTCATCCCCA
CCTTCCTCCGAGTTGACCCCGGCGGTCCCCCGTGAGTTCCCACCACGACGTGCTGGCAACACAGGGCGAGGGTTGC
GCTCGTTGCGGGACTTAACCCAACATCTCACGACACGAGCTGACGACGACCATGCACCACCTGTGAACCCGCCCCG
AAGGGAGGCCCCATCTCTGGGGCTGTCGGAACATGTCAAGCCCAGGTAAGGTTCTTCGCGTTGCATCGAATTAAT
CCGCATGCTCCGCCGCTTGTGCGGGCCCCCGTCAATTTCTTTGAGTTTTAGCCTTGCGGCCGTACTCCCCAGGCGG
GATGCTTAACGCGTTGGCTCCGACACGGAGACCGTGGAATGGTCCCCACATCCAGCATCCACCGTTTACGGCGTGG
ACTACCAGGGTATCTAATCCTGTTCGCTCCCCACGCTTTCGCTCCTCAGCGTCAGTGACGGCCCAGAGACCTGCCT
TCGCCATTGGTGTTCTTCCCGATATCTACACATTCCACCGTTACACCGGGAATTCCAGTCTCCCCTACCGCACTCA
AGCCCGCCCGTACCGGCGCGGATCCACCGTTAAGCGATGGACTTTCACACCGGACGCGACGAACCGCCTACGAGC
CCTTTACGCCCAATAATTCCGGATACGCTTGCACCCTACGTATTACCGCGGCTGCTGGCACGTAGTTAGCCGGTGC
TTATTCGAAAGGTACACTCACTCCGGAGGGCTTGCTTCCAGTCAAAA
```

>SEQ ID NO 5: Bifidobacterium_longum; Strain 30
```
GGGACGGATCTCCCTTAGACGGCTCCATCCCACAAGGGGTTAGGCCACCGGCTTCGGGTGCTGCCCACTTTCATGA
CTTGACGGGCGGTGTGTACAAGGCCCGGGAACGCATTCACCGCGACGTTGCTGATTCGCGATTACTAGCGACTCCG
CCCTTCACGCAGTCGAGTTGCAGACTGCGATCCGAACTGAGACCGGTTTTCAGGGATCCGCTCCGCGTCGCCGCGTC
GCATCCCGTTGTACCGGCCATTGTAGCATGCGTGAAGCCCTGGACGTAAGGGGCATGATGATCTGACGTCATCCCC
ACCTTCCTCCGAGTTAACCCCGGCGGTCCCCCGTGAGTTCCCGGCATAATCCGCTGGCAACACGGGGCGAGGGTTG
CGCTCGTTGCGGGACTTAACCCAACATCTCACGACACGAGCTGACGACGACCATGCACCACCTGTGAACCCGCCCC
GAAGGGAAGCCGTATCTCTACGACCGTCGGGAACATGTCAAGCCCAGGTAAGGTTCTTCGCGTTGCATCGAATTAA
TCCGCATGCTCCGCCGCATGTGCGGGCCCCCGTCAATTTCTTTGAGTTTTAGCCTTGCGGCCGTACTCCCCAGGCG
GGATGCTTAACGCGTTAGCTCCGACACGGAACCCGTGGAACGGGCCCCACATCCAGCATCCACCGTTTACGGCGTG
GACTACCAGGGTATCTAATCCTGTTCGCTCCCCACGCTTTCGCTCCTCAGCGTCAGTAACGGCCCAGAGACCTGCC
TTCGCCATTGGTGTTCTTCCCGATATCTACACATTCCACCGTTACACCGGGAATTCCAGTCTCCCCTACCGCACTC
AACCCGCCGTACCGGCGCGGATCCCCGGTAAGCGATGGACTTTCACACCGGACGCGAGG
```

>SEQ ID NO 8: Blautia_wexlerae; Strain 33
```
GNGANTGGCGGCGTGCTTACCATGCAGTCGAACGGGAAATACTTCATTGAAACTTCGGTGGATTTAATTTATTTCT
AGTGGCGGACGGGTGAGTAACGCGTGGGTAACCTGCCTTATACAGGGGATAACAGTCAGAAATGGCTGCTAATAC
CGCATAAGCGCACAGAGCTGCATGGCTCAGTGTGAAAAACTCCGGTGGTATAAGATGGACCCGCGTTGGATTAGCT
```

-continued

```
TGTTGGTGGGGTAACGGCCCACCAAGGCGACGATCCATAGCCGGCCTGAGAGGGTGAACGGCCACATTGGGACTGA

GACACGGCCCAGACTCCTACGGGAGGCAGCAGTGGGGAATATTGCACAATGGGGGAAACCCTGATGCAGCGACGCC

GCGTGAAGGAAGAAGTATCTCGGTATGTAAACTTCTATCAGCAGGGAAGATAGTGACGGTACCTGACTAAGAAGCC

CCGGCTAACTACGTGCCAGCAGCCGCGGTAATACGTAGGGGGCAAGCGTTATCCGGATTTACTGGGTGTAAAGGGA

GCGTAGACGGTGTGGCAAGTCTGATGTGAAAGGCATGGGCTCAACCTGTGGACTGCATTGGAAACTGTCATACTTG

AGTGCCGGAGGGGTAAGCGGAATTCCTAGTGTAGCGGTGAAATGCGTAGATATTAGGAGGAACACCAGTGGCGAAG

GCGGCTTACTGGACGGTAACTGACGTTGAGGCTCGAAAGCGTGGGGAGCAAACAGGATTAGATACCCTGGTAGTCC

ACGCCGTAAACGATGAATACTAGGTGTCGGGGGAGCATAGCTCTTCGGTGCCGTCGCAAACGCAGTAAGTATTCCA

CCTGGGGAGTACGTTCGCAAGAATGAAACTCAAAGGAATTGACGGGACCCGCACAAGCGGTGGAGCATGTGGTTT

AATTCGAAGCAACGCGAAGAACCTTACCAAGTCTTGACATCCGCCTGACCGGATCCTTAATCGGATCTTTCCTTC

GGGACAGGCGAGACAGGGGTGCATGGTTGTCGTCAGCTCGTGTCGTGAGATGTTGGGTAAGTCCGCACGAGCGCAA

CCCTATCCTCAGTAGCAGCATTTAAGTGGGCACTCTGGGGGAGACTGCC
```

>SEQ ID NO 2: *Bacteroides uniformis*; Strain 27
```
GAGCGCTAGGCTTACACATGCAAGTCGAGGGGCAGCATGAACTTAGCTTGCTAAGTTTGATGGCGACCGGCGCACG

GGTGAGTAACACGTATCCAACCTGCCGATGACTCGGGGATAGCCTTTCGAAAGAAAGATTAATACCCGATGGCATA

GTTCTTCCGCATGGTAGAACTATTAAAGAATTTCGGTCATCGATGGGGATGCGTTCCATTAGGTTGTTGGCGGGGT

AACGGCCCACCAAGCCTTCGATGGATAGGGGTTCTGAGAGGAAGGTCCCCCACATTGGAACTGAGACACGGTCCAA

ACTCCTACGGGAGGCAGCAGTGAGGAATATTGGTCAATGGACGAGAGTCTGAACCAGCCAAGTAGCGTGAAGGATG

ACTGCCCTATGGGTTGTAAACTTCTTTTATACGGGAATAAAGTGAGGCACGCGTGCCTTTTTGTATGTACCGTATG

AATAAGGATCGGCTAACTCCGTGCCAGCAGCCGCGGTAATACGGAGGATCCGAGCGTTATCCGGATTTATTGGGTT

TAAAGGGAGCGTAGGCGGACGCTTAAGTCAGTTGTGAAAGTTTGCGGCTCAACCGTAAAATTGCAGTTGATACTGG

GTGTCTTGAGTACAGTAGAGGCAGGCGGAATTCGTGGTGTAGCGGTGAAATGCTTAGATATCACGAAGAACTCCGA

TTGCGAAGGCAGCTTGCTGGACTGTAACTGACGCTGATGCTCGAAAGTGTGGGTATCAAACAGGATTAGATACCCT

GGTAGTCCACACAGTAAACGATGAATACTCGCTGTTTGCGATATACAGTAAGCGGCCAAGCGAAAGCGTTAAGTAT

TCCACCTGGGGAGTACGCCGGCAACGGTGAAACTCAAAGGAATTGACGGGGCCCGCACAAGCGGGAGGAACATGT

GGTTTAATTCGATGATACGCGAGGAACCTTACCCGGGCTTGAATTGCAACTGAATGATGTGGAGACATGTCAGCCG

CAAGCAGTTGTGAAGGTGCTGCATGGTTGTCGTCAGCTCGTGCCGTGAGGTGTCGGCTTAAGTGCCATAACGAGCG

CAACCCTATCGTAGTACCAT
```

>SEQ ID NO 14: *Coprococcus comes*; Strain 37
```
TGGCTGCGGCGTGCTTACCATGCAAGTCGAACGAAGCACTTATCTTTGATTCTTCGGATGAAGAGGTTTGTGACTG

AGTGGCGGACGGGTGAGTAACGCGTGGGTAACCTGCCTCATACAGGGGGATAACAGTTAGAAATGACTGCTAATAC

CGCATAAGACCACGGAGCCGCATGGCTCAGTGGGAAAAACTCCGGTGGTATGAGATGGACCCGCGTCTGATTAGGT

AGTTGGTGGGGTAACGGCCTACCAAGCCAACGATCAGTAGCCGACCTGAGAGGGTGACCGGCCACATTGGGACTGA

GACACGGCCCAAACTCCTACGGGAGGCAGCAGTGGGGAATATTGCACAATGGGGGAAACCCTGATGCAGCGACGCC

GCGTGAGCGAAGAAGTATTTCGGTATGTAAAGCTCTATCAGCAGGGAAGAAAATGACGGTACCTGACTAAGAAGCA

CCGGCTAAATACGTGCCAGCAGCCGCGGTAATACGTATGGTGCAAGCGTTATCCGGATTTACTGGGTGTAAAGGGA

GCGTAGACGGCTGTGTAAGTCTGAAGTGAAAGCCCGGGGCTCAACCCCGGGACTGCTTTGGAAACTATGCAGCTAG

AGTGTCGGAGAGGTAAGTGGAATTCCCAGTGTAGCGGTGAAATGCGTAGATATTGGGAGGAACACCAGTGGCGAAG

GCGGCTTACTGGACGATGACTGACGTTGAGGCTCGAAAGCGTGGGGAGCAAACAGGGATTAGATACCCTGGTAGTC
```

-continued
CACGCCGTAAACGATGACTACTAAGTGTCGGGGAGCAAAAGCTCTTCGGTGCCGCAGCAAACGCAATAAGTAGTCC

ACCTGGGGGAGTACGTCGCAAGAATGAAACTCAAAGGAATTGACCGGGGACCCGCACAACGGTGGAGCATGTGGTT

TAATTC

>SEQ ID NO 18: *Parabacteroides merdae*; Strain 41
TAGATTTACCTAGGCCGATCCTTGCGGTTACGGACTTCAGGTACCCCCGGCTCCCATGGCTTGACGGGCGGTGTGT

ACAAGGCCCGGGAACGTATTCACCGCGCCATGGCTGATGCGCGATTACTAGCGAATCCAGCTTCACGGAGTCGAGT

TGCAGACTCCGATCCGAACTGAGACATGGTTTGGAGATTAGCATCCTGTCACCAGGTAGCTGCCCTTTGTCCATGC

CATTGTAACACGTGTGTCGCCCCGGATGTAAGGGCCGTGCTGATTTGACGTCATCCCCACCTTCCTCACAGCTTAC

GCTGGCAGTCTCACCAGAGTCCTCAGCTTCACCTGTTAGTAACTAGTGATAAGGGTTGCGCTCGTTATGGCACTTA

AGCCGACACCTCACGGCACGAGCTGACGACAACCATGCAGCACCTCGTAATCTGCTATTGCTAGAAAGAGTGTTTC

CACTCCGGTCAGACTACGTTCAAACCCGGGTAAGGTTCCTCGCGTATCATCGAATTAAACCACATGTTCCTCCGCT

TGTGCGGGCCCCCGTCAATTCCTTTGAGTTTCACCGTTGCCGGCGTACTCCCCAGGTGGATTACTTAACGCTTTCG

CTGTAGAGCTTACATTGTATCGCAAACTCCTAGTAATCATCGTTTACTGCGTGGACTACCAGGGTATCTAATCCTG

TTTGATCCCCACGCTTTCGTGCTTCAGTGTCAGTTATGGTTTAGTAAGCTGCCTTCGCAATCGGAGTTCTGCGTGA

TATCTATGCATTTCACCGCTACACCACGCATTCCGCCTACCTCAAACACACTCAAGTAACCCAGTTTCAACGGCAA

TTTTATGGTTGAGCCACAAACTTTCACCGCTGACTTAAATCACCACCTACGCACCCTTTAAACCCAATAAATCCGG

ATAACGCTCGCATCCTCCGTATTACCGCGGCTGCTGGCACGGAGTTAGCCGATGCTTATTCATAGGGTACATACAA

AAAGACACGTCCTCCACTTTATTCCCCTTTA

>SEQ ID NO 3: *Bacteroides vulgatus*; Strain 28
ACAGGTTTTTTCCCTAAGGGCGCTCCTCGCGGTTACGCACTTCAGGTACCCCCGGCTCCCATGGCTTGACGGGCGG

TGTGTACAAGGCCCGGGAACGTATTCACCGCGCCGTGGCTGATGCGCGATTACTAGCGAATCCAGCTTCGTGGAGT

CGGGTTGCAGACTCCAGTCCGAACTGAGAGAGGTTTTTGGGATTGGCATCCACTCGCGTGGTAGCGGCCCTCTGTA

CCCCCCATTGTAACACGTGTGTAGCCCCGGACGTAAGGGCCGTGCTGATTTGACGTCATCCCCACCTTCCTCACAT

CTTACGATGGCAGTCTTGTCAGAGTCCTCAGCGGAACCTGTTAGTAACTGACAACAAGGGTTGCGCTCGTTATGGC

ACTTAAGCCGACACCTCACGGCACGAGCTGACGACAACCATGCAGCACCTTCACAGATGCCTTGCGGCTTACGGCT

TTCACCGTAATTCATCTGCAATTTAAGCCCGGGTAAGGTTCCTCGCGTATCATCGAATTAAACCACATGTTCCTCC

GCTTGTGCGGGCCCCCGTCAATTCCTTTGAGTTTCACCGTTGCCGGCGTACTCCCCAGGTGGAATACTTAACGCTT

TCGCTTGGCCGCTTGCTGTAATGCACAAACAGCGAGTATTCATCGTTTACCGTGTGGACTACCAGGGTATCTAAAT

CCTGTTTGATACCCACACTTTCGAGCCTCAATGTCAGTTGCAGCTTAGCAGGCTGCCTTTATTATCGGAGTTCTTC

GTGATATCT

>SEQ ID NO 15: *Dorea longicatena*; Strain 38
CGGATCGGTCACCTTCGGCAGCTCCCTCCTTACGGTTGGGTCACTGACTTCGGGCGTTACTGACTCCCATGGTGTG

ACGGGCGGTGTGTACAAGACCCGGGAACGTATTCACCGCAGCATTCTGATCTGCGATTACTAGCGATTCCAGCTTC

ATGTAGTCGAGTTGCAGACTACAATCCGAACTGAGACGTTATTTTTGAGATTTGCTTACCCTCGCGAGTTCGCTTC

TCTTTGTTTACGCCATTGTAGCACGTGTGTAGCCCTGGTCATAAGGGGCATGATGATTTGACGTCATCCCCACCTT

CCTCCAGGTTATCCCTGGCAGTCTCTCCAGAGTGCCCAGCTTAACCTGCTGGCTACTGAAGATAGGGGTTGCGCTC

GTTGCGGGACTTAACCCAACATCTCACGACACGAGCTGACGACAACCATGCACCACCTGTCACCGATGTTCCGAAG

AAAAGCTTCCATTACGAAGCGGTCATCGGGATGTCAAGATCAGGTAAGGTTCTTCGCGTTGCTTCGAATTAAACCA

CATGCTCCACCGCTTGTGCGGGTCCCCGTCAATTCCTTTGAGTTTCATTCTTGCGAACGTACTCCCCAGGTGGACT

GCTTATTGCGTTAGCTGCGGCACCGAATGGCTTTGCCACCCGACACCTAGCAGTCATCGTTTACGGCGTGGACTAC

CAGGGTATCTAATCCTGTTTGCTCCCCACGCTTTCGAGCCTCAACGTCAGTCATCGTCCAGCAAGCCGCCTTCGCC

ACTGGTGTTCCTCCTAATATCTACGCATTTCACCGCTACACTAGGAATTCCACTTGCCTCTCCGACACTCTAGCTC

```
AGCAGTTCCAAATGCAGTCCCGGGGTTGAGCCCCGGGCTTTCACATCTGGCTTGCCGTGCCGTCTACGCTCCCTTT

ACACCCAGTAAATCCCGGATAACGCTTGCCCCCTACGTATTACCGGCGGCTGCTGGCACGTAGTTAGCCCGGGGCT

TCTTAGTCAAGGTACCGTCAT

>SEQ ID NO 13: Collinsella aerofaciens; Strain 36
CCGTCAACCTTCGGCGCCTCCCCCCTCGCGGTTGGGCCGGCGACTTCGGGTGCAGACGACTCGGGTGGTGTGACGG

GCGGTGTGTACAAGGCCCGGGAACGCATTCACCGCGGCATGCTGATCCGCGATTACTAGCAACTCCGACTTCATGG

GGGCGGGTTGCAGCCCCAATCCGAACTGGGGCCGGCTTTCCGGGATCCGCTCCCCCTCGCGGGGTGGCATCCCTC

TGTACCGGCCATTGTAGCACGTGTGCAGCCCAGGGCATAAGGGGCATGATGACTTGACGTCGTCCCCGCCCTCCTC

CGCCTTGACGGCGGCGGTCCCGCGTGGGTTCCCGGCATCACCCGATGGCAACACGCGGCGGGGGTTGCGCTCGTTG

CGGGACTTAACCCAACATCTCACGACACGAGCTGACGACAGCCATGCACCACCTGTATGGGCTCCTCTCGGCCACG

GGGTCTCCCCCGCTTCACCCATATGTCAAGCCCTGGTAAGGTTCTTCGCGTTGCTTCGAATTAAGCCACATGCTCC

GCTGCTTGTGCGGGCCCCCGTCAATTCCTTTGAGTTTTAGCCTTGCGGCCGTACTCCCCAGGCGGGACGCTTAATG

CGTTGGCTGCGGCACGGGGGATCGTCCCCCCACACCTAGCGTCCATCGTTTACGGCTGGGACTACCAGGGTATCT

AATCCTGTTCGCTCCCCAGCTTTCGCGCCTCAGCGTCGGTCTCGGCCCAGAGGGCCGCCTTCGCCACCGGTGTTC

CACCCGATATCTGCGCATTCCACCGCTACACCGGGTGTTCCACCCTCCCCTACCGGACCCAAGCCGCGGAGGTTCC

GGGGGCTTCGGGGGGTTGAGCCCCCGCTTCGACCCCGGCCTGCCGGGCCGCCTACGCGCGCTTTACGCCCAATGA

ATCCGGATAACGCTCGCCCCCTACGTATTACGCGGCTGCTGGCACGTAGTTAGCCGGGGCTTCTTCTGCAGGTACA

GTCTTGACTCTTCCCTGCTGAAAGCGGTTTACGA

>SEQ ID NO 19: Parabacteroides distasonis; Strain 42
TCAGCATGACCTAGGCCGATCCTCGCGGTTACGGACTTCAGGTACCCCCGGCTCCCATGGCTTGACGGGCGGTGTG

TACAAGGCCCGGGAACGTATTCACCGCGCCATGGCTGATGCGCGATTACTAGCGAATCCAGCTTCACGGAGTCGGG

TTGCAGACTCCGATCCGAACTGAGACGTGGTTTGGGGATTCGCTCCCTGTCGCCAGGTGGCTTCCCTTTGTCCACG

CCATTGTAACACGTGTGTCGCCCCGGATGTAAGGGCCGTGCTGATTTGACGTCATCCCCGCCTTCCTCGCAGCTTA

CGCTGGCAGTCCCACCAGAGTCCTCAGCATCACCTGTTAGTAACTAGTGGCAAGGGTTGCGCTCGTTATGGCACTT

AAGCCGACACCTCACGGCACGAGCTGACGACAACCATGCAGCACCTCGCAAACGGCTATTGCTAGAAGAGGTGTTT

CCACCTCGGTCCGAATGCGTTCAAACCCGGGTAAGGTTCCTCGCGTATCATCGAATTAAACCACATGTTCCTCCGC

TTGTGCGGGCCCCCGTCAATTCCTTTGAGTTTCACCGTTGCCGGCGTACTCCCCAGGTGGATCACTTAACGCTTTC

GCTGTGCCGCTTACACTGTATCGCAAACAGCTAGTGATCATCGTTTACTGCGTGGACTACCAGGGTATCTAATCCT

GTTTGATCCCCACGCTTTCGTGCATCAGCGTCAGTCATGGCTTGGCAGGCTGCCTTCGCAATCGGGGTTCTGCGTG

ATATCTAAGCATTTCACCGCTACACCACGCATTCCGCCTGCCTCAAACATACTCAAGCCTCCCAGTTTCAACGGCA

ATTCTATGGTTGAGCCACAGACTTTCACCGCTGACTTAAAAGGCCGCCTACGCACCCTTTAAACCCAATAAATCCG

GATAACGCTCGGATCCTCCGTATTACCGCGGCTGCTGGCACGGAGTTAGCCGATCCTTATTCATAAGGTACATACA

AAACAGGAAACGTCCACAACTTTATTCCCTTATAAAGAGGTTTACGAT

>SEQ ID NO 20: Prevotella copri; Strain 43
CTTAGCTTTCGCCTAGGCCGCTCCTTACGGTCACGGACTTTAGGCGCCCCGGCTTTCATGGCTTGACGGGCGGTG

TGTACAAGGCCCGGGAACGTATTCACCGCGCCATGGCTGATGCGCGATTACTAGCGAATCCAGCTTCGTGGGTCG

GGTTGCAGACCCCAGTCCGAACTGAGACAGGCTTTAAGGATTTGATCCTTTTTGCAAGGGACCGTCTCTCTGTACC

TGCCATTGTAACACGTGTGTAGCCCCGGACGTAAGGGCCGTGCTGATTTGACGTCATCCCCACCTTCCTCACACCT

TACGGTGGCAGTGTCCCCAGAGTGCCCAGCTTAACCTGATGGCAACTAAGGAGAGGGGTTGCGCTCGTTATGGCAC

TTAAGCCGACACCTCACGGCACGAGCTGACGACAACCATGCAGCACCTTCACAGAGGCCCCGAAGGGCGTCATTGT

CTCCAAATCCTTCCTCTGCAATTCAAGCCCGGGTAAGGTTCCTCGCGTATCATCGAATTAAACCACATGTTCCTCC

GCTTGTGCGGGCCCCCGTCAATTCCTTTGAGTTTCACCGTTGCCGGCGTACTCCCCAGGTGGGATGCTTAATGCTT
```

-continued

TCGCTTGGCCGCTGACCTATTCAGACCAACAGCGGGCATCCATCGTTTACCGTGCGGACTACCAGGGTATCTAATC

CTGTTCGATACCCGCACTTTCGAGCTTCAGCGTCAGTTGCGCTCCAGTGAGCTGCCTTCGCAATCGGAGTTCTTCG

TGATATCTAAGCATTTCACCGCTACACCACGAATTCCGCCCACTTTGTGCGTACTCAAGGAAACCAGTTCGCGCTG

CAGTGCAACGTTGAGCGTCTAATTTCACAACACGCTTAATCTCCGGCTACGCTCCCTTTAACCAAAAAAACCAGAT

AACGCCGGACCTCCGTATTACCGCGGCTGCTGGCCGGAATTAGCCGGCCCTATCATAAGGTACATGCAAAAAGCTA

CCAAACTCACTTTTTCCCTTTACAAGAGTTACAACCATAGGCC

>SEQ ID NO 1: *Alistipes putredinis*; Strain 26
GCTCAGCTTGCCTAGGTCGCTCCTTGCGGTCACGAACTTCAGGCACCCCCGGCTCCCATGGCTTGACGGGCGGTGT

GTACAAGGCCCGGGAACGTATTCACCGCGCCATGGCTGATGCGCGATTACTAGCGAATCCAACTTCATGGAGGCGG

GTTTCAGCCTCCAATCCGAACTGAGATAGGCTTTCGAGATTCGCATCCCATCGCTGGGTAGCTGCCCTCTGTACCT

ACCATTGTAACACGTGTGTAGCCCCGGACGTAAGGGCCGTGCTGATTTGACGTCATCCCCACCTTCCTCTCGGCTT

ACACCGGCAGTCCCGCCAGAGTGCCCAGCTTCACCTGATGGCAACTAACGGTAGGGGTTGCGCTCGTTATGGGACT

TAACCCGACACCTCACGGCACGAGCTGACGACAACCATGCAGCACCTAGTTTCGCGCCCCGAAGGGAAATCCTCTT

TCAAGAATCGTCGCTAACTTTCAAGCCCGGGTAAGGTTCCTCGCGTATCATCGAATTAAACCACATGTTCCTCCGC

TTGTGCGGGCCCCCGTCAATTCCTTTGAGTTTCATTCTTGCAACGTACTCCCCAGGTGGATAACTTATCGCTTTC

GCTTAGTCACCGACTGTGTATCGCCGACAACGAGTTATCATCGTTTACTGCGTGGACTACCAGGGTATCTAATCCT

GTTTGCTCCCCACGCTTTCGTGCCTCAACGTCAGATATAGTTTGGTAAGCTGCCTTCGCAATCGGTGTTCTGTATG

ATCTCTAAGCATTTCACCGCTACACCATACATTCCGCCTACCGCAACTACTCTAGCTCAACAGTATTAGAGGCA

CGTTCAGGGTTGAGCCCCGAAATTTCACCTCTAACTTATCAAACCGCCTACGCACCCTTTAAACCCAATAAATCCG

GATAACGCTTGAATCCTCCGTATTACCGCGGCTGCTGGCACGGAGTTAGCCGATCCTTATTCGTACGATACTTTCA

GACAGATACACGTATCTGCGTTTACCCTCGTACA

>SEQ ID NO 16: *Eubacterium halli*; Strain 39
TCGGCTCCCTTCGAAGCTCCCTCCATAAAGGTTGGGTCACTGGCTTCGGGCATTTCCAACTCCCATGGTGTGACGG

GCGGTGTGTACAAAACCCGGGAACGTATTCACCGCGACATTCTGATTCGCGATTACTAGCGATTCCAGCTTCGTGT

AGTCGGGTTGCAAACTACAGTCCAAACTGGGACGGCCTTTTTGTGGTTTGCTCCCCCTCGCGGGTTTGCCTCACTC

TGTGACCGCCATTGTAGCACGTGTGTCGCCCAAATCATAAGGGGCATGATGATTTGACGTCGTCCCCACCTTCCTC

CAGGTTATCCCTGGCAGTCTCTCCAAAGTGCCCAGCCTTACCTGCTGGCTACTGAAAATAGGGGTTGCGCTCGTTG

CGGGACTTAACCCAACATCTCACAACACAAGCTGACAACAACCATGCACCACCTGTCTCTTCTGTCCCGAAGGAAA

ACTCCCATTACGGAGTGGTCAAAGGATGTCAAGACCTGGTAAGGTTCTTCGCGTTGCTTCAAATTAAACCACATG

CTCCACCGCTTGTGCGGGTCCCCGTCAATTCCTTTGAGTTTCATTCTTGCAAACGTACTCCCCAGGTGGAATACTT

ACTGCGTTAGCGGCGGCACCGAAGCCTATACGGCCCCGACACCTAGTATTCATCGTTTACGGCGTGGACTACCAGG

GTATCTAATCCTGTTTGCTCCCCACGCTTTCGTGCCTCAGTGTCAGTAACAGTCCAGCAGGCCGCCTTCGCCACTG

GTGTTCCTCCTAATATCTACGCATTTCACCGCTACACTAGGAATTCCGCCTGCTTCTCCTGTACTCTAGCTAAGCA

GTTTCAAATGCAGCTCCGGGGTTGAGCCCGGGCTTTCACATCTGACTTGCACTGCCACCTACGCACCCTTTACACC

AATAAATCCGGATAACGCTTGCTCCATACGTATTACCGCGGCTGCTGGCACGTATTAGCCCGGAGCTTCTAATCAG

GTACCGGCATTATCTCCCTGCTGATAGA

>SEQ ID NO 17: *Faecalibacterium prausnitzii*; Strain 40
TGGGCTGGCGGCGCGCTACACATGCAGTCGAACGAGCGAGAGAGAGCTTGCTTTCTCGAGCGAGTGGCGAACGGGT

GAGTAACGCGTGAGGAACCTGCCTCAAAGAGGGGGACAACAGTTGGAAACGACTGCTAATACCGCATAAGCCCACG

ACCCGGCATCGGGTAGAGGGAAAAGGAGCAATCCGCTTTGAGATGGCCTCGCGTCCGATTAGCTAGTTGGTGAGGT

AATGGCCCACCAAGGCGACGATCGGTAGCCGGACTGAGAGGTTGAACGGCCACATTGGGACTGAGACACGGCCCAG

ACTCCTACGGGAGGCAGCAGTGGGGAATATTGCACAATGGGGGAAACCCTGATGCAGCGACGCCGCGTGGAGGAAG

-continued

AAGGTCTTCGGATTGTAAACTCCTGTTGTTGAGGAAGATAATGACGGTACTCAACAAGGAAGTGACGGCTAACTAC

GTGCCAGCAGCCGCGGTAAAACGTAGGTCACAAGCGTTGTCCGGAATTACTGGGTGTAAAGGGAGCGCAGGCGGGA

AGACAAGTTGGAAGTGAAATCCATGGGCTCAACCCATGAACTGCTTTCAAAACTGTTTTTCTTGAGTAGTGCAGAG

GTAGGCGGAATTCCCGGTGTAGCGGTGGAATGCGTAGATATCGGGAGGAACACCAGTGGCGAAGGCGGCCTACTGG

GCACCAACTGACGCTGAGGCTCGAAAGTGTGGGTAGCAAACAGGATTAGATACCCTGGTAGTCCACACTGTAAACG

ATGATTACTAGGTGTTGGAGGATTGACCCCTTCAGTGCCGCAGTTAACACAATAAGTAATCCACCTGGGGAGTACG

ACCGCAAGGTTGAAACTCAAAGGAATTGACGGGGGCCCGCACAAGCAGTGGAGTATGTGGTTTAATTCGACGCAAC

GCGAAGAACCTTACCAAGTCTTGACATCCTTGTGACGATGCTAGAAATAGTATTTTTCTTCTGAACACAGAGACAG

GTGGTGCATGGTTGTCGTCAGCTCGTGTCGTGAGATGTTGGGTTAAGTCCCGCAACGAGCGCCAACCCTTATGGTC

AGTTACTACCGCA

>SEQ ID NO 7: *Blautia obeum*; Strain 37
CCAAAAAGCGCGGCGGCGTGCTTACCATGCAGTCGAACGGGAAACTTTTATTGAAGCTTCGGCAGATTTGGTTGGT

TTCTAGTGGCGGACGGGTGAGTAACGCGTGGGTAACCTGCCTTATACAGGGGGATAACAACCAGAAATGGTTGCTA

ATACCGCATAAGCGCACAGGACCGCATGGTCCGGTGTGAAAAACTCCGGTGGTATAAGATGGACCCGCGTTGGATT

AGCTAGTTGGCAGGGTAACGGCCTACCAAGGCGACGATCCATAGCCGGCCTGAGAGGGTGAACGGCCACATTGGGA

CTGAGACACGGCCCAGACTCCTACGGGAGGCAGCAGTGGGGAATATTGCACAATGGGGGAAACCCTGATGCAGCGA

CGCCGCGTGAAGGAAGAAGTATCTCGGTATGTAAACTTCTATCAGCAGGGAAGATAGTGACGGTACCTGACTAAGA

AGCCCCGGCTAACTACGTGCCAGCAGCCGCGGTAATACGTAGGGGGCAAGCGTTATCCGGATTTACTGGGTGTAAA

GGGAGCGTAGACGGACTGGCAAGTCTGATGTGAAAGGCGGGGGCTCAACCCCTGGACTGCATTGGAAACTGTTAGT

CTTGAGTGCCGGAGAGGTAAGCGGAATTCCTAGTGTAGCGGTGAAATGCGTAGATATTAGGAGGAACACCAGTGGC

GAAGGCGGCTTACTGGACGGTAACTGACGTTGAGGCTCGAAAGCGTGGGGAGCAAACAGGATTAGATACCCTG

>SEQ ID NO 12: *Parabacteroides distasonis*; Strain 35
TCGGGTTTTTTCCTAGGCCGATCCTTTCGGTTACTGACTTCAGGTACCCCCGGCTCCCATGGCTTGACGGGCGGTG

TGTACAAGGCCCGGGAACGTATTCACCGCGCCATGGCTGATGCGCGATTACTAGCGAATCCAGCTTCACGGAGTCG

GGTTGCAGACTCCGATCCTAACTGAGACGTGGTTTGGGGATTCGCTCCCTGTCGCCAGGTGGCCTCCCTTTGTCCA

CGCCATTGTAACACGTGTGTCGCCCCGGATGTAAGGGCCGTGCTGATTTGACGTCATCCCCGCCTTCCTCGCAGCT

TACGCTGGCAGTCCCACCAGAGTCCTCAGCTTTACCTGTTAGTAACTAGTGGCATGGGTTGCGCTCGTTATGGCAC

TTAAGCCGACACCTCACGGCACGAGCTGACAACAACCATGCACCACCTCGCAAACGGCTATTGCTAAAAAAGGTGT

TTCCACCTCGGTCCTAATGCTTTCAAACCCGGGTAAGGTTCCTCGCGTATCATCGAATTAAACCACATGTTCCTCC

GCTTGTGCTGGCCCCCGTCATTCCTTTGAGTTTCACCGTTGCCGGCGTACTCCCCAGGTGGATCACATAACGCTTT

CCCTGAGCCGCTTACTGTGTATCGTACACACCTAGTGATCATCTTTTACTGCGTGGACTAACAGGGTATCCTAATC

CTGTTTGATCCCCACGCTTTCGTGCATCACGTCAGTCATGGCTTGTGAGCTGCCTTCGCAAACTGGGTTCTGCAAG

A

>SEQ ID NO 11: *Clostridium bolteae*; Strain 34
GGGCGGGCGGCGTGCTACCATGCAAGTCGAACGAAGCAATTAAATGAAGTTTTCGGATGGAATTTGATTGACTGAG

TGGCGGACGGGTGAGTAACGCGTGGATAACCTGCCTCACACTGGGGGATAACAGTTAGAAATGACTGCTAATACCG

CATAAGCGCACAGTACCGCATGGTACGGTGTGAAAAACTCCGGTGGTGTGAGATGGATCCGCGTCTGATTAGCCAG

TTGGCGGGGTAACGGCCCACCAAAGCGACGATCAGTAGCCGACCTGAGAGGGTGACCGGCCACATTGGGACTGAGA

CACGGCCCAAACTCCTACGGGAGGCAGCAGTGGGGAATATTGCACAATGGGCGAAAGCCTGATGCAGCGACGCCGC

GTGAGTGAAGAAGTATTTCGGTATGTAAAGCTCTATCAGCAGGGAAGAAAATGACGGTACCTGACTAAGAAGCCCC

GGCTAACTACGTGCCAGCAGCCGCGGTAATACGTAGGGGGCAAGCGTTATCCGGATTTACTGGGTGTAAAGGGAGC

GTAGACGGCGAAGCAAGTCTGAAGTGAAAACCCAGGGCTCAACCCTGGGACTGCTTTGGAAACTGTTTTGCTAGAG

-continued

```
TGTCGGAGAGGTAAGTGGAATTCCTAGTGTAGCGGTGAAATGCGTAGATATTAGGAGGAACACCAGTGGCGAAGGC
GGCTTACTGGACGATAACTGACGTTGAGGCTCGAAAGCGTGGGGAGCAAACAGGATTAGATACCCTGGTAGTCCAC
GCCGTAAACGATGAATGCTAGGTGTTGGGGGGCAAAGCCCTTCGGTGCCGTCGCAAACGCAGTAAGCATTCCACCT
GGGGAGTACGTTCGCAAGAATGAAACTCAAGGAATTGACGGGGACCCGCACAAGCGGTGGAGCATGTGGTTTAATT
CGAAGCAACGCGAAGAACTTACCAAGTCTTGACATCCTCTTGACCGGCGTGTAACGGCGCCTTCTCTTCTGGGCAA
GAGAGACAGTGGTGCATGGTTGTCGTCAGCTCGTGTCGTGAGATGTTGGGTTAAGTCCCGCACGAGCGCAACCCTT
TTCCTTATATCACAGGTGAGCTGGGCCCTCTAGGAGACTGCCAGGATACTGAGGAA
```

>SEQ ID NO 4: Parabacteroides merdae; Strain 29

```
GTGCTCAGCTTTTACCCTAGGCCGATCCTTGCGGTTACGGACTTCAGGTACCCCCGGCTCCCATGGCTTGACGGGC
GGTGTGTACAAGGCCCGGGAACGTATTCACCGCGCCATGGCTGATGCGCGATTACTAGCGAATCCAGCTTCACGGA
GTCGAGTTGCAGACTCCGATCCGAACTGAGACATGGTTTGGAGATTAGCATCCTGTCGCCAGGTAGCTGCCCTTTG
TCCATGCCATTGTAACACGTGTGTCGCCCCGGATGTAAGGGCCGTGCTGATTTGACGTCATCCCCACCTTCCTCAC
AGCTTACGCTGGCAGTCTCACCAGAGTCCTCAGCTTCACCTGTTAGTAACTAGTGATAAGGGTTGCGCTCGTTATG
GCACTTAAGCCGACACCTCACGGCACGAGCTGACGACAACCATGCAGCACCTCGTAATCTGCTATTGCTAGAAGGA
GTGTTTCCACTCCGGTCAGACTACGTTCAAACCCGGGTAAGGTTCCTCGCGTATCATCGAATTAAACCACATGTTC
CTCCGCTTGTGCGGGCCCCCGTCAATTCCTTTGAGTTTCACCGTTGCCGGCGTACTCCCCAGGTGGATTACTTAAC
GCTTTCGCTGTAGAGCTTACATTGTATCGCAAACTCCTAGTAATCATCGTTTACTGCGTGGACTACCAGGGTATCT
AATCCTGTTTGATCCCCACGCTTTCGTGCTTCAGTGTCAGTTATGGTTTAGTAAGCTGCCTTCGCAATCGGAGTTC
TGCGTGATATCTATGCATTTCACCGCTACACCACGCATTCCGCCTACCTCAAACACACTCAAGTAACCCAGTTTCA
ACGGCAATTTTATGGTTGAGCCACAAACTTTCACCGCTGACTTAAATCACCACCTACGCACCCTTTAACCCAATAA
ATCCGATAACGCTCGCATCCTCCGTATTACCGCGGCTGCTGCCCGGAGTTAGCCGATGCTTATTCATAGGGTACAT
ACAAAAAGGACACGT
```

>SEQ ID NO 21: Roseburia faecis; Strain 44

```
GGGGCTGGGCGGCGTGCTTACCATGCAAGTCGAACGAAGCACTCTATTTGATTTTCTTCGGAAATGAAGATTTTGT
GACTGAGTGGCGGACGGGTGAGTAACGCGTGGGTAACCTGCCTCATACAGGGGGATAACAGTTGGAAACGACTGCT
AATACCGCATAAGCGCACAGGATCGCATGATCCGGTGTGAAAAACTCCGGTGGTATGAGATGGACCCGCGTCTGAT
TAGCCAGTTGGCAGGGTAACGGCCTACCAAAGCGACGATCAGTAGCCGACCTGAGAGGGTGACCGGCCACATTGGG
ACTGAGACACGGCCCAAACTCCTACGGGAGGCAGCAGTGGGGAATATTGCACAATGGGGGAAACCCTGATGCAGCG
ACGCCGCGTGAGCGAAGAAGTATTTCGGTATGTAAAGCTCTATCAGCAGGGAAGAAGAATGACGGTACCTGACTAA
GAAGCACCGGCTAAATACGTGCCAGCAGCCGCGGTAATACGTATGGTGCAAGCGTTATCCGGATTTACTGGGTGTA
AAGGGAGCGCAGGCGGTGCGGCAAGTCTGATGTGAAAGCCCGGGGCTCAACCCCGGTACTGCATTGGAAACTGTCG
TACTAGAGTGTCGGAGGGGTAAGTGGAATTCCTAGTGTAGCGGTGAAATGCGTAGATATTAGGAGGAACACCAGTG
GCGAAGGCGGCTTACTGGACGATAACTGACGCTGAGGCTCGAAAGCGTGGGGAGCAAACAGGATTAGATACCCTGG
TAGTCCACGCCGTAAACGATGAATACTAGGTGTCGGGGAGCATTGCTCTTCGGTGCCGCAGCAAACGCAATAAGTA
TTCCACCTGGGGAGTACGTTCGCAAGAATGAAACTCAAAGGAATTGACGGGACCCGCACAGCGGTGGAGCATGTG
GTTTATTCGAAGCAACGCGAAGAACCTTACCAAGTCTTGACATCCCGATGACAGAGTATGTAATGTACTTTCTCTT
CGAGCATCGGTGACAGTGGGTGCATGGTTGTCGTCACTCGTGTCGTGAGATGTTGGGTTAAGTCCGCAACGAGCGC
AACCCCTGTCCTTAGTAGCAGCGGTG
```

>SEQ ID NO: 9: Blautia producta/Blautia coccoides; Strain 2

```
AGAGTTTGATCCTGGCTCAGGATGAACGCTGGCGGCGTGCTTAACACATGCAAGTCGAGCGAAGCATTAAGACAGA
TTTCTTCGGATTGAAGTCTTTGTGACTGAGCGGCGGACGGGTGAGTAACGCGTGGGTAACCTGCCTCATACAGGGG
GATAACAGTTAGAAATGACTGCTAATACCGCATAAGCGCACAGGAcCGCATGGTCTGGTGTGAAAAACTCCGGTGG
```

TATGAGATGGACCCGCGTCTGATTAGCTAGTTGGAGGGGTAACGGCCCACCAAGGCGACGATCAGTAGCCGGCCTG
AGAGGGTGAACGGCCACATTGGGACTGAGACACGGCCCAGACTCCTACGGGAGGCAGCAGTGGGGAATATTGCACA
ATGGGGGAAACCCTGATGCAGCGACGCCGCGTGAAGGAAGAAGTATCTCGGTATGTAAACTTCTATCAGCAGGGAA
GAAAATGACGGTACCTGACTAAGAAGCCCCGGCTAACTACGTGCCAGCAGCCGCGGTAATACGTAGGGGGCAAGCG
TTATCCGGATTTACTGGGTGTAAAGGGAGCGTAGACGGAAGAGCAAGTCTGATGTGAAAGGCTGGGGCTTAACCCC
AGGACTGCATTGGAAACTGTTGTTCTAGAGTGCCGGAGAGGTAAGCGGAATTCCTAGTGTAGCGGTGAAATGCGTA
GATATTAGGAGGAACACCAGTGGCGAAGGCGGCTTACTGGACGGTAACTGACGTTGAGGCTCGAAAGCGTGGGGAG
CAAACAGGATTAGATACCCTGGTAGTCCACGCCGTAAACGATGAATACTAGGTGTCGGGTGGCAAAGCCATTCGGT
GCCGCAGCAAACGCAATAAGTATTCCACCTGGGGAGTACGTTCGCAAGAATGAAACTCAAAGGAATTGACGGGGAC
CCGCACAAGCGGTGGAGCATGTGGTTTAATTCGAAGCAACGCGAAGAACCTTACCAAGTCTTGACATCCCTCTGAC
CGTCCCGTAAtGGGGgCTTCCCTTCGGGGCAGAGGAGACAGGTGGTGCATGGTTGTCGTCAGCTCGTGTCGTGAGA
TGTTGGGTTAAGTCCCGCAACGAGCGCAACCCTTATCCTTAGTAGCCAGCACATGATGGTGGGCACTCTAGGGAGA
CTGCCGGGGATAACCCGGAGGAAGGCGGGGACGACGTCAAATCATCATGCCCCTTATGATTTGGGCTACACACGTG
CTACAATGGCGTAAACAAAGGGAAGCGAGACAGCGATGTTGAGCGAATCCCAAAAATAACGTCCCAGTTCGGACTG
CAGTCTGCAACTCGACTGCACGAAGCTGGAATCGCTAGTAATCGCGGATCAGAATGCCGCGGTGAATACGTTCCCG
GGTCTTGTACACACCGCCCGTCACACCATGGGAGTCAGTAACGCCCGAAGTCAGTGACCTAACCGAAAGGAAGGAG
CTGCCGAAGGCGGGACCGATAACTGGGGTGAAGTCGTAACAAGGTAGCCGTATCGGAAGGTGCGGCTGGATCACCT
CCTTTCTAAGGAAGAAGAAGTAGAGAAAAGTGTTTCACTGTTGAGTTACCAAGA

SEQ ID NO: 10: *Clostridium hathewayi/Hungatella effluvii* strain UB-B.2; Strain 20
ATGAGAGTTCGATCCTGGCTCAGGATGAACGCTGGCGGCGTGCTTAACACATGCAAGTCGAGCGAAGCGGTTTCGA
TGAAGTTTTCGGATGGATTTGAAATCGACTTAGCGGCGGACGGGTGAGTAACGCGTGGGTAACCTGCCTTACACTG
GGGGATAACAGTTAGAAATGACTGCTAATACCGCATAAGCGCACAGGGCCGCATGGTCTGGTGCGAAAAACTCCGG
TGGTGTAAGATGGACCCGCGTCTGATTAGGTAGTTGGTGGGGTAACGGCCCACCAAGCCGACGATCAGTAGCCGAC
CTGAGAGGGTGACCGGCCACATTGGGACTGAGACACGGCCCAAACTCCTACGGGAGGCAGCAGTGGGGAATATTGG
ACAATGGGCGAAAGCCTGATCCAGCGACGCCGCGTGAGTGAAGAAGTATTTCGGTATGTAAAGCTCTATCAGCAGG
GAAGAAAATGACGGTACCTGACTAAGAAGCCCCGGCTAACTACGTGCCAGCAGCCGCGGTAATACGTAGGGGGCAA
GCGTTATCCGGATTTACTGGGTGTAAAGGGAGCGTAGACGGTTAAGCAAGTCTGAAGTGAAAGCCCGGGGCTCAAC
CCCGGTACTGCTTTGGAAACTGTTTGACTTGAGTGCAGGAGAGGTAAGTGGAATTCCTAGTGTAGCGGTGAAATGC
GTAGATATTAGGAGGAACACCAGTGGCGAAGGCGGCTTACTGGACTGTAACTGACGTTGAGGCTCGAAAGCGTGGG
GAGCAAACAGGATTAGATACCCTGGTAGTCCACGCCGTAAACGATGAATACTAGGTGTCGGGGGACAACGTCCTTC
GGTGCCGCCGCTAACGCAATAAGTATTCCACCTGGGGAGTACGTTCGCAAGAATGAAACTCAAAGGAATTGACGGG
GACCCGCACAAGCGGTGGAGCATGTGGTTTAATTCGAAGCAACGCGAAGAACCTTACCAAGTCTTGACATCCCATT
GAAAATCATTTAACCGTGATCCCTCTTCGGAGCAATGGAGACAGGTGGTGCATGGTTGTCGTCAGCTCGTGTCGTG
AGATGTTGGGTTAAGTCCCGCAACGAGCGCAACCCTTATCCTTAGTAGCCAGCACATGATGGTGGGCACTCTGGGG
AGACTGCCAGGGATAACCTGGAGGAAGGTGGGGATGACGTCAAATCATCATGCCCCTTATGATTTGGGCTACACAC
GTGCTACAATGGCGTAAACAAAGGGAAGCAAGGAGCGATCTGGAGCAAACCCCAAAAATAACGTCTCAGTTCGGA
TTGCAGGCTGCAACTCGCCTGCATGAAGCTGGAATCGCTAGTAATCGCGAATCAGAATGTCGCGGTGAATACGTTC
CCGGGTCTTGTACACACCGCCCGTCACACCATGGGAGTTGGTAACGCCCGAAGTCAGTGACCCAACCGTAAGGAGG
GAGCTGCCGAAGGCGGGACTGATAACTGGGGTGAAGTCGTAACAAGGTAGCCGTATCGGAAGGTGCGGCTGGATCA
CCTCCTTT SEQ ID NO: 23 *Flavonifractor plautii* Strain 1
TATTGAGAGTTTGATCCTGGCTCAGGATGAACGCTGGCGGCGTGCTTAACACATGCAAGTCGAACGGGGTGCTCAT

GACGGAGGATTCGTCCAACGGATTGAGTTACCTAGTGGCGGACGGGTGAGTAACGCGTGAGGAACCTGCCTTGGAG

AGGGGAATAACACTCCGAAAGGAGTGCTAATACCGCATGATGCAGTTGGGTCGCATGGCTCTGACTGCCAAAGATT

TATCGCTCTGAGATGGCCTCGCGTCTGATTAGCTAGTAGGCGGGGTAACGGCCCACCTAGGCGACGATCAGTAGCC

GGACTGAGAGGTTGACCGGCCACATTGGGACTGAGACACGGCCCAGACTCCTACGGGAGGCAGCAGTGGGGAATAT

TGGGCAATGGGCGCAAGCCTGACCCAGCAACGCCGCGTGAAGGAAGAAGGCTTTCGGGTTGTAAACTTCTTTTGTC

GGGGACGAAACAAATGACGGTACCCGACGAATAAGCCACGGCTAACTACGTGCCAGCAGCCGCGGTAATACGTAGG

TGGCAAGCGTTATCCGGATTTACTGGGTGTAAAGGGCGTGTAGGCGGGATTGCAAGTCAGATGTGAAAACTGGGGG

CTCAACCTCCAGCCTGCATTTGAAACTGTAGTTCTTGAGTGCTGGAGAGGCAATCGGAATTCCGTGTGTAGCGGTG

AAATGCGTAGATATACGGAGGAACACCAGTGGCGAAGGCGGATTGCTGGACAGTAACTGACGCTGAGGCGCGAAAG

CGTGGGGAGCAAACAGGATTAGATACCCTGGTAGTCCACGCCGTAAACGATGGATACTAGGTGTGGGGGGTCTGAC

CCCCTCCGTGCCGCAGTTAACACAATAAGTATCCCACCTGGGGAGTACGATCGCAAGGTTGAAACTCAAAGGAATT

GACGGGGGCCCGCACAAGCGGTGGAGTATGTGGTTTAATTCGAAGCAACGCGAAGAACCTTACCAGGGCTTGACAT

CCCACTAACGAAGCAGAGATGCATTAGGTGCCCTTCGGGGAAAGTGGAGACAGGTGGTGCATGGTTGTCGTCAGCT

CGTGTCGTGAGATGTTGGGTTAAGTCCCGCAACGAGCGCAACCCTTATTGTTAGTTGCTACGCAAGAGCACTCTAG

CGAGACTGCCGTTGACAAAACGGAGGAAGGTGGGGACGACGTCAAATCATCATGCCCCTTATGTCCTGGGCCACAC

ACGTACTACAATGGTGGTTAACAGAGGGAGGCAATACCGCGAGGTGGAGCAAATCCCTAAAAGCCATCCCAGTTCG

GATTGCAGGCTGAAACCCGCCTGTATGAAGTTGGAATCGCTAGTAATCGCGGATCAGCATGCCGCGGTGAATACGT

TCCCGGGCCTTGTACACACCGCCCGTCACACCATGAGAGTCGGGAACACCCGAAGTCCGTAGCCTAACCGCAAGGA

GGGCGCGGCCGAAGGTGGGTTCGATAATTGGGGTGAAGTCGTAACAAGGTAGCCGTATCGGAAGGTGCGGCTGGAT

CACCTCCTTT

SEQ ID NO: 24 *Blautia producta*-2 Strain 3
TCAGAGAGTTTGATCCTGGCTCAGGATGAACGCTGGCGGCGTGCTTAACACATGCAAGTCGAGCGAAGCACTAAGA

CAGATTTCTTCGGATTGAAGTCTTTGTGACTGAGCGGCGGACGGGTGAGTAACGCGTGGGTAACCTGCCTCATACA

GGGGGATAACAGTTAGAAATGACTGCTAATACCGCATAAGCGCACAGGACCGCATGGTCTGGTGTGAAAAACTCCG

GTGGTATGAGATGGACCCGCGTCTGATTAGCTAGTTGGAGGGGTAACGGCCCACCAAGGCGACGATCAGTAGCCGG

CCTGAGAGGGTGAACGGCCACATTGGGACTGAGACACGGCCCAGACTCCTACGGGAGGCAGCAGTGGGGAATATTG

CACAATGGGGGAAACCCTGATGCAGCGACGCCGCGTGAAGGAAGAAGTATCTCGGTATGTAAACTTCTATCAGCAG

GGAAGAAAATGACGGTACCTGACTAAGAAGCCCCGGCTAACTACGTGCCAGCAGCCGCGGTAATACGTAGGGGGCA

AGCGTTATCCGGATTTACTGGGTGTAAAGGGAGCGTAGACGGAATAGCAAGTCTGATGTGAAAGGCTGGGGCTTAA

CCCCAGGACTGCATTGGAAACTGTTGTTCTAGAGTGCCGGAGAGGTAAGCGGAATTCCTAGTGTAGCGGTGAAATG

CGTAGATATTAGGAGGAACACCAGTGGCGAAGGCGGCTTACTGGACGGTAACTGACGTTGAGGCTCGAAAGCGTGG

GGAGCAAACAGGATTAGATACCCTGGTAGTCCACGCCGTAAACGATGAATACTAGGTGTCGGGTGGCAAAGCCATT

CGGTGCCGCAGCAAACGCAATAAGTATTCCACCTGGGGAGTACGTTCGCAAGAATGAAACTCAAAGGAATTGACGG

GGACCCGCACAAGCGGTGGAGCATGTGGTTTAATTCGAAGCAACGCGAAGAACCTTACCAAGTCTTGACATCCCTC

TGACCGTCCCGTAACGGGACTTCCCTTCGGGGCAGAGGAGACAGGTGGTGCATGGTTGTCGTCAGCTCGTGTCGT

GAGATGTTGGGTTAAGTCCCGCAACGAGCGCAACCCTTATCCTTAGTAGCCAGCACATGATGGTGGGCACTCTAGG

GAGACTGCCGGGGATAACCCGGAGGAAGGCGGGGACGACGTCAAATCATCATGCCCCTTATGATTTGGGCTACACA

CGTGCTACAATGGCGTAAACAAAGGGAAGCGAGACAGCGATGTTGAGCAATCCCAAAAATAACGTCCCAGTTCGG

ACTGCAGTCTGCAACTCGACTGCACGAAGCTGGAATCGCTAGTAATCGCGGATCAGAATGCCGCGGTGAATACGTT

```
CCCGGGTCTTGTACACACCGCCCGTCACACCATGGGAGTCAGTAACGCCCGAAGTCAGTGACCTAACCGAAAGGAA

GGAGCTGCCGAAGGCGGGACCGATAACTGGGGTGAAGTCGTAACAAGGTAGCCGTATCGGAAGGTGCGGCTGGATC

ACCTCCTTT

SEQ ID NO: 25 Blautia producta-3 Strain 4
TCAGAGAGTTTGATCCTGGCTCAGGATGAACGCTGGCGGCGTGCTTAACACATGCAAGTCGAGCGAAGCACTTAAG

TGGATCTCTTCGGATTGAAACTTATTTGACTGAGCGGCGGACGGGTGAGTAACGCGTGGGTAACCTGCCTCATACA

GGGGGATAACAGTTAGAAATGGCTGCTAATACCGCATAAGCGCACAGGACCGCATGGTCTGGTGTGAAAAACTCCG

GTGGTATGAGATGGACCCGCGTCTGATTAGCTAGTTGGAGGGGTAACGGCCCACCAAGGCGACGATCAGTAGCCGG

CCTGAGAGGGTGAACGGCCACATTGGGACTGAGACACGGCCCAGACTCCTACGGGAGGCAGCAGTGGGGAATATTG

CACAATGGGGGAAACCCTGATGCAGCGACGCCGCGTGAAGGAAGAAGTATCTCGGTATGTAAACTTCTATCAGCAG

GGAAGAAAATGACGGTACCTGACTAAGAAGCCCCGGCTAACTACGTGCCAGCAGCCGCGGTAATACGTAGGGGGCA

AGCGTTATCCGGATTTACTGGGTGTAAAGGGAGCGTAGACGGAAGAGCAAGTCTGATGTGAAAGGCTGGGGCTTAA

CCCCAGGACTGCATTGGAAACTGTTTTTCTAGAGTGCCGGAGAGGTAAGCGGAATTCCTAGTGTAGCGGTGAAATG

CGTAGATATTAGGAGGAACACCAGTGGCGAAGGCGGCTTACTGGACGGTAACTGACGTTGAGGCTCGAAAGCGTGG

GGAGCAAACAGGATTAGATACCCTGGTAGTCCACGCCGTAAACGATGAATACTAGGTGTCGGGTGGCAAAGCCATT

CGGTGCCGCAGCAAACGCAATAAGTATTCCACCTGGGGAGTACGTTCGCAAGAATGAAACTCAAAGGAATTGACGG

GGACCCGCACAAGCGGTGGAGCATGTGGTTTAATTCGAAGCAACGCGAAGAACCTTACCAAGTCTTGACATCCCTC

TGACCGGCCCGTAACGGGGCCTTCCCTTCGGGCAGAGGAGACAGGTGGTGCATGGTTGTCGTCAGCTCGTGTCGT

GAGATGTTGGGTTAAGTCCCGCAACGAGCGCAACCCCTATCCTTAGTAGCCAGCAGGTGAAGCTGGGCACTCTAGG

GAGACTGCCGGGGATAACCCGGAGGAAGGCGGGGACGACGTCAAATCATCATGCCCCTTATGATTTGGGCTACACA

CGTGCTACAATGGCGTAAACAAAGGGAAGCGAGACAGCGATGTTGAGCAAATCCCAAAAATAACGTCCCAGTTCGG

ACTGCAGTCTGCAACTCGACTGCACGAAGCTGGAATCGCTAGTAATCGCGAATCAGAATGTCGCGGTGAATACGTT

CCCGGGTCTTGTACACACCGCCCGTCACACCATGGGAGTCAGTAACGCCCGAAGTCAGTGACCCAACCTTATAGGA

GGGAGCTGCCGAAGGCGGGACCGATAACTGGGGTGAAGTCGTAACAAGGTAGCCGTATCGGAAGGTGCGGCTGGAT

CACCTCCTTT

SEQ ID NO: 26 Clostridium ramosum Strain 5
Gatgaacgctggcggcgtgcctaatacatgcaagtcgaacgcgagcacttgtgctcgagtggcgaacgggtgagta atacataagtaacctgccctagacaggggataactattggaaacgatagctaagaccgcataggtacggacactg catggtgaccgtattaaagtgcctcaaagcactggtagaggatggacttatggcgcattagctgttggcggggta acggcccaccaaggcgacgatgcgtagccgacctgagagggtgaccggccacactgggactgagacacggcccag SEQ ID NO: 27 Flavonifractor plautii Strain 6
gatgaacgctggcggcgtgcttaacacatgcaagtcgaacggggtgctcatgacggaggattcgtccaacggattg agttacccagtggcggacgggtgagtaacgcgtgaggaacctgccttggagaggggaataacactccgaaaggagt gctaataccgcatgatgcagttgggtcgcatggctctgactgccaaagatttatcgctctgagatggcctcgcgtc tgattagctagtaggcgggtaacggcccacctaggcgacgatcagtagccggactgagaggttgaccggccacat tgggactgagacacggccca SEQ ID NO: 28 Barnesiella/Parabacteroides spp Strain 7
GTGCTCAGCTTTTACCCTAGGCCGATCCTTGCGGTTACGGACTTCAGGTACCCCCGGCTCCCATGGCTTGACGGGC

GGTGTGTACAAGGCCCGGGAACGTATTCACCGCGCCATGGCTGATGCGCGATTACTAGCGAATCCAGCTTCACGGA

GTCGAGTTGCAGACTCCGATCCGAACTGAGACATGGTTTGGAGATTAGCATCCTGTCGCCAGGTAGCTGCCCTTTG

TCCATGCCATTGTAACACGTGTGTCGCCCCGGATGTAAGGGCCGTGCTGATTTGACGTCATCCCCACCTTCCTCAC

AGCTTACGCTGGCAGTCTCACCAGAGTCCTCAGCTTCACCTGTTAGTAACTAGTGATAAGGGTTGCGCTCGTTATG

GCACTTAAGCCGACACCTCACGGCACGAGCTGACGACAACCATGCAGCACCTCGTAATCTGCTATTGCTAGAAGGA
```

```
GTGTTTCCACTCCGGTCAGACTACGTTCAAACCCGGGTAAGGTTCCTCGCGTATCATCGAATTAAACCACATGTTC

CTCCGCTTGTGCGGGCCCCGTCAATTCCTTTGAGTTTCACCGTTGCCGGCGTACTCCCCAGGTGGATTACTTAAC

GCTTTCGCTGTAGAGCTTACATTGTATCGCAAACTCCTAGTAATCATCGTTTACTGCGTGGACTACCAGGGTATCT

AATCCTGTTTGATCCCCACGCTTTCGTGCTTCAGTGTCAGTTATGGTTTAGTAAGCTGCCTTCGCAATCGGAGTTC

TGCGTGATATCTATGCATTTCACCGCTACACCACGCATTCCGCCTACCTCAAACACACTCAAGTAACCCAGTTTCA

ACGGCAATTTTATGGTTGAGCCACAAACTTTCACCGCTGACTTAAATCACCACCTACGCACCCTTTAACCCAATAA

ATCCGATAACGCTCGCATCCTCCGTATTACCGCGGCTGCTGCCCGGAGTTAGCCGATGCTTATTCATAGGGTACAT

ACAAAAAGGACACGT

SEQ ID NO: 29 Clostridium symbiosum Strain 8
ATGAGAGTTTGATCCTGGCTCAGGATGAACGCTGGCGGCGTGCCTAACACATGCAAGTCGAACGAAGCGATTTAA

CGGAAGTTTTCGGATGGAAGTTGAATTGACTGAGTGGCGGACGGGTGAGTAACGCGTGGGTAACCTGCCTTGTAC

TGGGGGACAACAGTTAGAAATGACTGCTAATACCGCATAAGCGCACAGTATCGCATGATACAGTGTGAAAAACTC

CGGTGGTACAAGATGGACCCGCGTCTGATTAGCTAGTTGGTAAGGTAACGGCTTACCAAGGCGACGATCAGTAGC

CGACCTGAGAGGGTGACCGGCCACATTGGGACTGAGACACGGCCCAAACTCCTACGGGAGGCAGCAGTGGGGAAT

ATTGCACAATGGGCGAAAGCCTGATGCAGCGACGCCGCGTGAGTGAAGAAGTATTTCGGTATGTAAAGCTCTATC

AGCAGGGAAGAAAATGACGGTACCTGACTAAGAAGCCCCGGCTAACTACGTGCCAGCAGCCGCGGTAATACGTAG

GGGGCAAGCGTTATCCGGATTTACTGGGTGTAAAGGGAGCGTAGACGGTAAAGCAAGTCTGAAGTGAAAGCCCGC

GGCTCAACTGCGGGACTGCTTTGGAAACTGTTTAACTGGAGTGTCGGAGAGGTAAGTGGAATTCCTAGTGTAGCG

GTGAAATGCGTAGATATTAGGAGGAACACCAGTGGCGAAGGCGACTTACTGGACGATAACTGACGTTGAGGCTCG

AAAGCGTGGGGAGCAAACAGGATTAGATACCCTGGTAGTCCACGCCGTAAACGATGAATACTAGGTGTTGGGGAG

CAAAGCTCTTCGGTGCCGTCGCAAACGCAGTAAGTATTCCACCTGGGGAGTACGTTCGCAAGAATGAAACTCAAA

GGAATTGACGGGGACCCGCACAAGCGGTGGAGCATGTGGTTTAATTCGAAGCAACGCGAAGAACCTTACCAGGTC

TTGACATCGATCCGACGGGGAGTAACGTCCCCTTCCCTTCGGGGCGGAAGACAGGTGGTGCATGGTTGTCGT

CAGCTCGTGTCGTGAGATGTTGGGTTAAGTCCCGCAACGAGCGCAACCCTTATTCTAAGTAGCCAGCGGTTCGGC

CGGGAACTCTTGGGAGACTGCCAGGGATAACCTGGAGGAAGGTGGGGATGACGTCAAATCATCATGCCCCTTATG

ATCTGGGCTACACACGTGCTACAATGGCGTAAACAAAGAGAAGCAAGACCGCGAGGTGGAGCAAATCTCAAAAAT

AACGTCTCAGTTCGGACTGCAGGCTGCAACTCGCCTGCACGAAGCTGGAATCGCTAGTAATCGCGAATCAGAATG

TCGCGGTGAATACGTTCCCGGGTCTTGTACACACCGCCCGTCACACCATGGGAGTCAGTAACGCCCGAAGTCAGT

GACCCAACCGCAAGGAGGGAGCTGCCGAAGGCGGGACCGATAACTGGGGTGAAGTCGTAACAAGGTAGCCGTATC

GGAAGGTGCGGCTGGATCACCTCCTTT

SEQ ID NO: 30 Eubacterium fissicatena Strain 23
gatgaacgctggcggcgtgcttaacacatgcaagtcgagcgaagcgctttacttagatttcttcggattgaaagtt ttgcgactgagcggcggacgggtgagtaacgcgtgggtaacctgcctcatacaggggataacagttagaaatgac tgctaataccgcataagaccacagtaccgcatggtacagtgggaaaaactccggtggtatgagatggacccgcgtc tgattagctagttggtaaggtaacggcttaccaaggcgacgatcagtagccgacctgagagggtgaccggccacat tgggactgagacacggccca SEQ ID NO: 31 Lachnospiraceae bacterium Strain 25
agagtttgatcctggctcaggataaacgctggcggcgcacataagacatgcaagtcgaacggacttaactcattct tttagattgagagcggttagtggcggactggtgagtaacacgtaagcaacctgcctatcagaggggaataacagtg agaaatcattgctaataccgcatatgctcacagtatcacatgatacagtgaggaaaggagcaatccgctgatagat gggcttgcgcctgattagttagttggtggggtaacggcctaccaagacgacgatcagtagccggactgagaggttg aacggccacattgggactgagatacggcccagactcctacgggaggcagcagtcgggaatattgcgcaatggagga
```

-continued aactctgacgcagtgacgccgcgtataggaagaaggttttcggattgtaaactattgtcgttagggaagataaaag actgtacctaaggaggaagccccggctaactatgtgccagcagccgcggtaatacataggggggcaagcgttatccg gaattattgggtgtaaagggtgcgtagacggaagaacaagttggttgtgaaatccctcggctcaactgaggaactg caaccaaaactattctccttgagtgtcggagaggaaagtggaattcctagtgtagcggtgaaatgcgtagatatta ggaggaacaccagtggcgaaggcgactttctggacgataactgacgttgaggcacgaaagtgtggggagcaaacag gattagataccctggtagtccacactgtaaacgatggatactaggtgtagggtgtattaagcactctgtgccgccg ctaacgcattaagtatcccacctggggagtacgaccgcaaggttgaaactcaaaggaattgacggggcccgcaca agcagtggagtatgtggtttaattcgaagcaacgcgaagaaccttaccagggcttgacatataccggaatatacta gagatagtatagtccttcgggactggtatacaggtggtgcatggttgtcgtcagctcgtgtcgtgagatgttgggt taagtcccgcaacgagcgcaacccctatcgttagttgctagcaggtaatgctgagaactctagcgagactgccggt gataaatcggaggaaggtggggatgacgtcaaatcatcatgccctttatgtcctgggctacacacgtactacaatg gccgtaacagagggaagcaatatagtgatatggagcaaaaccctaaaagcggtctcagttcggattgaaggctgaa attcgccttcatgaagccggaattgctagtaatggcaggtcagcatactgccgtgaatacgttcccgggccttgta cacaccgcccgtcacaccatgagagttggaaatacccgaagcctgtgagctaactgtaaagaggcagcagtcgaag gtagagccaatgattggggtgaagtcgtaacaaggtagccgt SEQ ID NO: 32 Dorea Longicatena Strain 18
AACGAGAGTTTGATCCTGGCTCAGGATGAACGCTGGCGGCGTGCTTAACACATGCAAGTCGAGCGAAGCACTTTG

GAAGATTCTTCGGATGATTTCCTTTGTGACTGAGCGGCGGACGGGTGAGTAACGCGTGGGTAACCTGCCTCATAC

AGGGGGATAACAGTTAGAAATGACTGCTAATACCGCATAAGACCACGGTACCGCATGGTACAGTGGTAAAAACTC

CGGTGGTATGAGATGGACCCGCGTCTGATTAGGTAGTTGGTGGGGTAACGGCCTACCAAGCCGACGATCAGTAGC

CGACCTGAGAGGGTGACCGGCCACATTGGGACTGAGACACGGCCCAGACTCCTACGGGAGGCAGCAGTGGGGAAT

ATTGCACAATGGAGGAAACTCTGATGCAGCGACGCCGCGTGAAGGATGAAGTATTTCGGTATGTAAACTTCTATC

AGCAGGGAAGAAAATGACGGTACCTGACTAAGAAGCCCCGGCTAACTACGTGCCAGCAGCCGCGGTAATACGTAG

GGGGCAAGCGTTATCCGGATTTACTGGGTGTAAAGGGAGCGTAGACGGCACGGCAAGCCAGATGTGAAAGCCCGG

GGCTCAACCCCGGGACTGCATTTGGAACTGCTGAGCTAGAGTGTCGGAGAGGCAAGTGGAATTCCTAGTGTAGCG

GTGAAATGCGTAGATATTAGGAGGAACACCAGTGGCGAAGGCGGCTTGCTGGACGATGACTGACGTTGAGGCTCG

AAAGCGTGGGGAGCAAACAGGATTAGATACCCTGGTAGTCCACGCCGTAAACGATGACTGCTAGGTGTCGGGTGG

CAAAGCCATTCGGTGCCGCAGCTAACGCAATAAGCAGTCCACCTGGGGAGTACGTTCGCAAGAATGAAACTCAAA

GGAATTGACGGGGACCCGCACAAGCGGTGGAGCATGTGGTTTAATTCGAAGCAACGCGAAGAACCTTACCTGATC

TTGACATCCCGATGACCGCTTCGTAATGGAAGCTTTTCTTCGGAACATCGGTGACAGGTGGTGCATGGTTGTCGT

CAGCTCGTGTCGTGAGATGTTGGGTTAAGTCCCGCAACGAGCGCAACCCCTATCTTCAGTAGCCAGCAGGTTAAG

CTGGGCACTCTGGAGAGACTGCCAGGGATAACCTGGAGGAAGGTGGGGATGACGTCAAATCATCATGCCCCTTAT

GACCAGGGCTACACACGTGCTACAATGGCGTAAACAAAGAGAAGCGAACTCGCGAGGGTAAGCAAATCTCAAAAA

TAACGTCTCAGTTCGGATTGTAGTCTGCAACTCGACTACATGAAGCTGGAATCGCTAGTAATCGCAGATCAGAAT

GCTGCGGTGAATACGTTCCCGGGTCTTGTACACACCGCCCGTCACACCATGGGAGTCAGTAACGCCCGAAGTCAG

TGACCCAACCGTAAGGAGGGAGCTGCCGAAGGTGGGACCGATAACTGGGGTGAAGTCGTAACAAGGTAGCCGTAT

CGGAAGGTGCGGCTGGATCACCTCCTTT

SEQ ID NO: 33 Blautia producta-4 Strain 10
ATCAGAGAGTTTGATCCTGGCTCAGGATGAACGCTGGCGGCGTGCTTAACACATGCAAGTCGAGCGAAGCACTTA

AGTGGATCTCTTCGGATTGAAACTTATTTGACTGAGCGGCGGACGGGTGAGTAACGCGTGGGTAACCTGCCTCAT

ACAGGGGGATAACAGTTAGAAATGGCTGCTAATACCGCATAAGCGCACAGGACCGCATGGTCTGGTGTGAAAAAC

```
TCCGGTGGTATGAGATGGACCCGCGTCTGATTAGCTAGTTGGAGGGGTAACGGCCCACCAAGGCGACGATCAGTA

GCCGGCCTGAGAGGGTGAACGGCCACATTGGGACTGAGACACGGCCCAGACTCCTACGGGAGGCAGCAGTGGGGA

ATATTGCACAATGGGGGAAACCCTGATGCAGCGACGCCGCGTGAAGGAAGAAGTATCTCGGTATGTAAACTTCTA

TCAGCAGGGAAGAAAATGACGGTACCTGACTAAGAAGCCCCGGCTAACTACGTGCCAGCAGCCGCGGTAATACGT

AGGGGGCAAGCGTTATCCGGATTTACTGGGTGTAAAGGGAGCGTAGACGGAAGAGCAAGTCTGATGTGAAAGGCT

GGGGCTTAACCCCAGGACTGCATTGGAAACTGTTTTTCTAGAGTGCCGGAGAGGTAAGCGGAATTCCTAGTGTAG

CGGTGAAATGCGTAGATATTAGGAGGAACACCAGTGGCGAAGGCGGCTTACTGGACGGTAACTGACGTTGAGGCT

CGAAAGCGTGGGGAGCAAACAGGATTAGATACCCTGGTAGTCCACGCCGTAAACGATGAATACTAGGTGTCGGGT

GGCAAAGCCATTCGGTGCCGCAGCAAACGCAATAAGTATTCCACCTGGGGAGTACGTTCGCAAGAATGAAACTCA

AAGGAATTGACGGGGACCCGCACAAGCGGTGGAGCATGTGGTTTAATTCGAAGCAACGCGAAGAACCTTACCAAG

TCTTGACATCCCTCTGACCGGCCCGTAACGGGCCTTCCCTTCGGGGCAGAGGAGACAGGTGGTGCATGGTTGTC

GTCAGCTCGTGTCGTGAGATGTTGGGTTAAGTCCCGCAACGAGCGCAACCCCTATCCTTAGTAGCCAGCAGGTGA

AGCTGGGCACTCTAGGGAGACTGCCGGGGATAACCCGGAGGAAGGCGGGGACGACGTCAAATCATCATGCCCCTT

ATGATTTGGGCTACACACGTGCTACAATGGCGTAAACAAAGGGAAGCGAGACAGCGATGTTGAGCAAATCCCAAA

AATAACGTCCCAGTTCGGACTGCAGTCTGCAACTCGACTGCACGAAGCTGGAATCGCTAGTAATCGCGAATCAGA

ATGTCGCGGTGAATACGTTCCCGGGTCTTGTACACACCGCCCGTCACACCATGGGAGTCAGTAACGCCCGAAGTC

AGTGACCCAACCTTACAGGAGGGAGCTGCCGAAGGCGGGACCGATAACTGGGGTGAAGTCGTAACAAGGTAGCCG

TATCGGAAGGTGCGGCTGGATCACCTCCTTT

SEQ ID NO: 34 E. coli Strain 46
agtttgatcatggctcagattgaacgctggcggcaggcctaacacatgcaagtcgaacggtaacaggaacgagctt gctgctttgctgacgagtggcggacgggtgagtaatgtctgggaaactgcctgatggagggggataactactggaa acggtagctaataccgcataacgtcgcaagaccaaagaggggggaccttcgggcctcttgccatcggatgtgcccag atgggattagctagtaggtggggtaaaggctcacctaggcgacgatccctagctggtctgagaggatgaccagcca cactggaactgagacacggtccagactcctacgggaggcagcagtggggaatattgcacaatgggcgcaagcctga tgcagccatgccgcgtgtatgaagaaggccttcggggttgtaaagtactttcagcggggaggaagggagtaaagtta ataccttgctcattgacgttaccgcagaagaannaccggctaactccgtgccagcagccgcggtaatacggaggg tgcaagcgttaatcggaattactgggcgtaaagngcangcaggcggtttgttaagtcagatgtgaaatccccgggc tcaacctgggaactgcatctgatactggcaagcttgagtctcgtagaggggggtagaattccaggtgtagcggtga aatgcgtagagatctggaggaataccggtggcgaaggcggccccctggacgaagactgacgctcaggtgcgaaagc gtggggagcaaacaggattagataccctggtagtccacgccgtaaacgatgtcgacttggaggttgtgcccttgag gcgtggcttccggannntaacgcgttaagtcgaccgcctggggagtacggccgcaaggttaaaactcaaatgaattg acggggccgcacaagcggtggagcatgtggtttaattcgatgcaacgcgaagaaccttacctggtcttgacatcc acggaagttttcagagatgagaatgtgccttcgggaaccgtgagacaggtgctgcatggctgtcgtcagctcgtgt tgtgaaatgttgggttaagtcccgcaacgagcgcaacccttatcctttgttgccagcggtccggccgggaactcaa aggagactgccagtgataaactggaggaaggtggggatgacgtcaagtcatcatggcccttacgaccagggctaca cacgtgctacaatggcgcatacaaagagaagcgacctcgcgagagcaagcggacctcataaagtgcgtcgtagtcc ggattggagtctgcaactcgactccatgaagtcggaatcgctagtaatcgtggatcagaatgccacggtgaatacg ttcccgggccttgtacacaccgcccgtcacaccatgggagtgggttgcaaaagaagtaggtagcttaaccttcggg agggcgc SEQ ID NO: 35 Lactococcus lactis Strain 47
NNAATTTTTGTTGTGCTCATACGTGCAGTTGAGCGCTCGAAGGTTGGTACTTGTACCCTCTGGATGAGCAGCGAAC

GGGTGAGTAACGCGTGGGGAATCTGCCTTTGAGCGGGGGACCACATTTGGAAACGAATGCGAATACCGCATAAAAA
```

CTTTAAACACAAGTTTTAAGTTTGAAAGATGCAATTGCATCACTCCAAGATGATCCCGCGTTGTATTAGCTAGTTG

GTGAGGGAAAGGCTCCCCACGGCGATCATACATATCCGACCTGAGAGGGTGACCGGCCACATTGGGACTGAGCCAT

GATCAAACTCTGAAAAAGAGGCAGCAGTAGGGAATCTTCGGCAATGGACGAAAGTCTGACCGAGCAACGCCGCGTG

AGTGAAGAAGGTTTTCGGATCGTAAAACTCTGTTGGTAGAGAAGAACGTTGGTGAGAGTGGAAAGCTCATCAAGTG

ACGGTAACTACCCAGAAAGGGACGGCTAACTACGTGCCAGCAGCCGCGGTAATACGTAGGTCCCGAGCGTTGTCCG

GATTTATTGGGCGTAAAGCGAGCGCAGGTGGTTTATTAAGTCTGGTGTAAAAGGCAGTGGCTCAACCATTGTATGC

ATTGGAAACTGGTAGACTTGAGTGCAGGAGAGGAGAGTGGAATTCCATGTGTAGCGGGTGAAATGCGTAGATATAT

GGTAGGAACACCGGGTGGCGAAAGCGGCTCTCTGGCCTGTAACTGACACTGAGGCTCGAAAGCGTGGGGAGCAAA

AAGGATTAGATACCCTGGTAGTCCACGCCGTA

SEQ ID NO: 36 Lactobacillus ruminis Strain 48
NACTCTGTCACCTTAGGCGGCTGGCTCCAAAAGGTTACCCCACCGACTTTGGGTGTTACAAACTCTCATGGTGTGA

CGGGCGGTGTGTACAAGGCCCGGGAACGTATTCACCGCGACATGCTGATTCGCGATTACTAGCGATTCCGACTTCA

TGCAGGCGAGTTGCAGCCTGCAATCCGAACTGAGAACGGCTTTAAGAGATTAGCTTGCCCTCGCGAGTTAGCGACT

CGTTGTACCGTCCATTGTAGCACGTGTGTAGCCCAGGTCATAAGGGGCATGATGATTTGACGTCATCCCCACCTTC

CTCCGGTTTGTCACCGGCAGTCTCGCCAGAGTGCCCAACTTAATGATGGCAACTGACAATAAGGGTTGCGCTCGTT

GCGGGACTTAACCCAACATCTCACGACACGAGCTGACGACAACCATGCACCACCTGTCATTCTGTCCCCGAAGGGA

ACGTTCCATCTCTGGAATTGTCAGAAGATGTCAAGACCTGGTAAGGTTCTTCGCGTTGCTTCGAATTAAACCACAT

GCTCCACCGCTTGTGCGGGCCCCCGTCAATTCCTTTGAGTTTCAGTCTTGCGACCGTACTCCCCAGGCGGAGTGCT

TAATGCGTTAGCTGCAGCACTGAAGGGCGGAAACCCTCCAACACTTAGCACTCATCGTTTACGGCGTGGACTACCA

GGGTATCTAATCCTGTTTGCTACCCACGCTTTCGAACCTCAGCGTCAGTTACAGACCAGAGAGCCGCTTTCGCCAC

TGGTGTTCTTCCATATATCTACGCATTTCACCGCTACACATGGAGTTCCACTCTCCTCTTCTGCACTCAAGTCTTC

CAGTTTCCAATGCACTACTTCGGTTAAGCCGAAGGCTTTCACATCAGACTTAAAAGACCGCCTGCGTTCCCTTTAC

GCCCATAAATCCGGACACGCTCGCCACCTACGTATTACCGCGGCTGCTGGCACGTAGTTAGCCGTGGCTTTCTGGT

AGA

SEQ ID NO: 37 Lactobacillus ruminis Strain 49
ATTGAGAGTTTGATCCTGGCTCAGGACGAACGCTGGCGGCGTGCCTAATACATGCAAGTCGAACGAAGCTTTCTTT

CACCGAATGCTTGCATTCACCGAAAGAAGCTTAGTGGCGAACGGGTGAGTAACACGTAGGCAACCTGCCCAAAAGA

GGGGGATAACACTTGGAAACAGGTGCTAATACCGCATAACCATGAACACCGCATGATGTTCATGTAAAAGACGGCT

TTTGCTGTCACTTTTGGATGGGCCTGCGGCGTATTAACTTGTTGGTGGGGTAACGGCCTACCAAGGTGATGATACG

TAGCCGAACTGAGAGGTTGATCGGCCACATTGGGACTGAGACACGGCCCAAACTCCTACGGGAGGCAGCAGTAGGG

AATCTTCCACAATGGACGAAAGTCTGATGGAGCAACGCCGCGTGAATGAAGAAGGCCTTCGGGTCGTAAAATTCTG

TTGTCAGAGAAGAACGTGCGTGAGAGTAACTGTTCACGTATTGACGGTATCTGACCAGAAAGCCACGGCTAACTAC

GTGCCAGCAGCCGCGGTAATACGTAGGTGGCGAGCGTTGTCCGGATTTATTGGGCGTAAAGGGAACGCAGGCGGTC

TTTTAAGTCTGATGTGAAAGCCTTCGGCTTAACCGAAGTAGTGCATTGGAAACTGGAAGACTTGAGTGCAGAAGAG

GAGAGTGGAACTCCATGTGTAGCGGTGAAATGCGTAGATATATGGAAGAACACCAGTGGCGAAAGCGGCTCTCTGG

TCTGTAACTGACGCTGAGGTTCGAAAGCGTGGGTAGCAAACAGGATTAGATACCCTGGTAGTCCACGCCGTAAACG

ATGAGTGCTAAGTGTTGGAGGGTTTCCGCCCTTCAGTGCTGCAGCTAACGCATTAAGCACTCCGCCTGGGGAGTAC

GGTCGCAAGACTGAAACTCAAAGGAATTGACGGGGGCCCGCACAAGCGGTGGAGCATGTGGTTTAATTCGAAGCAA

CGCGAAGAACCTTACCAGGTCTTGACATCTTCTGACAATTCCAGAGATGGAACGTTCCCTTCGGGGACAGAATGAC

AGGTGGTGCATGGTTGTCGTCAGCTCGTGTCGTGAGATGTTGGGTTAAGTCCCGCAACGAGCGCAACCCTTATTGT

CAGTTGCCATCATTAAGTTGGGCACTCTGGCGAGACTGCCGGTGACAAACCGGAGGAAGGTGGGGATGACGTCAAA

-continued

TCATCATGCCCCTTATGACCTGGGCTACACACGTGCTACAATGGACGGTACAACGAGTCGCTAACTCGCGAGGGCA

AGCTAATCTCTTAAAGCCGTTCTCAGTTCGGATTGCAGGCTGCAACTCGCCTGCATGAAGTCGGAATCGCTAGTAA

TCGCGAATCAGCATGTCGCGGTGAATACGTTCCCGGGCCTTGTACACACCGCCCGTCACACCATGAGAGTTTGTAA

CACCCAAAGTCGGTGGGGTAACCTTTTGGAGCCAGCCGCCTAAGGTGGGACAGATGATTGGGGTGAAGTCGTAACA

AGGTAGCCGTAGGAGAACCTGCGGCTGGATCACCTCCTT

SEQ ID NO: 38 Lactobacillus animalis Strain 50
ATTGAGAGTTTGATCCTGGCTCAGGATGAACGCTGGCGGCGTGCCTAATACATGCAAGTCGAACGAAACTTCTTTA

TCACCGAGTGCTTGCACTCACCGATAAAGAGTTGAGTGGCGAACGGGTGAGTAACACGTGGGCAACCTGCCCAAAA

GAGGGGGATAACACTTGGAAACAGGTGCTAATACCGCATAACCATAGTTACCGCATGGTAACTATGTAAAAGGTGG

CTATGCTACCGCTTTTGGATGGGCCCGCGGCGCATTAGCTAGTTGGTGAGGTAAAGGCTTACCAAGGCAATGATGC

GTAGCCGAACTGAGAGGTTGATCGGCCACATTGGGACTGAGACACGGCCCAAACTCCTACGGGAGGCAGCAGTAGG

GAATCTTCCACAATGGGCGAAAGCCTGATGGAGCAACGCCGCGTGGGTGAAGAAGGTCTTCGGATCGTAAAACCCT

GTTGTTAGAGAAGAAAGTGCGTGAGAGTAACTGTTCACGTTTCGACGGTATCTAACCAGAAAGCCACGGCTAACTA

CGTGCCAGCAGCCGCGGTAATACGTAGGTGGCAAGCGTTATCCGGATTTATTGGGCGTAAAGGGAACGCAGGCGGT

CTTTTAAGTCTGATGTGAAAGCCTTCGGCTTAACCGGAGTAGTGCATTGGAAACTGGGAGACTTGAGTGCAGAAGA

GGAGAGTGGAACTCCATGTGTAGCGGTGAAATGCGTAGATATATGGAAGAACACCAGTGGCGAAAGCGGCTCTCTG

GTCTGTAACTGACGCTGAGGTTCGAAAGCGTGGGTAGCAAACAGGATTAGATACCCTGGTAGTCCACGCCGTAAAC

GATGAATGCTAAGTGTTGGAGGGTTTCCGCCCTTCAGTGCTGCAGCTAACGCAATAAGCATTCCGCCTGGGGAGTA

CGACCGCAAGGTTGAAACTCAAAGGAATTGACGGGGGCCCGCACAAGCGGTGGAGCATGTGGTTTAATTCGAAGCA

ACGCGAAGAACCTTACCAGGTCTTGACATCTTCTGACAATCCTAGAGATAGGACTTTCCCTTCGGGGACAGAATGA

CAGGTGGTGCATGGTTGTCGTCAGCTCGTGTCGTGAGATGTTGGGTTAAGTCCCGCAACGAGCGCAACCCTTATTG

TTAGTTGCCAGCATTAAGTTGGGCACTCTAGCAAGACTGCCGGTGACAAACCGGAGGAAGGTGGGGATGACGTCAA

ATCATCATGCCCCTTATGACCTGGGCTACACACGTGCTACAATGGACGGTACAACGAGTCGCAAGACCGCGAGGTT

TAGCAAATCTCTTAAAGCCGTTCTCAGTTCGGATTGTAGGCTGCAACTCGCCTACATGAAGTCGGAATCGCTAGTA

ATCGCGGATCAGCATGCCGCGGTGAATACGTTCCCGGGCCTTGTACACACCGCCCGTCACACCATGAGAGTTTGTA

ACACCCAAAGCCGGTGGGGTAACCTTTTGGAGCCAGCCGTCTAAGGTGGGACAGATGATTGGGGTGAAGTCGTAAC

AAGGTAGCCGTAGGAGAACCTGCGGCTGGATCACCTCCTTT

SEQ ID NO: 39 Lactobacillus rhamnosus Strain 51
NNCTCTGTTTTGCGTGTGATGCAGTCGACGAGTTCTGATTATTGAAAGGTGCTTGCATCTTGATTTAATTTTGAAC

GAGTGGCGGACGGGTGAGTAACACGTGGGTAACCTGCCCTTAAGTGGGGGATAACATTTGGAAACAGATGCTAATA

CCGCATAAATCCAAGAACCGCATGGTTCTTGGCTGAAAGATGGCGTAAGCTATCGCTTTTGGATGGACCCGCGGCG

TATTAGCTAGTTGGTGAGGTAACGGCTCACCAAGGCAATGATACGTAGCCGAACTGAGAGGTTGATCGGCCACATT

GGGACTGAGACACGGCCCAAACTCCTACGGGAGGCAGCAGTAGGGAATCTTCCACAATGGACGCAAGTCTGATGGA

GCAACGCCGCGTGAGTGAAGAAGGCTTTCGGGTCGTAAAACTCTGTTGTTGGAGAAGAATGGTCGGCAGAGTAACT

GTTGTCGGCGTGACGGTATCCAACCAGAAAGCCACGGCTAACTACGTGCCAGCAGCCGCGGTAATACGTAGGTGGC

AAGCGTTATCCGGATTTATTGGGCGTAAAGCGAGCGCAGGCGGTTTTTTAAGTCTGATGTGAAAGCCCTCGGCTTA

ACCGAGGAAGTGCATCGGAAACTGGGAAACTTGAGTGCAGAAGAGGACAGTGGAACTCCATGTGTAGCGGTGAAAT

GCGTAGATATATGGAAGAACACCAGTGGCGAGGCGGCTGTCTGGTCTGTAACTGACGCTGAGGCTCGAAAGCATGG

GTAGCGAACAGGATTAGATACCCTGGTAGTCCATGCCGTAAACGATGAATGCTAGGTGTTGGAGGGTTTCCGCCCT

TCAGTGCCGCGCTTACGCATTTAGCATTCGCCTGGGGAGTACGACCGCAGGTTGAACCTCAAAGGAATTG

-continued

SEQ ID NO: 40 *Lactobacillus rhamnosus* Strain 52
CCCNNTTGTGTCCTATACTGCAGTCTACAGTCTGAATATTGAAGGTGCTTGCATCTTGATTTAATTTTGAACGAGT

GGCGGACGGGTGAGTAACACGTGGGTAACCTGCCCTTAAGTGGGGGATAACATTTGGAAACAGATGCTAATACCGC

ATAAATCCAAGAACCGCATGGTTCTTGGCTGAAAGATGGCGTAAGCTATCGCTTTTGGATGGACCCGCGGCGTATT

AGCTAGTTGGTGAGGTAACGGCTCACCAAGGCAATGATACGTAGCCGAACTGAGAGGTTGATCGGCCACATTGGGA

CTGAGACACGGCCCAAACTCCTACGGGAGGCAGCAGTAGGGAATCTTCCACAATGGACGCAAGTCTGATGGAGCAA

CGCCGCGTGAGTGAAGAAGGCTTTCGGGTCGTAAAACTCTGTTGTTGGAAGAATGGTCGGCAGAGTAACTGTTG

TCGGCGTGACGGTATCCAACCAGAAAGCCACGGCTAACTACGTGCCAGCAGCCGCGGTAATACGTAGGTGGCAAGC

GTTATCCGGATTTATTGGGCGTAAAGCGAGCGCAGGCGGTTTTTTAAGTCTGATGTGAAAGCCCTCGGCTTAACCG

AGGAAGTGCATCGGAAACTGGGAAACTTGAGTGCAGAAGAGGACAGTGGAACTCCATGTGTAGCGGTGAAATGCGT

AGATATATGGAAGAACACCAGTGGCGAAGGCGGCTGTCTGGTCTGTAACTGACGCTGAGGCTCGAAAGCATGGGTA

GCGAACAGGATTAGATACCCTGGTAGTCCATGCCGTAAACGATGAATGCTAGGTGTTGGAGGGTTTCCGCCCTTCA

GTGCCGCAGCTAACGCATTAAGCATTCCGCCTGGGGAGTACGACCGCAAGGTTGAACTCAAAGGAATTGACGGGG

CCCGCACAAGCGGGGAGCATGTGGTTTAATTCGAAGCAACGCGAGGACCTTACCAGGTCTTGACATCTTTTGATC

ACCTGAGAGATCAGGTTTCCCCTTCGGGGCAAATGACAGTGGTGCATGGTTGTCGTCAGCTCCGTGTCTGAGATGT

TGGGTAAGTCCGCAACAAGCGCAACCCTTATGACTAGTTGCAGCTTAGTGGGCACTCCTAGTAGACTGCCGGTGAC

AACCGGAGGAAGGGTGGGGATGACTCAATCACTAGCCCTNGGACCTGGGCTACAACNNGTCCTCATG

SEQ ID NO: 41 *Lactobacillus rhamnosus* Strain 53
GNTCTGGTTTGTTTTGTTGGGGGGTGAAATCTAGTATTGAGGTGCTTGCATCTTGGTTTAATTGTGGAGGAGTGGC

GGACGGGTGAGTAACACGTGGGTAACCTGCCCTTAAGTGGGGGATAACATTTGGAAACAGATGCTAATACCGCATA

AATCCAAGAACCGCATGGTTCTTGGCTGAAAGATGGCGTAAGCTATCGCTTTTGGATGGACCCGCGGCGTATTAGC

TAGTTGGTGAGGTAACGGCTCACCAAGGCAATGATACGTAGCCGAACTGAGAGGTTGATCGGCCACATTGGGACTG

AGACACGGCCCAAACTCCTACGGGAGGCAGCAGTAGGGAATCTTCCACAATGGACGCAAGTCTGATGGAGCAACGC

CGCGTGAGTGAAGAAGGCTTTCGGGTCGTAAAACTCTGTTGTTGGAGAAGAATGGTCGGCAGAGTAACTGTTGTCG

GCGTGACGGTATCCAACCAGAAAGCCACGGCTAACTACGTGCCAGCAGCCGCGGTAATACGTAGGTGGCAAGCGTT

ATCCGGATTTATTGGGCGTAAAGCGAGCGCAGGCGGTTTTTTAAGTCTGATGTGAAAGCCCTCGGCTTAACCGAGG

AAGTGCATCGGAAACTGGGAAACTTGAGTGCAGAAGAGGACAGTGGAACTCCATGTGTAGCGGTGAAATGCGTAGA

TATATGGAAGAACACCAGTGGCGAAGGCGGCTGTCTGGTCTGTAACTGACGCTGAGGCTCGAAAGCATGGGTAGCG

AACAGGATTAGATACCCTGGTAGTCCATGCCGTAAACGATGAATGCTAGGTGTTGGAGGGTTTCCGCCCTTCAGTG

CCGCAGCTAACGCATTAAGCATCCGCCTGGGGAGTACGACCGCAAGGTTGAAACTCAAAGGAATTGACGGGGCCCG

CACAGCGTGGAGCATGTGGTTTAATTCGAAGCAACGCGAGAACCTTACCAGGTCTGACATCTTTGATCACTGAGAG

ATCAGGTTTCCCTTCGGGCAAATGACAGTGGTGCATGGTTGTCGTCAGCTCGTGTCTNGAGATGTTGGGTTAAT

SEQ ID NO: 42 *Bacteroides caccae* Strain 54
TGGCTCAGGATGAACGCTAGCTACAGGCTTAACACATGCAAGTCGAGGGGCATCAGTTTGGTTTGCTTGCAAACCA

AAGCTGGCGACCGGCGCACGGGTGAGTAACACGTATCCAACCTGCCTCATACTCGGGGATAGCCTTTCGAAAGAAA

GATTAATATCCGATAGCATATATTTCCCGCATGGGTTTTATATTAAAGAAATTCGGTATGAGATGGGGATGCGTTC

CATTAGTTTGTTGGGGGGTAACGGCCCACCAAGACTACGATGGATAGGGGTTCTGAGAGGAAGGTCCCCCACATT

GGAACTGAGACACGGTCCAAACTCCTACGGGAGGCAGCAGTGAGGAATATTGGTCAATGGACGCGAGTCTGAACCA

GCCAAGTAGCGTGAAGGATGACTGCCCTATGGGTTGTAAACTTCTTTTATATGGGAATAAAGTTGTCCACGTGTGG

ATTTTTGTATGTACCATATGAATAAGGATCGGCTAACTCCGTGCCAGCAGCCGCGGTAATACGGAGGATCCGAGCG

TTATCCGGATTTATTGGGTTTAAAGGGAGCGTAGGCGGATTGTTAAGTCAGTTGTGAAAGTTTGCGGCTCAACCGT

AAAATTGCAGTTGATACTGGCAGTCTTGAGTGCAGTAGAGGTGGGCGGAATTCGTGGTGTAGCGGTGAAATGCTTA

-continued

GATATCACGAAGAACTCCGATTGCGAAGGCAGCCACTGGAGTGTAACTGACGCTGATGCTCGAAAGTGTGGGTATC

AAACAGGATTAGATACCCTGGTAGTCCACACAGTAAACGATGAATACTCGCTGTTTGCGATATACAGTAAGCGGCC

AAGCGAAAGCATTAAGTATTCCACCTGGGGAGTACGCCGGCAACGGTGAAACTCAAAGGAATTGACGGGGGCCCGC

ACAAGCGGAGGAACATGTGGTTTAATTCGATGATACGCGAGGAACCTTACCCGGGCTTAAATTGCAAATGAATTAT

GGGGAAACCCATAGGCCGCAAGGCATTTGTGAAGGTGCTGCATGGTTGTCGTCAGCTCGTGCCGTGAGGTGTCGGC

TTAAGTGCCATAACGAGCGCAACCCTTATCTTCAGTTACTAACAGGTCATGCTGAGGACTCTGGAGAGACTGCCGT

CGTAAGATGTGAGGAAGGTGGGGATGACGTCAAATCAGCACGGCCCTTACGTCCGGGGCTACACACGTGTTACAAT

GGGGGGTACAGAAGGCCGCTACCTGGTGACAGGATGCCAATCCCAAAAACCTCTCTCAGTTCGGATCGAAGTCTGC

AACCCGACTTCGTGAAGCTGGATTCGCTAGTAATCGCGCATCAGCCATGGCGCGGTGAATACGTTCCCGGGCCTTG

TACACACCGCCCGTCAAGCCATGAAAGCCGGGGGTACCTGAAGTACGTAACCGCAAGGAGCGTCCTAGGGTAAAAC

TGGTAATTGGGGCTAAGTCGTAACAAGGTA

SEQ ID NO: 43 *Bacteroides cellulosilyticus* Strain 55
AGAGTTTGATCCTGGCTCAGGATGAACGCTAGCTACAGGCTTAACACATGCAAGTCGAGGGGCAGCATGACCTAGC

AATAGGTTGATGGCGACCGGCGCACGGGTGAGTAACACGTATCCAACCTACCGGTTATTCCGGGATAGCCTTTCGA

AAGAAAGATTAATACCGGATAGTATAACGAGAAGGCATCTTTTTGTTATTAAAGAATTTCGATAACCGATGGGGAT

GCGTTCCATTAGTTTGTTGGCGGGGTAACGGCCCACCAAGACATCGATGGATAGGGGTTCTGAGAGGAAGGTCCCC

CACATTGGAACTGAGACACGGTCCAAACTCCTACGGGAGGCAGCAGTGAGGAATATTGGTCAATGGACGAGAGTCT

GAACCAGCCAAGTAGCGTGAAGGATGACTGCCCTATGGGTTGTAAACTTCTTTTATATGGGAATAAAGTGAGCCAC

GTGTGGCTTTTTGTATGTACCATACGAATAAGGATCGGCTAACTCCGTGCCAGCAGCCGCGGTAATACGGAGGATC

CGAGCGTTATCCGGATTTATTGGGTTTAAAGGGAGCGTAGGCGGACTATTAAGTCAGCTGTGAAAGTTTGCGGCTC

AACCGTAAAATTGCAGTTGATACTGGTCGTCTTGAGTGCAGTAGAGGTAGGCGGAATTCGTGGTGTAGCGGTGAAA

TGCTTAGATATCACGAAGAACTCCGATTGCGAAGGCAGCTTACTGGACTGTAACTGACGCTGATGCTCGAAAGTGT

GGGTATCAAACAGGATTAGATACCCTGGTAGTCCACACAGTAAACGATGAATACTCGCTGTTTGCGATATACGCA

AGCGGCCAAGCGAAAGCATTAAGTATTCCACCTGGGGAGTACGCCGGCAACGGTGAAACTCAAAGGAATTGACGGG

GGCCCGCACAAGCGGAGGAACATGTGGTTTAATTCGATGATACGCGAGGAACCTTACCCGGGCTTAAATTGCAAAT

GAATATAGTGGAAACATTATAGCCGCAAGGCATTTGTGAAGGTGCTGCATGGTTGTCGTCAGCTCGTGCCGTGAGG

TGTCGGCTTAAGTGCCATAACGAGCGCAACCCTTATCTTTAGTTACTAACAGGTCATGCTGAGGACTCTAGAGAGA

CTGCCGTCGTAAGATGTGAGGAAGGTGGGGATGACGTCAAATCAGCACGGCCCTTACGTCCGGGGCTACACACGTG

TTACAATGGGGGGTACAGAAGGCAGCTACACAGCGATGTGATGCTAATCCCAAAAGCCTCTCTCAGTTCGGATTGG

AGTCTGCAACCCGACTCCATGAAGCTGGATTCGCTAGTAATCGCGCATCAGCCACGGCGCGGTGAATACGTTCCCG

GGCCTTGTACACACCGCCCGTCAAGCCATGAAAGCCGGGGGTACCTGAAGTCCGTAACCGTAAGGAGCGGCCTAGG

GTAAAACTGGTAATTGGGGCTAAGTCGTA

SEQ ID NO: 44 *Bacteroides faecis* Strain 56
CTCAGGATGAACGCTAGCTACAGGCTTAACACATGCAAGTCGAGGGGCAGCATTTCAGTTTGCTTGCAAACTGGAG

ATGGCGACCGGCGCACGGGTGAGTAACACGTATCCAACCTGCCGATAACTCGGGGATAGCCTTTCGAAAGAAAGAT

TAATACCCGATGGCATAATAGAACCGCATGGTTTTTTTATTAAAGAATTTCGGTTATCGATGGGGATGCGTTCCAT

TAGGCAGTTGGTGAGGTAACGGCTCACCAAACCTTCGATGGATAGGGGTTCTGAGAGGAAGGTCCCCCACATTGGA

ACTGAGACACGGTCCAAACTCCTACGGGAGGCAGCAGTGAGGAATATTGGTCAATGGACGAGAGTCTGAACCAGCC

AAGTAGCGTGAAGGATGACTGCCCTATGGGTTGTAAACTTCTTTTATATGGGAATAAAGTTTTCCACGTGTGGAAT

TTTGTATGTACCATATGAATAAGGATCGGCTAACTCCGTGCCAGCAGCCGCGGTAATACGGAGGATCCGAGCGTTA

TCCGGATTTATTGGGTTTAAAGGGAGCGTAGGTGGACAGTTAAGTCAGTTGTGAAAGTTTGCGGCTCAACCGTAAA

ATTGCAGTTGATACTGGCTGTCTTGAGTACAGTAGAGGTGGGCGGAATTCGTGGTGTAGCGGTGAAATGCTTAGAT

-continued

ATCACGAAGAACTCCGATTGCGAAGGCAGCTCACTGGACTGCAACTGACACTGATGCTCGAAAGTGTGGGTATCAA

ACAGGATTAGATACCCTGGTAGTCCACACAGTAAACGATGAATACTCGCTGTTTGCGATATACAGTAAGCGGCCAA

GCGAAAGCATTAAGTATTCCACCTGGGGAGTACGCCGGCAACGGTGAAACTCAAAGGAATTGACGGGGGCCCGCAC

AAGCGGAGGAACATGTGGTTTAATTCGATGATACGCGAGGAACCTTACCCGGGCTTAAATTGCATTTGAATATATT

GGAAACAGTATAGTCGTAAGACAAATGTGAAGGTGCTGCATGGTTGTCGTCAGCTCGTGCCGTGAGGTGTCGGCTT

AAGTGCCATAACGAGCGCAACCCTTATCTTTAGTTACTAACAGGTCATGCTGAGGACTCTAGAGAGACTGCCGTCG

TAAGATGTGAGGAAGGTGGGGATGACGTCAAATCAGCACGGCCCTTACGTCCGGGGCTACACACGTGTTACAATGG

GGGGTACAGAAGGCAGCTACCTGGTGACAGGATGCTAATCCCAAAAGCCTCTCTCAGTTCGGATCGAAGTCTGCAA

CCCGACTTCGTGAAGCTGGATTCGCTAGTAATCGCGCATCAGCCATGGCGCGGTGAATACGTTCCCGGGCCTTGTA

CACACCGCCCGTCAAGCCATGAAAGCCGGGGGTACCTGAAGTACGTAACCGCAAGGAGCGTCCTAGGGTAAAACTG

GTAATTGGGCTAAGTCGTAACAAGGTA

SEQ ID NO: 45 *Bacteroides ovatus* Strain 57
CGATATCCGGATTTATTGGAGTTT-

AAGGGAGCGTAGGTGGATTGTTAAGTCAGTTGTGAAAGTTTGCGGCTCAACCGTAAAATTGCAGTTGAAACTGGCA

GTCTTGAGTACAGTAGAGGTGGGCGGAATTCGTGGTGTAGCGGTGAAATGCTTAGATATCACGAAGAACTCCGATT

GCGAAGGCAGCTCACTAGACTGTCACTGACACTGATGCTCGAAAGTGTGGGTATCAAACAGGATTAGATACCCTGG

TAGTCCACACAGTAAACGATGAATACTCGCTGTTTGCGATATACAGTAAGCGGCCAAGCGAAAGCATTAAGTATTC

CACCTGGGGAGTACGCCGGCAACGGTGAAACTCAAAGGAATTGACGGGGGCCCGCACAAGCGGAGGAACATGTGGT

TTAATTCGATGATACGCGAGGAACCTTACCCGGGCTTAAATTGCAACAGAATATATTGGAAACAGTATAGCCGTAA

GGCTGTTGTGAAGGTGCTGCATGGTTGTCGTCAGCTCGTGCCGTGAGGTGTCGGCTTAAGTGCCATAACGAGCGCA

ACCCTTATCTTTAGTTACTAACAGGTKATGCTGAGGACTCTAGAGAGACTGCCGTCGTAAGATGTGAGGAAGGTGG

GGATGACGTCAAATCAGCACGGCCCTTACGTCCGGGGCTACACACGTGTTACAATGGGGGGTACAGAAGGCSGCTA

CCTGGTGACAGGATGCTAATCCCAAAAACCTCTCTCAGTTCGGATCGAAGTCTGCAACCCGACTTCGTGAAGCTGG

ATTCGCTAGTAATCGCGCATCAGCCATGGCGCGGTGAATACGTTCCCGGGCCTTGTACACACCGCCCGTCAAGCCA

TGAAAGCCGGGGGTACCTGAAGTACGTAACCGCAAGGAGCGTCCTAGGGGTAAAACTGGTAATTGGGGC

SEQ ID NO: 46 *Bacteroides thetaiotaomicron* Strain 58
TTTAAGGGAGCGTAGGTGGACAGTTAAGTCAGTTGTGAAAGTTTGCGGCTCAACCGTAAAATTGCAGTTGATACTG

GCTGTCTTGAGTACAGTAGAGGTGGGCGGAATTCGTGGTGTAGCGGTGAAATGCTTAGATATCACGAAGAACTCCG

ATTGCGAAGGCAGCTCACTGGACTGCAACTGACACTGATGCTCGAAAGTGTGGGTATCAAACAGGATTAGATACCC

TGGTAGTCCACACAGTAAACGATGAATACTCGCTGTTTGCGATATACAGTAAGCGGCCWAGCGAAAGCATTAAGTA

TTCCACCTGGGGAGTACGCCGGCAACGGTGAAACTCAAAGGAATTGACGGGGGCCCGCACAAGCGGAGGAACATGT

GGTTTAATTCGATGATACGCGAGGAACCTTACCCGGGCTTAAATTGCAWWTGAATAWWYTGGAAACAGKWTAGYCG

YAAGRCAWWTGTGAAGGTGCTGCATGGTTGTCGTCAGCTCGTGCCGTGAGGTGTCGGCTTAAGTGCCATAACGAGC

GCAACCCTTATCTTTAGTTACTAACAGGTCATGCTGAGGACTCTAGAGAGACTGCCGTCGTAAGATGTGAGGAAGG

TGGGGATGACGTCAAATCAGCACGGCCCTTACGTCCGGGGCTACACACGTGTTACAATGGGGGGTACAGAAGGCAG

CTACCTGGTGACAGGATGCTAATCCCAAAAGCCTCTCTCAGTTCGGATCGAAGTCTGCAACCCGACTTCGTGAAGC

TGGATTCGCTAGTAATCGCGCATCAGCCATGGCGCGGTGAATACGTTCCCGGGCCTTGTACACACCGCCCGTCAAG

CCATGAAAGCCGGGGGTACCTGAAGTACGTAACCGCA

SEQ ID NO: 47 *Bacteroides uniformis* Strain 59
CTGGCTCAGGATGAACGCTAGCTACAGGCTTAACACATGCAAGTCGAGGGGCAGCATGAACTTAGCTTGCTAAGTT

TGATGGCGACCGGCGCACGGGTGAGTAACACGTATCCAACCTGCCGATGACTCGGGGATAGCCTTTCGAAAGAAAG

ATTAATACCCGATGGCATAGTTCTTCCGCATGGTAGAACTATTAAAGAATTTCGGTCATCGATGGGGATGCGTTCC

-continued

```
ATTAGGTTGTTGGCGGGGTAACGGCCCACCAAGCCTTCGATGGATAGGGGTTCTGAGAGGAAGGTCCCCCACATTG

GAACTGAGACACGGTCCAAACTCCTACGGGAGGCAGCAGTGAGGAATATTGGTCAATGGACGAGAGTCTGAACCAG

CCAAGTAGCGTGAAGGATGACTGCCCTATGGGTTGTAAACTTCTTTTATACGGGAATAAAGTGAGGCACGTGTGCC

TTTTTGTATGTACCGTATGAATAAGGATCGGCTAACTCCGTGCCAGCAGCCGCGGTAATACGGAGGATCCGAGCGT

TATCCGGATTTATTGGGTTTAAAGGGAGCGTAGGCGGACGCTTAAGTCAGTTGTGAAAGTTTGCGGCTCAACCGTA

AAATTGCAGTTGATACTGGGTGTCTTGAGTACAGTAGAGGCAGGCGGAATTCGTGGTGTAGCGGTGAAATGCTTAG

ATATCACGAAGAACTCCGATTGCGAAGGCAGCTTGCTGGACTGTAACTGACGCTGATGCTCGAAAGTGTGGGTATC

AAACAGGATTAGATACCCTGGTAGTCCACACAGTAAACGATGAATACTCGCTGTTTGCGATATACAGTAAGCGGCC

AAGCGAAAGCGTTAAGTATTCCACCTGGGGAGTACGCCGGCAACGGTGAAACTCAAAGGAATTGACGGGGGCCCGC

ACAAGCGGAGGAACATGTGGTTTAATTCGATGATACGCGAGGAACCTTACCCGGGCTTGAATTGCAACTGAATGAT

GTGGAGACATGTCAGCCGCAAGGCAGTTGTGAAGGTGCTGCATGGTTGTCGTCAGCTCGTGCCGTGAGGTGTCGGC

TTAAGTGCCATAACGAGCGCAACCCTTATCGATAGTTACCATCAGGTTATGCTGGGGACTCTGTCGAGACTGCCGT

CGTAAGATGTGAGGAAGGTGGGGATGACGTCAAATCAGCACGGCCCTTACGTCCGGGGCTACACACGTGTTACAAT

GGGGGGTACAGAAGGCAGCTACACGGCGACGTGATGCTAATCCCTAAAGCCTCTCTCAGTTCGGATTGGAGTCTGC

AACCCGACTCCATGAAGCTGGATTCGCTAGTAATCGCGCATCAGCCACGGCGCGGTGAATACGTTCCCGGGCCTTG

TACACACCGCCCGTCAAGCCATGAAAGCCGGGGGTACCTGAAGTGCGTAACCGCGAGGAGCGCCCTAGGGTAAAAC

TGGTGATTGGGGCTAAGTCGTAACAAGGTA

SEQ ID NO: 48 Bacteroides vulgatus Strain 60
ATGAAGAGTTTGATCCTGGCTCAGGATGAACGCTAGCTACAGGCTTAACACATGCAAGTCGAGGGGCAGCATGGTC

TTAGCTTGCTAAGGCCGATGGCGACCGGCGCACGGGTGAGTAACACGTATCCAACCTGCCGTCTACTCTTGGACAG

CCTTCTGAAAGGAAGATTAATACAAGATGGCATCATGAGTTCACATGTTCACATGATTAAAGGTATTCCGGTAGAC

GATGGGGATGCGTTCCATTAGATAGTAGGCGGGGTAACGGCCCACCTAGTCTTCGATGGATAGGGGTTCTGAGAGG

AAGGTCCCCCACATTGGAACTGAGACACGGTCCAAACTCCTACGGGAGGCAGCAGTGAGGAATATTGGTCAATGGG

CGAGAGCCTGAACCAGCCAAGTAGCGTGAAGGATGACTGCCCTATGGGTTGTAAACTTCTTTTATAAAGGAATAAA

GTCGGGTATGCATACCCGTTTGCATGTACTTTATGAATAAGGATCGGCTAACTCCGTGCCAGCAGCCGCGGTAATA

CGGAGGATCCGAGCGTTATCCGGATTTATTGGGTTTAAAGGGAGCGTAGATGGATGTTTAAGTCAGTTGTGAAAGT

TTGCGGCTCAACCGTAAAATTGCAGTTGATACTGGATATCTTGAGTGCAGTTGAGGCAGGCGGAATTCGTGGTGTA

GCGGTGAAATGCTTAGATATCACGAAGAACTCCGATTGCGAAGGCAGCCTGCTAAGCTGCAACTGACATTGAGGCT

CGAAAGTGTGGGTATCAAACAGGATTAGATACCCTGGTAGTCCACACGGTAAACGATGAATACTCGCTGTTTGCGA

TATACGGCAAGCGGCCAAGCGAAAGCGTTAAGTATTCCACCTGGGGAGTACGCCGGCAACGGTGAAACTCAAAGGA

ATTGACGGGGCCCGCACAAGCGGAGGAACATGTGGTTTAATTCGATGATACGCGAGGAACCTTACCCGGGCTTAA

ATTGCAGATGAATTACGGTGAAAGCCGTAAGCCGCAAGGCATCTGTGAAGGTGCTGCATGGTTGTCGTCAGCTCGT

GCCGTGAGGTGTCGGCTTAAGTGCCATAACGAGCGCAACCCTTGTTGTCAGTTACTAACAGGTTCCGCTGAGGACT

CTGACAAGACTGCCATCGTAAGATGTGAGGAAGGTGGGGATGACGTCAAATCAGCACGGCCCTTACGTCCGGGGCT

ACACACGTGTTACAATGGGGGGTACAGAGGGCCGCTACCACGCGAGTGGATGCCAATCCCAAAAACCTCTCTCAGT

TCGGACTGGAGTCTGCAACCCGACTCCACGAAGCTGGATTCGCTAGTAATCGCGCATCAGCCACGGCGCGGTGAAT

ACGTTCCCGGGCCTTGTACACACCGCCCGTCAAGCCATGGGAGCCGGGGGTACCTGAAGTGCGTAACCGCGAGGAG

CGCCCTAGGGTAAAACTGGTGACTGGGGCTAAGTCGTAACAAGGTAGCCGTACCGGAAG

SEQ ID NO: 49 Bifidobacterium adolescentis Strain 61
GGGCTCGTAGKCGGTTCGTCGCGTCCGGTGTGAAAGTCCAYCGCTTAACGGTGGATCCGCGCCGGGTACGGGCGGG

CTTGAGTGCGGTAGGGGAGACTGGAATTCCCGGTGTAACGGTGGAATGTGTAGATATCGGGAAGAACACCAATGGC
```

-continued

GAAGGCAGGTCTCTGGGCCGTCACTGACGCTGAGGAGCGAAAGCGTGGGGAGCGAACAGGATTAGATACCCTGGTA

GTCCACGCCGTAAACGGTGGATGCTGGATGTGGGGACCATTCCACGGTCTCCGTGTCGGAGCCAACGCGTTAAGCA

TCCCGCCTGGGGAGTACGGCCGCAAGGCTAAAACTCAAAGAAATTGACGGGGGCCCGCACAAGCGGCGGAGCATGC

GGATTAATTCGATGCAACGCGAAGAACCTTACCTGGGCTTGACATGTTCCCGACAGCCCCAGAGATGGGGCCTCCC

TTCGGGGCGGGTTCACAGGTGGTGCATGGTCGTCGTCAGCTCGTGTCGTGAGATGTTGGGTTAAGTCCCGCAACGA

GCGCAACCCTCGCCCTGTGTTGCCAGCACGTCGTGGTGGGAACTCACGGGGACCGCCGGGGTCAACTCGGAGGAA

GGTGGGGATGACGTCAGATCATCATGCCCCTTACGTCCAGGGCTTCACGCATGCTACAATGGCCGGTACAACGGGA

TGCGACACT-

GTGAGGTGGAGCGGATCCCTTAAAACCGGTCTCAGTTCGGATTGGAGTCTGCAACCCGACTCCATGAAGGCGGAGT

CGCTAGTAATCGCGGATCAGCAACGCCGCGGTGAATGCGTTCCCGGGCCTTGTACACACCGCCCGTCAAGTCATGA

AAGTGGGTAGCACCCGAAGCCGGTGGCCCATCCTTTTTGGGG

SEQ ID NO: 50 *Bifidobacterium longum* Strain 62
TGGCTCAGGATGAACGCTGGCGGCGTGCTTAACACATGCAAGTCGAACGGGATCCATCAGGCTTTGCTTGGTGGTG

AGAGTGGCGAACGGGTGAGTAATGCGTGACCGACCTGCCCCATACACCGGAATAGCTCCTGGAAACGGGTGGTAAT

GCCGGATGCTCCAGTTGATCGCATGGTCTTCTGGGAAAGCTTTCGCGGTATGGGATGGGGTCGCGTCCTATCAGCT

TGACGGCGGGGTAACGGCCCACCGTGGCTTCGACGGGTAGCCGGCCTGAGAGGGCGACCGGCCACATTGGGACTGA

GATACGGCCCAGACTCCTACGGGAGGCAGCAGTGGGGAATATTGCACAATGGGCGCAAGCCTGATGCAGCGACGCC

GCGTGAGGGATGGAGGCCTTCGGGTTGTAAACCTCTTTTATCGGGGAGCAAGCGAGAGTGAGTTTACCCGTTGAAT

AAGCACCGGCTAACTACGTGCCAGCAGCCGCGGTAATACGTAGGGTGCAAGCGTTATCCGGAATTATTGGGCGTAA

AGGGCTCGTAGGCGGTTCGTCGCGTCCGGTGTGAAAGTCCATCGCTTAACGGTGGATCCGCGCCGGGTACGGGCGG

GCTTGAGTGCGGTAGGGGAGACTGGAATTCCCGGTGTAACGGTGGAATGTGTAGATATCGGGAAGAACACCAATGG

CGAAGGCAGGTCTCTGGGCCGTTACTGACGCTGAGGAGCGAAAGCGTGGGGAGCGAACAGGATTAGATACCCTGGT

AGTCCACGCCGTAAACGGTGGATGCTGGATGTGGGGCCCGTTCCACGGGTTCCGTGTCGGAGCTAACGCGTTAAGC

ATCCCGCCTGGGGAGTACGGCCGCAAGGCTAAAACTCAAAGAAATTGACGGGGGCCCGCACAAGCGGCGGAGCATG

CGGATTAATTCGATGCAACGCGAAGAACCTTACCTGGGCTTGACATGTTCCCGACGGTCGTAGAGATACGGCTTCC

CTTCGGGGCGGGTTCACAGGTGGTGCATGGTCGTCGTCAGCTCGTGTCGTGAGATGTTGGGTTAAGTCCCGCAACG

AGCGCAACCCTCGCCCCGTGTTGCCAGCGGATTATGCCGGGAACTCACGGGGACCGCCGGGGTTAACTCGGAGGA

AGGTGGGGATGACGTCAGATCATCATGCCCCTTACGTCCAGGGCTTCACGCATGCTACAATGGCCGGTACAACGGG

ATGCGACGCGGCGACGCGGAGCGGATCCCTGAAAACCGGTCTCAGTTCGGATCGCAGTCTGCAACTCGACTGCGTG

AAGGCGGAGTCGCTAGTAATCGCGAATCAGCAACGTCGCGGTGAATGCGTTCCCGGGCCTTGTACACACCGCCCGT

CAAGTCATGAAAGTGGGCAGCACCCGAAGCCGGTGGCCTAACCCCTTGTGGGATGGAGCCGTCTAAGGTGAGGCTC

GTGATTGGGACTAAGTCGTAACAAGGTAGCCGTACCGGAAGGTGCGGCTGG

SEQ ID NO: 51 *Bifidobacterium pseudocatenulatum* Strain 63
GGTTCGTCGCGTCCGGTGTGAAAGTCCATCGTTTAACGGTGGATCTGCGCCGGGTACGGGCGGGCTGGAGTGCGGT

AGGGGAGACTGGAATTCCCGGTGTAACGGTGGAATGTGTAGATATCGGGAAGAACACCAATGGCGAAGGCAGGTCT

CTGGGCCGTTACTGACGCTGAGGAGCGAAAGCGTGGGGAGCGAACAGGATTAGATACCCTGGTAGTCCACGCCGTA

AACGGTGGATGCTGGATGTGGGGCCCGTTCCACGGGTTCCGTGWCGGAGCTAACGCGTTAAGCATCCCGCCTGGGG

AGTACGGCCGCAAGGCTAAAACWMAAAKAAATTGACGGGGGCCCGCACAAGCGGCGGAGCATGCGGATTAATTCGA

TGCAACGCGAAGAACCTTACCTGGGCTTGACATGTTCCCGACAGCCGTAGAGATATGGCCTCCCTTCGGGGCGGGT

TCACAGGTGGTGCATGGTCGTCGTCAGCTCGTGTCGTGAGATGTTGGGTTAAGTCCCGCAACGAGCGCAACCCTCG

-continued

CCCTGTGTTGCCAGCACGTCATGGTGGGAACTCACGGGGACCGCCGGGGTCAACTCGGAGGAAGGTGGGGATGAC

GTCAGATCATCATGCCCCTTACGTTCAGGGCTTCACGCATGCTACAATGGCCGGTACAACGGGATGCGACACGGCG

ACGTG

SEQ ID NO: 52 Blautia coccoides Strain 64
TGTGACTGAGCGGCGGACGGGTGAGTAACGCGTGGGTAACCTGCCTCATACAGGGGGATAACAGTTAGAAATGACT

GCTAATACCGCATAAGCGCACAGGACCGCATGGTCTGGTGTGAAAAACTCCGGTGGTATGAGATGGACCCGCGTCT

GATTAGCTAGTTGGAGGGGTAACGGCCCACCAAGGCGACGATCAGTAGCCGGCCTGAGAGGGTGAACGGCCACATT

GGGACTGAGACACGGCCCAGACTCCTACGGGAGGCAGCAGTGGGGAATATTGCACAATGGGGGAAACCCTGATGCA

GCGACGCCGCGTGAAGGAAGAAGTATCTCGGTATGTAAACTTCTATCAGCAGGGAAGAAAATGACGGTACCTGACT

AAGAAGCCCCGGCTAACTACGTGCCAGCAGCCGCGGTAATACGTAGGGGGCAAGCGTTATCCGGATTTACTGGGTG

TAAAGGGAGCGTAGACGGAAGAGCAAGTCTGATGTGAAAGGCTGGGGCTTAACCCCAGGACTGCATTGGAAACTGT

TGTTCTAGAGTGCCGGAGAGGTAAGCGGAATTCCTAGTGTAGCGGTGAAATGCGTAGATATTAGGAGGAACACCAG

TGGCGAAGGCGGCTTACTGGACGGTAACTGACGTTGAGGCTCGAAAGCGTGGGGAGCAAACAGGATTAGATACCCT

GGTAGTCCACGCCGTAAACGATGAATACTAGGTGTCGGGTGGCAAAGCCATTCGGTGCCGCAGCAAACGCAATAAG

TATTCCACCTGGGGAGTACGTTCGCAAGAATGAAACTCAAAGGAATTGACGGGACCCGCACAAGCGGTGGAGCAT

GTGGTTTAATTCGAAGCAACGCGAAGAACCTTACCAAGTCTTGACATCCCTCTGACCGTCCCGTAACGGGGCTTC

CCTTCGGGGCAGAGGAGACAGGTGGTGCATGGTTGTCGTCAGCTCGTGTCGTGAGATGTTGGGTTAAGTCCCGCAA

CGAGCGCAACCCTTATCCTTAGTAGCCAGCACATGATGGTGGGCACTCTAGGGAGACTGCCGGGGATAACCCGGAG

GAAGGCGGGGACGACGTCAAATCATCATGCCCCTTATGATTTGGGCTACACACGTGCTACAATGGCGTAAACAAAG

GGAAGCGAGACAGCGATGTTGAGCGAATCCCAAAAATAACGTCCCAGTTCGGACTGCAGTCTGCAACTCGACTGCA

CGAAGCTGGAATCGCTAGTAATCGCGGATCAGAATGCCGCGGTGAATACGTTCCCGGGTCTTGTACACACCGCCCG

TCACACCATGGGAGTCAGTAACGCCCGAAGTCAGTGACCTAACCGAAAGGAAGGAGCTGCCGAAGGCGGGACCGAT

AACTGGGGTGAAGTCGTAACAAGGTA

SEQ ID NO: 53 Clostridium citroniae Strain 65
TCCGGATTTACTGGAGTAGT-

AAGGGAGCGTAGACGGCGAAGCAAGTCTGGAGTGAAAACCCAGGGCTCAACCCTGGGACTGCTTTGGAAACTGTTT

TGCTAGAGTGTCGGAGAGGTAAGTGGAATTCCTAGTGTAGCGGTGAAATGCGTAGATATTAGGAGGAACACCAGTG

GCGAAGGCGGCTTACTGGACGATAACTGACGTTGAGGCTCGAAAGCGTGGGGAGCAAACAGGATTAGATACCCTGG

TAGTCCACGCCGTAAACGATGAATGCTAGGTGTTGGGGGGCAAAGCCCTTCGGTGCCGTCGCAAACGCAATAAGCA

TTCCACCTGGGGAGTACGTTCGCAAGAATGAAACTCAAAGGAATTGACGGGGACCCGCACAAGCGGTGGAGCATGT

GGTTTAATTCGAAGCAACGCGAAGAACCTTACCAAGTCTTGACATCCCCCTGACCGGTCAGTAAAGTGACCTTTCC

TTCGGGACAGGGGAGACAGGTGGTGCATGGTTGTCGTCAGCTCGTGTCGTGAGATGTTGGGTTAAGTCCCGCAACG

AGCGCAACCCTTATCCTTAGTAGCCAGCAGGTAAAGCTGGGCACTCTAGGGAGACTGCCAGGGATAACCTGGAGGA

AGGTGGGGATGACGTCAAATCATCATGCCCCTTATGATTTGGGCTACACACGTGCTACAATGGCGTAAACAAAGGG

AAGCGACCCTGCGAAGGCAAGCAAATCCCAAAAATAACGTCCCAGTTCGGACTGTAGTCTGCAACCCGACTACACG

AAGCTGGAATCGCTAGTAATCGCGAATCAGAATGTCGCGGTGAATACGTTCCCGGGTCTTGTACACACCGCCCGTC

ACACCATGGGAGTCAGCAACGCCCGAAGTCAGTGACCCAACCGAAAGGAGGGAGCTGCCGAA

SEQ ID NO: 54 *Clostridium clostridioforme* Strain 66

TAATACCGCATAAGCGCACAGTGCCGCATGGCAGTGTGTGAAAAACTCCGGTGGTGTGAGATGGATCCGCGTCTGA

TTAGCCAGTTGGCGGGGTAACGGCCCACCAAAGCGACGATCAGTAGCCGACCTGAGAGGGTGACCGGCCACATTGG

GACTGAGACACGGCCCAAACTCCTACGGGAGGCAGCAGTGGGGAATATTGCACAATGGGCGAAAGCCTGATGCAGC

GACGCCGCGTGAGTGAAGAAGTATTTCGGTATGTAAAGCTCTATCAGCAGGGAAGAAAATGACGGTACCTGACTAA

-continued

GAAGCCCCGGCTAACTACGTGCCAGCAGCCGCGGTAATACGTAGGGGGCAAGCGTTATCCGGATTTACTGGGTGTA

AAGGGAGCGTAGACGGCGAAGCAAGTCTGAAGTGAAAACCCGGGGCTCAACCCTGGGACTGCTTTGGAAACTGTTT

TGCTAGAGTGTCGGAGAGGTAAGTGGAATTCCTAGTGTAGCGGTGAAATGCGTAGATATTAGGAGGAACACCAGTG

GCGAAGGCGGCTTACTGGACGATAACTGACGTTGAGGCTCGAAAGCGTGGGGAGCAAACAGGATTAGATACCCTGG

TAGTCCACGCCGTAAACGATGAATGCTAGGTGTTGGGGGCAAAGCCCTTCGGTGCCGCCGCAAACGCAGTAAGCA

TTCCACCTGGGGAGTACGTTCGCAAGAATGAAACTCAAAGGAATTGACGGGGACCCGCACAAGCGGTGGAGCATGT

GGTTTAATTCGAAGCAACGCGAAGAACCTTACCAAGTCTTGACATCCCCCTGACGGGCCGGTAACGCGGCCTTTCC

TTCGGGACAGGGGAGACAGGTGGTGCATGGTTGTCGTCAGCTCGTGTCGTGAGATGTTGGGTTAAGTCCCGCAACG

AGCGCAACCCTTATCCTTAGTAGCCAGCAGGTAGAGCCGGGCACTCTAGGGAGACTGCCAGGGATAACCTGGAGGA

AGGTGGGGATGACGTCAAATCATCATGCCCCTTATGATTTGGGCTACACACGTGCTACAATGGCGTAAACAAAGGG

AAGCGAGACAGTGATGTGGAGCAAATCCCAAAAATAACGTCCCAGTTCGGACTGTAGTCTGCAACCCGACTACACG

AAGCTGGAATCGCTAGTAATCGCGAATCAGAATGTCGCGGTGAATACGTTCCCGGGTCTTGTACACACCGCCCGTC

ACACCATGGGAGTCAGCAACGCCCGAAGTCAGTGACCCAACCGAAAGGAGGGAGCTGCCGAAGGCGGGGCAGGTAA

CTGGGGTGAAGTCGT

SEQ ID NO: 55 Clostridium innocuum Strain 67
ATGGAGAGTTTGATCCTGGCTCAGGATGAACGCTGGCGGCATGCCTAATACATGCAAGTCGAACGAAGT-

TTCGAGGAAGCTTGCTTCCAAAGAGACTTAGTGGCGAACGGGTGAGTAACACGTAGGTAACCTGCCCATGTGTCCG

GGATAACTGCTGGAAACGGTAGCTAAAACCGGATAGGTATACAGAGCGCATGCTCAGTATATTAAAGCGCCCATCA

AGGCGTGAACATGGATGGACCTGCGGCGCATTAGCTAGTTGGTGAGGTAACGGCCCACCAAGGCGATGATGCGTAG

CCGGCCTGAGAGGGTAAACGGCCACATTGGGACTGAGACACGGCCCAAACTCCTACGGGAGGCAGCAGTAGGGAAT

TTTCGTCAATGGGGGAAACCCTGAACGAGCAATGCCGCGTGAGTGAAGAAGGTCTTCGGATCGTAAAGCTCTGTTG

TAAGTGAAGAACGGCTCATAGAGGAAATGCTATGGGAGTGACGGTAGCTTACCAGAAAGCCACGGCTAACTACGTG

CCAGCAGCCGCGGTAATACGTAGGTGGCAAGCGTTATCCGGAATCATTGGGCGTAAAGGGTGCGTAGGTGGCGTAC

TAAGTCTGTAGTAAAAGGCAATGGCTCAACCATTGTAAGCTATGGAAACTGGTATGCTGGAGTGCAGAAGAGGGCG

ATGGAATTCCATGTGTAGCGGTAAAATGCGTAGATATATGGAGGAACACCAGTGGCGAAGGCGGTCGCCTGGTCTG

TAACTGACACTGAGGCACGAAAGCGTGGGGAGCAAATAGGATTAGATACCCTAGTAGTCCACGCCGTAAACGATGA

GAACTAAGTGTTGGAGGAATTCAGTGCTGCAGTTAACGCAATAAGTTCTCCGCCTGGGGAGTATGCACGCAAGTGT

GAAACTCAAAGGAATTGACGGGGCCCGCACAAGCGGTGGAGTATGTGGTTTAATTCGAAGCAACGCGAAGAACCT

TACCAGGCCTTGACATGGAAACAAATACCCTAGAGATAGGGGGATAATTATGGATCACACAGGTGGTGCATGGTTG

TCGTCAGCTCGTGTCGTGAGATGTTGGGTTAAGTCCCGCAACGAGCGCAACCCTTGTCGCATGTTACCAGCATCAA

GTTGGGACTCATGCGAGACTGCCGGTGACAAACCGGAGGAAGGTGGGGATGACGTCAAATCATCATGCCCCTTAT

GGCCTGGGCTACACACGTACTACAATGGCGGCCACAAAGAGCAGCGACACAGTGATGTGAAGCGAATCTCATAAAG

GTCGTCTCAGTTCGGATTGAAGTCTGCAACTCGACTTCATGAAGTCGGAATCGCTAGTAATCGCAGATCAGCATGC

TGCGGTGAATACGTTCTCGGGCCTTGTACACACCGCCCGTCAAACCATGGGAGTCAGTAATACCCGAAGCCGGTGG

CATAACCGTAAGGAGTGAGCCGTCGAAGGTAGGACCGA

SEQ ID NO: 56 Clostridium innocuum Strain 68
ATGGAGAGTTTGATCCTGGCTCAGGATGAACGCTGGCGGCATGCCTAATACATGCAAGTCGAACGAAGT-

TTCGAGGAAGCTTGCTTCCAAAGAGACTTAGTGGCGAACGGGTGAGTAACACGTAGGTAACCTGCCCATGTGTCCG

GGATAACTGCTGGAAACGGTAGCTAAAACCGGATAGGTATACAGAGCGCATGCTCAGTATATTAAAGCGCCCATCA

AGGCGTGAACATGGATGGACCTGCGGCGCATTAGCTAGTTGGTGAGGTAACGGCCCACCAAGGCGATGATGCGTAG

CCGGCCTGAGAGGGTAAACGGCCACATTGGGACTGAGACACGGCCCAAACTCCTACGGGAGGCAGCAGTAGGGAAT

TTTCGTCAATGGGGGAAACCCTGAACGAGCAATGCCGCGTGAGTGAAGAAGGTCTTCGGATCGTAAAGCTCTGTTG

-continued

```
TAAGTGAAGAACGGCTCATAGAGGAAATGCTATGGGAGTGACGGTAGCTTACCAGAAAGCCACGGCTAACTACGTG

CCAGCAGCCGCGGTAATACGTAGGTGGCAAGCGTTATCCGGAATCATTGGGCGTAAAGGGTGCGTAGGTGGCGTAC

TAAGTCTGTAGTAAAAGGCAATGGCTCAACCATTGTAAGCTATGGAAACTGGTATGCTGGAGTGCAGAAGAGGGCG

ATGGAATTCCATGTGTAGCGGTAAAATGCGTAGATATATGGAGGAACACCAGTGGCGAAGGCGGTCGCCTGGTCTG

TAACTGACACTGAGGCACGAAAGCGTGGGGAGCAAATAGGATTAGATACCCTAGTAGTCCACGCCGTAAACGATGA

GAACTAAGTGTTGGAGGAATTCAGTGCTGCAGTTAACGCAATAAGTTCTCCGCCTGGGGAGTATGCACGCAAGTGT

GAAACTCAAAGGAATTGACGGGGGCCCGCACAAGCGGTGGAGTATGTGGTTTAATTCGAAGCAACGCGAAGAACCT

TACCAGGCCTTGACATGGAAACAAATACCCTAGAGATAGGGGGATAATTATGGATCACACAGGTGGTGCATGGTTG

TCGTCAGCTCGTGTCGTGAGATGTTGGGTTAAGTCCCGCAACGAGCGCAACCCTTGTCGCATGTTACCAGCATCAA

GTTGGGGACTCATGCGAGACTGCCGGTGACAAACCGGAGGAAGGTGGGGATGACGTCAAATCATCATGCCCCTTAT

GGCCTGGGCTACACACGTACTACAATGGCGACCACAAAGAGCAGCGACACAGTGATGTGAAGCGAATCTCATAAAG

GTCGTCTCAGTTCGGATTGAAGTCTGCAACTCGACTTCATGAAGTCGGAATCGCTAGTAATCGCAGATCAGCATGC

TGCGGTGAATACGTTCTCGGGCCTTGTACACACCGCCCGTCAAACCATGGGAGTCAGTAATACCCGAAGCCGGTGG

CATAACCGTAAGGAGTGAGCCGTCGAAGGTAGGACCGA

SEQ ID NO: 57 *Clostridium sordellii* Strain 69
ACACATGCAAGTCGAGCGAACCCTTCGGGGTGAGCGGCGGACGGGTGAGTAACGCGTGGGTAACCTGCCCTGTACA
```

CACGGATAACATACCGAAAGGTATGCTAATACGGGATRAYATATGAGAGTCGCATGGCTTTTGTATCAAAGCTCCG

GCGGTACAGGATGGACCCGCGTCTGATTAGCTAGTTGGTAAGGTAACGGCTTACCAAGGCAACGATCAGTAGCCGA

CCTGAGAGGGTGATCGGCCACATTGGAACTGAGACACGGTCCAAACTCMTACGGGAGGCAGCAGTGGGGAATATTG

CACAATGGGCGAAAGCCTGATGCAGCAACGCCGCGTGAGCGATGAAGGCCTTCGGGTCGTAAAGCTCTGTCCTCAA

GGAAGATAATGACGGTACTTGAGGAGGAAGCCCCGGCTAACTACGTGCCAGCAGCCGCGGTAATACGTAGGGGGCT

AGCGTTATCCGGAATTACTGGGCGTAAAGGGTGCGTAGGCGGTCTTTCAAGCCAGAAGTGAAAGGCTACGGCTCAA

CCGTAGTAAGCTTTTGGAACTGTAGGACTTGAGTGCAGGAGAGGAGAGTGGAATTCCTAGTGTAGCGGTGAAATGC

GTAGATATTAGGAGGAACACCAGTAGCGAAGGCGGCTCTCTGGACTGTAACTGACGCTGAGGCACGAAAGCGTGGG

GAGCAAACAGGATTAGATACCCTGGTAGTCCACGCCGTAAACGATGAGTACTAGGTGTCGGGGGTTACCCCCCTCG

GTGCCGCAGCTAACGCATTAAGTACTCCGCCTGGGAAGTACGCTCGCAAGAGTGAAACTCAAAGGAATTGACGGGG

ACCCGCACAAGTAGCGGAGCATGTGGTTTAATTCGAAGCAACGCGAAGAACCTTATCTAARCTTGACATC

SEQ ID NO: 58 *Coprococcus comes* Strain 70
ACRGGAGGCAGCAGTGGGGAATATTGCACAATGGGGGAAACCCTGATGCAGCGACGCCRCGTGAGCGAAGAAGTAT

TKCGGTATGTAAAGCTCTATCAGCAGGGAAGAAAATGACGGTACCTGACTAAGAAGCACCGGCTAAATACGTGCCA

GCAGCCGCGGTAATACGTATGGTGCAAGCGTTATCCGGATTTACTGGGTGTAAAGGGAGCGTAGACGGCTGTGTAA

GTCTGAAGTGAAAGGCGGGGGCTCCCCCCCGGGGACTGCTTTGGAAACTATGCAGCTAGACTGTCGGACAGGTAAG

TGGAATTCCCAGTGTAGCGGTGAAATGCGTAGATATTGGGAGGAACAGCAKTGGGTAAGGCTSCTTACAGGACRAT

SEQ ID NO: 59 *Dorea longicatena* Strain 71
TAACGCGTGGGTAACCTGCCTCATACAGGGGGATAACAGTTAGAAATGACTGCTAATACCGCATAAGACCACGGTA

CCGCATGGTACAGTGGTAAAAACTCCGGTGGTATGAGATGGACCCGCGTCTGATTAGGTAGTTGGTGGGGTAACGG

CCTACCAAGCCGACGATCAGTAGCCGACCTGAGAGGGTGACCGGCCACATTGGGACTGAGACACGGCCCAGACTCC

TACGGGAGGCAGCAGTGGGGAATATTGCACAATGGAGGAAACTCTGATGCAGCGACGCCGCGTGAAGGATGAAGTA

TTTCGGTATGTAAACTTCTATCAGCAGGGAAGAAAATGACGGTACCTGACTAAGAAGCCCCGGCTAACTACGTGCC

AGCAGCCGCGGTAATACGTAGGGGGCAAGCGTTATCCGGATTTACTGGGTGTAAAGGGAGCGTAGACGGCACGGCA

AGCCAGATGTG-

AAAGCCCGGGGCTCAACCCCGGGACTGCATTTGGAACTGCTGAGCTAGAGTGTCGGAGAGGCAAGTGGAATTCCTA

-continued

GTGTAGCGGTGAAATGCGTAGATATTAGGAGGAACACCAGTGGCGAAGGCGGCTTGCTGGACGATGACTGACGTTG

AGGCTCGAAAGCGTGGGGAGCAAACAGGATTAGATACCCTGGTAGTCCACGCCGTAAACGATGACTGCTAGGTGTC

GGGTGGCAAAGCCATTCGGTGCCGCAGCTAACGCAATAAGCAGTCCACCTGGGGAGTACGTTCGCAAGAATGAAAC

TCAAAGGAATTGACGGGGACCCGCACAAGCGGTGGAGCATGTGGTTTAATTCGAAGCAACGCGAAGAACCTTACCT

GATCTTGACATCCCGATGACCGCTTCGTAATGGAAGCTTTTCTTCGGAACATCGGTGACAGGTGGTGCATGGTTGT

CGTCAGCTCGTGTCGTGAGATGTTGGGTTAAGTCCCGCAACGAGCGCAACCCCTATCTTCAGTAGCCAGCAGGTTA

AGCTGGGCACTCTGGAGAGACTGCCAGGGATAACCTGGAGGAAGGTGGGGATGACGTCAAATCATCATGCCCCTTA

TGACCAGGGCTACACACGTGCTACAATGGCGTAAACAAAGAGAAGCGAACTCGCGAGGGTAAGCAAATCTCAAAAA

TAACGTCTCAGTTCGGATTGTAGTCTGCAACTCGACTACATGAAGCTGGAATCGCTAGTAATCGCAGATCAGAATG

CTGCGGTGAATACGTTCCCGGGTCTTGTACACACCGCCCGTCACACCATGGGAGTCAGTAACGCCCGAAGTCAGTG

ACCCAACCGTAAGG

SEQ ID NO: 60 *Erysipelatoclostridium ramosum* Strain 72
GAGGGAGCAGGCGGCAGCAAGGGTCTGTGGTGAAAGCCTGAAGTTAAACTTCAGTAAGCCATAGAAACCAGGCAGC

TAGAGTGCAGGAGAGGAKCGTGGAATTCCATGTGTAGCGGTGAAATGCGTAGATATATGGAGGAACACCAGTGGCG

AAGGCGACGATCTGGCCTGCAACTGACGCTCAGTCCCGAAAGCGTGGGGAGCAAATAGGATTAGATACCCTAGTAG

TCCACGCCGTAAACGATGAGTACTRAGTGTTGGATGTCAAAGTTCAGTGCTGCAGTTAACGCAATAAGTACTCCGC

CTGAGTAGTACGTTCGCAAGAATGAAACTCAAAGGAATTGACGGGGCCCGCACAAGCGGTGGAGCATGTGGTTTA

ATTCGAAGCAACGCGAAGAACCTTACCAGGTCTTGACATACTCATAAAGGCTCCAGAGATGGAGAGATAGCTATAT

GAGATACAGGTGGTGCATGGTTGTCGTCAGCTCGTGTCGTGAGATGTTGGGTTAAGTCCCGCAACGAGCGCAACCC

TTATCGTTAGTTACCATCATTAAGTTGGGGACTCTAGCGAGACTGCCAGTGACAAGCTGGAGGAARGCGGGGATGA

CGTCAAATCATCATGCCCCTTATGACCTGGGCTACACACGTGCTACAATGGATGGTGCAGAGGGAAGCGAAGCCGC

GAGGTGAAGCAAAACCCATAAAACCATTCTCAGTTCGGATTGTAGTCTGCARCTCGACTACATGAAGTTGGAATCG

CTAGTAATCGCGAATCARCATGTCGCGATGAATAMGTTCTCGGGCCTT

SEQ ID NO: 61 *Eubacterium rectale* Strain 73
AGAGTTTGATCCTGGCTCAGGATGAACGCTGGCGGCGTGCTTAACACATGCAAGTCGAACGAAGCACTTTATTTGA

TTTCCTTCGGGACTGATTATTTTGTGACTGAGTGGCGGACGGGTGAGTAACGCGTGGGTAACCTGCCTTGTACAGG

GGGATAACAGTTGGAAACGGCTGCTAATACCGCATAAGCGCACGGCATCGCATGATGCAGTGTGAAAAACTCCGGT

GGTATAAGATGGACCCGCGTTGGATTAGCTAGTTGGTGAGGTAACGGCCCACCAAGGCGACGATCCATAGCCGACC

TGAGAGGGTGACCGGCCACATTGGGACTGAGACACGGCCCAAACTCCTACGGGAGGCAGCAGTGGGGAATATTGCA

CAATGGGCGAAAGCCTGATGCAGCGACGCCGCGTGAGCGAAGAAGTATTTCGGTATGTAAAGCTCTATCAGCAGGG

AAGATAATGACGGTACCTGACTAAGAAGCACCGGCTAAATACGTGCCAGCAGCCGCGGTAATACGTATGGTGCAAG

CGTTATCCGGATTTACTGGGTGTAAAGGGAGCGCAGGCGGTGCGGCAAGTCTGATGTGAAAGCCCGGGGCTCAACC

CCGGTACTGCATTGGAAACTGTCGTACTAGAGTGTCGGAGGGGTAAGCGGAATTCCTAGTGTAGCGGTGAAATGCG

TAGATATTAGGAGGAACACCAGTGGCGAAGGCGGCTTACTGGACGATAACTGACGCTGAGGCTCGAAAGCGTGGGG

AGCAAACAGGATTAGATACCCTGGTAGTCCACGCCGTAAACGATGAATACTAGGTGTTGGGAAGCATTGCTTCTCG

GTGCCGTCGCAAACGCAGTAAGTATTCCACCTGGGGAGTACGTTCGCAAGAATGAAACTCAAAGGAATTGACGGGG

ACCCGCACAAGCGGTGGAGCATGTGGTTTAATTCGAAGCAACGCGAAGAACCTTACCAAGTCTTGACATCCTTCTG

ACCGGTACTTAACCGTACCTTCTCTTCGGAGCAGGAGTGACAGGTGGTGCATGGTTGTCGTCAGCTCGTGTCGTGA

GATGTTGGGTTAAGTCCCGCAACGAGCGCAACCCTTATCTTTAGTAGCCAGCGGTTCGGCCGGGCACTCTAGAGAG

ACTGCCAGGGATAACCTGGAGGAAGGCGGGGATGACGTCAAATCATCATGCCCCTTATGACTTGGGCTACACACGT

GCTACAATGGCGTAAACAAAGGGAAGCAAAGCTGTGAAGCCGAGCAAATCTCAAAAATAACGTCTCAGTTCGGACT

-continued

GTAGTCTGCAACCCGACTACACGAAGCTGGAATCGCTAGTAATCGCAGATCAGAATGCTGCGGTGAATACGTTCCC

GGGTCTTGTACACACCGCCCGTCACACCATGGGAGTTGGGAATGCCCGAAGCCAGTGACCTAACCGAAAGGAAGGA

GCTGTCGAAGGCAGGCTCGATAACTGGGGTGAAGTCGTAACAAGGTAGCCGTATCGGAAGGTGCGGCTGGATCACC

T

SEQ ID NO: 62 *Odoribacter splanchnicus* Strain 74
AGAGTTTGATCCTGGCTCAGGATGAACGCTAGCGACAGGCTTAACACATGCAAGTCGAGGGGCATCATGAGGTAGC

AATACCTTGATGGCGACCGGCGCACGGGTGAGTAACGCGTATGCAACCTGCCCGATACCGGGGTATAGCCCATGGA

AACGTGGATTAACACCCCATAGTACTTTTATCCTGCATGGGATGTGAGTTAAATGTTTAAGGTATCGGATGGGCAT

GCGTCCTATTAGTTAGTTGGCGGGGTAACAGCCCACCAAGACGATGATAGGTAGGGGTTCTGAGAGGAAGGTCCCC

CACATTGGAACTGAGACACGGTCCAAACTCCTACGGGAGGCAGCAGTGAGGAATATTGGTCAATGGACGAGAGTCT

GAACCAGCCAAGTCGCGTGAGGGAAGACTGCCCTATGGGTTGTAAACCTCTTTTATAAGGGAAGAATAAGTTCTAC

GTGTAGAATGATGCCTGTACCTTATGAATAAGCATCGGCTAACTCCGTGCCAGCAGCCGCGGTAATACGGAGGATG

CGAGCGTTATCCGGATTTATTGGGTTTAAAGGGTGCGTAGGCGGTTTATTAAGTTAGTGGTTAAATATTTGAGCTA

AACTCAATTGTGCCATTAATACTGGTAAACTGGAGTACAGACGAGGTAGGCGGAATAAGTTAAGTAGCGGTGAAAT

GCATAGATATAACTTAGAACTCCGATAGCGAAGGCAGCTTACCAGACTGTAACTGACGCTGATGCACGAGAGCGTG

GGTAGCGAACAGGATTAGATACCCTGGTAGTCCACGCCGTAAACGATGCTCACTGGTTCTGTGCGATATATTGTAC

GGGATTAAGCGAAAGTATTAAGTGAGCCACCTGGGGAGTACGTCGGCAACGATGAAACTCAAAGGAATTGACGGGG

GCCCGCACAAGCGGAGGAACATGTGGTTTAATTCGATGATACGCGAGGAACCTTACCTGGGTTTAAATGGGAAATG

TCGTATTTGGAAACAGATATTCTCTTCGGAGCGTTTTTCAAGGTGCTGCATGGTTGTCGTCAGCTCGTGCCGTGAG

GTGTCGGGTTAAGTCCCATAACGAGCGCAACCCTTACCGTTAGTTGCTAGCATGTAATGATGAGCACTCTAACGGG

ACTGCCACCGTAAGGTGAGAGGAAGGCGGGGATGACGTCAAATCAGCACGGCCCTTACACCCAGGGCTACACACGT

GTTACAATGGCCGGTACAGAGGGCCGCTACCAGGTGACTGGATGCCAATCTCAAAAGCCGGTCGTAGTTCGGATTG

GAGTCTGTAACCCGACTCCATGAAGTTGGATTCGCTAGTAATCGCGCATCAGCCATGGCGCGGTGAATACGTTCCC

GGGCCTTGTACACACCGCCCGTCAAGCCATGGAAGCCGGGGGTGCCTGAAGTCCGTAACCGCGAGGATCGGCCTAG

GGCAAAACTGGTAACTGGGGCTAAGTCGTAACAAGGTA

SEQ ID NO: 63 *Parabacteroides distasonis* Strain 75
CGAGGGGCAGCRCAGGAGT-TAGCAATAC-

CSGGTGGCGACCGGCGCACGGGTGAGTAACGCGTATGCAACTTRCCTATCAGAGGGGGATAACCCGGCGAAAGTCG

GACTAATACCGCATGAAGCAGGGATYCCGCATGGGRATATTTGCTAAAGATTCATCGCTGATAGATAGGCATGCGT

TCCATTAGGCAGTTGGCGGGGTAACRGCCCACCAAACCGACGATGGATAGGGGTTCTGAGAGGAAGGTCCCCCACA

TTGGTACTGAGACACGGACCAAACTCCTACGGGAGGCAGCAGTGAGGAATATTGGTCAATGGSCGWRAGSCTGAAC

CAGCCAAGTCGCGTGAGGGATGAAGGTTCTATGGATCGTAAACCTCTTTTATAAGGGAATAAAGTGCGGGACGTGT

CCYRTTTTGTATGTACCTTATGAATAAGGATCGGCTAACTCCGTGCCAGCAGCCGCGGTAATACGGAGGATCCGAG

CGTTATCCGGATTTATTGGGTTTAAAGGGTGCGTAGGCGGCCTTTTAAGTCAGCGGTGAAAGTCTGTGGCTCAACC

ATAGAATTGCCGTTGAAACTGGGGGGCTTGAGTATGTTTGAGGCAGGCGGAATGCGTGGTGTAGCGGTGAAATGCA

TAGATATCACGCAGAACCCCGWTTGCGAAGGCAGCCTGCCAAGCCGTAACTGACGCGGATGCACGAAAGCGTGGGG

ATCAAACAGGATTAGATACCCTGGTA

SEQ ID NO: 64 *Parabacteroides merdae* Strain 76
CATGCAAGTCGAGGGGCAGCATGATTTGTAGCAATACAGATTGATGGCGACCGGCGCACGGGTGAGTAACGCGTAT

GCAACTTACCTATCAGAGGGGGATAGCCCGGCGAAAGTCGGATTAATACCCCATAAAACAGGGGTCCCGCATGGGA

ATATTTGTTAAAGATTCATCGCTGATAGATAGGCATGCGTTCCATTAGGCAGTTGGCGGGGTAACGGCCCACCAAA

CCGACGATGGATAGGGGTTCKGAGAGGAAGGTCCCCCACATTGGTACTGAGACACGGACCAAACTCCTACGGGAGG

```
CAGCAGTGAGGAATATTGGTCAATGGCCGAGAGGCTGAACCAGCCAAGTCGCGTGAAGGAAGAAGGATCTATGGTT

TGTAAACTTCTTTTATAGGGGAATAAAGTGGAGGACGTGTCCTTTTTTGTATGTACCCTATGAATAAGCATCGGCT

AACTCCGTGMSARCMGCCGCGGGAATACGGAAGATGCAGAGCGTTATCCGGATWTATTGGGGTTA
```

SEQ ID NO: 65 Bacteroides xylanisolvens Strain 77
```
CATGCAAGTCGAGGGGCAGCATTTTAGTTTGCTTGCAAACTAAAGATGGCGACCGGCGCACGGGTGAGTAACACGT

ATCCAACCTGCCGATAACTCGGGGATAGCCTTTCGAAAGAAAGATTAATATCCGATAGTATATTAAAACCGCATGG

TTTTACTATTAAAGAATTTCGGTTATCGATGGGGATGCGTTCCATTAGTTTGTTGGCGGGGTAACGGCCCACCAAG

ACTACGATGGATAGGGGTTCTGAGAGGAAGGTCCCCCACATTGGAACTGAGACACGGTCCAAACTCCTACGGGAGG

CAGCAGTGAGGAATATTGGTCAATGGACGAGAGTCTGAACCAGCCAAGTAGCGTGAAGGATGACTGCCCTATGGGT

TGTAAACTTCTTTTATATGGGAATAAAGTATTCCACGTGTGGGATTTTGTATGTACCATATGAATAAGGATCGGCT

AACTCCGTGCCAGCAGCCGCGGTAATACGGAGGATCCGAGCGTTATCCGGATTTATTGGGTTTAAAGGGAGCGTAG

GTGGATTGTTAAGTCAGTTGTGAAAGTTTGCGGCTCAACCGTAAAATTGCAGTTGAAACTGGCAGTCTTGAGTACA

GTAGAGGTGGGCGGAATTCGTGGTGTAGCGGTGAAATGCTTAGATATCACGAAGAACTCCGATTGCGAAGGCAGCT

CACTAGACTGCAACTGACACTGATGCTCGAAAGTGTGGGTATCAAACAGGATTAGATACCCTGGTAGTCCACACAG

TAAACGATGAATACTCGCTGTTTGCGATATACAGTAAGCGGCCAAGCGAAAGCATTAAGTATTCCACCTGGGGAGT

ACGCCGGCAACGGTGAAACTCAAAGGAATTGACGGGGGCCCGCACAAGCGGAGGAACATGTGGTTTAATTCGATGA

TACGCGAGGAACCTTACCCGGGCTTAAATTGCATTTGAATAATCTGGAAACAGGTTAGCCGCAAGGCAAATGTGAA

GGTGCTGCATGGTTGTCGTCAGCTCGTGCCGTGAGGTGTCGGCTTAAGTGCCATAACGAGCGCAACCCTTATCTTT

AGTTACTAACAGGTTATGCTGAGGACTCTAGAGAGACTGCCGTCGTAAGATGTGAGGAAGGTGGGGATGACGTCAA

ATCAGCACGGCCCTTACGTCCGGGGCTACACACGTGTTACAATGGGGGGTACAGAAGGCAGCTACCTGGCGACAGG

ATGCTAATCCCAAAAACCTCTCTCAGTTCGGATCGAAGTCTGCAACCCGACTTCGTGAAGCTGGATTCGCTAGTAA

TCGCGCATCAGCCATGGCGCGGTGAATACGTTCCCGGGCCTTGTACACACCGCCCGTCAAGCCATGAAAGCCGGGG
```

SEQ ID NO: 66 Blautia obeum Strain 78
```
GGCGTGCTTAACACATGCAAGTCGAACGGGAAACCTTTTATTGAAGCTTCGGCAGATTTAG-

CTGGTTTCTAGTGGCGGACGGGTGAGTAACGCGTGGGTAACCTGCCTTATACAGGGGGATAACAACCAGAAATGGT

TGCTAATACCGCATAAGCGCACAGGACCGCATGGTCCGGTGTGAAAAACTCCGGTGGTATAAGATGGACCCGCGTT

GGATTAGCTAGTTGGCAGGGTAACGGCCTACCAAGGCGACGATCCATAGCCGGCCTGAGAGGGTGAACGGCCACAT

TGGGACTGAGACACGGCCCAGACTCCTACGGGAGGCAGCAGTGGGGAATATTGCACAATGGGGGAAACCCTGATGC

AGCGACGCCGCGTGAAGGAAGAAGTATCTCGGTATGTAAACTTCTATCAGCAGGGAAGATAGTGACGGTACCTGAC

TAAGAAGCCCCGGCTAACTACGTGCCAGCAGCCGCGGTAATACGTAGGGGGCAAGCGTTATCCGGATTTACTGGGT

GTAAAGGGAGCGTAGACGGACTGGCAAGTCTGATGTGAAAGGCGGGGGCTCAACCCCTGGACTGCATTGGAAACTG

TTAGTCTTGAGTGCCGGAGAGGTAAGCGGAATTCCTAGTGTAGCGGTGAAATGCGTAGATATTAGGAGGAACACCA

GTGGCGAAGGCGGCTTACTGGACGGTAACTGACGTTGAGGCTCGAAAGCGTGGGGAGCAAACAGGATTAGATACCC

TGGTAGTCCACGCCGTAAACGATGAATACTAGGTGTTGGGGAGCAAAGCTCTTCGGTGCCGCCGCAAACGCATTAA

GTATTCCACCTGGGGAGTACGTTCGCAAGAATGAAACTCAAAGGAATTGACGGGACCCGCACAAGCGGTGGAGCA

TGTGGTTTAATTCGAAGCAACGCGAAGAACCTTACCAAGTCTTGACATCCCTCTGACCGTTCCTTAACCGGAACTT

TCCTTCGGGACAGGGGAGACAGGTGGTGCATGGTTGTCGTCAGCTCGTGTCGTGAGATGTTGGGTTAAGTCCCGCA

ACGAGCGCAACCCCTATCCCCAGTAGCCAGCAGTCCGGCTGGGCACTCTGAGGAGACTGCCAGGGATAACCTGGAG

GAAGGCGGGGATGACGTCAAATCATCATGCCCCTTATGATTTGGGCTACACACGTGCTACAATGGCGTAAACAAAG

GGAAGCAAGCCTGCGAAGGTAAGCAAATCCCAAAAATAACGTCCCAGTTCGGACTGCAGTCTGCAACTCGACTGCA

CGAAGCTGGAATCGCTAGTAATCGCGGATCAGAATGCCGCGGTGAATACGTTCCCGGGTCTTGTACACACCGCCCG

TCACACCATGGGAGTCAGTAACGCCCGAAGTCAGTGACCTAACTGC
```

SEQ ID NO: 67 *Alistipes putredinis* Strain 79
AGAGTTTGATCCTGGCTCAGGATGAACGCTAGCGGCAGGCTTAACACATGCAAGTCGAGGGGCAGCATAATGGATA

GCAATATCTATGGTGGCGACCGGCGCACGGGTGCGTAACGCGTATGCAACCTACCTTTAACAGGGGGATAACACTG

AGAAATTGGTACTAATACCCCATAATATCATAGAAGGCATCTTTTATGGTTGAAAATTCCGATGGTTAGAGATGGG

CATGCGTTGTATTAGCTAGTTGGTGGGGTAACGGCTCACCAAGGCGACGATACATAGGGGGACTGAGAGGTTAACC

CCCCACACTGGTACTGAGACACGGACCAGACTCCTACGGGAGGCAGCAGTGAGGAATATTGGTCAATGGACGCAAG

TCTGAACCAGCCATGCCGCGTGCAGGATGACGGCTCTATGAGTTGTAAACTGCTTTTGTACGAGGGTAAACGCAGA

TACGTGTATCTGTCTGAAAGTATCGTACGAATAAGGATCGGCTAACTCCGTGCCAGCAGCCGCGGTAATACGGAGG

ATTCAAGCGTTATCCGGATTTATTGGGTTTAAAGGGTGCGTAGGCGGTTTGATAAGTTAGAGGTGAAATTTCGGGG

CTCAACCCTGAACGTGCCTCTAATACTGTTGAGCTAGAGAGTAGTTGCGGTAGGCGGAATGTATGGTGTAGCGGTG

AAATGCTTAGAGATCATACAGAACACCGATTGCGAAGGCAGCTTACCAAACTATATCTGACGTTGAGGCACGAAAG

CGTGGGGAGCAAACAGGATTAGATACCCTGGTAGTCCACGCAGTAAACGATGATAACTCGTTGTCGGCGATACACA

GTCGGTGACTAAGCGAAAGCGATAAGTTATCCACCTGGGGAGTACGTTCGCAAGAATGAAACTCAAAGGAATTGAC

GGGGGCCCGCACAAGCGGAGGAACATGTGGTTTAATTCGATGATACGCGAGGAACCTTACCCGGGCTTGAAAGTTA

GCGACGATTCTTGAAAGAGGATTTCCCTTCGGGGCGCGAAACTAGGTGCTGCATGGTTGTCGTCAGCTCGTGCCGT

GAGGTGTCGGGTTAAGTCCCATAACGAGCGCAACCCCTACCGTTAGTTGCCATCAGGTGAAGCTGGGCACTCTGGC

GGGACTGCCGGTGTAAGCCGAGAGGAAGGTGGGGATGACGTCAAATCAGCACGGCCCTTACGTCCGGGGCTACACA

CGTGTTACAATGGTAGGTACAGAGGGCAGCTACCCAGCGATGGGATGCGAATCTCGAAAGCCTATCTCAGTTCGGA

TTGGAGGCTGAAACCCGCCTCCATGAAGTTGGATTCGCTAGTAATCGCGCATCAGCCATGGCGCGGTGAATACGTT

CCCGGGCCTTGTACACACCGCCCGTCAAGCCATGGGAGCCGGGGGTGCCTGAAGTTCGTGACCGCAAGGAGCGACC

TAGGGCAAAACTGGTGACTGGGGCTAAGTCGTAACAAGGTA

SEQ ID NO: 68 *Collinsella aerofaciens* Strain 80
AGAGTTCGATCCTGGCTCAGGATGAACGCTGGCGGCGCGCCTAACACATGCAAGTCGAACGGCACCTATCTTCGGA

TAGAAGCGAGTGGCGAACGGCTGAGTAACACGTGGAGAACCTGCCCCCTCCCCGGGATAGCCGCCCGAAAGGACG

GGTAATACCGGATACCCCGGGGTGCCGCATGGCACCCCGGCTAAAGCCCCGACGGGAGGGGATGGCTCCGCGGCCC

ATCAGGTAGACGGCGGGGTGACGGCCCACCGTGCCGACAACGGGTAGCCGGGTTGAGAGACCGACCGGCCAGATTG

GGACTGAGACACGGCCCAGACTCCTACGGGAGGCAGCAGTGGGGAATCTTGCGCAATGGGGGGAACCCTGACGCAG

CGACGCCGCGTGCGGGACGGAGGCCTTCGGGTCGTAAACCGCTTTCAGCAGGGAAGAGTCAAGACTGTACCTGCAG

AAGAAGCCCCGGCTAACTACGTGCCAGCAGCCGCGGTAATACGTAGGGGGCGAGCGTTATCCGGATTCATTGGGCG

TAAAGCGCGCGTAGGCGGCCCGGCAGGCCGGGGGTCGAAGCGGGGGGCTCAACCCCCCGAAGCCCCCGGAACCTCC

GCGGCTTGGGTCCGGTAGGGGAGGGTGGAACACCCGGTGTAGCGGTGGAATGCGCAGATATCGGTGGAACACCGG

TGGCGAAGGCGGCCCTCTGGGCCGAGACCGACGCTGAGGCGCGAAAGCTGGGGAGCGAACAGGATTAGATACCCT

GGTAGTCCCAGCCGTAAACGATGGACGCTAGGTGTGGGGGGACGATCCCCCCGTGCCGCAGCCAACGCATTAAGCG

TCCCGCCTGGGGAGTACGGCCGCAAGGCTAAAACTCAAAGGAATTGACGGGGGCCCGCACAAGCAGCGGAGCATGT

GGCTTAATTCGAAGCAACGCGAAGAACCTTACCAGGGCTTGACATATGGGTGAAGCGGGGAGACCCCGTGGCCGA

GAGGAGCCCATACAGGTGGTGCATGGCTGTCGTCAGCTCGTGTCGTGAGATGTTGGGTTAAGTCCCGCAACGAGCG

CAACCCCCGCCGCGTGTTGCCATCGGGTGATGCCGGGAACCCACGCGGGACCGCCGCCGTCAAGGCGGAGGAGGGC

GGGGACGACGTCAAGTCATCATGCCCCTTATGCCCTGGGCTGCACACGTGCTACAATGGCCGGTACAGAGGGATGC

CACCCCGCGAGGGGAGCGGATCCCGGAAAGCCGGCCCCAGTTCGGATTGGGGCTGCAACCCGCCCCCATGAAGT

CGGAGTTGCTAGTAATCGCGGATCAGCATGCCGCGGTGAATGCGTTCCCGGGCCTTGTACACACCGCCCGTCACAC

CACCCGAGTCGTCTGCACCCGAAGTCGCCGGCCCAACCGAGAGGGGGGAGGCGCCGAAGGTGTGGAGGGTGAGGGG

GGTGAAGTCGTAACAAGGTA

SEQ ID NO: 69 *Bacteroides faecis* Strain 81
CTCAGGATGAACGCTAGCTACAGGCTTAACACATGCAAGTCGAGGGGCAGCATTCCAGTTTGCTTGCAAACTGGAG

ATGGCGACCGGCGCACGGGTGAGTAACACGTATCCAACCTGCCGATAACTCGGGGATAGCCTTTCGAAAGAAAGAT

TAATACCCGATGGCATAATAGAACCGCATGGTTTGATTATTAAAGAATTTCGGTTATCGATGGGGATGCGTTCCAT

TAGGCAGTTGGTGGGGTAACGGCCCACCAAACCTTCGATGGATAGGGGTTCTGAGAGGAAGGTCCCCCACATTGGA

ACTGAGACACGGTCCAAACTCCTACGGGAGGCAGCAGTGAGGAATATTGGTCAATGGACGAGAGTCTGAACCAGCC

AAGTAGCGTGAAGGATGACTGCCCTATGGGTTGTAAACTTCTTTTATATGGGAATAAAGTGGTCCACGTGTGGATT

TTTGTATGTACCATATGAATAAGGATCGGCTAACTCCGTGCCAGCAGCCGCGGTAATACGGAGGATCCGAGCGTTA

TCCGGATTTATTGGGTTTAAAGGGAGCGTAGGTGGACAGTTAAGTCAGTTGTGAAAGTTTGCGGCTCAACCGTAAA

ATTGCAGTTGATACTGGCTGTCTTGAGTACAGTAGAGGCGGGCGGAATTCGTGGTGTAGCGGTGAAATGCTTAGAT

ATCACGAAGAACTCCGATTGCGAAGGCAGCTCACTGGACTGCAACTGACACTGATGCTCGAAAGTGTGGGTATCAA

ACAGGATTAGATACCCTGGTAGTCCACACAGTAAACGATGAATACTCGCTGTTTGCGATATACAGTAAGCGGCCAA

GCGAAAGCATTAAGTATTCCACCTGGGGAGTACGCCGGCAACGGTGAAACTCAAAGGAATTGACGGGGCCCGCAC

AAGCGGAGGAACATGTGGTTTAATTCGATGATACGCGAGGAACCTTACCCGGGCTTAAATTGCATTTGAATATATT

GGAAACAGTATAGTCGTAAGACAAATGTGAAGGTGCTGCATGGTTGTCGTCAGCTCGTGCCGTGAGGTGTCGGCTT

AAGTGCCATAACGAGCGCAACCCTTATCTTTAGTTACTAACAGGTCATGCTGAGGACTCTGGAGAGACTGCCGTCG

TAAGATGTGAGGAAGGTGGGGATGACGTCAAATCAGCACGGCCCTTACGTCCGGGGCTACACACGTGTTACAATGG

GGGGTACAGAAGGCCGCTACCTGGTGACAGGATGCTAATCCCAAAAGCCTCTCTCAGTTCGGATCGAAGTCTGCAA

CCCGACTTCGTGAAGCTGGATTCGCTAGTAATCGCGCATCAGCCATGGCGCGGTGAATACGTTCCCGGGCCTTGTA

CACACCGCCCGTCAAGCCATGAAAGCCGGGGGTACCTGAAGTACGTAACCGCAAGGAGCGTCCTAGGGTAAAACTG

GTAATTGGGGCTAAGTCGTAACAAGGTA

SEQ ID NO: 70 *Alistipes shahii* Strain 82
ACATAGGGGGWSTGWKAGGTTWRCCSCCCACATTSRTACTGAGMCA-

TGAWCMAACTCTMTACGGGARGSAGSAGTGAGGAATATTGGTCRRTGGACGCAAGTCTGAACCAGCCATGCCGSGT

GCRGGAAGACGGCTCKATGAGTKGKAAACTGCTTTTGTACRARRGTAAACGCTCTTACGTGTAAGAGCCTGAAAGT

ATSGTACRAATGAGGATCGGCTAACTCCGTGCCAGCAGCCGCGGTAATACGGAGGATCCAAGCGTTATCCGGATTT

ATTGGGTTTAAAGGGTGCGTAGGCGGGTTGATAAAGTTAGRGG

SEQ ID NO: 71 *Anaerostipes caccae* Strain 83
GCTT-ACACATG-

CAAGTCGAACGAAGCATTTARGATTGAAGTTTTCGGATGGATTTCCTATATGACTGAGTGGCGGACGGGTGAGTAA

CGCGTGGGGAACCTGCCCTATACAGGGGGATAACAGCTGGAAACGGCTGCTAATACCGCATAAGCGCACAGAATCG

CATGATTCAGTGTGAAAAGCCCTGGCAGTATAGGATGGTCCCGCGTCTGATTAGCTGGTTGGTGAGGTAACGGCTC

ACCAAGGCGACGATCAGTAGCCGGCTTGAGAGAGTGAACGGCCACATTGGGACTGAGACACGGCCCAAACTCCTAC

GGGAGGCAGCAGTGGGGAATATTGCACAATGGGGG-

AAACCCTGATGCAGCGACGCCGCGTGAGTGAAGAAGTATTTCGGTATGTAAAGCTCTATCAGCAGGGAAGAAAACA

GACGGTACCTGACTAAGAAGCCCCGGCTAACTACGTGCCAGCAGCCGCGGTAATACGTAGGGGGCAAGCGTTATCC

GGAATTACTGGGTGTAAAGGGTGCGTAGGTGGCATGGTAAGTCAGAAGTGAAAGCCCGGGGCTTAACCCCGGGACT

GCTTTTGAAACTGTCATGCTGGAGTGCAGGAGAGGTAAGCGGAATTCCTAGTGTAGCGGTGAAATGCGTAGATATT

AGGAGGAACACCAGTGGCGAAGGCGGCTTACTGGACTGTCACTGACACTGATGCACGAAAGCGTGGGGAGCAAACA

GGATTAGATACCCTGGTAGTCCACGCCGTAAACGATGAATACTAGGTGTCGGGGCCGTAGAGGCTTCGGTGCCGCA

GCAAA

SEQ ID NO: 72 Phascolarctobacterium faecium Strain 84
CGGAGAATTTTCATTTCGGTAGAATTCTTAGTGGCGAACGGGTGAGTAACGCGTAGGCAACCTGCCCTTTAGACGG

GGACAACATTCCGAAAGGAGTGCTAATACCGGATGTGATCATCGTGCCGCATGGCAGGATGAAGAAAGATGGCCTC

TACAAGTAAGCTATCGCTAAAGGATGGGCCTGCGTCTGATTAGCTAGTTGGTAGTGTAACGGACTACCAAGGCGAT

GATCAGTAGCCGGTCTGAGAGGATGAACGGCCACATTGGGACTGAGACACGGCCCAAACTCCTACGGGAGGCAGCA

GTGGGGAATCTTCCGCAATGGACGAAAGTCTGACAGAGCAACGCCGCGTGAGTGATGAAGGATTTCGGTCTGTAAA

GCTCTGTTGTTTATGACGAACGTGCAGTGTGTGAACAATGCATTGCAATGACGGTAGTAAACGAGGAAGCCACGGC

TAACTACGTGCCAGCAGCCGCGGTAATACGTAGGTGGCGAGCGTTGTCCGGAATTATTGGGCGTAAAGAGCATGTA

GGCGGCTTAATAAGTCGAGCGTGAAAAATGCGGGGCTCAACCCCGTATGGCGCTGGAAACTGTTAGGCTTGAGTGC

AGGAGAGGAAAGGGGAATTCCCAGTGTAGCGGTGAAATGCGTAGATATTGGGAGGAACACCAGTGGCGAAGGCGCC

TTTCTGGACTGTGTTTGACGCTGAGATGCGAAAGCCAGGGTAGC

SEQ ID NO: 73 Agathobaculum butyriciproducens Strain 85
TAGTGGCGGACGGGTGAGTAACGCGTGAGCAATCTGCCTTTAAGAGGGGGATAACAGTCGGAAACGGCTGCTAATA

CCGCATAAAGCATTGAATTCGCATGTTTTCGATGCCAAAGGAGCAATCCGCTTTTAGATGAGCTCGCGTCTGATTA

GCTAGTTGGCGGGGTAACGGCCCACCAAGGCGACGATCAGTAGCCGGACTGAGAGGTTGAACGGCCACATTGGGAC

TGAGACACGGCCCAGACTCCTACGGGAGGCAGCAGTGGGGAATATTGCGCAATGGGGGRAACCCTGACGCAGCAAC

GCCGCGTGATTGAAGAAGGCCTTCGGGTTGTAAAGATCTTTAATCAGGGACGAA--

AMATGACGGTACCTGAAGAATAAGCTCCGGCTAACTACGTGCCAGCAGCCGCGGTAATACGTAGGGAGCAAGCGTT

ATCCGGATTTACTGGGTGTAAAGGGCGCGCAGGCGGGCCGGCAAGTTGGAAGTGAAATCCGGGGGCTTAACCCCCG

AACTGCTTTCAAAACTGCTGGTCTTGAGTGATGGAGAGGCAGGCGGAATTCCGTGTGTAGCGGTGAAATGCGTAGA

TATACGGAGGAACACCAGTGGCGAAGGCGGCCTGCTGGACATTAACTGACGCTGAGGCGCGAAAGCGTGGGGAGCA

AACAGGATTAGATACCCTGGTAGTCCACGCCGTAAACGATGGATA

SEQ ID NO: 74 Bacteroides fragilis Strain 86
ATGAAGAGTTTGATCCTGGCTCAGGATGAACGCTAGCTACAGGCTTAACACATGCAAGTCGAGGGGCATCAGGAAG

AAAGCTTGCTTTCTTTGCTGGCGACCGGCGCACGGGTGAGTAACACGTATCCAACCTGCCCTTTACTCGGGGATAG

CCTTTCGAAAGAAAGATTAATACCCGATGGCATAATGATTCCGCATGGTTTCATTATTAAAGGATTCCGGTAAAGG

ATGGGGATGCGTTCCATTAGGTTGTTGGTGAGGTAACGGCTCACCAAGCCTTCGATGGATAGGGGTTCTGAGAGGA

AGGTCCCCCACATTGGAACTGAGACACGGTCCAAACTCCTACGGGAGGCAGCAGTGAGGAATATTGGTCAATGGGC

GCTAGCCTGAACCAGCCAAGTAGCGTGAAGGATGAAGGCTCTATGGGTCGTAAACTTCTTTTATATAAGAATAAAG

TGCAGTATGTATACTGTTTTGTATGTATTATATGAATAAGGATCGGCTAACTCCGTGCCAGCAGCCGCGGTAATAC

GGAGGATCCGAGCGTTATCCGGATTTATTGGGTTTAAAGGGAGCGTAGGTGGACTGGTAAGTCAGTTGTGAAAGTT

TGCGGCTCAACCGTAAAATTGCAGTTGATACTGTCAGTCTTGAGTACAGTAGAGGTGGGCGGAATTCGTGGTGTAG

CGGTGAAATGCTTAGATATCACGAAGAACTCCGATTGCGAAGGCAGCTCACTGGACTGCAACTGACACTGATGCTC

GAAAGTGTGGGTATCAAACAGGATTAGATACCCTGGTAGTCCACACAGTAAACGATGAATACTCGCTGTTTGCGAT

ATACAGTAAGCGGCCAAGCGAAAGCATTAAGTATTCCACCTGGGGAGTACGCCGGCAACGGTGAAACTCAAAGGAA

TTGACGGGGGCCCGCACAAGCGGAGGAACATGTGGTTTAATTCGATGATACGCGAGGAACCTTACCCGGGCTTAAA

TTGCAGTGGAATGATGTGGAAACATGTCAGTGAGCAATCACCGCTGTGAAGGTGCTGCATGGTTGTCGTCAGCTCG

TGCCGTGAGGTGTCGGCTTAAGTGCCATAACGAGCGCAACCCTTATCTTTAGTTACTAACAGGTTATGCTGAGGAC

TCTAGAGAGACTGCCGTCGTAAGATGTGAGGAAGGTGGGGATGACGTCAAATCAGCACGGCCCTTACGTCCGGGGC

TACACACGTGTTACAATGGGGGGTACAGAAGGCAGCTAGCGGGTGACCGTATGCTAATCCCAAAAGCCCTCTCAG

-continued

TTCGGATCGAAGTCTGCAACCCGACTTCGTGAAGCTGGATTCGCTAGTAATCGCGCATCAGCCACGGCGCGGTGAA

TACGTTCCCGGGCCTTGTACACACCGCCCGTCAAGCCATGGGAGCCGGGGGTACCTGAAGTACGTAACCGCAAGGA

TCGTCCTAGGGTAAAACTGGTGACTGGGGCTAAGTCGTAACAAGGTAGCCGTACCGGAAGGTGCGGCTGGAACACC

TCCTT

SEQ ID NO: 75 *Fusobacterium mortiferum* Strain 87
TGGCTCAGGATGAACGCTGACAGAATGCTTAACACATGCAAGTCTACTTGATCCTTCGGGTGATGGTGGCGGACGG

GTGAGTAACGCGTAAAGAACTTGCCCTGCAGTCTGGGACAACATTTGGAAACGAATGCTAATACCGGATATTATGT-

ATTTCTCGCATGAGTTTTACATGAAAGCTATATGCGCTGCAGGAGAGCTTTGCGTCCTATTAGCTAGTTGGTGAGG

TAACGGCTCACCAAGGCCATGATAGGTAGCCGGCCTGAGAGGGTGAACGGCCACAAGGGGACTGAGACACGGCCCT

TACTCCTACGGGAGGCAGCAGTGGGGAATATTGGACAATGGACCAAAAGTCTGATCCAGCAATTCTGTGTGCACGA

TGAAGTTTTTCGGAATGTAAAGTGCTTTCAGTTGGGACGAAGTAAGTGACGGTACCAACAGAAGAAGCGACGGCTA

AATACGTGCCAGCAGCCGCGGTAATACGTATGTCGCAAGCGTTATCCGGATTTATTGGGCGTAAAGCGCGTCTAGG

CGGTTTGGTAAGTCTGATGTGAAAATGCGGGGCTCAACTCCGTATTGCGTTGGAAACTGCTAAACTAGAGTACTGG

AGAGGTGGGCGGAACTACAAGTGTAGAGGTGAAATTCGTAGATATTTGTAGGAATGCCGATGGGGAAGCCAGCCCA

CTGGACAGATACTGACGCTAAAGCGCGAAAGCGTGGGTAGCAAACAGGATTAGATACCCTGGTAGTCCACGCCGTA

AACGATGATTACTAGGTGTTGGGGGTCGAACCTCAGCGCCCAAGCTAACGCGATAAGTAATCCGCCTGGGGAGTAC

GTACGCAAGTATGAAACTCAAAGGAATTGACGGGGACCCGCACAAGCGGTGGAGCATGTGGTTTAATTCGACGCAA

CGCGAGGAACCTTACCAGCGTTTGACATCCTAAGAAATTAGCAGAGATGCTTTTGTGCCCCTTCGGGGGAACTTAG

TGACAGGTGGTGCATGGCTGTCGTCAGCTCGTGT

SEQ ID NO: 76 *Paraclostridium benzoelyticum* Strain 88
AGAGTTTGATCCTGGCTCAGGATGAACGCTGGCGGCGTGCCTAACACATGCAAGTCGAGCGATCTCTTCGGAGAGA

GCGGCGGACGGGTGAGTAACGCGTGGGTAACCTGCCCTGTACACACGGATAACATACCGAAAGGTATACTAATACG

GGATAACATACGAAAGTCGCATGGCTTTTGTATCAAAGCTCCGGCGGTACAGGATGGACCCGCGTCTGATTAGCTA

GTTGGTAAGGTAATGGCTTACCAAGGCAACGATCAGTAGCCGACCTGAGAGGGTGATCGGCCACACTGGAACTGAG

ACACGGTCCAGACTCCTACGGGAGGCAGCAGTGGGGAATATTGCACAATGGGCGAAAGCCTGATGCAGCAACGCCG

CGTGAGCGATGAAGGCCTTCGGGTCGTAAAGCTCTGTCCTCAAGGAAGATAATGACGGTACTTGAGGAGGAAGCCC

CGGCTAACTACGTGCCAGCAGCCGCGGTAATACGTAGGGGGCTAGCGTTATCCGGAATTACTGGGCGTAAAGGGTG

CGTAGGTGGTTTTTTAAGTCAGAAGTGAAAGGCTACGGCTCAACCGTAGTAAGCTTTTGAAACTAGAGAACTTGAG

TGCAGGAGAGGAGAGTAGAATTCCTAGTGTAGCGGTGAAATGCGTAGATATTAGGAGGAATACCAGTAGCGAAGGC

GGCTCTCTGGACTGTAACTGACACTGAGGCACGAAAGCGTGGGGAGCAAACAGGATTAGATACCCTGGTAGTCCAC

GCCGTAAACGATGAGTACTAGGTGTCGGGGGTTACCCCCCTCGGTGCCGCAGCTAACGCATTAAGTACTCCGCCTG

GGAAGTACGCTCGCAAGAGTGAAACTCAAAGGAATTGACGGGACCCGCACAAGTAGCGGAGCATGTGGTTTAATT

CGAAGCAACGCGAAGAACCTTACCTAAGCTTGACATCCCACTGACCTCTCCCTAATCGGAGATTTCCCTTCGGGGA

CAGTGGTGACAGGTGGTGCATGGTTGTCGTCAGCTCGTGTCGTGAGATGTTGGGTTAAGTCCCGCAACGAGCGCAA

CCCTTGCCTTTAGTTGCCAGCATTAAGTTGGGCACTCTAGAGGGACTGCCGAGGATAACTCGGAGGAAGGTGGGGA

TGACGTCAAATCATCATGCCCCTTATGCTTAGGGCTACACACGTGCTACAATGGGTGGTACAGAGGGTTGCCAAGC

CGCGAGGTGGAGCTAATCCCTTAAAGCCATTCTCAGTTCGGATTGTAGGCTGAAACTCGCCTACATGAAGCTGGAG

TTACTAGTAATCGCAGATCAGAATGCTGCGGTGAATGCGTTCCCGGGTCTTGTACACACCGCCCGTCACACCATGG

AAGTTGGGGCGCCCGAAGCCGGTTAGCTAACCTTTTAGGAAGCGGCCGTCGAAGGTGAAACCAATGACTGGGGTG

AAGTCGTAACAAGGTAGCCGTATCGGAAGGTGCGGCTGGATCACCT

-continued
SEQ ID NO: 77 Escherichia fergusonii Strain 89
TTGAAGAGTTTGATCATGGCTCAGATTGAACGCTGGCGGCAGGCCTAACACATGCAAGTCGAACGGTAACAGGAAG

CAGCTTGCTGCTTTGCTGACGAGTGGCGGACGGGTGAGTAATGTCTGGGAAACTGCCTGATGGAGGGGGATAACTA

CTGGAAACGGTAGCTAATACCGCATAACGTCGCAAGACCAAAGAGGGGGACCTTCGGGCCTCTTGCCATCGGATGT

GCCCAGATGGGATTAGCTAGTAGGTGGGGTAACGGCTCACCTAGGCGACGATCCCTAGCTGGTCTGAGAGGATGAC

CAGCCACACTGGAACTGAGACACGGTCCAGACTCCTACGGGAGGCAGCAGTGGGGAATATTGCACAATGGGCGCAA

GCCTGATGCAGCCATGCCGCGTGTATGAAGAAGGCCTTCGGGTTGTAAAGTACTTTCAGCGGGGAGGAAGGGAGTA

AAGTTAATACCTTTGCTCATTGACGTTACCCGCAGAAGAAGCACCGGCTAACTCCGTGCCAGCAGCCGCGGTAATA

CGGAGGGTGCAAGCGTTAATCGGAATTACTGGGCGTAAAGCGCACGCAGGCGGTTTGTTAAGTCAGATGTGAAATC

CCCGGGCTCAACCTGGGAACTGCATCTGATACTGGCAAGCTTGAGTCTCGTAGAGGGGGGTAGAATTCCAGGTGTA

GCGGTGAAATGCGTAGAGATCTGGAGGAATACCGGTGGCGAAGGCGGCCCCCTGGACGAAGACTGACGCTCAGGTG

CGAAAGCGTGGGGAGCAAACAGGATTAGATACCCTGGTAGTCCACGCCGTAAACGATGTCGACTTGGAGGTTGTGC

CCTTGAGGCGTGGCTTCCGGAGCTAACGCGTTAAGTCGACCGCCTGGGGAGTACGGCCGCAAGGTTAAAACTCAAA

TGAATTGACGGGGGCCCGCACAAGCGGTGGAGCATGTGGTTTAATTCGATGCAACGCGAAGAACCTTACCTGGTCT

TGACATCCACGGAAGTTTTCAGAGATGAGAATGTGCCTTCGGGAACCGTGAGACAGGTGCTGCATGGCTGTCGTCA

GCTCGTGTTGTGAAATGTTGGGTTAAGTCCCGCAACGAGCGCAACCCTTATCCTTTGTTGCCAGCGGTCCGGCCGG

GAACTCAAAGGAGACTGCCAGTGATAAACTGGAGGAAGGTGGGGATGACGTCAAGTCATCATGGCCCTTACGACCA

GGGCTACACACGTGCTACAATGGCGCATACAAAGAGAAGCGACCTCGCGAGAGCAAGCGGACCTCATAAAGTGCGT

CGTAGTCCGGATTGGAGTCTGCAACTCGACTCCATGAAGTCGGAATCGCTAGTAATCGTGGATCAGAATGCCACGG

TGAATACGTTCCCGGGCCTTGTACACACCGCCCGTCACACCATGGGAGTGGGTTGCAAAAGAAGTAGGTAGCTTAA

CCTTCGGGAGGGCGCTTACCACTTTGTGATTCATGACTGGGGTGAAGTCGTAACAAGGTAACCGTAGGGGAACCTG

CGGTTGGATCACCTCCTT

The invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Unless otherwise defined herein, scientific and technical terms used in connection with the present disclosure shall have the meanings that are commonly understood by those of ordinary skill in the art. Further, unless otherwise required by context, singular terms shall include pluralities and plural terms hall include the singular. The methods and techniques of the present disclosure are generally performed according to conventional methods well-known in the art. Generally, nomenclatures used in connection with, and techniques of biochemistry, enzymology, molecular and cellular biology, microbiology, virology, cell or tissue culture, genetics and protein and nucleic chemistry described herein are those well-known and commonly used in the art. The methods and techniques of the present disclosure are generally performed according to conventional methods well known in the art and as described in various general and more specific references that are cited and discussed throughout the present specification unless otherwise indicated.

The present invention is further illustrated by the following Examples, which in no way should be construed as further limiting. The entire contents of all of the references (including literature references, issued patents, published patent applications, and co-pending patent applications) cited throughout this application are hereby expressly incorporated by reference, in particular for the teaching that is referenced hereinabove. However, the citation of any reference is not intended to be an admission that the reference is prior art.

EXAMPLES

Example 1: Mouse Model of Vancomycin-Resistant Enterococcus faecium and Carbapenem-Resistant Klebsiella pneumoniae Mouse models of vancomycin-resistant Enterococcus faecium (VRE) and carbapenem-resistant Klebsiella pneumoniae (CRE) colonization were established using the methodology used by Ubeda et al. (JCI 2010 120 (12): 4332) and Caballero et al. (PLoS Pathog. (2015) 11(9): 1005). As shown in FIG. 1A, C57BL/6 mice were treated with broad-spectrum antibiotics (e.g., ampicillin) for seven days prior to the pathogen challenge. The antibiotic treatment created a niche for VRE/CRE to colonize. On day 0, the ampicillin treatment was terminated. Mice were single-housed and challenged with $10^4$-$10^5$ CFU of VRE or CRE (mono-colonized) or both VRE and CRE (co-colonized). Fecal samples (pellets) were collected from each mouse at various time points following the challenge to quantify CFUs as a measure of pathogen colonization. The fecal samples were plated on selective media. Mice challenged with VRE, CRE, or both remained densely colonized for 21 days in the absence of continued antibiotic treatment (FIGS. 1B-1E). No spontaneous clearance was observed. CRE and VRE colonized the intestine to the same level following mono- or co-challenge (FIGS. 1B-1E).

Example 2: Carbapenem-Resistant *Klebsiella pneumoniae*

As described in Example 1, mouse models of CRE colonization were established following the methodology used by Ubeda et al. (*JCI* 2010 120 (12): 4332) and Caballero et al. (*PLoS Pathog.* (2015) 11(9). As shown in FIG. 2A, mice were treated with broad-spectrum antibiotics (ampicillin) for seven days prior to the CRE challenge. On day −7, the ampicillin treatment was terminated. Mice were single-housed and challenged with $10^4$-$10^5$ CFU of CRE. Three days after the pathogen challenge (on day 0), mice were randomized into groups, and the first of three treatment doses of fecal microbiota treatment (FMT) or stool fraction library (SFL) was administered. The three-day period between CRE challenge and FMT/SFL administration served as a washout period to clear residual antibiotics and establish CRE colonization in the intestine. Fecal samples were collected at various time points post-treatment to quantify CRE levels (plating on selective media) and to determine strain engraftment by metagenomic sequencing.

First, the model for CRE colonization and clearance was validated. As shown in FIG. 2B, administration of FMT from a donor reduced the CRE burden from densely-colonized mice.

Stool fractions were generated to identify fractions having potent pathogen-antagonistic activity. The stool fraction library, SFL, was used to reduce the time to defined and optimized live bacterial product, LBP, by creating donor-derived bacterial fractions that are less complex, culturable, and stable. To generate stool fractions enriched in non-spore forming (NSP) bacterial including members of the *Bacteroidetes, Firmicutes* (non-spore and spore-formers), *Proteobacteria*, and *Actinobacteria* phyla, a 10% fecal slurry was diluted and plated onto rich solid media. After a three day incubation under anaerobic conditions, multiple plates from the same dilution containing well-separated colonies with distinct morphology were scraped and pooled. Aliquots were frozen at −80° C. until ready for use. Likewise, to generate stool fractions enriched in spore-forming (SP) bacteria, a 10% fecal slurry was treated with 100% ethanol for 60 minutes. Following ethanol treatment, the stool suspension was diluted and plated as described above. Stool fractions and FMT were tested for their ability to reduce the CRE burden (decolonize) in mice colonized with CRE as shown in FIG. 3A.

As shown in FIG. 3B, the stool fractions were able to reduce the CRE burden.

Example 2A: Composition of Stool Fractions

The stool fractions from two example donors were sequenced to identify the bacterial species present in the fractions. Genomic DNA (gDNA) was extracted from each frozen stool fraction library (SFL) using a modified protocol based on the MasterPure DNA extraction kit (Lucigen). In brief, SFL cells were pelleted and resuspended in lysis buffer containing lysozyme. gDNA was then extracted and purified from the SFL lysate following the manufacturers protocol. The SFL gDNA was then sequenced on the Illumina platform. Sequencing libraries were prepared using the Nextera XT Library Prep kit and sequenced on the Illumina NextSeq instrument. Raw metagenomic FASTQ files for each SFL sample were filtered to remove adapters and low quality sequences then reads were assigned to the nearest taxonomic relative using the One Codex database and software (Minot S S, BioRxiv. 2015 Sep. 25). After every sequence read has been assigned, the One Codex software was used to estimate the relative abundance of the microbial species in each SFL. The One Codex software takes the number of sequences assigned to each species and the relative coverage of those sequences to the reference genome as inputs and applies a non-negative least squares algorithm to calculate the relative abundance of each species. These resulting relative abundance estimates are more accurate than other methods when evaluated against a broad set of known composition communities (McIntyre ABR Genome Biol. 2017 Sep. 21; 18(1):182; blog.onecodex.com/2017/06/30/tool-off/).

The species estimated to be greater than 0.1% abundant in each SFL are shown in Tables 8-11. The taxonomic ID can be matched with a particular species, e.g., on the NCBI taxonomy database. The number in the abundance column in the Tables is in fraction (i.e., 0.1=10%)

The abundance of the indicated bacterial species in the stool fractions of the donors is presented in Tables 8-11. The bolded entries had an abundance of greater than 0.001 (greater than 0.1%).

TABLE 8

Donor 1 Spore fraction

| Species | Tax ID | Abundance as fraction (i.e., 0.1 = 10%) |
| --- | --- | --- |
| *Ruminococcus* sp. CAG:60 | 1262964 | 0.114254371 |
| *Ruminococcus* sp. 5_1_39BFAA | 457412 | 0.084642189 |
| Lachnospiraceae bacterium 5_1_63FAA | 658089 | 0.081860554 |
| *Ruminococcus* sp. CAG:9 | 1262967 | 0.067730475 |
| *Blautia wexlerae* | 418240 | 0.058207328 |
| *Intestinibacter bartlettii* | 261299 | 0.049859469 |
| *Clostridium* sp. 1_1_41A1FAA | 457397 | 0.036767771 |
| *Flavonifractor plautii* | 292800 | 0.035268356 |
| *Intestinimomas butyriciproducens* | 1297617 | 0.032495136 |
| *Clostridium* sp. ATCC BAA-442 | 649724 | 0.03102409 |
| Clostridiales bacterium VE202-13 | 1530202013 | 0.028246039 |
| *Clostridium perfringens* | 1502 | 0.027743555 |
| *Anaerostipes hadrus* | 649756 | 0.027352897 |
| *Blautia obeum* | 40520 | 0.02699018 |
| *Blautia* sp. KLE 1732 | 1226324 | 0.025347561 |
| *Blautia* sp. GD8 | 1737424 | 0.024798118 |
| Firmicutes bacterium CAG:56 | 1263031 | 0.023695258 |
| *Ruminococcus* sp. SR1/5 | 657323 | 0.019906629 |
| [*Ruminococcus*] *torques* | 33039 | 0.01812662 |
| *Ruminococcus faecis* | 592978 | 0.016073097 |
| *Clostridium* sp. JCC | 1414720 | 0.014201016 |
| *Clostridium bartlettii* CAG:1329 | 1263063 | 0.014122199 |
| *Anaerotruncus colihominis* | 169435 | 0.01240539 |
| *Faecalibacterium prausnitzii* | 853 | 0.012192349 |
| *Ruminococcus* sp. CAG:55 | 1262960 | 0.010879193 |
| Lachnospiraceae bacterium 7_1_58FAA | 658087 | 0.010548055 |
| [*Clostridium*] *symbiosum* | 1512 | 0.010286688 |
| Firmicutes bacterium CAG:270 | 1263014 | 0.009651414 |
| *Agathobacter rectalis* | 39491 | 0.008499925 |
| Clostridia bacterium UC5.1-2F7 | 1697792 | 0.008295436 |
| *Roseburia faecis* | 301302 | 0.006803593 |
| *Clostridium* sp. GD3 | 1650661 | 0.005870841 |
| Firmicutes bacterium CAG:41 | 1263021 | 0.005576561 |
| *Coprococcus* sp. ART55/1 | 751585 | 0.005199271 |
| Firmicutes bacterium CAG:145 | 1263005 | 0.003379299 |
| Firmicutes bacterium CAG:212 | 1263009 | 0.003028622 |
| Butyrate-producing bacterium SS3/4 | 245014 | 0.00289582 |
| *Turicibacter* sp. H121 | 1712675 | 0.002635766 |

TABLE 8-continued

Donor 1 Spore fraction

| Species | Tax ID | Abundance as fraction (i.e., 0.1 = 10%) |
|---|---|---|
| Coprococcus catus | 116085 | 0.00249742 |
| [Clostridium] sordellii | 1505 | 0.002380229 |
| Dorea longicatena | 88431 | 0.002363233 |
| Turicibacter sanguinis | 154288 | 0.001913638 |
| Clostridia bacterium UC5.1-1D1 | 1697794 | 0.001771593 |
| Coprobacillus sp. CAG:235 | 1262854 | 0.001381104 |
| [Eubacterium] eligens | 39485 | 0.001321584 |
| Bifidobacterium longum | 216816 | 0.001284171 |
| Clostridium sp. CAG:7 | 1262832 | 0.001101715 |
| Roseburia sp. CAG:18 | 1262941 | 0.001092103 |
| Blautia sp. CAG:37 | 1262757 | 0.000352532 |
| Eubacterium sp. CAG:202 | 1262884 | 0.000334486 |
| Eubacterium eligens CAG:72 | 1263077 | 0.000263831 |
| Collinsella sp. CAG:166 | 1262850 | 0.000173492 |
| Collinsella sp. 4_8_47FAA | 742722 | 0.000171706 |
| Collinsella aerofaciens | 74426 | 0.000167991 |

TABLE 9

Donor 1 Non-spore fraction

| Species | Tax ID | Abundance (i.e., 0.1 = 10%) |
|---|---|---|
| Bacteroides fragilis | 817 | 0.240030795 |
| Bacteroides sp. 1_1_6 | 469586 | 0.109915096 |
| Bacteroides ovatus | 28116 | 0.057356484 |
| Bacteroides vulgatus | 821 | 0.057027174 |
| Parabacteroides merdae CAG:48 | 1263094 | 0.04539845 |
| Bacteroides sp. D20 | 585543 | 0.040816026 |
| Streptococcus salivarius CAG:79 | 1263109 | 0.037047843 |
| Bacteroides uniformis | 820 | 0.036665374 |
| Bifidobacterium longum | 216816 | 0.034175394 |
| Bacteroides sp. 3_1_19 | 469592 | 0.031930786 |
| Parabacteroides sp. D26 | 658662 | 0.030863579 |
| Streptococcus salivarius | 1304 | 0.028772724 |
| Parabacteroides merdae | 46503 | 0.020672573 |
| Parabacteroides distasonis | 823 | 0.019996753 |
| Bifidobacterium bifidum | 1681 | 0.01694393 |
| Bacteroides eggerthii | 28111 | 0.016877293 |
| Parabacteroides johnsonii | 387661 | 0.01683543 |
| Streptococcus sp. SR4 | 1161417 | 0.015911045 |
| Bacteroides sp. UNK.MGS-14 | 1638780 | 0.013589416 |
| Bifidobacterium adolescentis | 1680 | 0.013578653 |
| Bacteroides eggerthii CAG:109 | 1263043 | 0.010184478 |
| Collinsella sp. CAG:166 | 1262850 | 0.0086852 |
| Collinsella sp. 4_8_47FAA | 742722 | 0.008097428 |
| Bilophila wadsworthia | 35833 | 0.007388944 |
| Collinsella aerofaciens | 74426 | 0.007276615 |
| Coprococcus comes CAG:19 | 1263070 | 0.006906287 |
| Odoribacter splanchnicus | 28118 | 0.006038242 |
| Carnobacterium sp. N15.MGS-207 | 1637504 | 0.005593854 |
| Bacteroides salyersiae | 291642 | 0.005332525 |
| Parabacteroides goldsteinii | 328812 | 0.004365227 |
| Phascolarctobacterium sp. CAG:207 | 1262914 | 0.00354678 |
| [Ruminococcus] torques | 33039 | 0.003338547 |
| Coprococcus comes | 410072 | 0.003244754 |
| Odoribacter sp. UNK.MGS-12 | 1638778 | 0.002983057 |
| Ruminococcus sp. CAG:55 | 1262960 | 0.00259416 |
| Bacteroides sp. CAG:189 | 1262737 | 0.001677158 |
| Bacteroides sp. 1_1_30 | 457387 | 0.001649594 |
| Ruminococcus sp. CAG:90 | 1262968 | 0.001606256 |
| Ruminococcus faecis | 592978 | 0.00158367 |
| Ruminococcus sp. SR1/5 | 657323 | 0.00113882 |
| Blautia sp. GD8 | 1737424 | 0.00111962 |
| Bilophila sp. 4_1_30 | 693988 | 0.00111359 |
| Blautia obeum | 40520 | 0.00092913 |
| Blautia wexlerae | 418240 | 0.00083038 |
| Ruminococcus sp. CAG:17 | 1262951 | 0.000670423 |
| Blautia sp. KLE 1732 | 1226324 | 0.000633229 |

TABLE 9-continued

Donor 1 Non-spore fraction

| Species | Tax ID | Abundance (i.e., 0.1 = 10%) |
|---|---|---|
| Dorea longicatena | 88431 | 0.00057183 |
| Ruminococcus sp. CAG:60 | 1262964 | 0.000463894 |
| Ruminococcus sp. 5_1_39BFAA | 457412 | 0.000382035 |
| [Eubacterium] hallii | 39488 | 0.000215007 |
| Clostridium sp. JCC | 1414720 | 9.92671E-05 |

TABLE 10

Donor 2 Spore fraction

| Species | Tax ID | Abundance (i.e., 0.1 = 10%) |
|---|---|---|
| Ruminococcus sp. N15.MGS-57 | 1637508 | 0.246389057 |
| Ruminococcus bicirculans | 1160721 | 0.228445766 |
| Ruminococcus sp. CAG:57 | 1262962 | 0.208089003 |
| Firmicutes bacterium CAG:41 | 1263021 | 0.066550215 |
| Ruminococcus sp. CAG:9 | 1262967 | 0.040836711 |
| Ruminococcus sp. 5139BFAA | 457412 | 0.027095679 |
| Blautia wexlerae | 418240 | 0.01887964 |
| Ruminococcus sp. CAG:90 | 1262968 | 0.017475529 |
| Roseburia sp. CAG:197 | 1262943 | 0.015525608 |
| Intestinibacter bartlettii | 261299 | 0.01380223 |
| Turicibacter sp. HGF1 | 910310 | 0.011074177 |
| Staphylococcus aureus | 1280 | 0.009583571 |
| Turicibacter sanguinis | 154288 | 0.009314866 |
| Lachnospiraceae bacterium 5_1_63FAA | 658089 | 0.007625159 |
| Anaerostipes hadrus | 649756 | 0.006875226 |
| Ruminococcus sp. SR1/5 | 657323 | 0.006627311 |
| Clostridium sp. 1_1_41A1FAA | 457397 | 0.006165961 |
| Ruminococcus sp. CAG:17 | 1262951 | 0.005129445 |
| Eubacterium hallii CAG:12 | 1263078 | 0.004980707 |
| Eubacterium eligens CAG:72 | 1263077 | 0.004801422 |
| Eubacterium sp. CAG:202 | 1262884 | 0.004712347 |
| Clostridium sp. JCC | 1414720 | 0.004664514 |
| Clostridium bartlettii CAG:1329 | 1263063 | 0.002897256 |
| [Ruminococcus] torques | 33039 | 0.002887768 |
| [Clostridium] sordellii | 1505 | 0.002760016 |
| [Eubacterium] hallii | 39488 | 0.002577268 |
| Coprococcus sp. ART55/1 | 751585 | 0.002478733 |
| Ruminococcus callidus | 40519 | 0.002243859 |
| Blautia sp. GD8 | 1737424 | 0.002118038 |
| Coprococcus sp. CAG:131 | 1262862 | 0.002021396 |
| Clostridium celatum | 36834 | 0.001931035 |
| Ruminococcus sp. JC304 | 1095771 | 0.001888972 |
| Blautia sp. KLE 1732 | 1226324 | 0.001503377 |
| Roseburia faecis | 301302 | 0.001314441 |
| [Eubacterium] eligens | 39485 | 0.001179972 |
| Blautia obeum | 40520 | 0.000867666 |
| Firmicutes bacterium CAG:212 | 1263009 | 0.000684508 |
| Dorea longicatena | 88431 | 0.000498219 |
| Faecalibacterium prausnitzii | 853 | 0.000370047 |
| Turicibacter sp. H121 | 1712675 | 0.000332562 |
| Bacteroides vulgatus | 821 | 0.000312006 |
| Bifidobacterium longum | 216816 | 0.000302065 |
| Collinsella aerofaciens | 74426 | 7.31707E-05 |
| Collinsella sp. 4_8_47FAA | 742722 | 7.29356E-05 |

TABLE 11

Donor 2 Non-spore fraction

| Species | Tax ID | Abundance (i.e., 0.1 = 10%) |
|---|---|---|
| Bifidobacterium longum | 216816 | 0.222453009 |
| Bifidobacterium adolescentis | 1680 | 0.204814337 |
| Bifidobacterium stercoris | 592977 | 0.19792986 |
| Collinsella sp. 4 8 47FAA | 742722 | 0.041064039 |
| Collinsella sp. CAG:166 | 1262850 | 0.040920779 |

TABLE 11-continued

Donor 2 Non-spore fraction

| Species | Tax ID | Abundance (i.e., 0.1 = 10%) |
|---|---|---|
| Collinsella aerofaciens | 74426 | 0.038585301 |
| Faecalibacterium prausnitzii | 853 | 0.027117182 |
| Collinsella sp. CAG:289 | 1262851 | 0.021343728 |
| Collinsella sp. MS5 | 1499681 | 0.017218285 |
| Bacteroides sp. 2_1_16 | 469587 | 0.016754777 |
| Butyrate-producing bacterium SSC/2 | 245018 | 0.014826459 |
| Bacteroides uniformis | 820 | 0.01088125 |
| Bacteroides vulgatus | 821 | 0.009174624 |
| Roseburia sp. CAG:18 | 1262941 | 0.009066265 |
| Parabacteroides merdae CAG:48 | 1263094 | 0.007515988 |
| Ruminococcus sp. CAG:55 | 1262960 | 0.007419941 |
| Blautia sp. CAG:37 | 1262757 | 0.006862496 |
| Bacteroides faecis | 674529 | 0.006664491 |
| Dorea formicigenerans CAG:28 | 1263073 | 0.006638101 |
| Coprococcus comes CAG:19 | 1263070 | 0.006034677 |
| Roseburia faecis | 301302 | 0.005997385 |
| Coprococcus comes | 410072 | 0.005897654 |
| [Ruminococcus] torques | 33039 | 0.004537152 |
| Ruminococcus sp. 5_1_39BFAA | 457412 | 0.004245095 |
| Staphylococcus aureus | 1280 | 0.004122705 |
| Coprococcus sp. ART55/1 | 751585 | 0.003809693 |
| Ruminococcus sp. CAG:9 | 1262967 | 0.003691574 |
| Parabacteroides merdae | 46503 | 0.003687796 |
| Ruminococcus faecis | 592978 | 0.003599944 |
| Dorea longicatena | 88431 | 0.003502778 |
| Blautia wexlerae | 418240 | 0.003439925 |
| Coprococcus sp. CAG:131 | 1262862 | 0.003276343 |
| Bacteroides sp. D20 | 585543 | 0.003271357 |
| Lachnospiraceae bacterium CAG:25 | 1262984 | 0.003054647 |
| Dorea formicigenerans | 39486 | 0.002973301 |
| Bacteroides fragilis | 817 | 0.002092517 |
| Parabacteroides distasonis | 823 | 0.002063842 |
| Ruminococcus sp. CAG:17 | 1262951 | 0.001718271 |
| Sutterella sp. CAG:397 | 1262976 | 0.001636647 |
| Ruminococcus sp. JC304 | 1095771 | 0.001289925 |
| Bacteroides massiliensis | 204516 | 0.001287539 |
| Blautia obeum | 40520 | 0.0012123 |
| Eubacterium hallii CAG:12 | 1263078 | 0.001142996 |
| [Eubacterium] hallii | 39488 | 0.000968696 |
| Odoribacter splanchnicus | 28118 | 0.000792204 |
| Bacteroides eggerthii | 28111 | 0.000777778 |
| Anaerostipes hadrus | 649756 | 0.000741052 |
| Bacteroides ovatus | 28116 | 0.000498587 |
| Agathobacter rectalis | 39491 | 0.000470219 |
| Butyrate-producing bacterium SS3/4 | 245014 | 0.000469715 |
| Firmicutes bacterium CAG:270 | 1263014 | 0.000404282 |
| Parabacteroides sp. D26 | 658662 | 0.000322602 |
| Streptococcus salivarius | 1304 | 0.000287024 |
| Eubacterium sp. CAG:202 | 1262884 | 0.000275057 |
| [Clostridium] sordellii | 1505 | 8.86088E−05 |
| Eubacterium eligens CAG:72 | 1263077 | 6.0261E−05 |
| Ruminococcus sp. CAG:60 | 1262964 | 2.47064E−05 |

Figure 23:
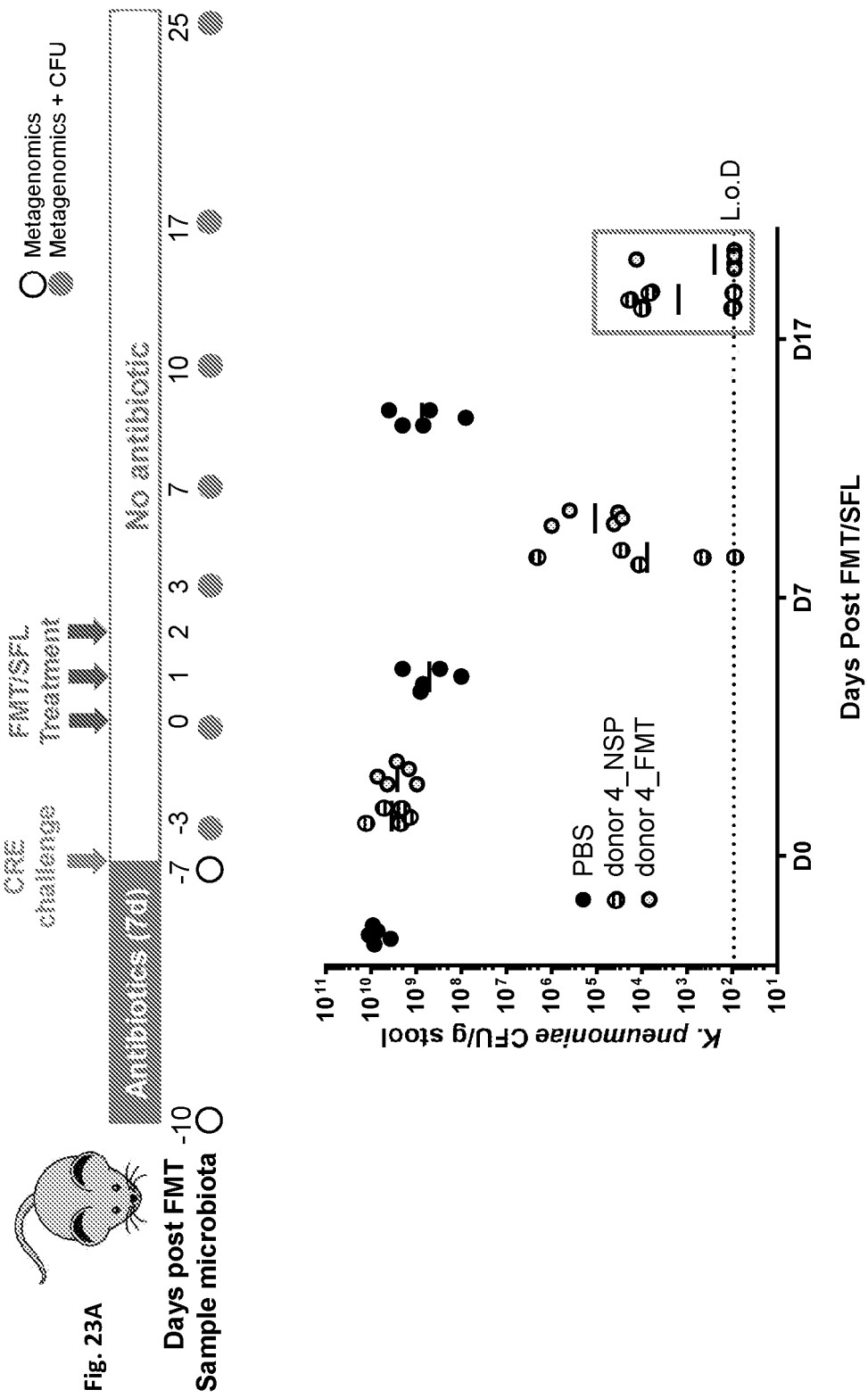
FIGS. 23A and 23B show FMT and stool fractions enriched in non-spore-forming ("NSP") bacteria from a healthy donor (donor 4, also referred to as "D14") reduce the CRE burden in colonized mice.

Example 2B: Non-Spore Forming Stool Fractions are as Effective as FMT in CRE Clearance As described herein, stool samples from healthy donors have been found to promote clearance of multidrug-resistant *Klebsiella pneumoniae* colonization. Non-spore forming (NSP) stool fractions and FMT from healthy donors were tested for their ability to reduce the CRE burden (decolonize) in mice colonized with CRE as shown in FIG. 23A. As shown in FIG. 23B, the NSP fractions were as effective as FMT at reducing the CRE burden. Mice that received the NSP fractions exhibited comparable CRE decolonization rates as mice that received FMT.

Example 2C: Live Bacterial Products (LBPs) Directed Against CRE

Bacterial strains were assembled into various live bacterial products (LBPs) shown in FIG. 4. The LBPs were tested in the CRE colonization mouse model. As shown in FIGS. 5A-5D, the LBPs and FMT reduced the CRE burden as compared to PBS control.

Example 2D: Clearance of CRE

Figure 6:
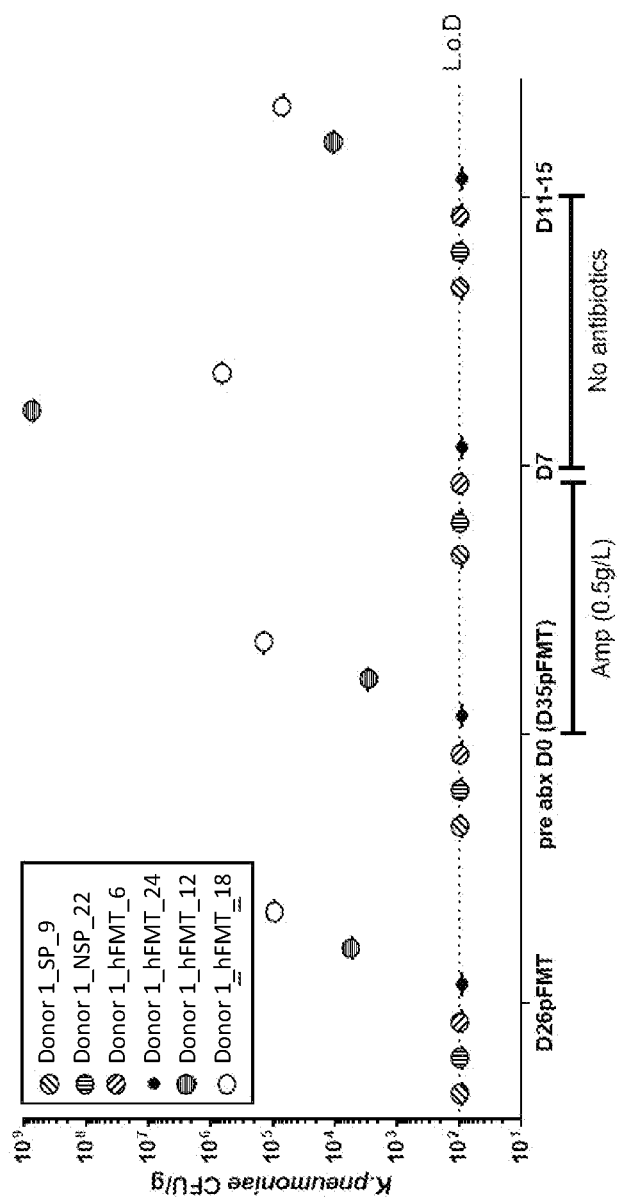
FIG. 6 shows the *K. pneumoniae* levels in fecal samples of decolonized mice on day 26 post fecal matter treatment ("D26pFMT"), prior to antibiotic treatment ("pre abx D0", corresponding to day 35 post fecal matter treatment ("D35pFMT")), day 7 ("D7") following antibiotic treatment, and days 11-15 ("D11-15") following antibiotic treatment. Ampicillin ("Amp") was administered from day 0 to day 7.

To determine whether CRE clearance by FMT and SFL was true clearance of CRE or an inability to detect low CRE levels, mice that cleared CRE in the experiments described previously received a second round of ampicillin on day 35 post-FMT/SFL treatment. Ampicillin treatment was terminated after 7 days. Mice that had detectable CRE levels ($10^4$-$10^5$ CFU range) were also ampicillin-treated and used as controls. Fecal samples were collected from each mouse pre-antibiotic administration, on day 7 of ampicillin treatment, and at 2 weeks post-ampicillin treatment to assess the re-expansion, or lack thereof, of CRE. As shown in FIG. 6, CRE levels did not increase following antibiotic treatment of decolonized mice, indicating that FMT/SFL-mediated decolonization of CRE is sufficient to eradicate CRE from the intestines.

Example 2E: Identification of CRE-Antagonistic Strains

In vitro assays were performed to identify CRE pathogen-antagonistic strains. Soft agar overlay assays are commonly used in classical antibiotic drug discovery programs, and a zone of inhibition indicates suppression of the target strain. The assay complements other in vitro screening systems (e.g., growth competition assay). The top agar layer is embedded with the target strain, which is poured over plate containing a sterile disc spotted with a test strain. After an incubation period, a zone of inhibition surrounding the disc can be measured, and the level of activity of different test strains can be examined.

Figure 8:
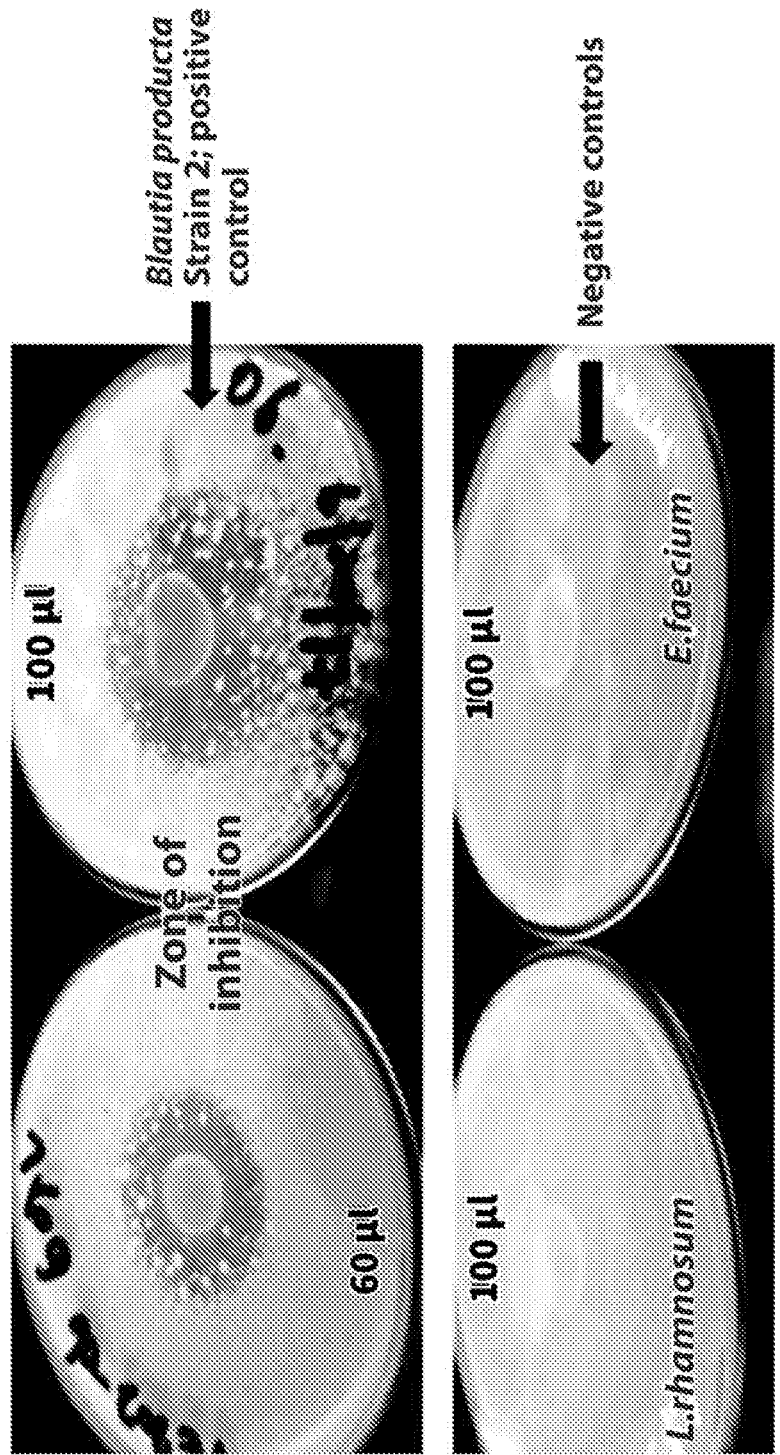
FIG. 8 shows examples of a soft agar overlay assay to identify strains having pathogen-antagonistic activity against CRE.

In the example soft agar overlays of FIG. 8, *Blautia producta* inhibits *K. pneumoniae* 2814 (CRE) in the assay, shown by the zone of inhibition. The inhibitory activity is both dose-dependent and *bacterium*-specific. Neither *L. rhamnosum* nor *E. faecium* resulted in a zone of inhibition in the assay. FIG. 9 presents a table showing bacterial strains that had CRE suppressing activity in the soft agar overlay assays.

Figure 10:
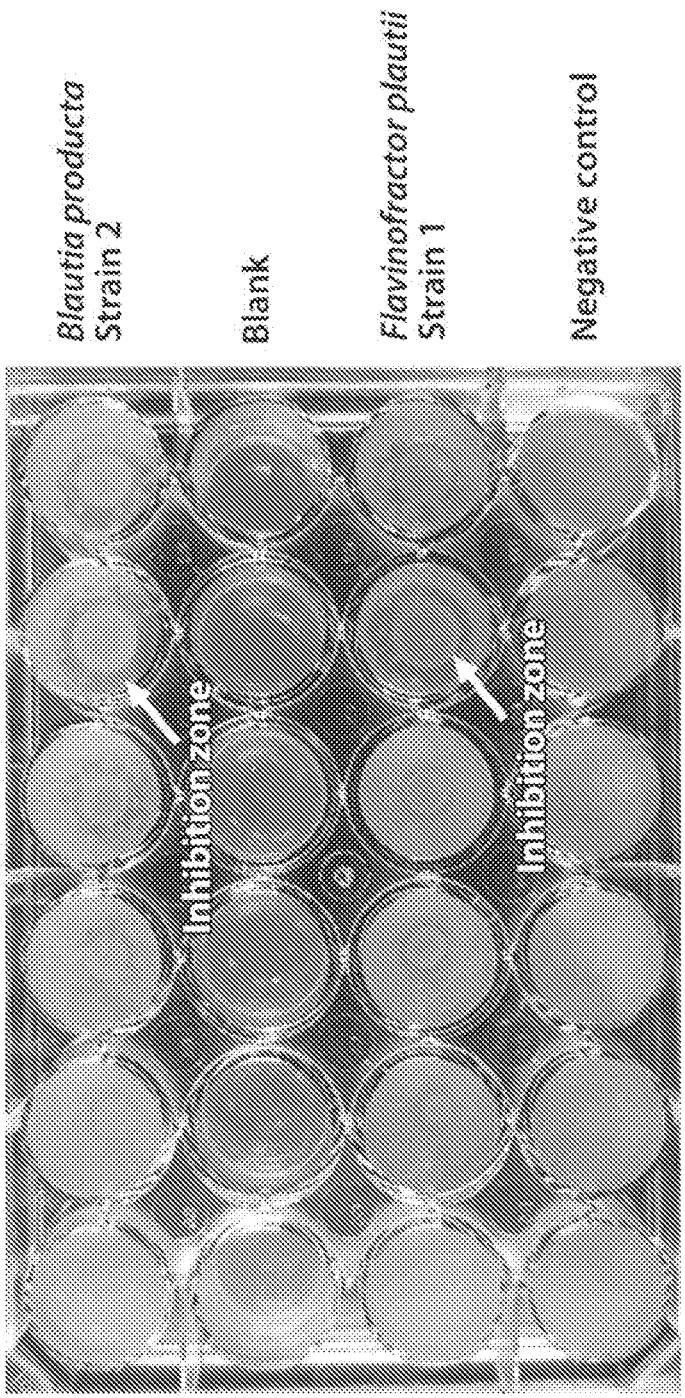
FIG. 10 shows an example agar overlay screen to identify pathogen-antagonistic strains.

The soft agar overlay assay was performed using a medium throughput screening method, shown in FIG. 10. Using 24-well plates, 72 bacterial strains can be screened per day per pathogen to identify strains that have antagonistic activity against pathogenic organisms.

Figure 11:
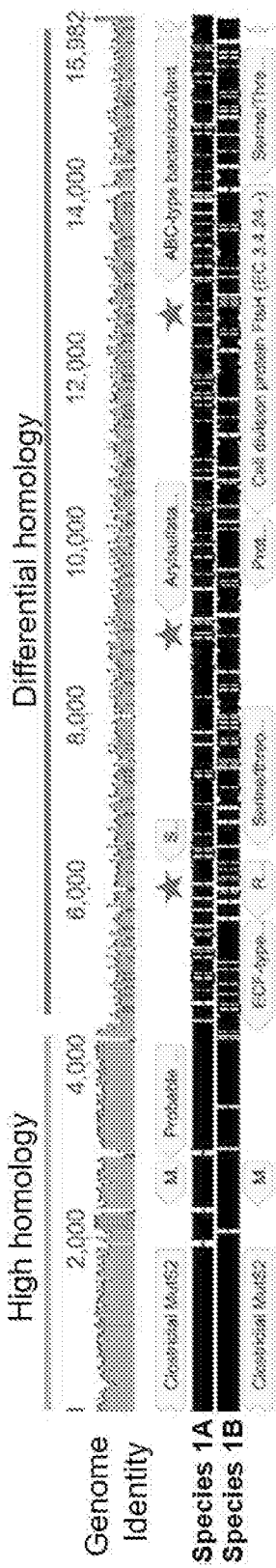
FIG. 11 show a schematic depicting a genome alignment between two strains of the *Blautia producta* species, a first strain having pathogen-antagonizing activity (Strain 2) and a second strain of the same bacterial species that does not have pathogen-antagonizing activity (Strain 10). The alignment identified a region of differential homology encoding bacteriocin-associated genes that were present in Strain 2 but absent in Strain 10.

Finally, genomic information from the bacterial strains was examined to determine reveal potential mechanisms of action for the pathogen-antagonistic activity. For example, two bacterial strains of the same species (*Blautia producta*) were identified having differential pathogen-antagonistic activity. In particular, Strain 2 had pathogen-antagonistic activity and Strain 10 did not. A genome alignment revealed the presence of bacteriocin-associated genes (indicated by stars in FIG. 11) in Strain 2 that were absent in Strain 10. The analysis was performed using anti-SMASH (antibiotics and secondary metabolite analysis shell; Weber et al., 2015).

Example 3: Colonization Resistance is Maintained Following Clearance of CRE

Figure 24:
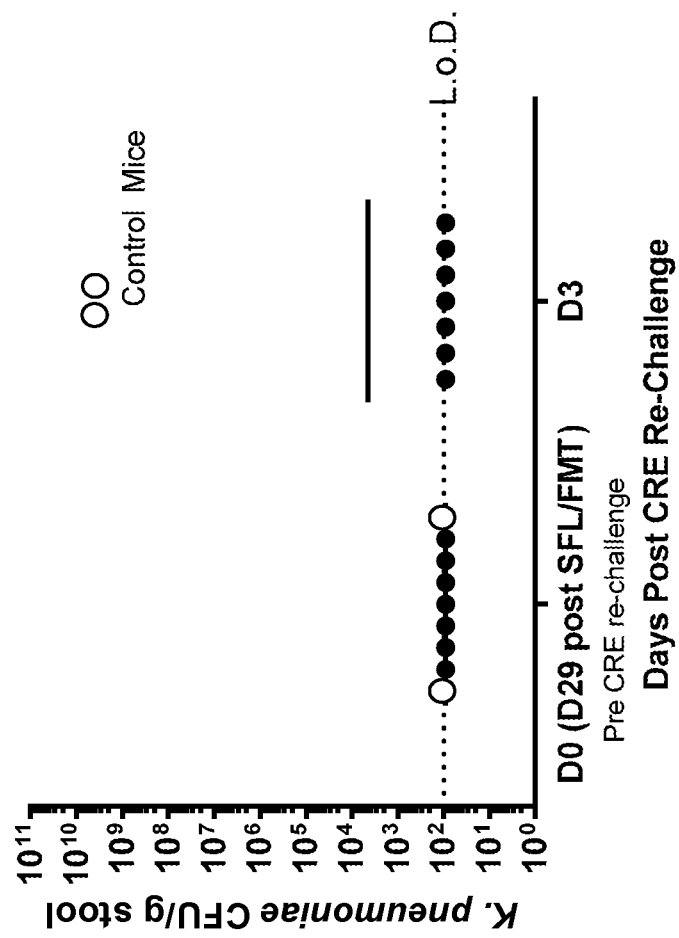
FIG. 24 shows CRE CFU levels in fecal samples from mice that previously cleared CRE and were re-challenged with CRE. CRE CFU levels are shown prior to the second challenged with CRE (day 0, corresponding to day 29 post stool fraction treatment/fecal matter treatment ("D29 post SFL/FMT") and three days after the second challenge ("D3").

Mice that had previously cleared CRE colonization in the FMT/SFL experiments described in Example 2B (FIGS. 23A and 23B) were assessed to determine if the mice could be re-colonized with subsequent CRE challenge. A subset of mice that had cleared CRE in FIG. 23B at various time points post-FMT/SFL administration were re-challenged with $10^5$ CRE CFU on day 29 post-FMT/SFL treatment. To ensure viability of the CRE inoculum and its ability to expand in the intestine, a cohort of untreated mice were administered ampicillin for 7 days and challenged with CRE. Fecal samples were collected three days post-challenge to assess CRE expansion. As shown in FIG. 24, the mice that had previously cleared CRE were resistant to re-colonization with CRE.

Example 4: Vancomycin-Resistant *Enterococcus faecium*

Figure 12:
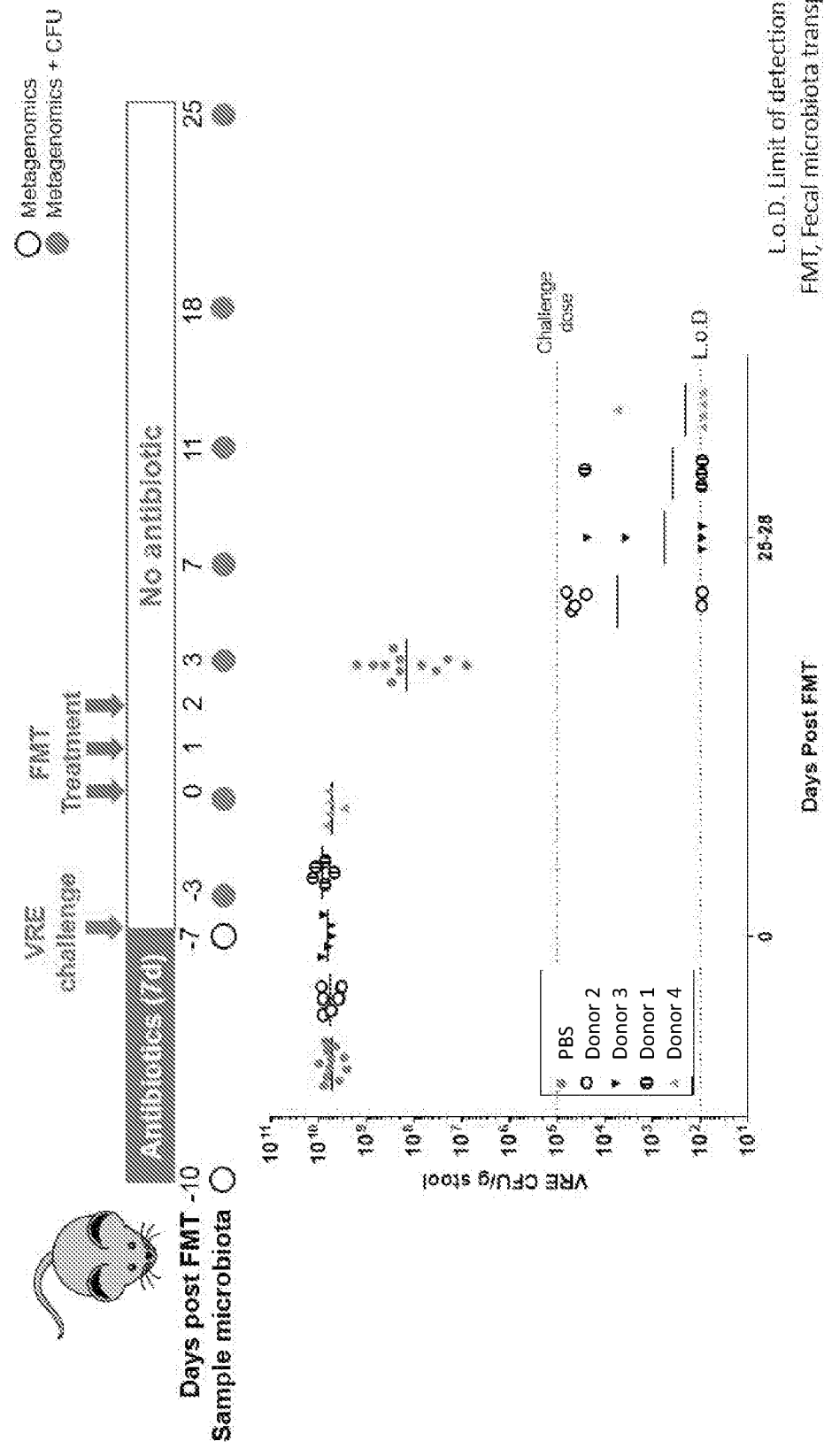
FIGS. 12A and 12B show FMT samples from a donor reduce the VRE burden in colonized mice.

As described in Example 1, mouse models of vancomycin-resistant *Enterococcus faecium* (VRE) colonization were established. As shown in FIG. 12A, mice were treated with broad-spectrum antibiotics (ampicillin) for seven days prior to the VRE challenge. On day −7, the ampicillin treatment was terminated. Mice were single-housed and challenged with $10^4$-$10^5$ CFU of VRE. Seven days after the pathogen challenge (on day 0), mice were randomized into groups, and the first of three treatment doses of fecal microbiota treatment (FMT) or stool fraction library (SFL) was administered on the third day after pathogen challenge. The three day period between VRE challenge and FMT/SPL administration served as a washout period to clear residual antibiotics and establish VRE colonization in the intestine. Fecal samples were collected at various time points post-treatment to quantify VRE levels (plating on selective media) and to determine strain engraftment by metagenomic sequencing. As shown in FIG. 12B, administration of FMT from donors reduced the VRE burden from densely-colonized mice.

Figure 13:
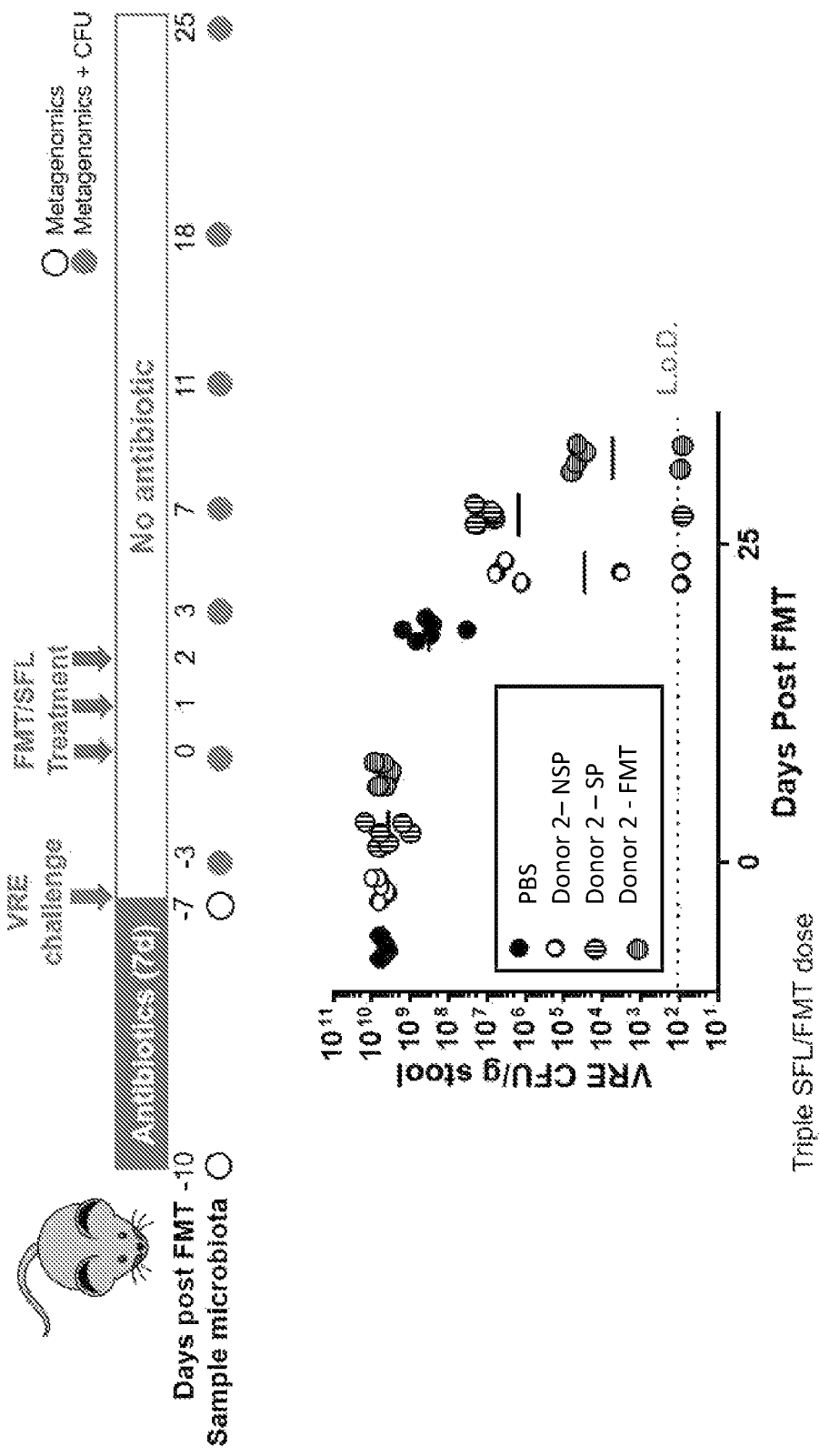
FIGS. 13A and 13B show stool fractions from a donor reduce the VRE burden in colonized mice.

Stool fractions were generated from donors with potent pathogen-antagonistic activity, as described in Example 2. The stool fractions were tested for their ability to reduce the VRE burden (decolonize) in mice colonized with VRE as shown in FIG. 13A. As shown in FIG. 13B, the stool fractions were able to reduce the VRE burden.

Figure 14:
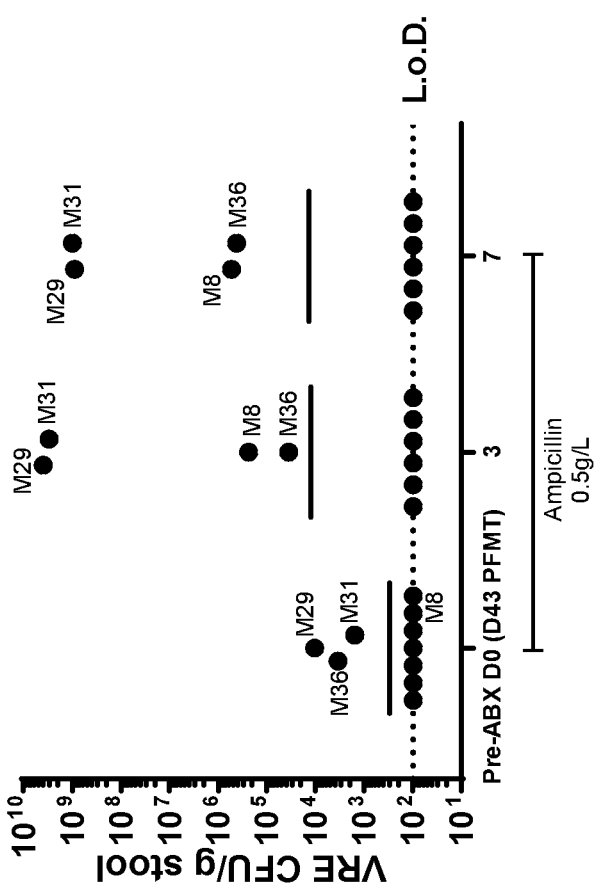
FIG. 14 shows VRE CFU levels in fecal samples of mice prior to antibiotic treatment ("pre abx D0", corresponding to day 43 post fecal matter treatment ("D43PFMT")), day 3 ("D3") following antibiotic treatment, and day 7 ("D7") following antibiotic treatment. Ampicillin was administered from day 0 to day 7. Mice that were not decolonized are labeled with identification numbers at each of the time points.

To determine whether VRE clearance by FMT and SFL was true clearance of VRE or an inability to detect low VRE levels, mice that cleared VRE in the experiments described above received a second round of ampicillin on day 43 post-FMT/SPL treatment. Ampicillin treatment was terminated after 7 days. Mice that had detectable CRE levels ($10^3$-$10^4$ CFU range) were also ampicillin-treated and used as controls. Fecal samples were collected from each mouse pre-antibiotic administration and on days 3 and 7 post-ampicillin treatment to assess the re-expansion, or lack thereof, of VRE. As shown in FIG. 14, VRE levels did not increase following antibiotic treatment of the majority of decolonized mice, indicating that FMT/SFL-mediated decolonization of VRE was sufficient to eradicate VRE from the intestines. In particular, 90% of the decolonized mice remained VRE-free despite 7 days of ampicillin treatment, whereas VRE expanded significantly in mice with detectable VRE levels.

Figure 15:
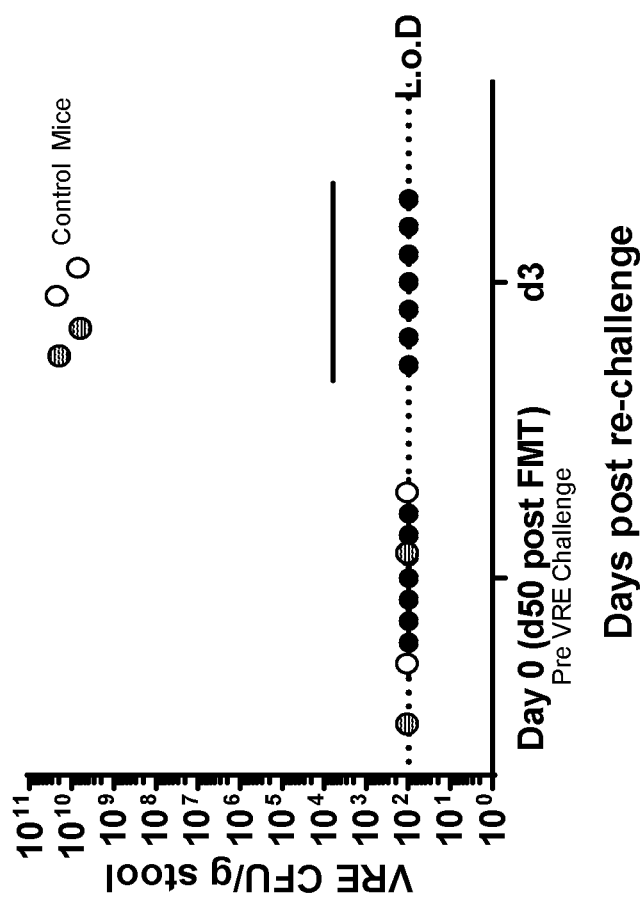
FIG. 15 shows VRE CFU levels in fecal samples from mice that previously cleared VRE and were re-challenged with VRE. VRE CFU levels are shown prior the second challenge with VRE (day 0, corresponding to day 50 post fecal matter treatment "d50 post FMT") and three days after the second challenge ("d3").

Mice that had cleared VRE colonization in the FMT experiment (FIG. 12) were assessed to determine if the mice could be re-colonized with subsequent VRE challenges. A subset of mice that had cleared VRE in FIG. 12 at various time points post-FMT administration were re-challenged with $10^4$ VRE CFU on day 0, corresponding to day 50 post-FMT. To ensure viability of the VRE inoculum and its ability to expand in the intestine, a cohort of untreated mice were administered ampicillin for 7 days to ensure viability of the VRE inoculum. Fecal samples were collected three days post-challenge to assess VRE expansion. As shown in FIG. 15, the mice that had previously cleared VRE were resistant to re-colonization with VRE.

Figure 16:
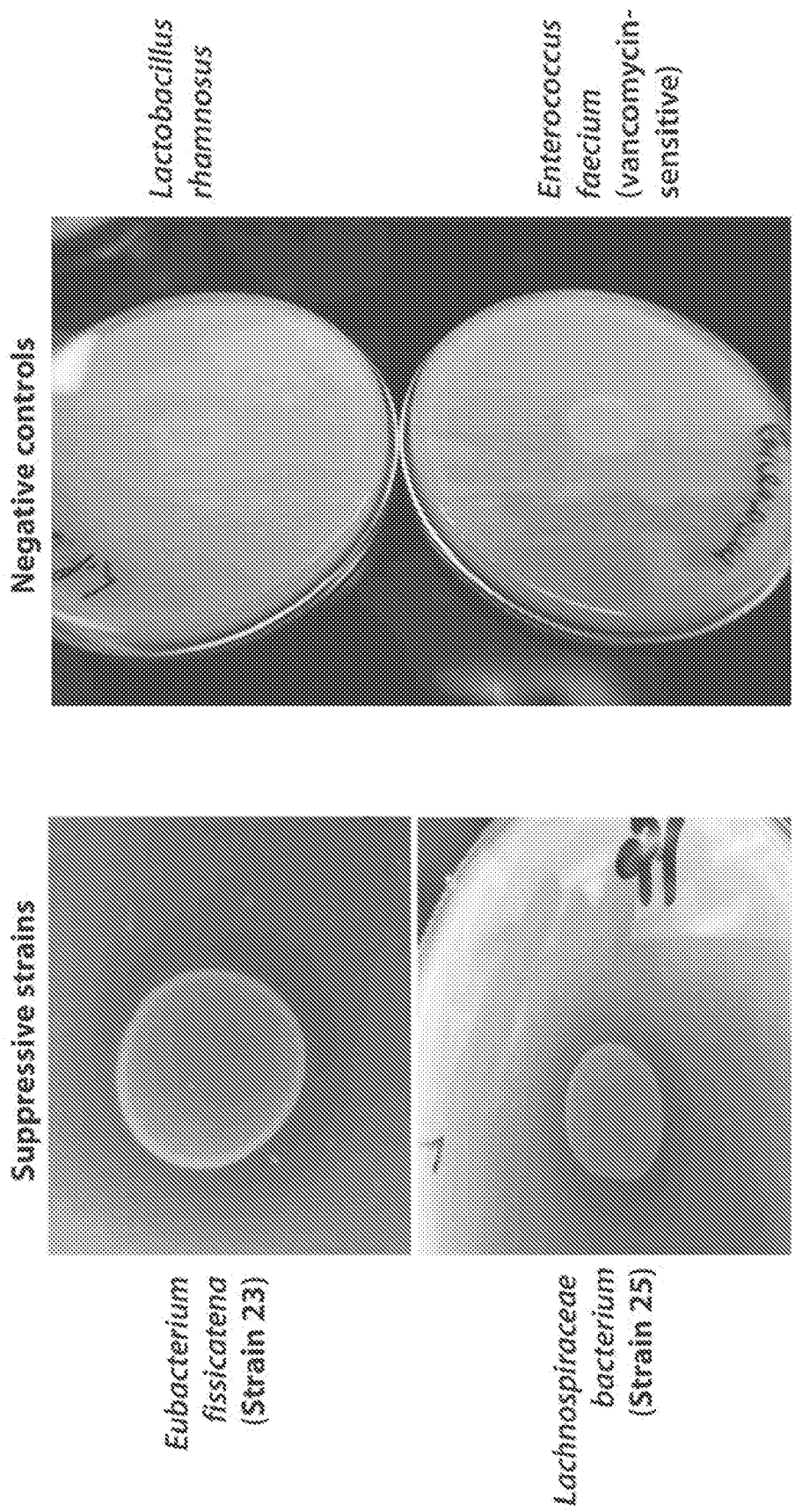
FIG. 16 shows examples of a soft agar overlay assay to identify strains with pathogen-antagonistic activity against VRE.

In vitro soft agar assays were performed, as described in Example 2, to identify pathogen-antagonistic bacterial strains having activity against VRE. Example soft agar overlays are presented in FIG. 16 in which *Eubacterium fissicatena* and *Lachnospiraceae bacterium* had zones of inhibition whereas *Lactobacillus rhamnosus* and *Enterococcus faecium* did not. Results from the soft agar overlay assays are presented in FIG. 17.

Example 5: Broth Based Competition Assays

Figure 18:
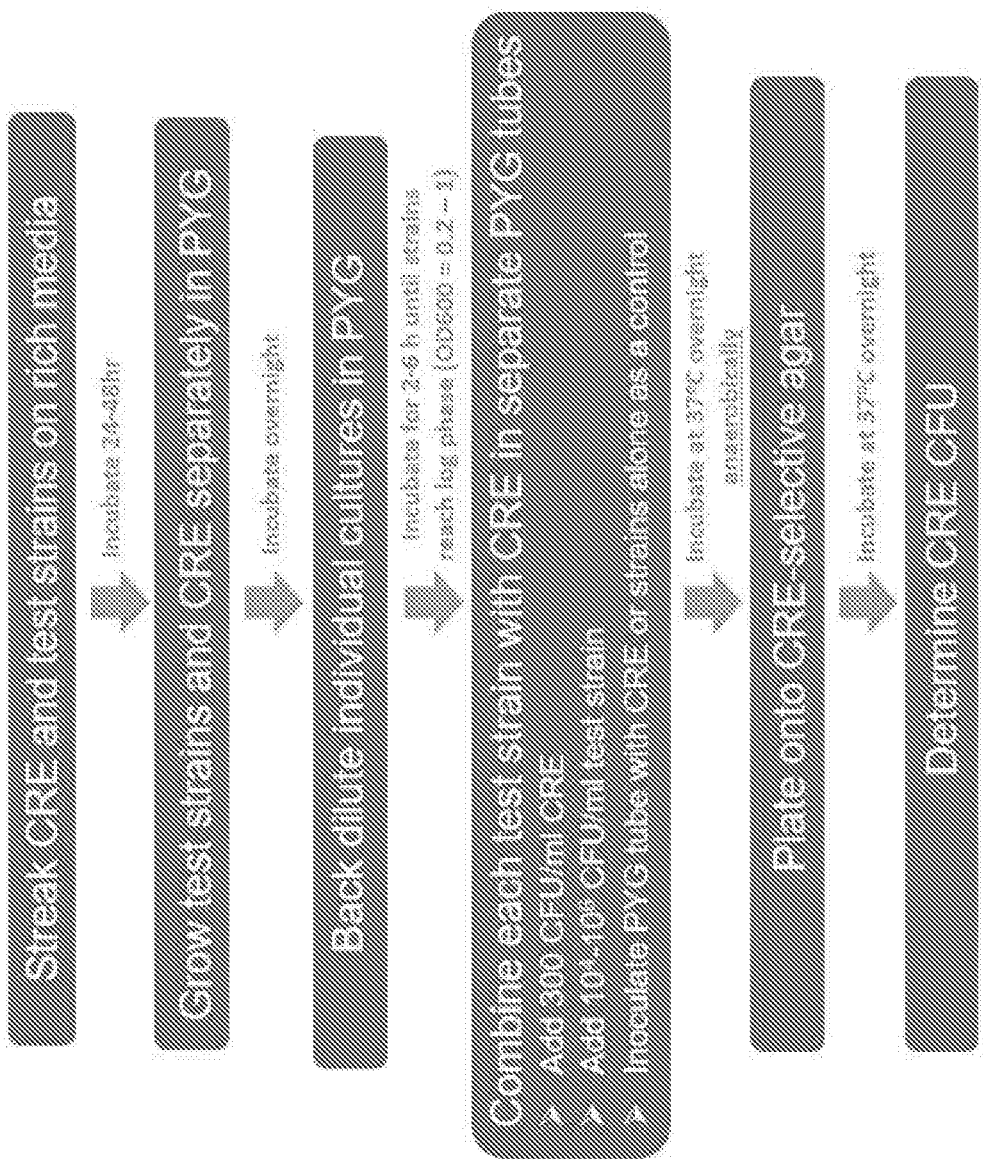
FIG. 18 shows a work-flow diagram of a broth-based competition assay, as described in Example 5.
Figure 19:
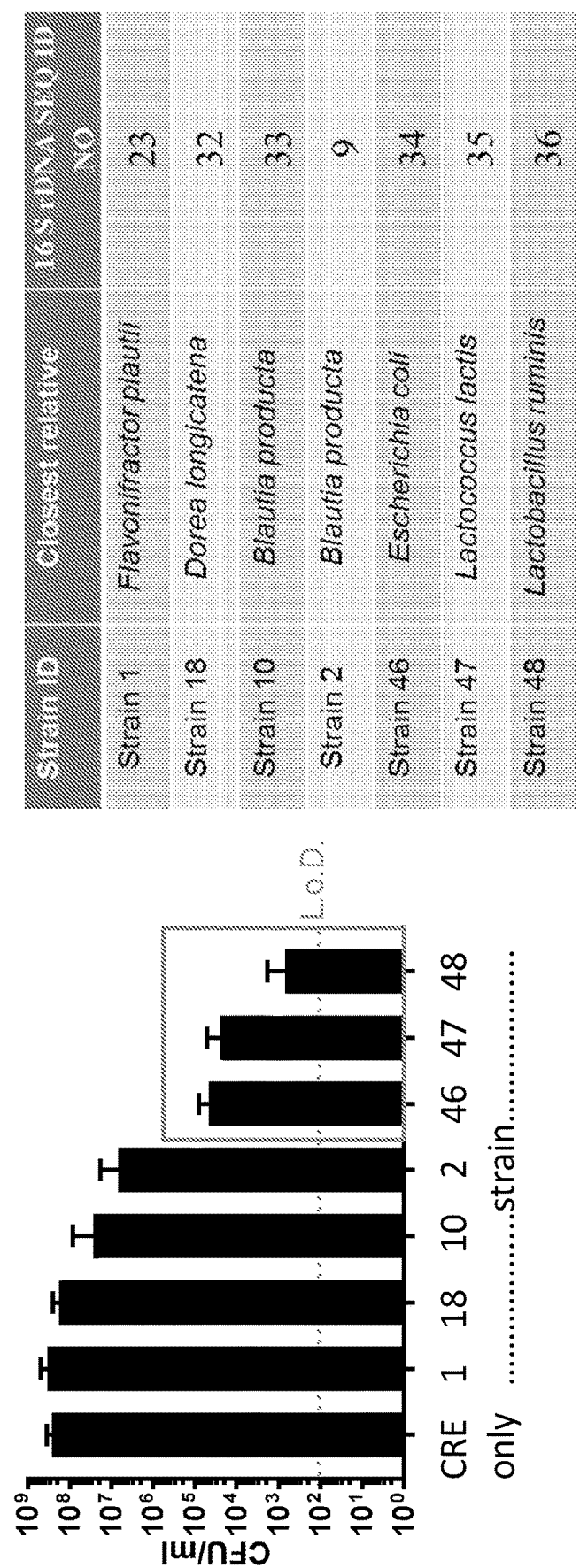
FIGS. 19 and 20 show the ability of the indicated bacterial strains to suppress CRE growth (L.o.D. is Limit of Detection).
Figure 20:
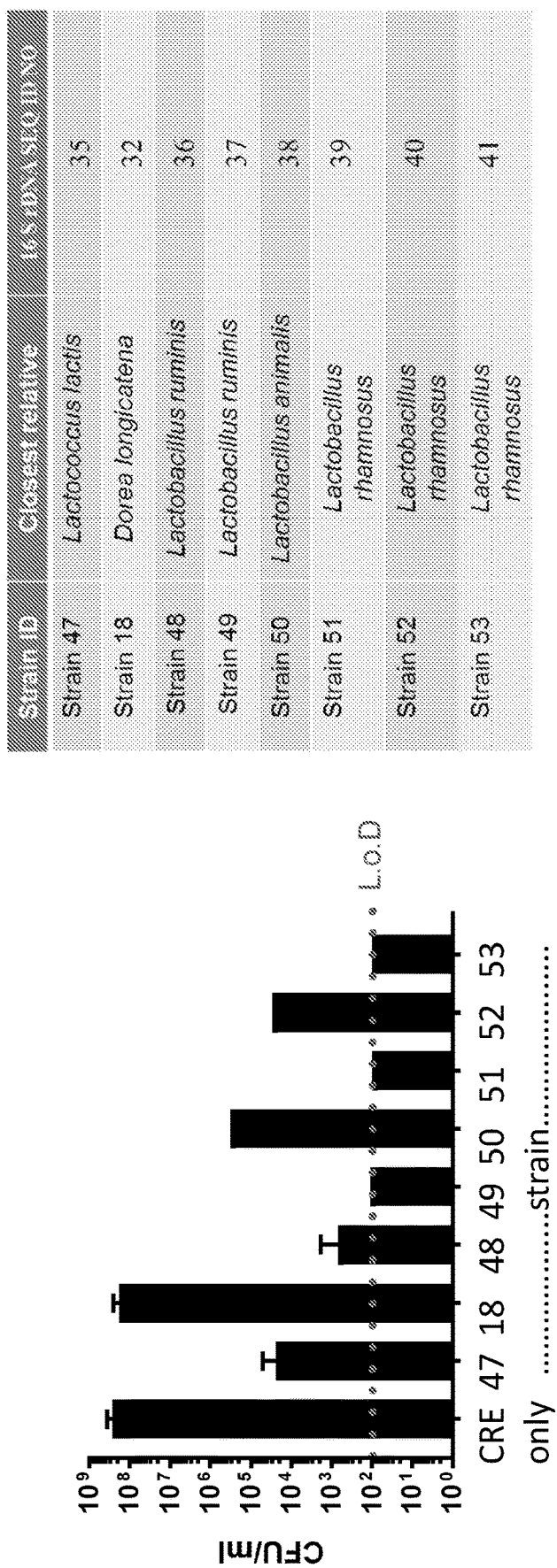

A broth-based competition assay was developed to allow for the determination of MDRO (e.g., CRE and VRE) suppressing ability of bacterial strains of interest. Individual bacterial strains to be tested were grown as a co-culture from early stationary phase liquid cultures with a defined CRE or VRE inoculum under anaerobic conditions. The culture was plated onto CRE or VRE selective media and the number of Colony Forming Units (CFUs) was determined. FIG. 18 shows a schematic of the workflow of this broth-based competition assay with CRE as the MDRO. The results are shown in FIGS. 19, 20, and 25A. FIGS. 19 and 25A shows that *Lactobacillus ruminus* provided the highest level of suppression of CRE. FIG. 20 shows that some strains of *Lactobacillus rhamnosus* provided a similar level of suppression as *Lactobacillus ruminus*. All strains evaluated were donor-derived strains except for *E. coli* (ATCC-25922) and *Lactococcus lactis* (ATCC-11454).

The bacterial strains were also assessed for their ability to suppress different CRE strains, including *K. pneumoniae* ATCC BAA-2814 (KPC), *K. pneumoniae* ATCC BAA-1705 (KPC), and *K. pneumoniae* ATCC BAA-2146 (NDM-1). As shown in FIGS. 25A-25C, several of the bacterial strains had broad-spectrum activity in inhibiting CRE strains.

Figure 21:
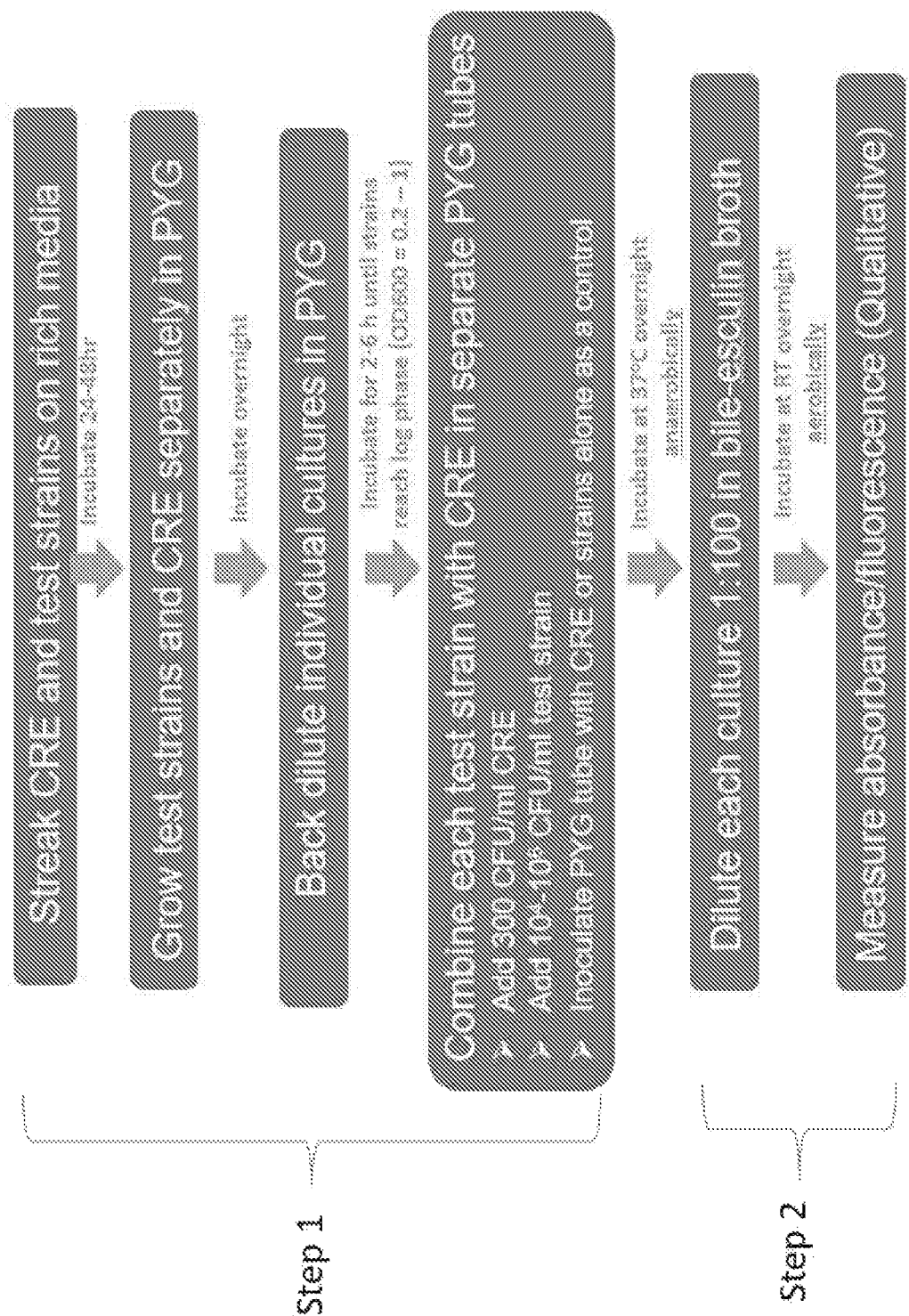
FIG. 21 shows a work-flow diagram of a broth-based competition assay with optical detection, as described in Example 5.
Figure 22:
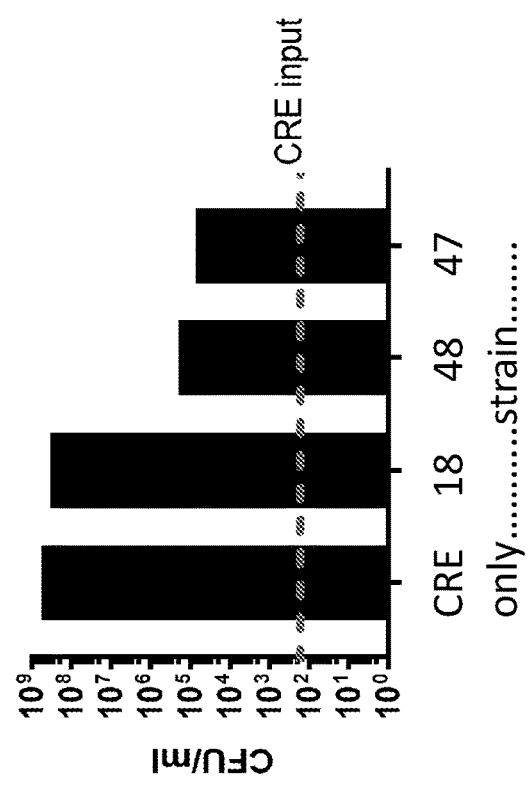
FIG. 22 shows the ability of the indicated bacterial strains to suppress CRE growth (RFU is Relative Fluorescence Unit).

The broth-based competition assay was developed further to allow for suppression level readout through color observation or relative fluorescence units (RFUs). FIG. 21 shows a schematic of the workflow of the broth-based competition assay with visual readout. Individual bacterial strains to be tested were grown as a co-culture from early stationary phase liquid cultures with a defined CRE or VRE inoculum under anaerobic conditions. After growth overnight, a small aliquot of each co-culture was transferred into chromogenic, selective media (bio-esculin broth) that changes color from clear to dark as a result of CRE or VRE expansion. Eight hours after transfer into the bio-esculin broth, any change in chromogenicity, which is indicative of CRE/VRE growth, was assessed visually and measured by fluorescence intensity as relative fluorescence units (RFU). The results of a representative experiment are shown in FIG. 22. Pathogens cultured alone or in the presence of inactive strains expanded to $10^8$-$10^9$ CFU which corresponded to $10^3$ RFU. Pathogens grown in the presence of highly suppressive strains resulted in ≥3 log reduction in pathogen expansion and corresponded to $10^5$ RFU, which was similar to the RFU control of the media alone. The assay with visual readout therefore has a sufficient dynamic range to evaluate the suppressive activity of bacterial strains of interest. Similar to the outcome of the CFU broth assay, *Lactobacillus rhamnosus* and *Lactobacillus ruminus* provided the strongest level of suppression.

The assay therefore has a sufficient dynamic range to evaluate the suppressive activity of bacterial strains of interest.

Example 6: FMT Efficacy Against VRE and CRE—Single Dose Vs. Triple Dose

Figures 26A, 26B:
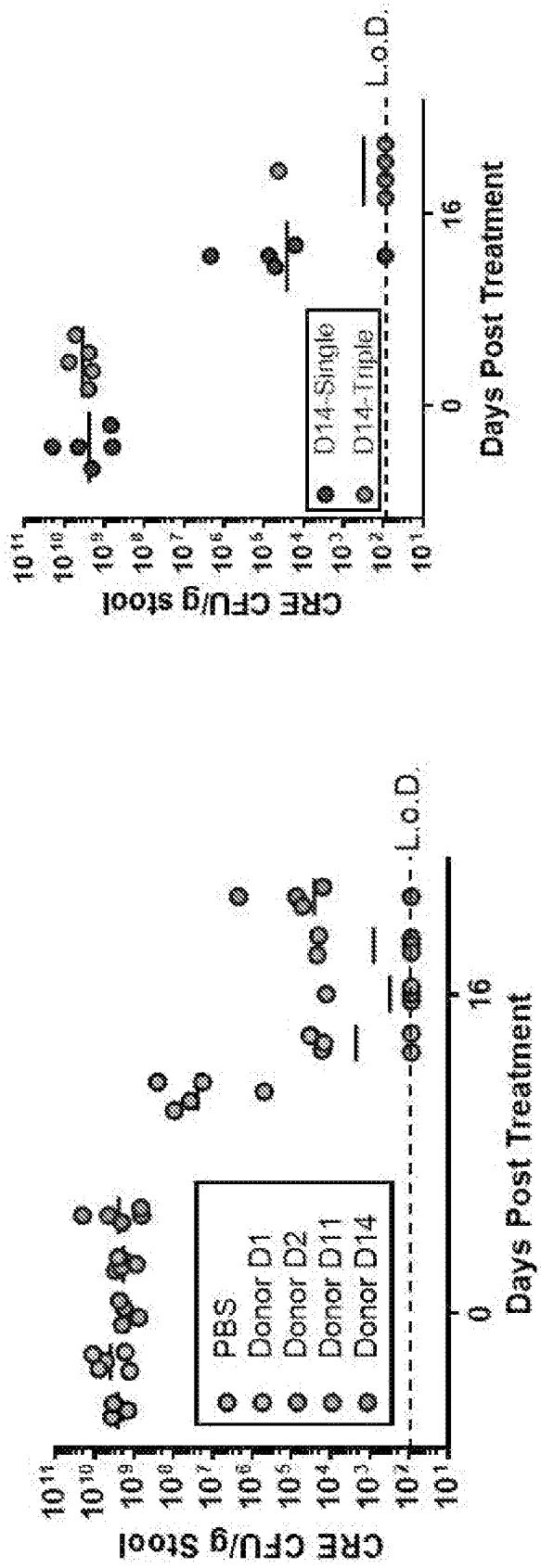
FIGS. 26A-26C show the efficacy of FMT against CRE.
Figure 26C:
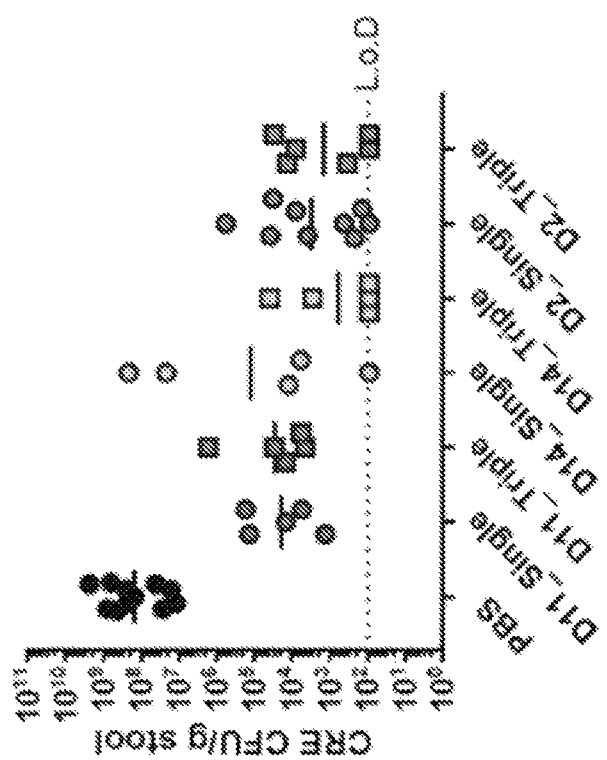

To investigate the efficacy of FMT treatment against vancomycin resistant *Enterococci* (VRE) and carbapenem resistant *Enterobacteriaceae* (CRE), C57BL/6 mice were treated with 0.5 g of ampicillin in the drinking water for 7 days and challenged with $10^5$ colony-forming units (CFU) of either VRE (ATCC 700221) or CR-KP (ATCC BAA-2814) on day 7, at which point antibiotic treatment was discontinued. Three days following challenge, subsets of mice were administered a single dose or three consecutive FMT doses from each of four well-characterized donors. CR-KP and VRE colonization levels were measured in fecal samples collected from each mouse longitudinally following the first FMT dose by plating on selective media. While control mice (PBS-treated) remained densely colonized for the duration of the experiment, mice treated with fecal material from all four donors exhibited reduced levels of CR-KP (see FIGS. 26A and 26C) and VRE that were comparable to, or higher than, mouse derived FMT. Notably, a single FMT dose was as efficacious as a triple dose at clearing CR-KP (FIGS. 26A and 26C) and VRE for 3 of the 4 donors. Donor D14, on the other hand, achieved a 75% clearance rate for both CR-KP and VRE when administered to mice as a triple dose compared to 25% when administered as a single dose (see FIGS. 26B and 26C).

Example 7: Stool Fraction Efficacy Against VRE and CRE

Figure 27:
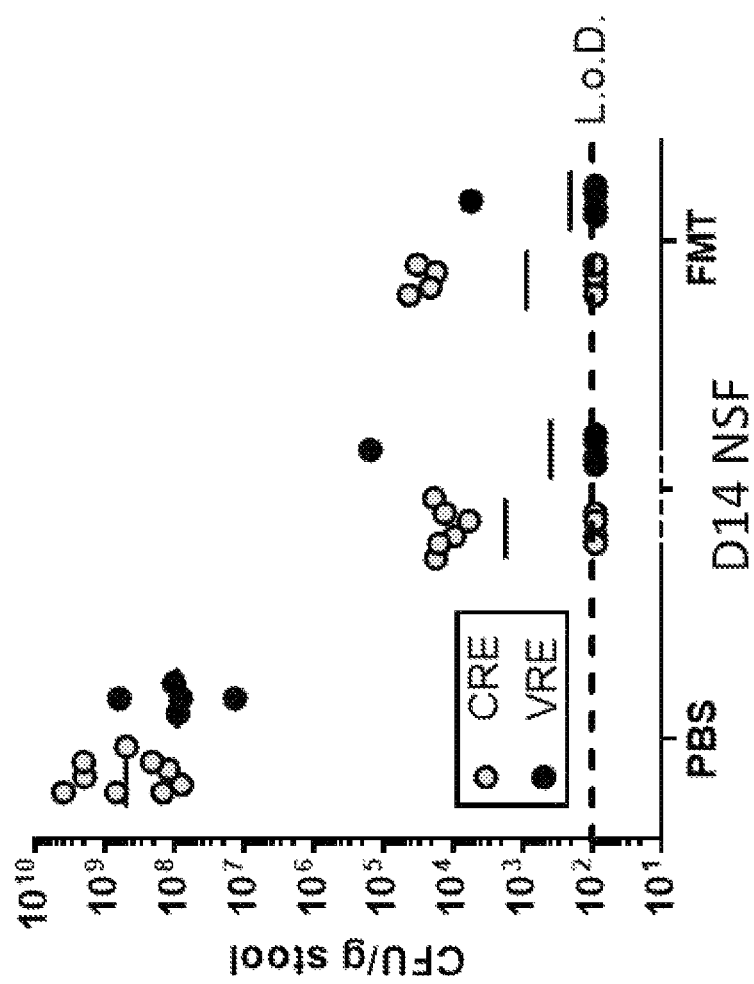
FIG. 27 shows that a non-spore forming ("NSF") enriched stool fraction from a donor (donor 4, "D14") reduces the CRE and VRE CFU levels in mice at day 25 following the three doses of the fecal matter/stool fraction treatment. CRE and VRE CFU levels for control (PBS) and FMT are also shown. L.o.D. is Limit of Detection.
Figure 29:
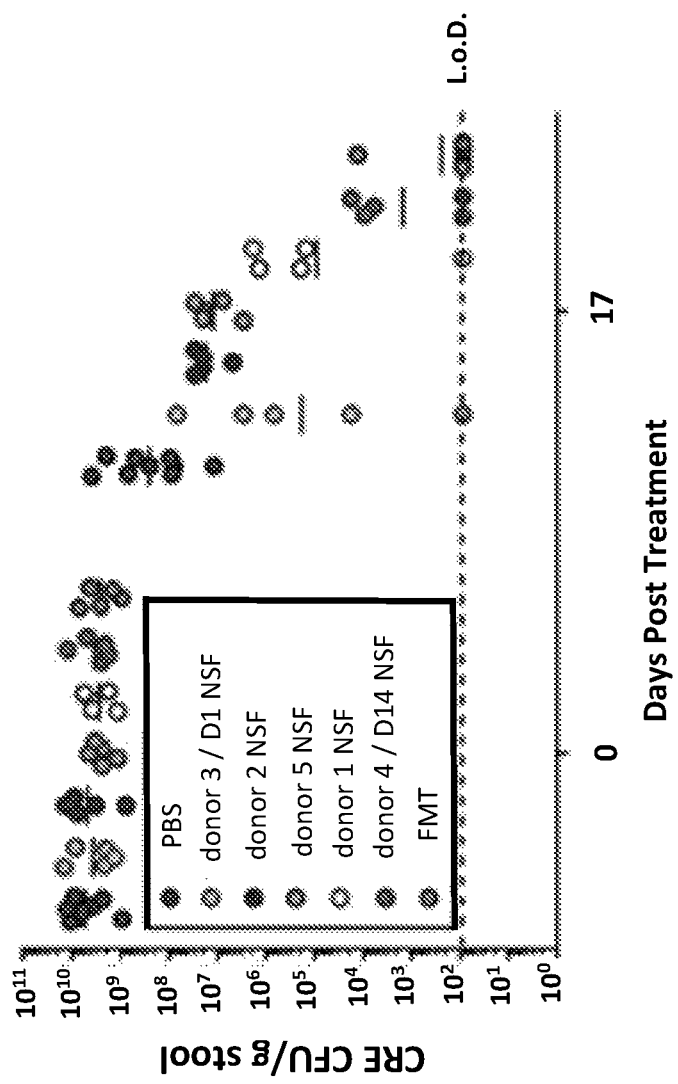
FIG. 29 shows non-spore forming ("NSF") enriched stool fractions or FMT reduce the CRE burden in mice that were treated with ampicillin for 7 days and then challenged with CRE. Three days following CRE challenge, mice were administered 3 consecutive doses of control (PBS), bacterial compositions from donors (donor 3 ("D1"), donor 2, donor 5, donor 1, or donor 4 ("D14")) or human fecal material (FMT). CRE CFU levels were quantified at 0 and 17 days post administration ("post-treatment"). At each time point, the data from left-to-right are control (PBS), donor 3 ("D1"), donor 2, donor 5, donor 1, donor 4 ("D14"), and FMT. L.o.D. is Limit of Detection.

Non-spore forming fractions were generated from donor 3, donor 2, donor 5, donor 1, and donor 4 ("D14"), as described in Example 2. The stool fractions were tested for their ability to reduce the CRE burden in mice colonized with CRE after 17 days of treatment (FIG. 29). The stool fractions were then tested for their ability to reduce the VRE and CRE burden (decolonize) in mice colonized with VRE as shown in FIG. 13A, or CRE, after 25 days of treatment. As shown in FIG. 27, the non-spore forming stool fraction (D14 NSF) was able to reduce the VRE and CRE burdens.

Example 8: In Vitro Hits for CRE in a Broth-Based Competition Assay

Figure 28:
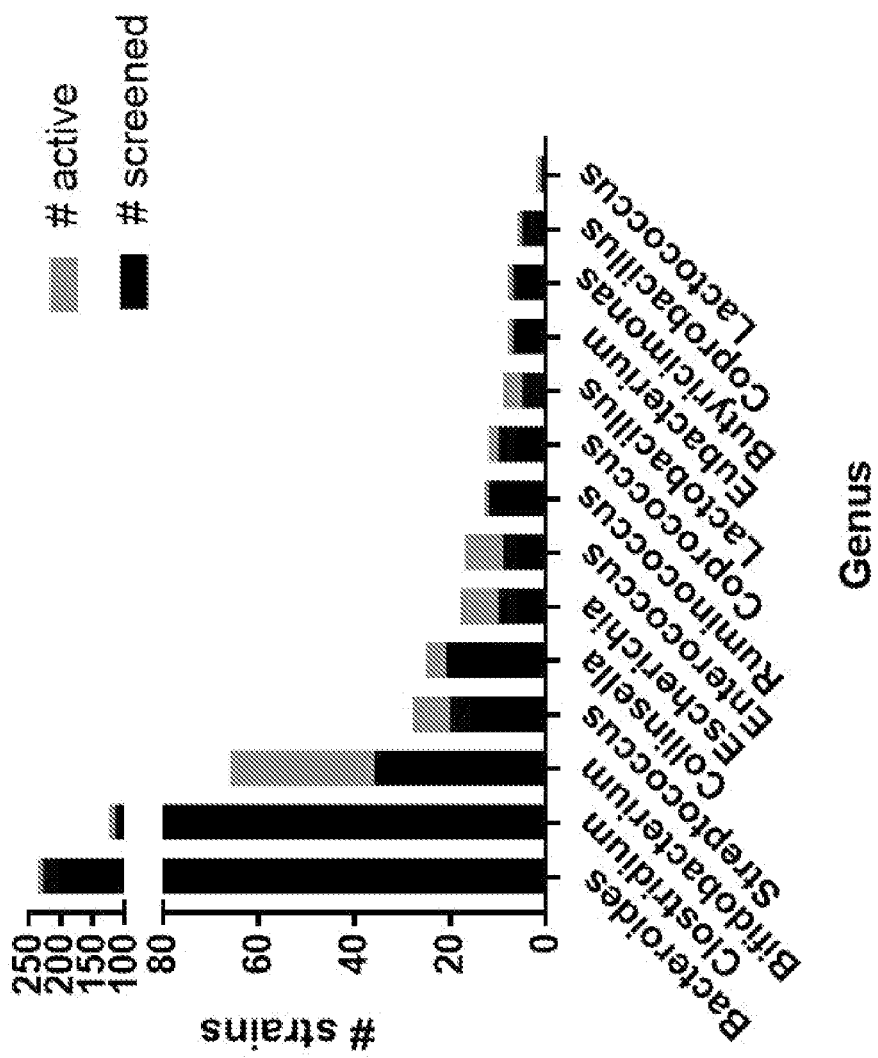
FIG. 28 shows the number of screened strains and number of strains in the listed bacterial genera that are active against 5 *Klebsiella* strains.

For the broth-based competition assay, individual test strains from early stationary phase liquid cultures first were co-cultured with a defined CR-KP or VRE inoculum anaerobically. The following day, a small aliquot of each co-culture was transferred into chromogenic, selective media that changes color from clear to black as a result of CRE or VRE expansion. Eight hours later, chromogenic changes, indicative of CRE/VRE growth, were assessed visually and measured by fluorescence intensity as relative fluorescence units (RFU). Pathogens cultured alone or in the presence of inactive strains expanded to $10^8$-$10^9$ CFU/ml which corresponded to $10^3$ RFU. Pathogens grown in the presence of highly suppressive strains resulted in ≥3 log reduction in pathogen expansion and corresponded to $10^5$ RFU, which was also the RFU of the media alone. Thus, a RFU scale of $10^3$ (least active) to $10^5$ (most active) was used to determine the CRE and VRE suppressive activity of test strains. FIG. 28 shows the number of screened strains in the listed bacterial genera and the number of those strains that are active against 5 *Klebsiella* strains.

Example 9: Assessing the Relative Abundance and Persistence of Bacterial Strains from Donor 4 (D14) in the Mouse Intestine The colonization and persistence of bacterial strains from non-spore forming stool fractions from donor 4 (D14 NSF) were investigated in the intestines of mice. C57BL/6 mice were treated with antibiotics for 7 days, challenged with $10^5$ colony-forming units (CFU) of carbapenem-resistant *Klebsiella pneumoniae* (CR-KP), and administered D14 NSF. The fecal samples were collected at various time points ("output") and sequenced by whole-genome sequencing, and the bacterial strains were taxonomically classified. D14 NSF ("input") was also sequenced.

Figure 30:
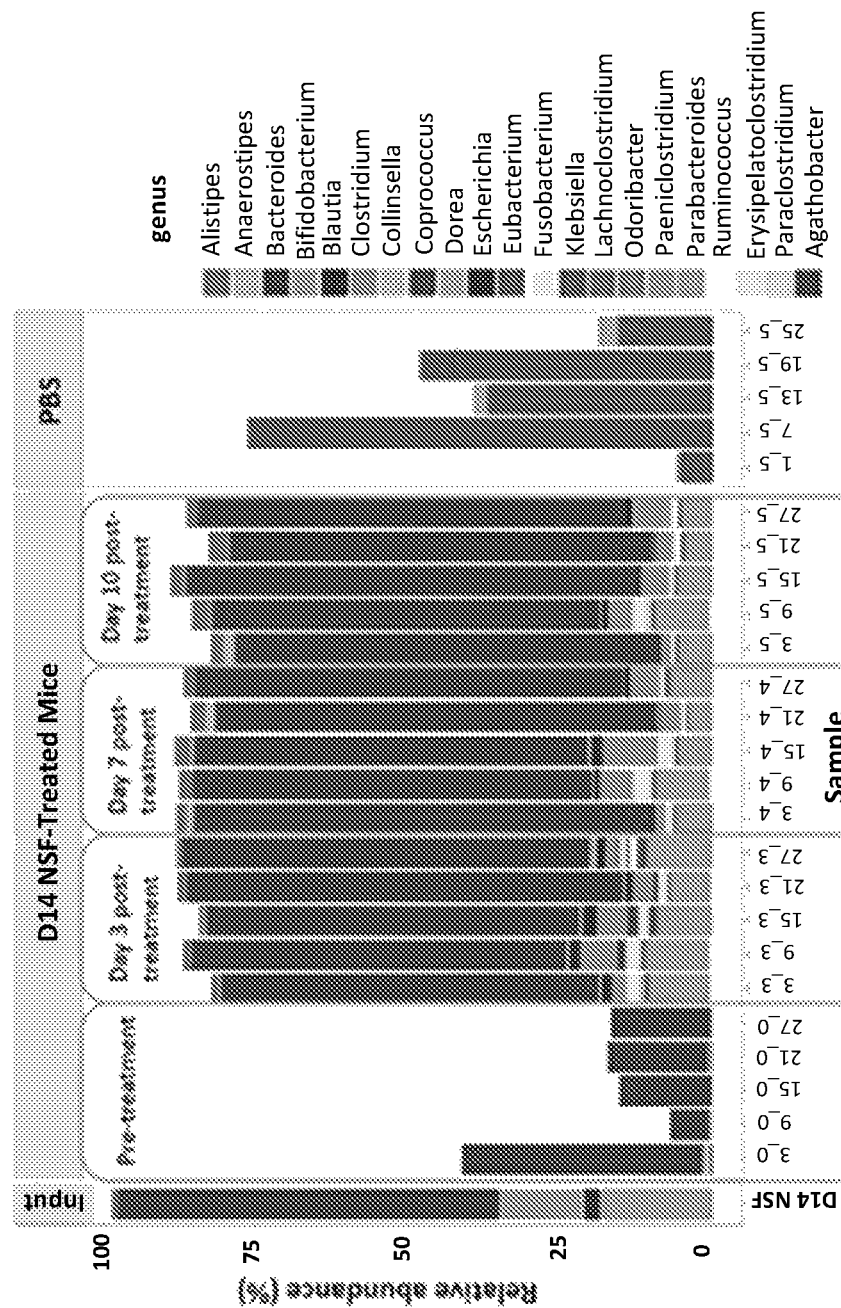
FIG. 30 shows the relative abundance and persistence of strains from the non-spore forming fraction from donor 4 "D14" in mice. Mice were treated with antibiotics, challenged with carbapenem-resistant *Klebsiella pneumoniae*, and then administered the non-spore forming fraction ("NSF") from donor 4 "D14". Fecal samples were collected from the mice treated with D4 NSF at the indicated treatment time points (pre-donor 4 "D14" NSF, day 3 post-NSF administration ("post treatment"), day 7 post-NSF administration, and day 10 post-NSF administration). The NSF inoculum (input) and fecal samples collected from the mice were whole-genome sequenced using an Illumina MiSeq sequencer, and the bacterial were taxonomically classified for organism relative abundances by One Codex. The relative abundances are shown at the genus level. Due to filtering of the data, the genera do not sum to 100%.

Mice prior to administration of D14 NSF (but after antibiotic treatment and CR-KP colonization) were densely colonized with CR-KP (data not shown), however following D14 NSF administration, the microbiota resembled that of the D14 NSF inoculum (input) and was drastically different from the mouse endogenous microbiota (pre-treatment). FIG. 30. Mice that were administered D14 NSF had undetectable levels of CR-KP on days 7 and 10 following treatment, which correlated with the 4 log reduction or clearance of CP-KP as determined by CFU levels (FIG. 29). The relative abundance of CR-KP ranged from 10-80% in control mice treated with PBS only at day 10 post treatment.

Analysis of the microbiota composition of these mice allowed identification of D14 NSF strains that stably colonized the intestine following complete clearance or significant reduction (≥4 log compared to PBS controls) of CRE fecal burden. As shown in Table 12, 36 bacterial strains from D14 NSF were found to be present at days 3, 7, and 10 post D4 NSF administration.

TABLE 12

Bacterial strains of compositions of 36 bacterial strains and 23 bacterial strains from non-spore forming fraction from donor 4 (D14) and the prevalence/abundance of each in a larger samples size of healthy donors:

| D14 36 strains | D14 23 strains | % Identity by 16S | SEQ ID NO: | Strain |
|---|---|---|---|---|
| *Bacteroides caccae* | X | 99.7 | 42 | 54 |
| *Bacteroides intestinalis/ Bacteroides cellulosyticus* | X | 99.2 | 43 | 55 |
| *Bacteroides_faecis* | X | 99.3 | 44 | 56 |
| *Bacteroides_ovatus* | X | 99.1 | 45 | 57 |
| *Bacteroides_thetaiotaomicron* | X | 98.4 | 46 | 58 |
| *Bacteroides uniformis* | X | 99.9 | 47 | 59 |
| *Bacteroides vulgatus* | X | 99.7 | 48 | 60 |
| *Bifidobacterium_adolescentis* | | 99.324 | 49 | 61 |
| *Bifidobacterium_longum* | | 99.6 | 50 | 62 |
| *Bifidobacterium_pseudocatenulatum* | | 99.1 | 51 | 63 |
| Clostridiales bacterium VE202-06/ *Blautia coccoides/ Blautia producta* | X | 100 | 52 | 64 |
| *Clostridium_citroniae* | X | 99.7 | 53 | 65 |
| *Clostridium* sp. C105KSO14/ *Clostridium clostridioforme* | X | 99.77 | 54 | 66 |
| Clostridiales bacterium VE202-212/ *Clostridium innocuum/ Eubacterium contortum* | X | 98.6 | 55 | 67 |
| Erysipelotrichaceae bacterium 6_1_45/ *Clostridium innocuum* | X | 98.7 | 56 | 68 |
| *Paeniclostridium sordellii/ Clostridium sordelli* | | 99.0 | 57 | 69 |
| *Coprococcus comes* | X | 95.3 | 58 | 70 |

TABLE 12-continued

Bacterial strains of compositions of 36 bacterial strains and 23 bacterial strains from non-spore forming fraction from donor 4 (D14) and the prevalence/abundance of each in a larger samples size of healthy donors:

| D14 36 strains | D14 23 strains | % Identity by 16S | SEQ ID NO: | Strain |
|---|---|---|---|---|
| *Dorea longicatena* | X | 99.7 | 59 | 71 |
| *Erysipelatoclostridium_ramosum* | X | 98.9 | 60 | 72 |
| *Eubacterium_rectale* | X | 100 | 61 | 73 |
| *Odoribacter* sp. UNK.MGS-12/ *Odoribacter splanchnicus* | | 99.6 | 62 | 74 |
| *Bacteroides* sp. 1__1__14/ *Parabacteroides merdae*/ *Parabacteroides distasonis* | | 96.9 | 63 | 75 |
| *Bacteroides* sp. UNK.MGS-14/ *Parabacteroides merdae* | | 98.1 | 64 | 76 |
| *Bacteroides xylanisolvens* | X | 99.708 | 65 | 77 |
| *Blautia obeum* | X | 98.8 | 66 | 78 |
| *Alistipes putredinis* | X | 100.0 | 67 | 79 |
| *Collinsella aerofaciens* | | 99.5 | 68 | 80 |
| *Eubacterium hallii*/ *Bacteroides faecis* | X | 99.932 | 69 | 81 |
| *Alistipes shahii* | X | 89.0 | 70 | 82 |
| *Anaerostipes caccae* | | 99.4 | 71 | 83 |
| *Phascolarctobacterium faecis*/ *Phascolarctobacterium faecium* | | 99.3 | 72 | 84 |
| *Agathobaculum*/ *Agathobaculum butyriciproducens* | | 98.0 | 73 | 85 |
| *Bacteroides* sp. 2__1__56FAA (*Bacteroides fragilis*) | | 99.9 | 74 | 86 |
| *Fusobacterium mortiferum* | X | 99.022 | 75 | 87 |
| *Paraclostridium bifermentans*/ *Paraclostridium benzoelyticum* | | 100.0 | 76 | 88 |
| *Escherichia* sp. 3__2__53FAA/ *Escherichia_fergusonii* | X | 99.87 | 77 | 89 |

Figure 31:
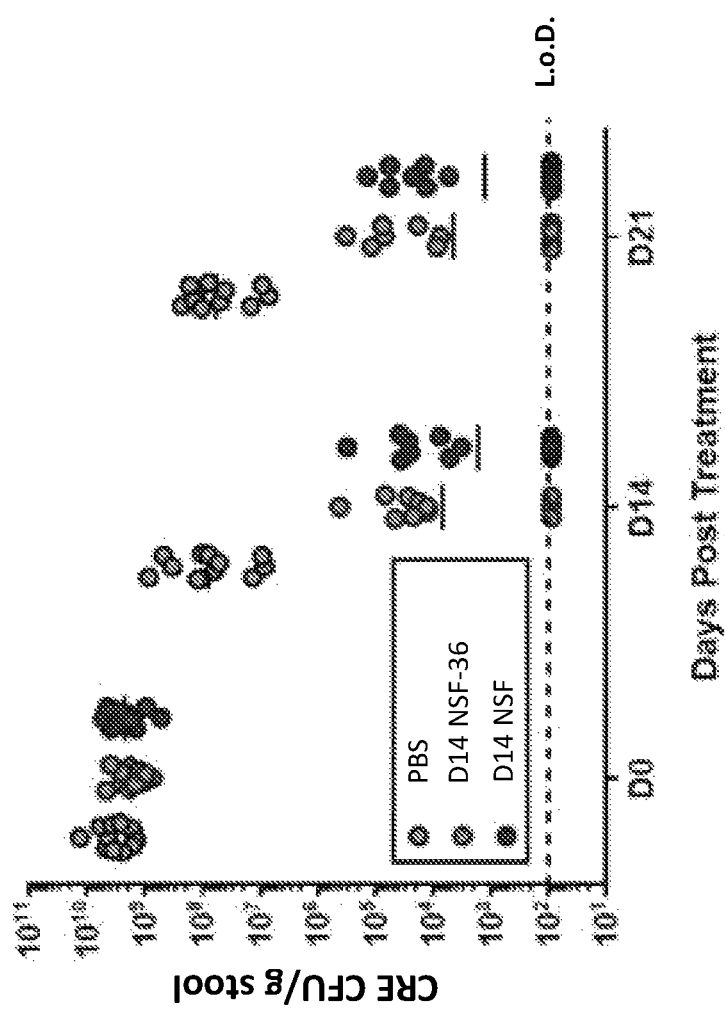
FIG. 31 shows that administration of the non-spore forming fraction from donor 4 (D14 NSF) or a composition of 36 bacterial strains that correspond to 36 strains found in donor 4 (D14 NSF-36) reduced CRE CFU levels. CRE CFU levels were quantified at day 0 and days 14 and 21 following administration of 3 doses of the treatment, shown from left to right for each time point: control (PBS), D14 NSF-36, and D14 NSF. L.o.D. is Limit of Detection.

Example 10: In Vivo Testing of a Composition of 23 and 36 Bacterial Strains from D14 NSF The composition of 36 bacterial strains from D14 NSF (D14 NSF-36) shown in Table 12 was tested to determine whether it could efficiently promote decolonization of carbapenem-resistant *Klebsiella pneumoniae* (CR-KP, CRE) from the mouse intestine. The composition was established by isolating individual donor strains and combining the individual donor strains into a composition consisting of the 36 bacterial strains. Each of the strains was cultured and combined into a composition prior to administration to antibiotic-treated mice that had been challenged with $10^5$ colony-forming units (CFU) of CR-KP. As shown in FIG. 31, all mice were colonized with CR-KP prior to administration of the composition or D14 NSF (D0). 100% of mice treated with the composition of 36 strains from D14 NSF exhibited, on average, a ≥4 log reduction in CRE CFU levels at days 14 and 21 post treatment, with clearance observed in 40% of mice. The results with the composition of 36 strains were comparable to the decolonization/clearance efficacy observed following administration of D14 NSF.

Figure 33:
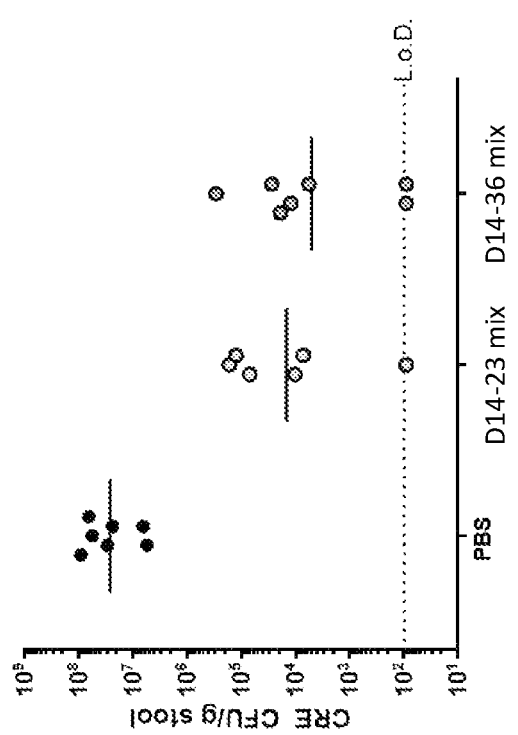
FIG. 33 shows C57BL/6J mice that were treated with antibiotics in the drinking water and challenged with $10^5$ CFU of CRE (*K. pneumoniae* ATCC BAA-2814) and administered 3 consecutive doses of one of the following three treatments beginning on day 3 post challenge: PBS; D14-23mix (23 strains found in donor 4 ("D14")), or D14-36mix (36 strains found in donor 4 ("D14")). Fecal pellets from all mice were collected various time points post treatment and plated on selective media for CRE quantification. Data shown represents D22 post treatment. L. o. D., limit of detection.

A subset of 23 strains of the 36 strains was also evaluated, using the same experimental setup and conditions. The results are shown in FIG. 33 which compares the results of the 23 strains versus the 36 strains. The 23 strains are indicated in Table 12

Figure 32:
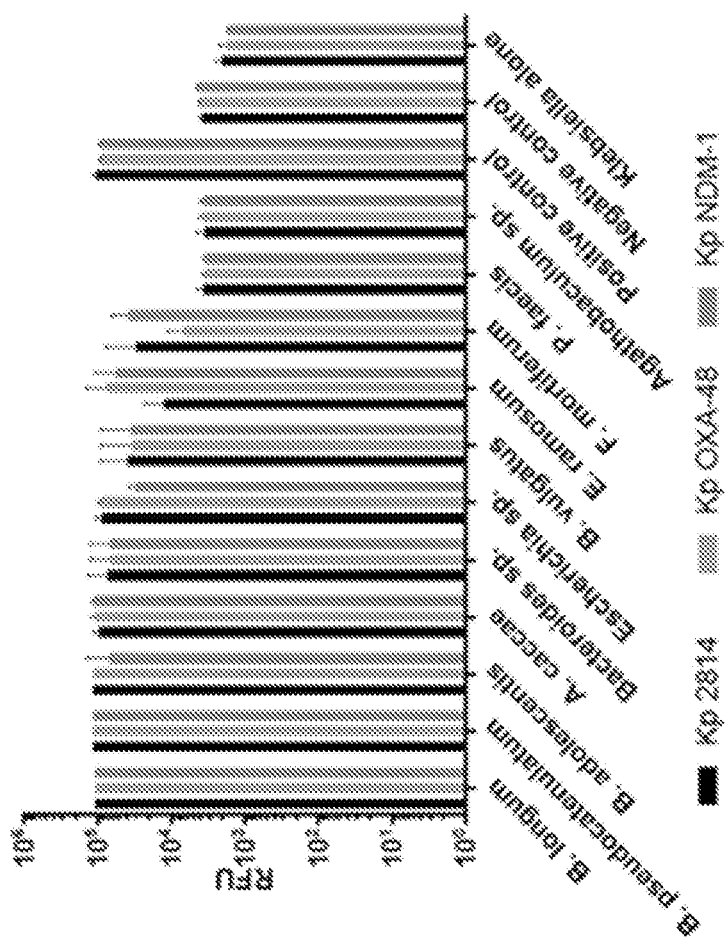
FIG. 32 shows the in vitro activity of a subset of bacterial strains from the composition of 36 bacterial strains found in donor 4 (shown on the x-axis) against 3 different *Klebsiella pneumoniae* strains (from left to right for each candidate strain: Kp 2814, Kp OXA-48, and Kp NDM-1) (RFU≥5× $10^4$). *P. faeces* and *Agathobaculum* sp. are representative inactive strains. Positive and negative controls for in vitro activity against *Klebsiella pneumoniae* are also shown. RFU is relative fluorescence units.

Example 11: In Vitro Activity of a Composition of 36 Bacterial Strains from D4 NSF The in vitro activity of a subset of the bacterial strains of the 36 bacterial strain composition (D14 NSF-36, Table 12) against *Klebsiella pneumoniae* strains was examined as in Example 8. FIG. 32 shows that at least 9 of the 36 strains had direct activity against 4 different *Klebsiella pneumoniae* strains (Kp 2814, Kp OXA-48, Kp NDM-1, and Kp NDM-2 (data not shown)).

Example 12: In Vivo Testing of a Composition of 36 and Non-Spore Forming Fraction from D14

Compositions of 36 bacterial strains from D14 (donor 4; "D14-36 mix") or from the non-spore forming fraction from D14 (donor 4; "D14-NSF") were tested for the ability to promote decolonization of *Klebsiella pneumoniae* 2H7 (KP 2H7) from the mouse intestine. The compositions were prepared by combining individual bacterial strains into a composition consisting of the 36 bacterial strains (see, Table 12) or a composition consisting of the non-spore forming fractions. The compositions (or PBS control) were administered to antibiotic-treated mice that had been challenged with $10^5$ colony-forming units (CFU) of KP 2H7, and the bacterial burden of KP 2H7 was quantified.

Figure 34:
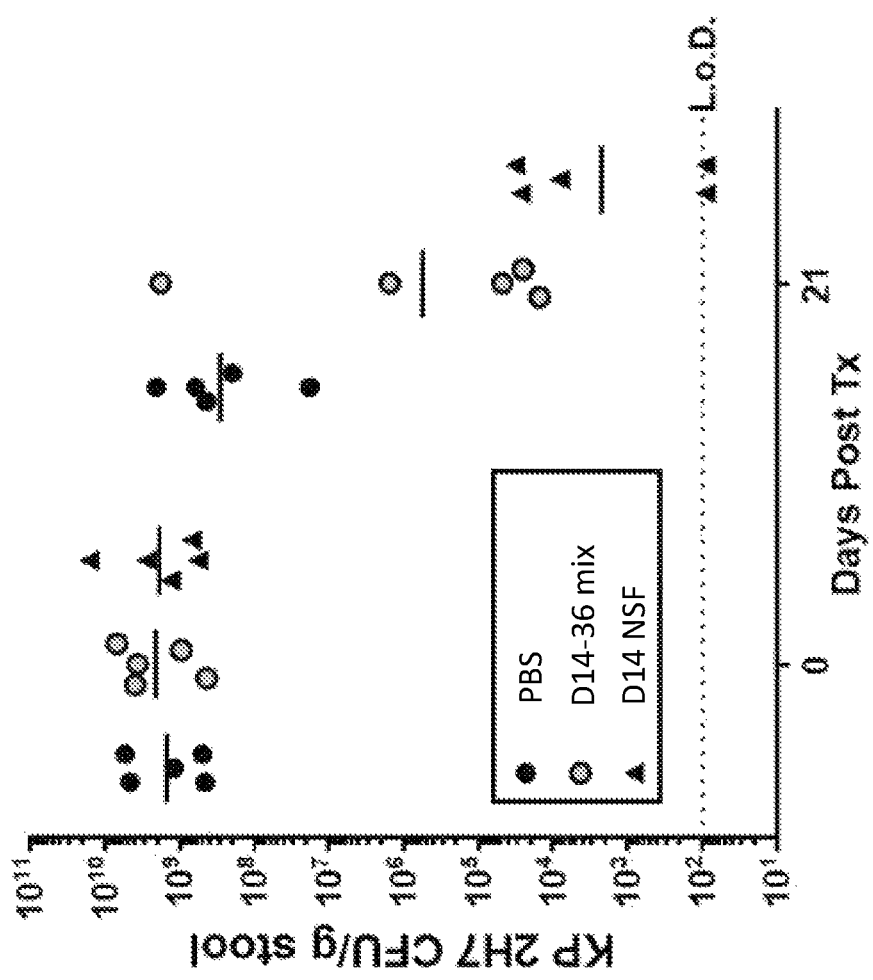
FIG. 34 shows that administration of a composition of 36 bacterial strains that correspond to 36 strains found in donor 4 (D14-36 mix) or the non-spore forming fraction of donor 4 (D14-NSF) reduced colonization with *Klebsiella pneumoniae* 2H7 (KP 2H7). KP 2H7 levels were quantified at days 0 and 21. For each time point, from left to right: control (PBS), D14-36 mix, and D14-NSF. L.o.D. is Limit of Detection.

As shown in FIG. 34, mice treated with the D14-36 mix composition exhibited, on average, a ≥3 log reduction in KP 2H7 CFU levels at day 21 post treatment, and mice treated with the non-spore forming fraction exhibited, on average, a ≥5 log reduction in KP 2H7 CFU levels at day 21 post treatment.

What is claimed is:

1. A composition comprising:
   (i) a purified bacterial strain comprising a 16S rDNA sequence having at least 99% sequence identity with the nucleic acid sequence of SEQ ID NO: 48;
   (ii) a purified bacterial strain comprising a 16S rDNA sequence having at least 99% sequence identity with the nucleic acid sequence of SEQ ID NO: 52;
   (iii) a purified bacterial strain comprising a 16S rDNA sequence having at least 99% sequence identity with the nucleic acid sequence of SEQ ID NO: 55;
   (iv) a purified bacterial strain comprising a 16S rDNA sequence having at least 99% sequence identity with the nucleic acid sequence of SEQ ID NO: 62;
   (v) a purified bacterial strain comprising a 16S rDNA sequence having at least 99% sequence identity with the nucleic acid sequence of SEQ ID NO: 67;
   (vi) a purified bacterial strain comprising a 16S rDNA sequence having at least 99% sequence identity with the nucleic acid sequence of SEQ ID NO: 72;
   (vii) a purified bacterial strain comprising a 16S rDNA sequence having at least 99% sequence identity with the nucleic acid sequence of SEQ ID NO: 75; and
   (viii) a purified bacterial strain comprising a 16S rDNA sequence having at least 99% sequence identity with the nucleic acid sequence of SEQ ID NO: 77,
   wherein the bacterial strains are lyophilized.

2. The composition of claim 1, wherein the composition comprises bacterial strains that originate from more than one human donor.

3. The composition of claim 1, wherein the composition comprises at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, or at least 36 purified bacterial strains.

4. The composition of claim 1, wherein the composition suppresses replication, survival, and/or colonization of one or more pathogenic organisms.

5. The composition of claim 1, further comprising:
   (i) a purified bacterial strain comprising a 16S rDNA sequence having at least 99% sequence identity with the nucleic acid sequence of SEQ ID NO: 23; and
   (ii) a purified bacterial strain comprising a 16S rDNA sequence having at least 99% sequence identity with the nucleic acid sequence of SEQ ID NO: 25.

6. The composition of claim 1, further comprising one or more enteric polymers.

7. The composition of claim 1, wherein the composition comprises $1 \times 10^7$ and $1 \times 10^{10}$ colony forming units (CFUs) per bacterial strain.

8. The composition of claim 1, wherein the composition comprises:
   (i) a purified bacterial strain comprising a 16S rDNA sequence having at least 99% sequence identity with the nucleic acid sequence of SEQ ID NO: 48;
   (ii) a purified bacterial strain comprising a 16S rDNA sequence having at least 100% sequence identity with the nucleic acid sequence of SEQ ID NO: 52;
   (iii) a purified bacterial strain comprising a 16S rDNA sequence having at least 100% sequence identity with the nucleic acid sequence of SEQ ID NO: 55;
   (iv) a purified bacterial strain comprising a 16S rDNA sequence having at least 100% sequence identity with the nucleic acid sequence of SEQ ID NO: 62;
   (v) a purified bacterial strain comprising a 16S rDNA sequence having at least 99% sequence identity with the nucleic acid sequence of SEQ ID NO: 67;
   (vi) a purified bacterial strain comprising a 16S rDNA sequence having at least 99% sequence identity with the nucleic acid sequence of SEQ ID NO: 72;
   (vii) a purified bacterial strain comprising a 16S rDNA sequence having at least 99% sequence identity with the nucleic acid sequence of SEQ ID NO: 75;
   (viii) a purified bacterial strain comprising a 16S rDNA sequence having at least 99% sequence identity with the nucleic acid sequence of SEQ ID NO: 77;
   (ix) a purified bacterial strain comprising a 16S rDNA sequence having at least 100% sequence identity with the nucleic acid sequence of SEQ ID NO: 23;
   (x) a purified bacterial strain comprising a 16S rDNA sequence having at least 100% sequence identity with the nucleic acid sequence of SEQ ID NO: 25; and
   (xi) a purified bacterial strain comprising a 16S rDNA sequence having at least 99% sequence identity with the nucleic acid sequence of SEQ ID NO: 26.

9. A pharmaceutical composition comprising the composition of claim 1 and a pharmaceutically acceptable excipient.

10. The pharmaceutical composition of claim 9, wherein the pharmaceutical composition is formulated for oral delivery or rectal delivery.

11. The pharmaceutical composition of claim 9, wherein the pharmaceutical composition is formulated for delivery to the intestine or the colon.

12. The composition of claim 9, wherein the pharmaceutical composition is in the form of capsule.

* * * * *

SEQUENCE LISTING

<160> NUMBER OF SEQ ID NOS: 77

<210> SEQ ID NO 1
<211> LENGTH: 1022
<212> TYPE: DNA
<213> ORGANISM: Alistipes putredinis

<400> SEQUENCE: 1

```
gctcagcttg cctaggtcgc tccttgcggt cacgaacttc aggcaccccc ggctcccatg      60
gcttgacggg cggtgtgtac aaggcccggg aacgtattca ccgcgccatg gctgatgcgc     120
gattactagc gaatccaact tcatggaggc gggtttcagc ctccaatccg aactgagata     180
ggctttcgag attcgcatcc catcgctggg tagctgccct ctgtacctac cattgtaaca     240
cgtgtgtagc cccggacgta agggccgtgc tgatttgacg tcatccccac cttcctctcg     300
```

```
gcttacaccg gcagtcccgc cagagtgccc agcttcacct gatggcaact aacggtaggg    360
gttgcgctcg ttatgggact aacccgaca cctcacggca cgagctgacg acaaccatgc    420
agcacctagt ttcgcgcccc gaagggaaat cctctttcaa gaatcgtcgc taactttcaa    480
gcccgggtaa ggttcctcgc gtatcatcga attaaaccac atgttcctcc gcttgtgcgg    540
gcccccgtca attcctttga gtttcattct tgcgaacgta ctccccaggt ggataactta    600
tcgctttcgc ttagtcaccg actgtgtatc gccgacaacg agttatcatc gtttactgcg    660
tggactacca gggtatctaa tcctgtttgc tccccacgct ttcgtgcctc aacgtcagat    720
atagtttggt aagctgcctt cgcaatcggt gttctgtatg atctctaagc atttcaccgc    780
tacaccatac attccgccta ccgcaactac tctctagctc aacagtatta gaggcacgtt    840
cagggttgag ccccgaaatt tcacctctaa cttatcaaac cgcctacgca ccctttaaac    900
ccaataaatc cggataacgc ttgaatcctc cgtattaccg cggctgctgg cacggagtta    960
gccgatcctt attcgtacga tactttcaga cagatacacg tatctgcgtt taccctcgta   1020
ca                                                                  1022
```

<210> SEQ ID NO 2
<211> LENGTH: 1084
<212> TYPE: DNA
<213> ORGANISM: Bacteroides uniformis

<400> SEQUENCE: 2

```
gagcgctagg cttacacatg caagtcgagg ggcagcatga acttagcttg ctaagtttga     60
tggcgaccgg cgcacgggtg agtaacacgt atccaacctg ccgatgactc ggggatagcc    120
tttcgaaaga aagattaata cccgatggca tagttcttcc gcatggtaga actattaaag    180
aatttcggtc atcgatgggg atgcgttcca ttaggttgtt ggcggggtaa cggcccacca    240
agccttcgat ggatagggt tctgagagga aggtccccca cattggaact gagacacggt    300
ccaaactcct acgggaggca gcagtgagga atattggtca atggacgaga gtctgaacca    360
gccaagtagc gtgaaggatg actgccctat gggttgtaaa cttcttttat acgggaataa    420
agtgaggcac gcgtgcctt ttgtatgtac cgtatgaata aggatcggct aactccgtgc    480
cagcagccgc ggtaatacgg aggatccgag cgttatccgg atttattggg tttaaaggga    540
gcgtaggcgg acgcttaagt cagttgtgaa agtttgcggc tcaaccgtaa aattgcagtt    600
gatactgggt gtcttgagta cagtagaggc aggcggaatt cgtggtgtag cggtgaaatg    660
cttagatatc acgaagaact ccgattgcga aggcagcttg ctggactgta actgacgctg    720
atgctcgaaa gtgtgggtat caaacaggat tagataccct ggtagtccac acagtaaacg    780
atgaatactc gctgtttgcg atatacagta agcggccaag cgaaagcgtt aagtattcca    840
cctggggagt acgccggcaa cggtgaaact caaaggaatt gacggggggcc cgcacaagcg    900
gaggaacatg tggtttaat tcgatgatac gcgaggaacc ttacccggc ttgaattgca    960
actgaatgat gtggagacat gtcagccgca agcagttgtg aaggtgctgc atggttgtcg   1020
tcagctcgtg ccgtgaggtg tcggcttaag tgccataacg agcgcaaccc tatcgtagta   1080
ccat                                                               1084
```

<210> SEQ ID NO 3
<211> LENGTH: 769
<212> TYPE: DNA
<213> ORGANISM: Bacteroides vulgatus

<400> SEQUENCE: 3

```
acaggttttt tccctaaggg cgctcctcgc ggttacgcac ttcaggtacc cccggctccc    60
atggcttgac gggcggtgtg tacaaggccc gggaacgtat tcaccgcgcc gtggctgatg   120
cgcgattact agcgaatcca gcttcgtgga gtcgggttgc agactccagt ccgaactgag   180
agaggttttt gggattggca tccactcgcg tggtagcggc cctctgtacc ccccattgta   240
acacgtgtgt agccccggac gtaagggccg tgctgatttg acgtcatccc caccttcctc   300
acatcttacg atggcagtct tgtcagagtc ctcagcggaa cctgttagta actgacaaca   360
agggttgcgc tcgttatggc acttaagccg acacctcacg gcacgagctg acgacaacca   420
tgcagcacct tcacagatgc cttgcggctt acggctttca ccgtaattca tctgcaattt   480
aagcccgggt aaggttcctc gcgtatcatc gaattaaacc acatgttcct ccgcttgtgc   540
gggcccccgt caattccttt gagtttcacc gttgccggcg tactcccccag gtggaatact   600
taacgctttc gcttggccgc ttgctgtaat gcacaaacag cgagtattca tcgtttaccg   660
tgtggactac cagggtatct aaatcctgtt tgatacccac actttcgagc ctcaatgtca   720
gttgcagctt agcaggctgc ctttattatc ggagttcttc gtgatatct             769
```

<210> SEQ ID NO 4
<211> LENGTH: 1003
<212> TYPE: DNA
<213> ORGANISM: Parabacteroides merdae

<400> SEQUENCE: 4

```
gtgctcagct tttaccctag gccgatcctt gcggttacgg acttcaggta cccccggctc    60
ccatggcttg acgggcggtg tgtacaaggc ccgggaacgt attcaccgcg ccatggctga   120
tgcgcgatta ctagcgaatc cagcttcacg gagtcgagtt gcagactccg atccgaactg   180
agacatggtt tggagattag catcctgtcg ccaggtagct gccctttgtc catgccattg   240
taacacgtgt gtcgccccgg atgtaagggc cgtgctgatt gacgtcatcc ccaccttcc   300
tcacagctta cgctggcagt ctcaccagag tcctcagctt cacctgttag taactagtga   360
taagggttgc gctcgttatg cacttaagcc gacacctcac ggcacgagct gacgacaac   420
catgcagcac ctcgtaatct gctattgcta gaaggagtgt ttccactccg gtcagactac   480
gttcaaaccc gggtaaggtt cctcgcgtat catcgaatta aaccacatgt tcctccgctt   540
gtgcgggccc ccgtcaattc ctttgagttt caccgttgcc ggcgtactcc ccaggtggat   600
tacttaacgc tttcgctgta gagcttacat tgtatcgcaa actcctagta atcatcgttt   660
actgcgtgga ctaccagggt atctaatcct gtttgatccc cacgctttcg tgcttcagtg   720
tcagttatgg tttagtaagc tgccttcgca atcggagttc tgcgtgatat ctatgcattt   780
caccgctaca ccacgcattc cgcctacctc aaacacactc aagtaaccca gtttcaacgg   840
caatttatg gttgagccac aaactttcac cgctgactta atcaccacc tacgcaccct   900
ttaacccaat aaatccgata acgctcgcat cctccgtatt accgcggctg ctgcccggag   960
ttagccgatg cttattcata gggtacatac aaaaaggaca cgt                   1003
```

<210> SEQ ID NO 5
<211> LENGTH: 895
<212> TYPE: DNA
<213> ORGANISM: Bifidobacterium longum

<400> SEQUENCE: 5

```
gggacggatc tcccttagac ggctccatcc cacaaggggt taggccaccg gcttcgggtg    60
```

```
ctgcccactt tcatgacttg acgggcggtg tgtacaaggc ccgggaacgc attcaccgcg      120
acgttgctga ttcgcgatta ctagcgactc cgccttcacg cagtcgagtt gcagactgcg      180
atccgaactg agaccggttt tcagggatcc gctccgcgtc gccgcgtcgc atcccgttgt      240
accggccatt gtagcatgcg tgaagccctg gacgtaaggg gcatgatgat ctgacgtcat      300
ccccaccttc ctccgagtta acccggcgg tccccgtga gttcccggca taatccgctg       360
gcaacacggg gcgaggggttg cgctcgttgc gggacttaac ccaacatctc acgacacgag     420
ctgacgacga ccatgcacca cctgtgaacc cgccccgaag ggaagccgta tctctacgac      480
cgtcgggaac atgtcaagcc caggtaaggt tcttcgcgtt gcatcgaatt aatccgcatg      540
ctccgccgca tgtgcgggcc ccgtcaatt tctttgagtt ttagccttgc ggccgtactc       600
cccaggcggg atgcttaacg cgttagctcc gacacggaac ccgtggaacg ggccccacat     660
ccagcatcca ccgtttacgg cgtggactac cagggtatct aatcctgttc gctccccacg     720
ctttcgctcc tcagcgtcag taacggccca gagacctgcc ttcgccattg gtgttcttcc     780
cgatatctac acattccacc gttacaccgg gaattccagt ctcccctacc gcactcaacc     840
cgccgtaccg gcgcggatcc ccggtaagcg atggactttc acaccggacg cgagg          895

<210> SEQ ID NO 6
<211> LENGTH: 1035
<212> TYPE: DNA
<213> ORGANISM: Bifidobacterium adolescentis

<400> SEQUENCE: 6
gaattcgagt ctcaccttag acggctcccc ccaaaaggtt gggccaccgg cttcgggtgc       60
tacccacttt catgacttga cgggcggtgt gtacaaggcc cgggaacgca ttcaccgcgg      120
cgttgctgat ccgcgattac tagcgactcc gccttcatgg agtcggggttg cagactccaa     180 tccgaactga gaccggtttt aagggatccg ctccacctcg cggtgtcgca tcccgttgta      240
ccggccattg tagcatgcgt gaagccctgg acgtaagggg catgatgatc tgacgtcatc      300
cccaccttcc tccgagttga ccccggcggt ccccgtgag ttcccaccac gacgtgctgg       360
caacacaggg cgagggttgc gctcgttgcg ggacttaacc caacatctca cgacacgagc      420
tgacgacgac catgcaccac ctgtgaaccc gccccgaagg gaggccccat ctctgggct      480 gtcgggaaca tgtcaagccc aggtaaggtt cttcgcgttg catcgaatta atccgcatgc     540
tccgccgctt gtgcgggccc cgtcaatttc tttgagtttt agccttgcg gccgtactcc      600 ccaggcggga tgcttaacgc gttggctccg acacggagac cgtggaatgg tccccacatc     660
cagcatccac cgtttacggc gtggactacc agggtatcta atcctgttcg ctccccacgc     720
tttcgctcct cagcgtcagt gacgcccag agacctgcct tcgccattgg tgttcttccc     780
gatatctaca cattccaccg ttacaccggg aattccagtc tcccctaccg cactcaagcc     840 cgccgtacc ggcgcggat ccaccgttaa gcgatggact tcacaccgg acgcgacgaa       900 ccgcctacga gcctttacg cccaataatt ccggatacgc ttgcaccta cgtattaccg      960 cggctgctgg cacgtagtta gccggtgctt attcgaaagg tacactcact ccggagggct    1020
tgcttccagt caaaa                                                    1035

<210> SEQ ID NO 7
<211> LENGTH: 757
<212> TYPE: DNA
<213> ORGANISM: Blautia obeum
```

<400> SEQUENCE: 7

```
ccaaaaagcg cggcggcgtg cttaccatgc agtcgaacgg gaaacttttta ttgaagcttc    60
ggcagatttg gttggtttct agtggcggac gggtgagtaa cgcgtgggta acctgcctta   120
tacaggggga taacaaccag aaatggttgc taataccgca taagcgcaca ggaccgcatg   180
gtccggtgtg aaaaactccg gtggtataag atggacccgc gttggattag ctagttggca   240
gggtaacggc ctaccaaggc gacgatccat agccggcctg agagggtgaa cggccacatt   300
gggactgaga cacggcccag actcctacgg gaggcagcag tggggaatat tgcacaatgg   360
gggaaaccct gatgcagcga cgccgcgtga aggaagaagt atctcggtat gtaaacttct   420
atcagcaggg aagatagtga cggtacctga ctaagaagcc ccggctaact acgtgccagc   480
agccgcggta atacgtaggg ggcaagcgtt atccggattt actgggtgta aagggagcgt   540
agacggactg gcaagtctga tgtgaaaggc gggggctcaa cccctggact gcattggaaa   600
ctgttagtct tgagtgccgg agaggtaagc ggaattccta gtgtagcggt gaaatgcgta   660
gatattagga ggaacaccag tggcgaaggc ggcttactgg acggtaactg acgttgaggc   720
tcgaaagcgt ggggagcaaa caggattaga taccctg                            757
```

<210> SEQ ID NO 8
<211> LENGTH: 1113
<212> TYPE: DNA
<213> ORGANISM: Blautia wexlerae
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (5)..(5)
<223> OTHER INFORMATION: n is a, c, g, or t

<400> SEQUENCE: 8

```
gngantggcg gcgtgcttac catgcagtcg aacgggaaat acttcattga aacttcggtg    60
gatttaattt atttctagtg gcggacgggt gagtaacgcg tgggtaacct gccttataca   120
gggggataac agtcagaaat ggctgctaat accgcataag cgcacagagc tgcatggctc   180
agtgtgaaaa actccggtgg tataagatgg accgcgttg gattagcttg ttggtggggt   240
aacggcccac caaggcgacg atccatagcc ggcctgagag ggtgaacggc cacattggga   300
ctgagacacg gcccagactc ctacgggagg cagcagtggg gaatattgca caatgggga   360
aaccctgatg cagcgacgcc gcgtgaagga agaagtatct cggtatgtaa acttctatca   420
gcagggaaga tagtgacggt acctgactaa gaagcccgg ctaactacgt gccagcagcc   480
gcggtaatac gtagggggca agcgttatcc ggatttactg ggtgtaaagg gagcgtagac   540
ggtgtggcaa gtctgatgtg aaaggcatgg gctcaacctg tggactgcat ggaaactgt   600
catacttgag tgccgaggg gtaagcgaa ttcctagtgt agcggtgaaa tgcgtagata   660
ttaggaggaa caccagtggc gaaggcggct tactggacgg taactgacgt tgaggctcga   720
aagcgtgggg agcaaacagg attagatacc ctggtagtcc acgccgtaaa cgatgaatac   780
taggtgtcgg gggagcatag ctcttcggtg ccgtcgcaaa cgcagtaagt attccacctg   840
gggagtacgt tcgcaagaat gaaactcaaa ggaattgacg ggacccgca caagcggtgg   900
agcatgtggt ttaattcgaa gcaacgcgaa gaaccttacc aagtcttgac atccgctga   960
ccggatcctt aatcgggatc tttccttcgg gacaggcgag acaggggtgc atggttgtcg  1020
tcagctcgtg tcgtgagatg ttgggtaagt ccgcacgagc gcaaccctat cctcagtagc  1080
```

```
agcatttaag tgggcactct gggggagact gcc                            1113

<210> SEQ ID NO 9
<211> LENGTH: 1574
<212> TYPE: DNA
<213> ORGANISM: Blautia producta

<400> SEQUENCE: 9
agagtttgat cctggctcag gatgaacgct ggcggcgtgc ttaacacatg caagtcgagc   60
gaagcattaa gacagatttc ttcggattga agtctttgtg actgagcggc ggacgggtga  120
gtaacgcgtg gtaacctgc ctcatacagg gggataacag ttagaaatga ctgctaatac  180
cgcataagcg cacaggaccg catggtctgg tgtgaaaaac tccggtggta tgagatggac  240
ccgcgtctga ttagctagtt ggaggggtaa cggcccacca aggcgacgat cagtagccgg  300
cctgagaggg tgaacggcca cattgggact gagacacggc ccagactcct acgggaggca  360
gcagtgggga atattgcaca atgggggaaa ccctgatgca gcgacgccgc gtgaaggaag  420
aagtatctcg gtatgtaaac ttctatcagc agggaagaaa atgacggtac ctgactaaga  480
agccccggct aactacgtgc cagcagccgc ggtaatacgt aggggcaag cgttatccgg  540 atttactggg tgtaaaggga gcgtagacgg aagagcaagt ctgatgtgaa aggctggggc  600
ttaaccccag gactgcattg gaaactgttg ttctagagtg ccggagaggt aagcggaatt  660
cctagtgtag cggtgaaatg cgtagatatt aggaggaaca ccagtggcga aggcggctta  720
ctggacggta actgacgttg aggctcgaaa gcgtggggag caaacaggat tagataccct  780
ggtagtccac gccgtaaacg atgaatacta ggtgtcgggt ggcaaagcca ttcggtgccg  840
cagcaaacgc aataagtatt ccacctgggg agtacgttcg caagaatgaa actcaaagga  900
attgacgggg acccgcacaa gcggtggagc atgtggttta attcgaagca acgcgaagaa  960
ccttaccaag tcttgacatc cctctgaccg tcccgtaatg ggcttccc ttcggggcag  1020 aggagacagg tggtgcatgg ttgtcgtcag ctcgtgtcgt gagatgttgg gttaagtccc 1080
gcaacgagcg caaccttat ccttagtagc cagcacatga tggtgggcac tctagggaga 1140
ctgccgggga taacccggag gaaggcgggg acgacgtcaa atcatcatgc cccttatgat 1200
ttgggctaca cacgtgctac aatggcgtaa acaaagggaa gcgagacagc gatgttgagc 1260
gaatcccaaa aataacgtcc cagttcggac tgcagtctgc aactcgactg cacgaagctg 1320
gaatcgctag taatcgcgga tcagaatgcc gcggtgaata cgttcccggg tcttgtacac 1380
accgcccgtc acaccatggg agtcagtaac gcccgaagtc agtgacctaa ccgaaaggaa 1440
ggagctgccg aaggcgggac cgataactgg ggtgaagtcg taacaaggta gccgtatcgg 1500
aaggtgcggc tggatcacct cctttctaag gaagaagaag tagagaaaag tgtttcactg 1560
ttgagttacc aaga                                                   1574

<210> SEQ ID NO 10
<211> LENGTH: 1528
<212> TYPE: DNA
<213> ORGANISM: Clostridium hathewayi
<220> FEATURE:
<223> OTHER INFORMATION: Hungatella effluvii strain

<400> SEQUENCE: 10
atgagagttc gatcctggct caggatgaac gctggcggcg tgcttaacac atgcaagtcg   60
agcgaagcgg tttcgatgaa gttttcggat ggatttgaaa tcgacttagc ggcggacggg  120
```

-continued

```
tgagtaacgc gtgggtaacc tgccttacac tgggggataa cagttagaaa tgactgctaa      180
taccgcataa gcgcacaggg ccgcatggtc tggtgcgaaa actccggtg gtgtaagatg       240
gacccgcgtc tgattaggta gttggtgggg taacggccca ccaagccgac gatcagtagc     300
cgacctgaga gggtgaccgg ccacattggg actgagacac ggcccaaact cctacgggag     360
gcagcagtgg ggaatattgg acaatgggcg aaagcctgat ccagcgacgc cgcgtgagtg     420
aagaagtatt tcggtatgta aagctctatc agcagggaag aaaatgacgg tacctgacta     480
agaagcccg gctaactacg tgccagcagc cgcggtaata cgtaggggc aagcgttatc       540
cggatttact gggtgtaaag ggagcgtaga cggttaagca agtctgaagt gaaagcccgg     600
ggctcaaccc cggtactgct ttggaaactg tttgacttga gtgcaggaga ggtaagtgga     660
attcctagtg tagcggtgaa atgcgtagat attaggagga acaccagtgg cgaaggcggc     720
ttactggact gtaactgacg ttgaggctcg aaagcgtggg gagcaaacag gattagatac     780
cctggtagtc cacgccgtaa acgatgaata ctaggtgtcg ggggacaacg tccttcggtg     840
ccgccgctaa cgcaataagt attccacctg gggagtacgt tcgcaagaat gaaactcaaa     900
ggaattgacg gggaccccgca caagcggtgg agcatgtggt ttaattcgaa gcaacgcgaa     960
gaaccttacc aagtcttgac atcccattga aaatcattta accgtgatcc ctcttcggag    1020
caatggagac aggtggtgca tggttgtcgt cagctcgtgt cgtgagatgt tgggttaagt    1080
cccgcaacga gcgcaaccct tatccttagt agccagcaca tgatggtggg cactctgggg    1140
agactgccag ggataacctg gaggaaggtg gggatgacgt caaatcatca tgcccttat    1200
gatttgggct acacacgtgc tacaatggcg taaacaaagg gaagcaaagg agcgatctgg    1260
agcaaacccc aaaaataacg tctcagttcg gattgcaggc tgcaactcgc ctgcatgaag    1320
ctggaatcgc tagtaatcgc gaatcagaat gtcgcggtga atacgttccc gggtcttgta    1380
cacaccgccc gtcacaccat gggagttggt aacgcccgaa gtcagtgacc caaccgtaag    1440
gagggagctg ccaaggcgg gactgataac tggggtgaag tcgtaacaag gtagccgtat    1500
cggaaggtgc ggctggatca cctcctttt                                    1528
```

<210> SEQ ID NO 11
<211> LENGTH: 1120
<212> TYPE: DNA
<213> ORGANISM: Clostridium bolteae

<400> SEQUENCE: 11

```
gggcgggcgg cgtgctacca tgcaagtcga acgaagcaat taaatgaagt tttcggatgg      60
aatttgattg actgagtggc ggacgggtga gtaacgcgtg gataacctgc ctcacactgg     120
gggataacag ttagaaatga ctgctaatac cgcataagcg cacagtaccg catggtacgg     180
tgtgaaaaac tccggtggtg tgagatggat ccgcgtctga ttagccagtt ggcggggtaa     240
cggcccacca aagcgacgat cagtagccga cctgagaggg tgaccggcca cattgggact     300
gagacacggc ccaaactcct acgggaggca gcagtgggga atattgcaca atgggcgaaa     360
gcctgatgca gcgacgccgc gtgagtgaag aagtatttcg gtatgtaaag ctctatcagc     420
agggaagaaa atgacggtac ctgactaaga gccccggct aactacgtgc cagcagccgc     480
ggtaatacgt agggggcaag cgttatccgg atttactggg tgtaaaggga gcgtagacgg     540
cgaagcaagt ctgaagtgaa aacccagggc tcaaccctgg gactgctttg gaaactgttt     600
tgctagagtg tcgagaggt aagtggaatt cctagtgtag cggtgaaatg cgtagatatt     660
aggaggaaca ccagtggcga aggcggctta ctggacgata actgacgttg aggctcgaaa     720
```

```
gcgtggggag caaacaggat tagataccct ggtagtccac gccgtaaacg atgaatgcta    780
ggtgttgggg ggcaaagccc ttcggtgccg tcgcaaacgc agtaagcatt ccacctgggg    840
agtacgttcg caagaatgaa actcaaggaa ttgacgggga cccgcacaag cggtggagca    900
tgtggtttaa ttcgaagcaa cgcgaagaac ttaccaagtc ttgacatcct cttgaccggc    960
gtgtaacggc gccttctctt ctgggcaaga gagacagtgg tgcatggttg tcgtcagctc    1020
gtgtcgtgag atgttgggtt aagtcccgca cgagcgcaac ccttttcctt atatcacagg    1080
tgagctgggc cctctaggag actgccagga tactgaggaa                         1120
```

<210> SEQ ID NO 12
<211> LENGTH: 761
<212> TYPE: DNA
<213> ORGANISM: Parabacteroides distasonis

<400> SEQUENCE: 12

```
tcgggttttt tcctaggccg atcctttcgg ttactgactt caggtacccc cggctcccat      60
ggcttgacgg gcggtgtgta caaggcccgg gaacgtattc accgcgccat ggctgatgcg     120
cgattactag cgaatccagc ttcacggagt cgggttgcag actccgatcc taactgagac     180
gtggtttggg gattcgctcc ctgtcgccag gtggcctccc tttgtccacg ccattgtaac     240
acgtgtgtcg ccccggatgt aagggccgtg ctgatttgac gtcatccccg ccttcctcgc     300
agcttacgct ggcagtccca ccagagtcct cagctttacc tgttagtaac tagtggcatg     360
ggttgcgctc gttatggcac ttaagccgac acctcacggc acgagctgac aacaaccatg     420
caccacctcg caaacggcta ttgctaaaaa aggtgtttcc acctcggtcc taatgctttc     480
aaacccgggt aaggttcctc gcgtatcatc gaattaaacc acatgttcct ccgcttgtgc     540
tggcccccgt cattcctttg agtttcaccg ttgccggcgt actcccagg tggatcacat      600 aacgctttcc ctgagccgct tactgtgtat cgtacacacc tagtgatcat cttttactgc     660
gtggactaac agggtatcct aatcctgttt gatccccacg ctttcgtgca tcacgtcagt     720
catggcttgt gagctgcctt cgcaaactgg gttctgcaag a                        761
```

<210> SEQ ID NO 13
<211> LENGTH: 1022
<212> TYPE: DNA
<213> ORGANISM: Collinsella aerofaciens

<400> SEQUENCE: 13

```
ccgtcaacct tcggcgcctc ccccctcgcg gttgggccgg cgacttcggg tgcagacgac      60
tcgggtggtg tgacgggcgg tgtgtacaag gcccgggaac gcattcaccg cggcatgctg     120
atccgcgatt actagcaact ccgacttcat ggggcgggt tgcagccccc aatccgaact     180
ggggccggct ttccgggatc cgctcccccct cgcggggtgg catccctctg taccggccat     240
tgtagcacgt gtgcagccca gggcataagg ggcatgatga cttgacgtcg tccccgccct     300
cctccgcctt gacggcggcg gtcccgcgtg ggttcccggc atcccgat ggcaacacgc      360 ggcgggggtt gcgctcgttg cgggacttaa cccaacatct cacgacacga gctgacgaca     420
gccatgcacc acctgtatgg gctcctctcg gccacggggt ctccccgct tcacccatat      480 gtcaagccct ggtaaggttc ttcgcgttgc ttcgaattaa gccacatgct ccgctgcttg     540
tgcgggcccc cgtcaattcc tttgagtttt agccttgcgg ccgtactccc caggcgggac     600
gcttaatgcg ttggctgcgg cacggggga tcgtcccccc acacctagcg tccatcgttt     660
```

```
acggctggga ctaccagggt atctaatcct gttcgctccc ccagctttcg cgcctcagcg    720
tcggtctcgg cccagagggc cgccttcgcc accggtgttc cacccgatat ctgcgcattc    780
caccgctaca ccgggtgttc caccctcccc taccggaccc aagccgcgga ggttccgggg    840
gcttcggggg gttgagcccc ccgcttcgac cccggcctgc cgggccgcct acgcgcgctt    900
tacgcccaat gaatccggat aacgctcgcc ccctacgtat tacgcggctg ctggcacgta    960
gttagccggg gcttcttctg caggtacagt cttgactctt ccctgctgaa agcggtttac   1020
ga                                                                  1022

<210> SEQ ID NO 14
<211> LENGTH: 918
<212> TYPE: DNA
<213> ORGANISM: Coprococcus comes

<400> SEQUENCE: 14
tggctgcggc gtgcttacca tgcaagtcga acgaagcact tatctttgat tcttcggatg     60
aagaggtttg tgactgagtg gcggacgggt gagtaacgcg tgggtaacct gcctcataca    120
gggggataac agttagaaat gactgctaat accgcataag accacggagc cgcatggctc    180
agtgggaaaa actccggtgg tatgagatgg acccgcgtct gattaggtag ttggtggggt    240
aacggcctac caagccaacg atcagtagcc gacctgagag ggtgaccggc cacattggga    300
ctgagacacg gcccaaactc ctacgggagg cagcagtggg gaatattgca caatggggga    360
aaccctgatg cagcgacgcc gcgtgagcga agaagtattt cggtatgtaa agctctatca    420
gcagggaaga aaatgacggt acctgactaa gaagcaccgg ctaaatacgt gccagcagcc    480
gcggtaatac gtatggtgca agcgttatcc ggatttactg ggtgtaaagg gagcgtagac    540
ggctgtgtaa gtctgaagtg aaagcccggg gctcaaccc gggactgctt tggaaactat    600
gcagctagag tgtcggagag gtaagtggaa ttcccagtgt agcggtgaaa tgcgtagata    660
ttgggaggaa caccagtggc gaaggcggct tactggacga tgactgacgt tgaggctcga    720
aagcgtgggg agcaaacagg gattagatac cctggtagtc cacgccgtaa acgatgacta    780
ctaagtgtcg gggagcaaaa gctcttcggt gccgcagcaa acgcaataag tagtccacct    840
gggggagtac gtcgcaagaa tgaaactcaa aggaattgac cggggacccg cacaacggtg    900
gagcatgtgg tttaattc                                                 918

<210> SEQ ID NO 15
<211> LENGTH: 1009
<212> TYPE: DNA
<213> ORGANISM: Dorea longicatena

<400> SEQUENCE: 15
cggatcggtc accttcggca gctccctcct tacggttggg tcactgactt cgggcgttac     60
tgactcccat ggtgtgacgg gcggtgtgta caagacccgg gaacgtattc accgcagcat    120
tctgatctgc gattactagc gattccagct tcatgtagtc gagttgcaga ctacaatccg    180
aactgagacg ttattttga gatttgctta ccctcgcgag ttcgcttctc tttgtttacg    240
ccattgtagc acgtgtgtag ccctggtcat aagggggcatg atgatttgac gtcatcccca    300
ccttcctcca ggttatccct ggcagtctct ccagagtgcc cagcttaacc tgctggctac    360
tgaagatagg ggttgcgctc gttgcgggac ttaacccaac atctcacgac acgagctgac    420
gacaaccatg caccacctgt caccgatgtt ccgaagaaaa gcttccatta cgaagcggtc    480
atcgggatgt caagatcagg taaggttctt cgcgttgctt cgaattaaac cacatgctcc    540
```

```
accgcttgtg cgggtcccg tcaattcctt tgagtttcat tcttgcgaac gtactcccca      600
ggtggactgc ttattgcgtt agctgcggca ccgaatggct tgccacccg acacctagca      660 gtcatcgttt acggcgtgga ctaccagggt atctaatcct gtttgctccc cacgctttcg    720
agcctcaacg tcagtcatcg tccagcaagc cgccttcgcc actggtgttc ctcctaatat     780
ctacgcattt caccgctaca ctaggaattc cacttgcctc tccgacactc tagctcagca    840
gttccaaatg cagtcccggg gttgagcccc gggctttcac atctggcttg ccgtgccgtc    900
tacgctccct ttacacccag taaatcccgg ataacgcttg cccctacgt attaccggcg     960 gctgctggca cgtagttagc ccggggcttc ttagtcaagg taccgtcat               1009

<210> SEQ ID NO 16
<211> LENGTH: 1016
<212> TYPE: DNA
<213> ORGANISM: Eubacterium halli

<400> SEQUENCE: 16
tcggctccct tcgaagctcc ctccataaag gttgggtcac tggcttcggg catttccaac    60
tcccatggtg tgacgggcgg tgtgtacaaa acccgggaac gtattcaccg cgacattctg    120
attcgcgatt actagcgatt ccagcttcgt gtagtcgggt tgcaaactac agtccaaact    180
gggacggcct ttttgtggtt tgctccccct cgcgggtttg cctcactctg tgaccgccat    240
tgtagcacgt gtgtcgccca atcataagg ggcatgatga tttgacgtcg tccccacctt    300
cctccaggtt atccctggca gtctctccaa agtgcccagc cttacctgct ggctactgaa    360 aatagggggtt gcgctcgttg cgggacttaa cccaacatct cacaacacaa gctgacaaca    420
accatgcacc acctgtctct tctgtcccga aggaaaactc ccattacgga gtggtcaaaa    480
ggatgtcaag acctggtaag gttcttcgcg ttgcttcaaa ttaaaccaca tgctccaccg    540
cttgtgcggg tccccgtcaa ttcctttgag tttcattctt gcaaacgtac tccccaggtg    600
gaatacttac tgcgttagcg gcggaccgga agcctatacg gccccgacac ctagtattca    660
tcgtttacgg cgtggactac cagggtatct aatcctgttt gctccccacg ctttcgtgcc    720
tcagtgtcag taacagtcca gcaggccgcc ttcgccactg gtgttcctcc taatatctac    780
gcatttcacc gctacactag gaattccgcc tgcttctcct gtactctagc taagcagttt    840
caaatgcagc tccggggttg agcccgggct ttcacatctg acttgcactg ccacctacgc    900
accctttaca ccaataaatc cggataacgc ttgctccata cgtattaccg cggctgctgg    960
cacgtattag cccggagctt ctaatcaggt accggcatta tctccctgct gataga       1016

<210> SEQ ID NO 17
<211> LENGTH: 1077
<212> TYPE: DNA
<213> ORGANISM: Faecalibacterium prausnitzii

<400> SEQUENCE: 17
tgggctggcg gcgcgctaca catgcagtcg aacgagcgag agagagcttg ctttctcgag    60
cgagtggcga acgggtgagt aacgcgtgag gaacctgcct caaagagggg gacaacagtt   120
ggaaacgact gctaataccg cataagccca cgacccggca tcgggtagag ggaaaaggag    180
caatccgctt tgagatggcc tcgcgtccga ttagctagtt ggtgaggtaa tggcccacca    240
aggcgacgat cggtagccgg actgagaggt tgaacggcca cattgggact gagacacggc    300
ccagactcct acgggaggca gcagtgggga atattgcaca atgggggaaa ccctgatgca    360
```

```
gcgacgccgc gtggaggaag aaggtcttcg gattgtaaac tcctgttgtt gaggaagata    420
atgacggtac tcaacaagga agtgacggct aactacgtgc cagcagccgc ggtaaaacgt    480
aggtcacaag cgttgtccgg aattactggg tgtaaaggga gcgcaggcgg aagacaagt    540
tggaagtgaa atccatgggc tcaacccatg aactgctttc aaaactgttt ttcttgagta    600
gtgcagaggt aggcggaatt cccggtgtag cggtggaatg cgtagatatc gggaggaaca    660
ccagtggcga aggcggccta ctgggcacca actgacgctg aggctcgaaa gtgtgggtag    720
caaacaggat tagataccct ggtagtccac actgtaaacg atgattacta ggtgttggag    780
gattgacccc ttcagtgccg cagttaacac aataagtaat ccacctgggg agtacgaccg    840
caaggttgaa actcaaagga attgacgggg gcccgcacaa gcagtggagt atgtggttta    900
attcgacgca acgcgaagaa ccttaccaag tcttgacatc cttgtgacga tgctagaaat    960
agtattttc ttctgaacac agagacaggt ggtgcatggt tgtcgtcagc tcgtgtcgtg   1020
agatgttggg ttaagtcccg caacgagcgc aacccttat ggtcagttac taccgca      1077
```

<210> SEQ ID NO 18
<211> LENGTH: 1019
<212> TYPE: DNA
<213> ORGANISM: Parabacteroides merdae

<400> SEQUENCE: 18

```
tagatttacc taggccgatc cttgcggtta cggacttcag gtaccccgg ctcccatggc     60
ttgacgggcg gtgtgtacaa ggcccgggaa cgtattcacc gcgccatggc tgatgcgcga   120
ttactagcga atccagcttc acggagtcga gttgcagact ccgatccgaa ctgagacatg   180
gtttggagat tagcatcctg tcaccaggta gctgcccttt gtccatgcca ttgtaacacg   240
tgtgtcgccc cggatgtaag ggccgtgctg atttgacgtc atccccacct tcctcacagc   300
ttacgctggc agtctcacca gagtcctcag cttcacctgt tagtaactag tgataagggt   360
tgcgctcgtt atggcactta agccgacacc tcacggcacg agctgacgac aaccatgcag   420
cacctcgtaa tctgctattg ctagaaagag tgtttccact ccggtcagac tacgttcaaa   480
cccgggtaag gttcctcgcg tatcatcgaa ttaaaccaca tgttcctccg cttgtgcggg   540
ccccccgtcaa ttcctttgag tttcaccgtt gccggcgtac tccccaggtg gattacttaa   600
cgctttcgct gtagagctta cattgtatcg caaactccta gtaatcatcg tttactgcgt   660
ggactaccag ggtatctaat cctgtttgat ccccacgctt tcgtgcttca gtgtcagtta   720
tggtttagta agctgccttc gcaatcggag ttctgcgtga tatctatgca tttcaccgct   780
acaccacgca ttccgcctac ctcaaacaca ctcaagtaac ccagtttcaa cggcaatttt   840
atggttgagc cacaaacttt taccgctgac ttaaatcacc acctacgcac cctttaaacc   900
caataaatcc ggataacgct cgcatcctcc gtattaccgc ggctgctggc acggagttag   960
ccgatgctta ttcataggt acatacaaaa agacacgtcc tccactttat tccccttta   1019
```

<210> SEQ ID NO 19
<211> LENGTH: 1036
<212> TYPE: DNA
<213> ORGANISM: Parabacteroides distasonis

<400> SEQUENCE: 19

```
tcagcatgac ctaggccgat cctcgcggtt acggacttca ggtaccccg gctcccatgg    60
cttgacgggc ggtgtgtaca aggcccggga acgtattcac cgcgccatgg ctgatgcgcg   120
attactagcg aatccagctt cacggagtcg ggttgcagac tccgatccga actgagacgt   180
```

```
ggtttgggga ttcgctccct gtcgccaggt ggcttccctt tgtccacgcc attgtaacac      240
gtgtgtcgcc ccggatgtaa gggccgtgct gatttgacgt catccccgcc ttcctcgcag      300
cttacgctgg cagtcccacc agagtcctca gcatcacctg ttagtaacta gtggcaaggg      360
ttgcgctcgt tatggcactt aagccgacac ctcacggcac gagctgacga caaccatgca      420
gcacctcgca aacggctatt gctagaagag gtgtttccac ctcggtccga atgcgttcaa      480
acccgggtaa ggttcctcgc gtatcatcga attaaaccac atgttcctcc gcttgtgcgg      540
gcccccgtca attcctttga gtttcaccgt tgccggcgta ctccccaggt ggatcactta      600
acgctttcgc tgtgccgctt acactgtatc gcaaacagct agtgatcatc gtttactgcg      660
tggactacca gggtatctaa tcctgtttga tccccacgct ttcgtgcatc agcgtcagtc      720
atggcttggc aggctgcctt cgcaatcggg gttctgcgtg atatctaagc atttcaccgc      780
tacaccacgc attccgcctg cctcaaacat actcaagcct cccagtttca acggcaattc      840
tatggttgag ccacagactt tcaccgctga cttaaaaggc cgcctacgca ccctttaaac      900
ccaataaatc cggataacgc tcggatcctc cgtattaccg cggctgctgg cacggagtta      960
gccgatcctt attcataagg tacatacaaa acaggaaacg tccacaactt tattccctta     1020
taaagaggtt tacgat                                                      1036

<210> SEQ ID NO 20
<211> LENGTH: 1031
<212> TYPE: DNA
<213> ORGANISM: Prevotella copri

<400> SEQUENCE: 20
cttagctttc gcctaggccg ctccttacgg tcacggactt taggcgcccc cggctttcat       60
ggcttgacgg gcggtgtgta caaggcccgg gaacgtattc accgcgccat ggctgatgcg      120
cgattactag cgaatccagc ttcgtggggt cgggttgcag accccagtcc gaactgagac      180
aggctttaag gatttgatcc tttttgcaag ggaccgtctc tctgtacctg ccattgtaac      240
acgtgtgtag ccccggacgt aagggccgtg ctgatttgac gtcatcccca ccttcctcac      300
accttacggt ggcagtgtcc ccagagtgcc cagcttaacc tgatggcaac taaggagagg      360
ggttgcgctc gttatggcac ttaagccgac acctcacggc acgagctgac gacaaccatg      420
cagcaccttc acagaggccc cgaagggcgt cattgtctcc aaatccttcc tctgcaattc      480
aagcccgggt aaggttcctc gcgtatcatc gaattaaacc acatgttcct ccgcttgtgc      540
gggcccccgt caattccttt gagtttcacc gttgccggcg tactccccag gtgggatgct      600
taatgctttc gcttggccgc tgacctattc agaccaacag cgggcatcca tcgtttaccg      660
tgcggactac cagggtatct aatcctgttc gatacccgca ctttcgagct tcagcgtcag      720
ttgcgctcca gtgagctgcc ttcgcaatcg gagttcttcg tgatatctaa gcatttcacc      780
gctacaccac gaattccgcc cactttgtgc gtactcaagg aaaccagttc gcgctgcagt      840
gcaacgttga gcgtctaatt tcacaacacg cttaatctcc ggctacgctc cctttaacca      900
aaaaaaccag ataacgccgg acctccgtat taccgcggct gctggccgga attagccggc      960
cctatcataa ggtacatgca aaaagctacc aaactcactt tttccccttta caagagttac     1020 aaccataggc c                                                           1031

<210> SEQ ID NO 21
<211> LENGTH: 1090
<212> TYPE: DNA
```

<213> ORGANISM: Roseburia faecis

<400> SEQUENCE: 21

```
ggggctgggc ggcgtgctta ccatgcaagt cgaacgaagc actctatttg attttcttcg      60
gaaatgaaga ttttgtgact gagtggcgga cgggtgagta acgcgtgggt aacctgcctc     120
atacaggggg ataacagttg gaaacgactg ctaataccgc ataagcgcac aggatcgcat     180
gatccggtgt gaaaaactcc ggtggtatga gatggacccg cgtctgatta gccagttggc     240
agggtaacgg cctaccaaag cgacgatcag tagccgacct gagagggtga ccggccacat     300
tgggactgag acacggccca aactcctacg ggaggcagca gtgggaata ttgcacaatg      360
ggggaaaccc tgatgcagcg acgccgcgtg agcgaagaag tatttcggta tgtaaagctc     420
tatcagcagg gaagaagaat gacggtacct gactaagaag caccggctaa atacgtgcca     480
gcagccgcgg taatacgtat ggtgcaagcg ttatccggat ttactgggtg taaagggagc     540
gcaggcggtg cggcaagtct gatgtgaaag cccggggctc aaccccgta ctgcattgga      600
aactgtcgta ctagagtgtc ggagggtaa gtggaattcc tagtgtagcg gtgaaatgcg      660
tagatattag gaggaacacc agtggcgaag gcggcttact ggacgataac tgacgctgag     720
gctcgaaagc gtggggagca aacaggatta gataccctgg tagtccacgc cgtaaacgat     780
gaatactagg tgtcggggag cattgctctt cggtgccgca gcaaacgcaa taagtattcc     840
acctggggag tacgttcgca agaatgaaac tcaaaggaat tgacggggac cgcacagcg      900
gtggagcatg tggtttattc gaagcaacgc gaagaacctt accaagtctt gacatcccga     960
tgacagagta tgtaatgtac tttctcttcg agcatcggtg acagtgggtg catggttgtc    1020
gtcactcgtg tcgtgagatg ttgggttaag tccgcaacga gcgcaacccc tgtccttagt    1080
agcagcggtg                                                           1090
```

<210> SEQ ID NO 22
<211> LENGTH: 1056
<212> TYPE: DNA
<213> ORGANISM: Ruminococcus faecis
<220> FEATURE:
<221> NAME/KEY: misc_feature
<222> LOCATION: (4)..(4)
<223> OTHER INFORMATION: n is a, c, g, or t

<400> SEQUENCE: 22

```
gcgntcggtc accttcggca gctccctcct tacggttggg tcactgactt cgggcgttac      60
tgactcccat ggtgtgacgg gcggtgtgta caagacccgg gaacgtattc accgcgacat     120
tctgattcgc gattactagc gattccagct tcatgtagtc gagttgcaga ctacaatccg     180
aactgagacg ttattttttgg gatttgctcg acctcgcggt tctgcctccc tttgtttacg     240
ccattgtagc acgtgtgtag ccctgctcat aagggcatg atgatttgac gtcatcccca      300
ccttcctcca ggttatccct ggcagtctct ctagagtgcc cggccaaacc gctggctact     360
aaagataggg gttgcgctcg ttgcgggact aacccaaca tctcacgaca cgagctgacg      420
acaaccatgc accacctgtc atccctgtcc cgaaggaaag gcaacattac ttgccggtca     480
gggagatgtc aagagcaggt aaggttcttc gcgttgcttc gaattaaacc acatgctcca     540
ccgcttgtgc gggtccccgt caattccttt gagtttcatt cttgcgaacg tactccccag     600
gtggactact tattgcgttt gctgcggcac cgaacagctt tgctgcccga cacctagtag     660
tcatcgttta cggcgtggac taccagggta tctaatcctg tttgctcccc acgctttcga     720
gcctcaacgt cagttaccgt ccagtaagcc gccttcgcca ctggtgttcc tcctaatatc     780
```

```
tacgcatttc accgctacac taggaattcc gcttacctct ccggtactct agattgacag    840
tttccaatgc agtcccgggg ttgagccccg ggttttcaca tcagacttgc cactccgtct    900
acgctccctt tacacccagt aaatccggat aacgcttgca ccatacgtat taccgcggct    960
gctggcacgt atttagcctg tgcttctagt caggtaccgt catttttcttc cctgctgata   1020 gagctttaca taccgaatac ttcatcccct cccgcg                              1056
```

<210> SEQ ID NO 23
<211> LENGTH: 1530
<212> TYPE: DNA
<213> ORGANISM: Flavonifractor plautii

<400> SEQUENCE: 23

```
tattgagagt ttgatcctgg ctcaggatga acgctggcgg cgtgcttaac acatgcaagt     60
cgaacggggt gctcatgacg gaggattcgt ccaacggatt gagttaccta gtggcggacg    120
ggtgagtaac gcgtgaggaa cctgccttgg agagggaat aacactccga aaggagtgct     180
aataccgcat gatgcagttg ggtcgcatgg ctctgactgc caaagattta tcgctctgag    240
atggcctcgc gtctgattag ctagtaggcg gggtaacggc ccacctaggc gacgatcagt    300
agccggactg agaggttgac cggccacatt gggactgaga cacggcccag actcctacgg    360
gaggcagcag tggggaatat tgggcaatgg gcgcaagcct gacccagcaa cgccgcgtga    420
aggaagaagg ctttcgggtt gtaaacttct tttgtcgggg acgaaacaaa tgacggtacc    480
cgacgaataa gccacggcta actacgtgcc agcagccgcg gtaatacgta ggtggcaagc    540
gttatccgga tttactgggt gtaaagggcg tgtaggcggg attgcaagtc agatgtgaaa    600
actgggggct caacctccag cctgcatttg aaactgtagt tcttgagtgc tggagaggca    660
atcggaattc cgtgtgtagc ggtgaaatgc gtagatatac ggaggaacac cagtggcgaa    720
ggcggattgc tggacagtaa ctgacgctga ggcgcgaaag cgtggggagc aaacaggatt    780
agataccctg gtagtccacg ccgtaaacga tggatactag gtgtgggggg tctgaccccc    840
tccgtgccgc agttaacaca ataagtatcc cacctgggga gtacgatcgc aaggttgaaa    900
ctcaaaggaa ttgacggggg cccgcacaag cggtggagta tgtggtttaa ttcgaagcaa    960
cgcgaagaac cttaccaggg cttgacatcc cactaacgaa gcagagatgc attaggtgcc   1020 cttcgggaa agtggagaca ggtggtgcat ggttgtcgtc agctcgtgtc gtgagatgtt   1080
gggttaagtc ccgcaacgag cgcaacccct attgttagtt gctacgcaag agcactctag   1140
cgagactgcc gttgacaaaa cggaggaagg tggggacgac gtcaaatcat catgcccctt   1200
atgtcctggg ccacacacgt actacaatgg tggttaacag agggaggcaa taccgcgagg   1260
tggagcaaat cctaaaagc catcccagtt cggattgcag gctgaaaccc gcctgtatga   1320
agttggaatc gctagtaatc gcggatcagc atgccgcggt gaatacgttc ccgggccttg   1380
tacacaccgc ccgtcacacc atgagagtcg gaacacccg aagtccgtag cctaaccgca   1440
aggagggcgc ggccgaaggt gggttcgata attggggtga agtcgtaaca aggtagccgt   1500
atcggaaggt gcggctggat cacctccttt                                    1530
```

<210> SEQ ID NO 24
<211> LENGTH: 1529
<212> TYPE: DNA
<213> ORGANISM: Blautia producta

<400> SEQUENCE: 24

```
tcagagagtt tgatcctggc tcaggatgaa cgctggcggc gtgcttaaca catgcaagtc    60
gagcgaagca ctaagacaga tttcttcgga ttgaagtctt tgtgactgag cggcggacgg   120
gtgagtaacg cgtgggtaac ctgcctcata caggggata acagttagaa atgactgcta   180
ataccgcata agcgcacagg accgcatggt ctggtgtgaa aaactccggt ggtatgagat   240
ggacccgcgt ctgattagct agttggaggg gtaacggccc accaaggcga cgatcagtag   300
ccggcctgag agggtgaacg gccacattgg gactgagaca cggcccagac tcctacggga   360
ggcagcagtg gggaatattg cacaatgggg gaaaccctga tgcagcgacg ccgcgtgaag   420
gaagaagtat ctcggtatgt aaacttctat cagcagggaa gaaaatgacg gtacctgact   480
aagaagcccc ggctaactac gtgccagcag ccgcggtaat acgtaggggg caagcgttat   540
ccggatttac tgggtgtaaa gggagcgtag acggaatagc aagtctgatg tgaaaggctg   600
gggcttaacc ccaggactgc attggaaact gttgttctag agtgccggag aggtaagcgg   660
aattcctagt gtagcggtga atgcgtaga tattaggagg aacaccagtg gcgaaggcgg   720
cttactggac ggtaactgac gttgaggctc gaaagcgtgg ggagcaaaca ggattagata   780
ccctggtagt ccacgccgta acgatgaat actaggtgtc gggtggcaaa gccattcggt   840
gccgcagcaa acgcaataag tattccacct ggggagtacg ttcgcaagaa tgaaactcaa   900
aggaattgac ggggacccgc acaagcggtg gagcatgtgg tttaattcga gcaacgcga   960 agaaccttac caagtcttga catccctctg accgtcccgt aacggggact tcccttcggg  1020
gcagaggaga caggtggtgc atggttgtcg tcagctcgtg tcgtgagatg ttgggttaag  1080
tcccgcaacg agcgcaaccc ttatccttag tagccagcac atgatggtgg gcactctagg  1140
gagactgccg gggataaccc ggaggaaggc ggggacgacg tcaaatcatc atgcccctta  1200
tgatttgggc tacacacgtg ctacaatggc gtaaacaaag gaagcgaga cagcgatgtt  1260 gagcgaatcc caaaaataac gtcccagttc ggactgcagt ctgcaactcg actgcacgaa  1320
gctggaatcg ctagtaatcg cggatcagaa tgccgcggtg aatacgttcc cgggtcttgt  1380
acacaccgcc cgtcacacca tgggagtcag taacgcccga agtcagtgac ctaaccgaaa  1440
ggaaggagct gccgaaggcg ggaccgataa ctggggtgaa gtcgtaacaa ggtagccgta  1500
tcggaaggtg cggctggatc acctcctttt                                    1529
```

<210> SEQ ID NO 25
<211> LENGTH: 1530
<212> TYPE: DNA
<213> ORGANISM: Blautia producta

<400> SEQUENCE: 25

```
tcagagagtt tgatcctggc tcaggatgaa cgctggcggc gtgcttaaca catgcaagtc    60
gagcgaagca cttaagtgga tctcttcgga ttgaaactta tttgactgag cggcggacgg   120
gtgagtaacg cgtgggtaac ctgcctcata caggggata acagttagaa atggctgcta   180
ataccgcata agcgcacagg accgcatggt ctggtgtgaa aaactccggt ggtatgagat   240
ggacccgcgt ctgattagct agttggaggg gtaacggccc accaaggcga cgatcagtag   300
ccggcctgag agggtgaacg gccacattgg gactgagaca cggcccagac tcctacggga   360
ggcagcagtg gggaatattg cacaatgggg gaaaccctga tgcagcgacg ccgcgtgaag   420
gaagaagtat ctcggtatgt aaacttctat cagcagggaa gaaaatgacg gtacctgact   480
aagaagcccc ggctaactac gtgccagcag ccgcggtaat acgtaggggg caagcgttat   540
ccggatttac tgggtgtaaa gggagcgtag acggaagagc aagtctgatg tgaaaggctg   600
```

```
gggcttaacc ccaggactgc attggaaact gttttctag agtgccggag aggtaagcgg      660
aattcctagt gtagcggtga aatgcgtaga tattaggagg aacaccagtg gcgaaggcgg      720
cttactggac ggtaactgac gttgaggctc gaaagcgtgg ggagcaaaca ggattagata      780
ccctggtagt ccacgccgta aacgatgaat actaggtgtc gggtggcaaa gccattcggt      840
gccgcagcaa acgcaataag tattccacct ggggagtacg ttcgcaagaa tgaaactcaa      900
aggaattgac ggggacccgc acaagcggtg gagcatgtgg tttaattcga agcaacgcga      960
agaaccttac caagtcttga catccctctg accggcccgt aacggggcct tccttcggg      1020 gcagaggaga caggtggtgc atggttgtcg tcagctcgtg tcgtgagatg ttgggttaag     1080
tcccgcaacg agcgcaaccc ctatccttag tagccagcag gtgaagctgg cactctagg     1140 gagactgccg gggataaccc ggaggaaggc ggggacgacg tcaaatcatc atgccccta     1200 tgatttgggc tacacacgtg ctacaatggc gtaaacaaag ggaagcgaga cagcgatgtt    1260
gagcaaatcc caaaataac gtcccagttc ggactgcagt ctgcaactcg actgcacgaa     1320
gctggaatcg ctagtaatcg cgaatcagaa tgtcgcggtg aatacgttcc cgggtcttgt    1380
acacaccgcc cgtcacacca tgggagtcag taacgcccga agtcagtgac ccaaccttat    1440
aggagggagc tgccgaaggc gggaccgata actgggtga agtcgtaaca aggtagccgt     1500
atcggaaggt gcggctggat cacctccttt                                     1530
```

<210> SEQ ID NO 26
<211> LENGTH: 303
<212> TYPE: DNA
<213> ORGANISM: Clostridium ramosum

<400> SEQUENCE: 26

```
gatgaacgct ggcggcgtgc ctaatacatg caagtcgaac gcgagcactt gtgctcgagt      60
ggcgaacggg tgagtaatac ataagtaacc tgccctagac aggggataa ctattggaaa     120 cgatagctaa gaccgcatag gtacggacac tgcatggtga ccgtattaaa gtgcctcaaa    180
gcactggtag aggatggact tatgcgcat tagctggttg gcggggtaac ggcccaccaa      240
ggcgacgatg cgtagccgac ctgagagggt gaccggccac actgggactg agacacggcc    300
cag                                                                  303
```

<210> SEQ ID NO 27
<211> LENGTH: 324
<212> TYPE: DNA
<213> ORGANISM: Flavonifractor plautii

<400> SEQUENCE: 27

```
gatgaacgct ggcggcgtgc ttaacacatg caagtcgaac ggggtgctca tgacggagga     60
ttcgtccaac ggattgagtt acccagtggc ggacgggtga gtaacgcgtg aggaacctgc    120
cttggagagg ggaataacac tccgaaagga gtgctaatac cgcatgatgc agttgggtcg    180
catggctctg actgccaaag atttatcgct ctgagatggc ctcgcgtctg attagctagt    240 aggcgggta acggcccacc taggcgacga tcagtagccg gactgagagg ttgaccggcc    300
acattgggac tgagacacgg ccca                                          324
```

<210> SEQ ID NO 28
<211> LENGTH: 1003
<212> TYPE: DNA
<213> ORGANISM: Unknown
<220> FEATURE:

<223> OTHER INFORMATION: Barnesiella/Parabacteroides spp

<400> SEQUENCE: 28

| | | | | | |
|---|---|---|---|---|---|
| gtgctcagct | tttaccctag | gccgatcctt | gcggttacgg | acttcaggta | cccccggctc | 60 |
| ccatggcttg | acgggcggtg | tgtacaaggc | ccgggaacgt | attcaccgcg | ccatggctga | 120 |
| tgcgcgatta | ctagcgaatc | cagcttcacg | gagtcgagtt | gcagactccg | atccgaactg | 180 |
| agacatggtt | tggagattag | catcctgtcg | ccaggtagct | gcccttttgtc | catgccattg | 240 |
| taacacgtgt | gtcgccccgg | atgtaagggc | cgtgctgatt | tgacgtcatc | cccaccttcc | 300 |
| tcacagctta | cgctggcagt | ctcaccagag | tcctcagctt | cacctgttag | taactagtga | 360 |
| taagggttgc | gctcgttatg | gcacttaagc | cgacacctca | cggcacgagc | tgacgacaac | 420 |
| catgcagcac | ctcgtaatct | gctattgcta | gaaggagtgt | ttccactccg | gtcagactac | 480 |
| gttcaaaccc | gggtaaggtt | cctcgcgtat | catcgaatta | aaccacatgt | tcctccgctt | 540 |
| gtgcgggccc | ccgtcaattc | ctttgagttt | caccgttgcc | ggcgtactcc | ccaggtggat | 600 |
| tacttaacgc | tttcgctgta | gagcttacat | tgtatcgcaa | actcctagta | atcatcgttt | 660 |
| actgcgtgga | ctaccagggt | atctaatcct | gtttgatccc | cacgctttcg | tgcttcagtg | 720 |
| tcagttatgg | tttagtaagc | tgccttcgca | atcggagttc | tgcgtgatat | ctatgcattt | 780 |
| caccgctaca | ccacgcattc | cgcctacctc | aaacacactc | aagtaaccca | gtttcaacgg | 840 |
| caattttatg | gttgagccac | aaactttcac | cgctgactta | aatcaccacc | tacgcaccct | 900 |
| ttaacccaat | aaatccgata | acgctcgcat | cctccgtatt | accgcggctg | ctgcccggag | 960 |
| ttagccgatg | cttattcata | gggtacatac | aaaaaggaca | cgt | | 1003 |

<210> SEQ ID NO 29
<211> LENGTH: 1527
<212> TYPE: DNA
<213> ORGANISM: Clostridium symbiosum

<400> SEQUENCE: 29

| | | | | | |
|---|---|---|---|---|---|
| atgagagttt | gatcctggct | caggatgaac | gctggcggcg | tgcctaacac | atgcaagtcg | 60 |
| aacgaagcga | tttaacggaa | gttttcggat | ggaagttgaa | ttgactgagt | ggcggacggg | 120 |
| tgagtaacgc | gtgggtaacc | tgccttgtac | tgggggacaa | cagttagaaa | tgactgctaa | 180 |
| taccgcataa | gcgcacagta | tcgcatgata | cagtgtgaaa | aactccggtg | gtacaagatg | 240 |
| gacccgcgtc | tgattagcta | gttggtaagg | taacggctta | ccaaggcgac | gatcagtagc | 300 |
| cgacctgaga | gggtgaccgg | ccacattggg | actgagacac | ggcccaaact | cctacgggag | 360 |
| gcagcagtgg | ggaatattgc | acaatgggcg | aaagcctgat | gcagcgacgc | cgcgtgagtg | 420 |
| aagaagtatt | tcggtatgta | aagctctatc | agcagggaag | aaaatgacgg | tacctgacta | 480 |
| agaagcccg | gctaactacg | tgccagcagc | cgcggtaata | cgtaggggc | aagcgttatc | 540 |
| cggatttact | gggtgtaaag | ggagcgtaga | cggtaaagca | agtctgaagt | gaaagcccgc | 600 |
| ggctcaactg | cgggactgct | ttggaaactg | tttaactgga | gtgtcggaga | ggtaagtgga | 660 |
| attcctagtg | tagcggtgaa | atgcgtagat | attaggagga | acaccagtgg | cgaaggcgac | 720 |
| ttactggacg | ataactgacg | ttgaggctcg | aaagcgtggg | gagcaaacag | gattagatac | 780 |
| cctggtagtc | cacgccgtaa | acgatgaata | ctaggtgttg | gggagcaaag | ctcttcggtg | 840 |
| ccgtcgcaaa | gcagtaagt | attccacctg | gggagtacgt | tcgcaagaat | gaaactcaaa | 900 |
| ggaattgacg | gggacccgca | caagcggtgg | agcatgtggt | ttaattcgaa | gcaacgcgaa | 960 |
| gaaccttacc | aggtcttgac | atcgatccga | cggggagta | acgtcccctt | cccttcgggg | 1020 |

```
cggagaagac aggtggtgca tggttgtcgt cagctcgtgt cgtgagatgt tgggttaagt   1080
cccgcaacga gcgcaaccct tattctaagt agccagcggt tcggccggga actcttggga   1140
gactgccagg gataacctgg aggaaggtgg ggatgacgtc aaatcatcat gccccttatg   1200
atctgggcta cacacgtgct acaatggcgt aaacaaagag aagcaagacc gcgaggtgga   1260
gcaaatctca aaaataacgt ctcagttcgg actgcaggct gcaactcgcc tgcacgaagc   1320
tggaatcgct agtaatgcgc aatcagaatg tcgcggtgaa tacgttcccg ggtcttgtac   1380
acaccgcccg tcacaccatg ggagtcagta cgcccgaag tcagtgaccc aaccgcaagg   1440
agggagctgc cgaaggcggg accgataact ggggtgaagt cgtaacaagg tagccgtatc   1500
ggaaggtgcg gctggatcac ctcctttt                                     1527
```

<210> SEQ ID NO 30
<211> LENGTH: 324
<212> TYPE: DNA
<213> ORGANISM: Eubacterium fissicatena

<400> SEQUENCE: 30

```
gatgaacgct ggcggcgtgc ttaacacatg caagtcgagc gaagcgcttt acttagattt     60
cttcggattg aaagttttgc gactgagcgg cggacgggtg agtaacgcgt gggtaacctg    120
cctcatacag ggggataaca gttagaaatg actgctaata ccgcataaga ccacagtacc    180
gcatggtaca gtgggaaaaa ctccggtggt atgagatgga cccgcgtctg attagctagt    240
tggtaaggta acggcttacc aaggcgacga tcagtagccg acctgagagg gtgaccggcc    300
acattgggac tgagacacgg ccca                                          324
```

<210> SEQ ID NO 31
<211> LENGTH: 1486
<212> TYPE: DNA
<213> ORGANISM: Lachnospiraceae bacterium

<400> SEQUENCE: 31

```
agagtttgat cctggctcag gataaacgct ggcggcgcac ataagacatg caagtcgaac     60
ggacttaact cattctttta gattgagagc ggttagtggc ggactggtga gtaacacgta    120
agcaacctgc ctatcagagg ggaataacag tgagaaatca ttgctaatac cgcatatgct    180
cacagtatca catgatacag tgaggaaagg agcaatccgc tgatagatgg gcttgcgcct    240
gattagttag ttggtggggt aacggcctac caagacgacg atcagtagcc ggactgagag    300
gttgaacggc cacattggga ctgagatacg gcccagactc ctacgggagg cagcagtcgg    360
gaatattgcg caatggagga aactctgacg cagtgacgcc gcgtatagga agaaggtttt    420
cggattgtaa actattgtcg ttagggaaga taaaagactg tacctaagga ggaagccccg    480
gctaactatg tgccagcagc cgcggtaata catgggggc aagcgttatc cggaattatt    540
gggtgtaaag ggtgcgtaga cggaagaaca agttggttgt gaaatccctc ggctcaactg    600
aggaactgca accaaaacta ttctccttga gtgtcggaga ggaaagtgga attcctagtg    660
tagcggtgaa atgcgtagat attaggagga acaccagtgg cgaaggcgac tttctggacg    720
ataactgacg ttgaggcacg aaagtgtggg gagcaaacag gattagatac cctggtagtc    780
cacactgtaa acgatggata ctaggtgtag ggtgtattaa gcactctgtg ccgccgctaa    840
cgcattaagt atcccacctg gggagtacga ccgcaaggtt gaaactcaaa ggaattgacg    900
ggggcccgca caagcagtgg agtatgtggt ttaattcgaa gcaacgcgaa gaaccttacc    960
```

```
agggcttgac atataccgga atatactaga gatagtatag tccttcggga ctggtataca    1020
ggtggtgcat ggttgtcgtc agctcgtgtc gtgagatgtt gggttaagtc ccgcaacgag    1080
cgcaacccct atcgttagtt gctagcaggt aatgctgaga actctagcga gactgccggt    1140
gataaatcgg aggaaggtgg ggatgacgtc aaatcatcat gcccttatg tcctgggcta     1200 cacacgtact acaatggccg taacagaggg aagcaatata gtgatatgga gcaaaccct     1260 aaaagcggtc tcagttcgga ttgaaggctg aaattcgcct tcatgaagcc ggaattgcta    1320
gtaatggcag gtcagcatac tgccgtgaat acgttcccgg gccttgtaca caccgcccgt    1380
cacaccatga gagttggaaa tacccgaagc ctgtgagcta actgtaaaga ggcagcagtc    1440
gaaggtagag ccaatgattg gggtgaagtc gtaacaaggt agccgt                   1486

<210> SEQ ID NO 32
<211> LENGTH: 1528
<212> TYPE: DNA
<213> ORGANISM: Dorea Longicatena

<400> SEQUENCE: 32
aacgagagtt tgatcctggc tcaggatgaa cgctggcggc gtgcttaaca catgcaagtc      60
gagcgaagca ctttggaaga ttcttcggat gatttccttt gtgactgagc ggcggacggg     120
tgagtaacgc gtgggtaacc tgcctcatac aggggataaa cagttagaaa tgactgctaa     180
taccgcataa gaccacggta ccgcatggta cagtggtaaa aactccggtg gtatgagatg     240
gacccgcgtc tgattaggta gttggtgggg taacggccta ccaagccgac gatcagtagc     300
cgacctgaga gggtgaccgg ccacattggg actgagacac ggcccagact cctacgggag     360
gcagcagtgg ggaatattgc acaatggagg aaactctgat gcagcgacgc cgcgtgaagg     420
atgaagtatt tcggtatgta aacttctatc agcaggaag aaaatgacgg tacctgacta      480
agaagccccg gctaactacg tgccagcagc cgcggtaata cgtaggggc aagcgttatc      540 cggatttact gggtgtaaag ggagcgtaga cggcacggca agccagatgt gaaagcccgg     600
ggctcaaccc cgggactgca tttggaactg ctgagctaga gtgtcggaga ggcaagtgga     660
attcctagtg tagcggtgaa atgcgtagat attaggagga acaccagtgg cgaaggcggc     720
ttgctggacg atgactgacg ttgaggctcg aaagcgtggg gagcaaacag gattagatac     780
cctggtagtc cacgccgtaa acgatgactg ctaggtgtcg ggtggcaaag ccattcggtg     840
ccgcagctaa cgcaataagc agtccacctg gggagtacgt tcgcaagaat gaaactcaaa     900
ggaattgacg ggacccgca caagcggtgg agcatgtggt ttaattcgaa gcaacgcgaa      960
gaaccttacc tgatcttgac atcccgatga ccgcttcgta atggaagctt tcttcggaa     1020 catcggtgac aggtggtgca tggttgtcgt cagctcgtgt cgtgagatgt gggttaagt    1080 cccgcaacga gcgcaacccc tatcttcagt agccagcagg ttaagctggg cactctggag    1140
agactgccag ggataacctg gaggaaggtg gggatgacgt caaatcatca tgccccttat    1200
gaccagggct acacacgtgc tacaatggcg taaacaaaga gaagcgaact cgcgagggta    1260
agcaaatctc aaaaataacg tctcagttcg gattgtagtc tgcaactcga ctacatgaag    1320
ctggaatcgc tagtaatcgc agatcagaat gctgcggtga atacgttccc gggtcttgta    1380
cacaccgccc gtcacaccat gggagtcagt aacgcccgaa gtcagtgacc caaccgtaag    1440
gagggagctg ccgaaggtgg gaccgataac tggggtgaag tcgtaacaag gtagccgtat    1500
cggaaggtgc ggctggatca cctcctttt                                      1528
```

<210> SEQ ID NO 33
<211> LENGTH: 1531
<212> TYPE: DNA
<213> ORGANISM: Blautia producta

<400> SEQUENCE: 33

```
atcagagagt tgatcctgg ctcaggatga acgctggcgg cgtgcttaac acatgcaagt        60
cgagcgaagc acttaagtgg atctcttcgg attgaaactt atttgactga gcggcggacg      120
ggtgagtaac gcgtgggtaa cctgcctcat acaggggat aacagttaga aatggctgct       180
aataccgcat aagcgcacag gaccgcatgg tctggtgtga aaaactccgg tggtatgaga      240
tggacccgcg tctgattagc tagttggagg ggtaacggcc caccaaggcg acgatcagta      300
gccggcctga gagggtgaac ggccacattg gactgagac acggcccaga ctcctacggg       360
aggcagcagt ggggaatatt gcacaatggg ggaaaccctg atgcagcgac gccgcgtgaa      420
ggaagaagta tctcggtatg taaacttcta tcagcaggga agaaaatgac ggtacctgac      480
taagaagccc cggctaacta cgtgccagca gccgcggtaa tacgtagggg gcaagcgtta      540
tccggattta ctgggtgtaa agggagcgta gacggaagag caagtctgat gtgaaaggct      600
ggggcttaac cccaggactg cattggaaac tgtttttcta gagtgccgga gaggtaagcg      660
gaattcctag tgtagcggtg aaatgcgtag atattaggag gaacaccagt ggcgaaggcg      720
gcttactgga cggtaactga cgttgaggct cgaaagcgtg gggagcaaac aggattagat      780
accctggtag tccacgccgt aaacgatgaa tactaggtgt cgggtggcaa agccattcgg      840
tgccgcagca aacgcaataa gtattccacc tggggagtac gttcgcaaga atgaaactca      900
aaggaattga cggggacccg cacaagcggt ggagcatgtg gtttaattcg aagcaacgcg      960 aagaaccta ccaagtcttg acatccctct gaccggcccg taacgggcc ttcccttcgg      1020 ggcagaggag acaggtggtg catggttgtc gtcagctcgt gtcgtgagat gttgggttaa     1080
gtcccgcaac gagcgcaacc cctatcctta gtagccagca ggtgaagctg ggcactctag     1140
ggagactgcc ggggataacc cggaggaagg cggggacgac gtcaaatcat catgccctt      1200 atgatttggg ctacacacgt gctacaatgg cgtaaacaaa gggaagcgag acagcgatgt     1260
tgagcaaatc ccaaaaataa cgtcccagtt cggactgcag tctgcaactc gactgcacga     1320
agctggaatc gctagtaatc gcgaatcaga atgtcgcggt gaatacgttc ccgggtcttg     1380
tacacaccgc ccgtcacacc atgggagtca gtaacgcccg aagtcagtga cccaacctta     1440
caggagggag ctgccgaagg cgggaccgat aactggggtg aagtcgtaac aaggtagccg     1500
tatcggaagg tgcggctgga tcacctcctt t                                    1531
```

<210> SEQ ID NO 34
<211> LENGTH: 1451
<212> TYPE: DNA
<213> ORGANISM: E. coli
<220> FEATURE:
<221> NAME/KEY: misc_feature
<222> LOCATION: (490)..(491)
<223> OTHER INFORMATION: n is a, c, g, or t
<220> FEATURE:
<221> NAME/KEY: misc_feature
<222> LOCATION: (566)..(566)
<223> OTHER INFORMATION: n is a, c, g, or t
<220> FEATURE:
<221> NAME/KEY: misc_feature
<222> LOCATION: (570)..(570)
<223> OTHER INFORMATION: n is a, c, g, or t
<220> FEATURE:
<221> NAME/KEY: misc_feature
<222> LOCATION: (851)..(852)

<223> OTHER INFORMATION: n is a, c, g, or t

<400> SEQUENCE: 34

```
agtttgatca tggctcagat tgaacgctgg cggcaggcct aacacatgca agtcgaacgg      60
taacaggaac gagcttgctg ctttgctgac gagtggcgga cgggtgagta atgtctggga     120
aactgcctga tggaggggga taactactgg aaacggtagc taataccgca taacgtcgca     180
agaccaaaga gggggacctt cgggcctctt gccatcggat gtgcccagat gggattagct     240
agtaggtggg gtaaaggctc acctaggcga cgatccctag ctggtctgag aggatgacca     300
gccacactgg aactgagaca cggtccagac tcctacggga ggcagcagtg gggaatattg     360
cacaatgggc gcaagcctga tgcagccatg ccgcgtgtat gaagaaggcc ttcgggttgt     420
aaagtacttt cagcggggag aagggagta aagttaatac ctttgctcat tgacgttacc     480
gcagaagaan naccggctaa ctccgtgcca gcagccgcgg taatacgag ggtgcaagcg     540
ttaatcggaa ttactgggcg taaagngcan gcaggcggtt tgttaagtca gatgtgaaat     600
ccccgggctc aacctgggaa ctgcatctga tactggcaag cttgagtctc gtagaggggg     660
gtagaattcc aggtgtagcg gtgaaatgcg tagagatctg gaggaatacc ggtggcgaag     720
gcggccccct ggacgaagac tgacgctcag gtgcgaaagc gtggggagca acaggatta     780
gatacctgg tagtccacgc cgtaaacgat gtcgacttgg aggttgtgcc cttgaggcgt     840
ggcttccgga nntaacgcgt taagtcgacc gcctggggag tacggccgca aggttaaaac     900
tcaaatgaat tgacggggc cgcacaagcg gtggagcatg tggtttaatt cgatgcaacg     960
cgaagaacct tacctggtct tgacatccac ggaagttttc agagatgaga atgtgccttc    1020
gggaaccgtg agacaggtgc tgcatggctg tcgtcagctc gtgttgtgaa atgttgggtt    1080
aagtcccgca acgagcgcaa cccttatcct ttgttgccag cggtccggcc gggaactcaa    1140
aggagactgc cagtgataaa ctggaggaag gtggggatga cgtcaagtca tcatggccct    1200
tacgaccagg gctacacacg tgctacaatg gcgcatacaa agagaagcga cctcgcgaga    1260
gcaagcggac ctcataaagt gcgtcgtagt ccggattgga gtctgcaact cgactccatg    1320
aagtcggaat cgctagtaat cgtggatcag aatgccacgg tgaatacgtt cccgggcctt    1380
gtacacaccg cccgtcacac catgggagtg ggttgcaaaa gaagtaggta gcttaacctt    1440
cgggagggcg c                                                         1451
```

<210> SEQ ID NO 35
<211> LENGTH: 792
<212> TYPE: DNA
<213> ORGANISM: Lactococcus lactis
<220> FEATURE:
<221> NAME/KEY: misc_feature
<222> LOCATION: (1)..(2)
<223> OTHER INFORMATION: n is a, c, g, or t

<400> SEQUENCE: 35

```
nnaatttttg ttgtgctcat acgtgcagtt gagcgctcga aggttggtac ttgtaccctc      60
tggatgagca gcgaacgggt gagtaacgcg tggggaatct gcctttgagc gggggaccac     120
atttggaaac gaatgcgaat accgcataaa aactttaaac acaagttta agtttgaaag     180
atgcaattgc atcactccaa gatgatcccg cgttgtatta gctagttggt gagggaaagg     240
ctccccacgg cgatcataca tatccgacct gagagggtga ccggccacat tgggactgag     300
ccatgatcaa actctgaaaa agaggcagca gtagggaatc ttcggcaatg gacgaaagtc     360
tgaccgagca acgccgcgtg agtgaagaag gttttcggat cgtaaaactc tgttggtaga     420
```

```
gaagaacgtt ggtgagagtg gaaagctcat caagtgacgg taactaccca gaaagggacg      480
gctaactacg tgccagcagc cgcggtaata cgtaggtccc gagcgttgtc cggatttatt      540
gggcgtaaag cgagcgcagg tggtttatta agtctggtgt aaaaggcagt ggctcaacca      600
ttgtatgcat tggaaactgg tagacttgag tgcaggagag gagagtggaa ttccatgtgt      660
agcgggtgaa atgcgtagat atatggtagg aacaccgggt ggcgaaagcg gctctctggc      720
ctgtaactga cactgaggct cgaaaagcgt ggggagcaaa aaggattaga taccctggta      780
gtccacgccg ta                                                          792
```

<210> SEQ ID NO 36
<211> LENGTH: 991
<212> TYPE: DNA
<213> ORGANISM: Lactobacillus ruminis
<220> FEATURE:
<221> NAME/KEY: misc_feature
<222> LOCATION: (1)..(1)
<223> OTHER INFORMATION: n is a, c, g, or t

<400> SEQUENCE: 36

```
nactctgtca ccttaggcgg ctggctccaa aaggttaccc caccgacttt gggtgttaca       60
aactctcatg gtgtgacggg cggtgtgtac aaggcccggg aacgtattca ccgcgacatg      120
ctgattcgcg attactagcg attccgactt catgcaggcg agttgcagcc tgcaatccga      180
actgagaacg gctttaagag attagcttgc cctcgcgagt tagcgactcg ttgtaccgtc      240
cattgtagca cgtgtgtagc ccaggtcata aggggcatga tgatttgacg tcatccccac      300
cttcctccgg tttgtcaccg gcagtctcgc cagagtgccc aacttaatga tggcaactga      360
caataagggt tgcgctcgtt gcgggactta acccaacatc tcacgacacg agctgacgac      420
aaccatgcac cacctgtcat tctgtccccg aagggaacgt tccatctctg gaattgtcag      480
aagatgtcaa gacctggtaa ggttcttcgc gttgcttcga attaaaccac atgctccacc      540
gcttgtgcgg gccccgtca attcctttga gtttcagtct tgcgaccgta ctccccaggc      600
ggagtgctta atgcgttagc tgcagcactg aagggcggaa accctccaac acttagcact      660
catcgtttac ggcgtggact accagggtat ctaatcctgt ttgctaccca cgctttcgaa      720
cctcagcgtc agttacagac cagagagccg cttttcgccac tggtgttctt ccatatatct      780
acgcatttca ccgctacaca tggagttcca ctctcctctt ctgcactcaa gtcttccagt      840
ttccaatgca ctacttcggt taagccgaag gctttcacat cagacttaaa agaccgcctg      900
cgttcccttt acgcccataa atccggacac gctcgccacc tacgtattac cgcggctgct      960
ggcacgtagt tagccgtggc tttctggtag a                                     991
```

<210> SEQ ID NO 37
<211> LENGTH: 1559
<212> TYPE: DNA
<213> ORGANISM: Lactobacillus ruminis

<400> SEQUENCE: 37

```
attgagagtt tgatcctggc tcaggacgaa cgctggcggc gtgcctaata catgcaagtc       60
gaacgaagct ttctttcacc gaatgcttgc attcaccgaa agaagcttag tggcgaacgg      120
gtgagtaaca cgtaggcaac ctgcccaaaa gaggggggata acacttggaa acaggtgcta      180
ataccgcata accatgaaca ccgcatgatg ttcatgtaaa agacggcttt tgctgtcact      240
tttggatggg cctgcggcgt attaacttgt tggtggggta acggcctacc aaggtgatga      300
```

```
tacgtagccg aactgagagg ttgatcggcc acattgggac tgagacacgg cccaaactcc    360
tacgggaggc agcagtaggg aatcttccac aatggacgaa agtctgatgg agcaacgccg    420
cgtgaatgaa gaaggccttc gggtcgtaaa attctgttgt cagagaagaa cgtgcgtgag    480
agtaactgtt cacgtattga cggtatctga ccagaaagcc acggctaact acgtgccagc    540
agccgcggta atacgtaggt ggcgagcgtt gtccggattt attgggcgta aagggaacgc    600
aggcggtctt ttaagtctga tgtgaaagcc ttcggcttaa ccgaagtagt gcattggaaa    660
ctggaagact tgagtgcaga agaggagagt ggaactccat gtgtagcggt gaaatgcgta    720
gatatatgga agaacaccag tggcgaaagc ggctctctgg tctgtaactg acgctgaggt    780
tcgaaagcgt gggtagcaaa caggattaga taccctggta gtccacgccg taaacgatga    840
gtgctaagtg tttggagggtt tccgcccttc agtgctgcag ctaacgcatt aagcactccg    900
cctggggagt acggtcgcaa gactgaaact caaaggaatt gacggggcc cgcacaagcg    960
gtggagcatg tggtttaatt cgaagcaacg cgaagaacct taccaggtct tgacatcttc   1020
tgacaattcc agagatggaa cgttcccttc ggggacagaa tgacaggtgg tgcatggttg   1080
tcgtcagctc gtgtcgtgag atgttgggtt aagtcccgca acgagcgcaa cccttattgt   1140
cagttgccat cattaagttg ggcactctgg cgagactgcc ggtgacaaac cggaggaagg   1200
tggggatgac gtcaaatcat catgcccctt atgacctggg ctacacacgt gctacaatgg   1260
acggtacaac gagtcgctaa ctcgcgaggg caagctaatc tcttaaagcc gttctcagtt   1320
cggattgcag gctgcaactc gcctgcatga agtcggaatc gctagtaatc gcgaatcagc   1380
atgtcgcggt gaatacgttc ccgggccttg tacacaccgc ccgtcacacc atgagagttt   1440
gtaacaccca agtcggtgg ggtaacctttt ggagccagc cgcctaaggt gggacagatg   1500
attggggtga agtcgtaaca aggtagccgt aggagaacct gcggctggat cacctccctt   1559

<210> SEQ ID NO 38
<211> LENGTH: 1561
<212> TYPE: DNA
<213> ORGANISM: Lactobacillus animalis

<400> SEQUENCE: 38
attgagagtt tgatcctggc tcaggatgaa cgctggcggc gtgcctaata catgcaagtc     60
gaacgaaact tctttatcac cgagtgcttg cactcaccga taaagagttg agtggcgaac    120
gggtgagtaa cacgtgggca acctgcccaa agagggggga taacacttgg aaacaggtgc    180
taataccgca taaccatagt taccgcatgg taactatgta aaaggtggct atgctaccgc    240
ttttggatgg gcccgcggcg cattagctag ttggtgaggt aaaggcttac caaggcaatg    300
atgcgtagcc gaactgagag gttgatcggc cacattggga ctgagacacg gcccaaactc    360
ctacgggagg cagcagtagg gaatcttcca caatgggcga aagcctgatg gagcaacgcc    420
gcgtgggtga agaaggtctt cggatcgtaa aaccctgttg ttagagaaga agtgcgtga    480
gagtaactgt tcacgttttcg acggtatcta accagaaagc cacggctaac tacgtgccag    540
cagccgcggt aatacgtagg tggcaagcgt tatccggatt tattgggcgt aaagggaacg    600
caggcggtct tttaagtctg atgtgaaagc cttcggctta accggagtag tgcattggaa    660
actgggagac ttgagtgcag aagaggagag tggaactcca tgtgtagcgg tgaaatgcgt    720
agatatatgg aagaacacca gtggcgaaag cggctctctg gtctgtaact gacgctgagg    780
ttcgaaagcg tgggtagcaa acaggattag ataccctggt agtccacgcc gtaaacgatg    840
aatgctaagt gttggagggt ttccgccctt cagtgctgca gctaacgcaa taagcattcc    900
```

```
gcctggggag tacgaccgca aggttgaaac tcaaaggaat tgacgggggc ccgcacaagc    960
ggtggagcat gtggtttaat tcgaagcaac gcgaagaacc ttaccaggtc ttgacatctt   1020
ctgacaatcc tagagatagg actttcccttt cggggacaga atgacaggtg gtgcatggtt   1080
```
(Note: line 1080 should match original)

```
gcctggggag tacgaccgca aggttgaaac tcaaaggaat tgacgggggc ccgcacaagc    960
ggtggagcat gtggtttaat tcgaagcaac gcgaagaacc ttaccaggtc ttgacatctt   1020
ctgacaatcc tagagatagg actttcccct tcggggacaga atgacaggtg gtgcatggtt   1080
gtcgtcagct cgtgtcgtga gatgttgggt taagtcccgc aacgagcgca acccttattg   1140
ttagttgcca gcattaagtt gggcactcta gcaagactgc cggtgacaaa ccggaggaag   1200
gtggggatga cgtcaaatca tcatgcccct tatgacctgg gctacacacg tgctacaatg   1260
gacggtacaa cgagtcgcaa gaccgcgagg tttagcaaat ctcttaaagc cgttctcagt   1320
tcggattgta ggctgcaact cgcctacatg aagtcggaat cgctagtaat cgcggatcag   1380
catgccgcgg tgaatacgtt cccgggcctt gtacacaccg cccgtcacac catgagagtt   1440
tgtaacaccc aaagccggtg gggtaacctt ttggagccag ccgtctaagg tgggacagat   1500
gattggggtg aagtcgtaac aaggtagccg taggagaacc tgcggctgga tcacctcctt   1560
t                                                                   1561

<210> SEQ ID NO 39
<211> LENGTH: 906
<212> TYPE: DNA
<213> ORGANISM: Lactobacillus rhamnosus
<220> FEATURE:
<221> NAME/KEY: misc_feature
<222> LOCATION: (1)..(2)
<223> OTHER INFORMATION: n is a, c, g, or t

<400> SEQUENCE: 39
nnctctgttt tgcgtgtgat gcagtcgacg agttctgatt attgaaaggt gcttgcatct     60
tgatttaatt ttgaacgagt ggcggacggg tgagtaacac gtgggtaacc tgcccttaag    120
tggggggataa catttggaaa cagatgctaa taccgcataa atccaagaac cgcatggttc    180
ttggctgaaa gatggcgtaa gctatcgctt ttggatggac ccgcggcgta ttagctagtt    240
ggtgaggtaa cggctcacca aggcaatgat acgtagccga actgagaggt tgatcggcca    300
cattgggact gagacacggc ccaaactcct acgggaggca gcagtaggga atcttccaca    360
atggacgcaa gtctgatgga gcaacgccgc gtgagtgaag aaggctttcg ggtcgtaaaa    420
ctctgttgtt ggagaagaat ggtcggcaga gtaactgttg tcggcgtgac ggtatccaac    480
cagaaagcca cggctaacta cgtgccagca gccgcggtaa tacgtaggtg gcaagcgtta    540
tccggattta tgggcgtaaa gcgagcgcag gcggttttt taagtctgat gtgaaagccc    600
tcggcttaac cgaggaagtg catcggaaac tgggaaactt gagtgcagaa gaggacagtg    660
gaactccatg tgtagcggtg aaatgcgtag atatatggaa gaacaccagt ggcgaggcgg    720
ctgtctggtc tgtaactgac gctgaggctc gaaagcatgg gtagcgaaca ggattagata    780
ccctggtagt ccatgccgta aacgatgaat gctaggtgtt ggagggtttc cgcccttcag    840
tgccgcgctt acgcatttag cattcgcctg gggagtacga ccgcaggttg aacctcaaag    900
gaattg                                                               906

<210> SEQ ID NO 40
<211> LENGTH: 1207
<212> TYPE: DNA
<213> ORGANISM: Lactobacillus rhamnosus
<220> FEATURE:
<221> NAME/KEY: misc_feature
<222> LOCATION: (4)..(5)
<223> OTHER INFORMATION: n is a, c, g, or t
<220> FEATURE:
```

```
<221> NAME/KEY: misc_feature
<222> LOCATION: (1180)..(1180)
<223> OTHER INFORMATION: n is a, c, g, or t
<220> FEATURE:
<221> NAME/KEY: misc_feature
<222> LOCATION: (1197)..(1198)
<223> OTHER INFORMATION: n is a, c, g, or t

<400> SEQUENCE: 40
cccnnttgtg tcctatactg cagtctacag tctgaatatt gaaggtgctt gcatcttgat      60
ttaattttga acgagtggcg gacgggtgag taacacgtgg gtaacctgcc cttaagtggg     120
ggataacatt tggaaacaga tgctaatacc gcataaatcc aagaaccgca tggttcttgg     180
ctgaaagatg gcgtaagcta tcgcttttgg atggacccgc ggcgtattag ctagttggtg     240
aggtaacggc tcaccaaggc aatgatacgt agccgaactg agaggttgat cggccacatt     300
gggactgaga cacggcccaa actcctacgg gaggcagcag tagggaatct tccacaatgg     360
acgcaagtct gatggagcaa cgccgcgtga gtgaagaagg ctttcgggtc gtaaaactct     420
gttgttggag aagaatggtc ggcagagtaa ctgttgtcgg cgtgacggta tccaaccaga     480
aagccacggc taactacgtg ccagcagccg cggtaatacg taggtggcaa gcgttatccg     540
gatttattgg gcgtaaagcg agcgcaggcg gttttttaag tctgatgtga aagccctcgg     600
cttaaccgag gaagtgcatc ggaaactggg aaacttgagt gcagaagagg acagtggaac     660
tccatgtgta gcggtgaaat gcgtagatat atggaagaac accagtggcg aaggcggctg     720
tctggtctgt aactgacgct gaggctcgaa agcatgggta gcgaacagga ttagataccc     780
tggtagtcca tgccgtaaac gatgaatgct aggtgttgga gggtttccgc ccttcagtgc     840
cgcagctaac gcattaagca ttccgcctgg gggagtacga ccgcaaggtt gaactcaaag     900
gaattgacgg ggcccgcaca agcggggag catgtggttt aattcgaagc aacgcgagga     960
ccttaccagg tcttgacatc ttttgatcac ctgagagatc aggtttcccc ttcggggcaa    1020
atgacagtgt gcatggttg tcgtcagctc cgtgtctgag atgttgggta agtccgcaac    1080
aagcgcaacc cttatgacta gttgcagctt agtgggcact cctagtagac tgccggtgac    1140
aaccggagga agggtgggga tgactcaatc actagccctn ggacctgggc tacaacnngt    1200
cctcatg                                                              1207

<210> SEQ ID NO 41
<211> LENGTH: 1062
<212> TYPE: DNA
<213> ORGANISM: Lactobacillus rhamnosus
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (1046)..(1046)
<223> OTHER INFORMATION: n is a, c, g, or t

<400> SEQUENCE: 41
gntctggttt gttttgttgg ggggtgaaat ctagtattga ggtgcttgca tcttggttta      60
attgtggagg agtggcggac gggtgagtaa cacgtgggta acctgccctt aagtggggga     120
taacatttgg aaacagatgc taataccgca taaatccaag aaccgcatgg ttcttggctg     180
aaagatggcg taagctatcg cttttggatg gacccgcggc gtattagcta gttggtgagg     240
taacggctca ccaaggcaat gatacgtagc cgaactgaga ggttgatcgg ccacattggg     300
actgagacac ggcccaaact cctacgggag gcagcagtag ggaatcttcc acaatggacg     360
```

```
caagtctgat ggagcaacgc cgcgtgagtg aagaaggctt tcgggtcgta aaactctgtt      420
gttggagaag aatggtcggc agagtaactg ttgtcggcgt gacggtatcc aaccagaaag      480
ccacggctaa ctacgtgcca gcagccgcgg taatacgtag gtggcaagcg ttatccggat      540
ttattgggcg taaagcgagc gcaggcggtt ttttaagtct gatgtgaaag ccctcggctt      600
aaccgaggaa gtgcatcgga aactgggaaa cttgagtgca gaagaggaca gtggaactcc      660
atgtgtagcg gtgaaatgcg tagatatatg gaagaacacc agtggcgaag gcggctgtct      720
ggtctgtaac tgacgctgag gctcgaaagc atgggtagcg aacaggatta gataccctgg      780
tagtccatgc cgtaaacgat gaatgctagg tgttggaggg tttccgccct tcagtgccgc      840
agctaacgca ttaagcatcc gcctgggag tacgaccgca aggttaaaac tcaaaggaat      900
tgacggggcc cgcacagcgt ggagcatgtg gtttaattcg aagcaacgcg agaaccttac      960
caggtctgac atctttgatc actgagagat caggtttccc ttcgggcaaa tgacagtggt     1020
gcatggttgt cgtcagctcg tgtctngaga tgttgggtta at                        1062

<210> SEQ ID NO 42
<211> LENGTH: 1474
<212> TYPE: DNA
<213> ORGANISM: Bacteroides caccae

<400> SEQUENCE: 42
tggctcagga tgaacgctag ctacaggctt aacacatgca agtcgagggg catcagtttg       60
gtttgcttgc aaaccaaagc tggcgaccgg cgcacgggtg agtaacacgt atccaacctg      120
cctcatactc ggggatagcc tttcgaaaga aagattaata tccgatagca tatatttccc      180
gcatgggttt tatattaaag aaattcggta tgagatgggg atgcgttcca ttagtttgtt      240
gggggggtaa cggcccacca agactacgat ggataggggt tctgagagga aggtccccca      300
cattggaact gagacacggt ccaaactcct acgggaggca gcagtgagga atattggtca      360
atggacgcga gtctgaacca gccaagtagc gtgaaggatg actgccctat ggggttgtaaa      420 cttcttttat atgggaataa agttgtccac gtgtggattt ttgtatgtac catatgaata      480
aggatcggct aactccgtgc cagcagccgc ggtaatacga aggatccgag cgttatccgg      540
atttattggg tttaaaggga gcgtaggcgg attgttaagt cagttgtgaa agtttgcggc      600
tcaaccgtaa aattgcagtt gatactggca gtcttgagtg cagtagaggt gggcggaatt      660
cgtggtgtag cggtgaaatg cttagatatc acgaagaact ccgattgcga aggcagccac      720
tggagtgtaa ctgacgctga tgctcgaaag tgtgggtatc aaacaggatt agataccctg      780
gtagtccaca cagtaaacga tgaatactcg ctgtttgcga tatacagtaa gcggccaagc      840
gaaagcatta agtattccac ctggggagta cgccggcaac ggtgaaactc aaaggaattg      900 acggggccc gcacaagcgg aggaacatgt ggtttaattc gatgatacgc gaggaacctt      960
acccgggctt aaaattgcaaa tgaattatgg ggaaacccat aggccgcaag gcatttgtga     1020
aggtgctgca tggttgtcgt cagctcgtgc cgtgaggtgt cggcttaagt gccataacga     1080
gcgcaaccct tatcttcagt tactaacagg tcatgctgag gactctggag agactgccgt     1140
cgtaagatgt gaggaaggtg gggatgacgt caaatcagca cggcccttac gtccggggct     1200
acacacgtgt tacaatgggg ggtacagaag gccgctacct ggtgacagga tgccaatccc     1260
aaaaacctct ctcagttcgg atcgaagtct gcaaccgac ttcgtgaagc tggattcgct     1320
agtaatcgcg catcagccat ggcgcggtga atacgttccc gggccttgta cacaccgccc     1380
```

| | |
|---|---|
| gtcaagccat gaaagccggg ggtacctgaa gtacgtaacc gcaaggagcg tcctagggta | 1440 |
| aaactggtaa ttggggctaa gtcgtaacaa ggta | 1474 |

<210> SEQ ID NO 43
<211> LENGTH: 1473
<212> TYPE: DNA
<213> ORGANISM: Bacteroides cellulosilyticus

<400> SEQUENCE: 43

| | |
|---|---|
| agagtttgat cctggctcag gatgaacgct agctacaggc ttaacacatg caagtcgagg | 60 |
| ggcagcatga cctagcaata ggttgatggc gaccggcgca cgggtgagta acacgtatcc | 120 |
| aacctaccgg ttattccggg atagcctttc gaaagaaaga ttaataccgg atagtataac | 180 |
| gagaaggcat cttttgtta ttaaagaatt tcgataaccg atggggatgc gttccattag | 240 |
| tttgttggcg gggtaacggc ccaccaagac atcgatggat aggggttctg agaggaaggt | 300 |
| cccccacatt ggaactgaga cacggtccaa actcctacgg gaggcagcag tgaggaatat | 360 |
| tggtcaatgg acgagagtct gaaccagcca agtagcgtga aggatgactg ccctatgggt | 420 |
| tgtaaacttc ttttatatgg gaataaagtg agccacgtgt ggcttttgt atgtaccata | 480 |
| cgaataagga tcggctaact ccgtgccagc agccgcggta atacggagga tccgagcgtt | 540 |
| atccggattt attgggttta aagggagcgt aggcggacta ttaagtcagc tgtgaaagtt | 600 |
| tgcggctcaa ccgtaaaatt gcagttgata ctggtcgtct tgagtgcagt agaggtaggc | 660 |
| ggaattcgtg gtgtagcggt gaaatgctta gatatcacga gaactccga ttgcgaaggc | 720 |
| agcttactgg actgtaactg acgctgatgc tcgaaagtgt gggtatcaaa caggattaga | 780 |
| taccctggta gtccacacag taaacgatga atactcgctg tttgcgatat acggcaagcg | 840 |
| gccaagcgaa agcattaagt attccacctg gggagtacgc cggcaacggt gaaactcaaa | 900 |
| ggaattgacg ggggcccgca caagcggagg aacatgtggt ttaattcgat gatacgcgag | 960 |
| gaaccttacc cgggcttaaa ttgcaaatga atatagtgga acattatag ccgcaaggca | 1020 |
| tttgtgaagg tgctgcatgg ttgtcgtcag ctcgtgccgt gaggtgtcgg cttaagtgcc | 1080 |
| ataacgagcg caacccttat ctttagttac taacaggtca tgctgaggac tctagagaga | 1140 |
| ctgccgtcgt aagatgtgag gaaggtgggg atgacgtcaa atcagcacgg cccttacgtc | 1200 |
| cggggctaca cacgtgttac aatgggggt acagaaggca gctacacagc gatgtgatgc | 1260 |
| taatcccaaa agcctctctc agttcggatt ggagtctgca acccgactcc atgaagctgg | 1320 |
| attcgctagt aatcgcgcat cagccacggc gcggtgaata cgttcccggg ccttgtacac | 1380 |
| accgcccgtc aagccatgaa agccgggggt acctgaagtc cgtaaccgta aggagcggcc | 1440 |
| tagggtaaaa ctggtaattg gggctaagtc gta | 1473 |

<210> SEQ ID NO 44
<211> LENGTH: 1472
<212> TYPE: DNA
<213> ORGANISM: Bacteroides faecis

<400> SEQUENCE: 44

| | |
|---|---|
| ctcaggatga acgctagcta caggcttaac acatgcaagt cgaggggcag catttcagtt | 60 |
| tgcttgcaaa ctggagatgg cgaccggcgc acgggtgagt aacacgtatc caacctgccg | 120 |
| ataactcggg gatagccttt cgaaagaaag attaataccc gatggcataa tagaaccgca | 180 |
| tggttttttt attaaagaat ttcggttatc gatggggatg cgttccatta ggcagttggt | 240 |
| gaggtaacgg ctcaccaaac cttcgatgga taggggttct gagaggaagg tccccccacat | 300 |

```
tggaactgag acacggtcca aactcctacg ggaggcagca gtgaggaata ttggtcaatg    360
gacgagagtc tgaaccagcc aagtagcgtg aaggatgact gccctatggg ttgtaaactt    420
cttttatatg ggataaaagt tttccacgtg tggaattttg tatgtaccat atgaataagg    480
atcggctaac tccgtgccag cagccgcggt aatacgagg atccgagcgt tatccggatt    540
tattgggttt aaagggagcg taggtggaca gttaagtcag ttgtgaaagt ttgcggctca    600
accgtaaaat tgcagttgat actggctgtc ttgagtacag tagaggtggg cggaattcgt    660
ggtgtagcgg tgaaatgctt agatatcacg aagaactccg attgcgaagg cagctcactg    720
gactgcaact gacactgatg ctcgaaagtg tgggtatcaa acaggattag ataccctggt    780
agtccacaca gtaaacgatg aatactcgct gtttgcgata tacagtaagc ggccaagcga    840
aagcattaag tattccacct ggggagtacg ccggcaacgg tgaaactcaa aggaattgac    900
gggggcccgc acaagcggag gaacatgtgg tttaattcga tgatacgcga ggaaccttac    960
ccgggcttaa attgcatttg aatatattgg aaacagtata gtcgtaagac aaatgtgaag   1020
gtgctgcatg gttgtcgtca gctcgtgccg tgaggtgtcg gcttaagtgc cataacgagc   1080 gcaacccta tctttagtta ctaacaggtc atgctgagga ctctagagag actgccgtcg   1140
taagatgtga ggaaggtggg gatgacgtca aatcagcacg cccttacgt ccggggctac   1200 acacgtgtta caatgggggg tacagaaggc agctacctgg tgacaggatg ctaatcccaa   1260
aagcctctct cagttcggat cgaagtctgc aacccgactt cgtgaagctg gattcgctag   1320
taatcgcgca tcagccatgg cgcggtgaat acgttcccgg gccttgtaca caccgcccgt   1380
caagccatga aagccggggg tacctgaagt acgtaaccgc aaggagcgtc ctagggtaaa   1440
actggtaatt ggggctaagt cgtaacaagg ta                                1472

<210> SEQ ID NO 45
<211> LENGTH: 929
<212> TYPE: DNA
<213> ORGANISM: Bacteroides ovatus
<220> FEATURE:
<221> NAME/KEY: misc_feature
<222> LOCATION: (583)..(583)
<223> OTHER INFORMATION: k is g or t
<220> FEATURE:
<221> NAME/KEY: misc_feature
<222> LOCATION: (704)..(704)
<223> OTHER INFORMATION: s is g or c

<400> SEQUENCE: 45
cgatatccgg atttattgga gtttaaggga gcgtaggtgg attgttaagt cagttgtgaa     60
agtttgcggc tcaaccgtaa aattgcagtt gaaactggca gtcttgagta cagtagaggt    120
gggcggaatt cgtggtgtag cggtgaaatg cttagatatc acgaagaact ccgattgcga    180
aggcagctca ctagactgtc actgacactg atgctcgaaa gtgtgggtat caaacaggat    240
tagataccct ggtagtccac acagtaaacg atgaatactc gctgtttgcg atatacagta    300
agcggccaag cgaaagcatt aagtattcca cctggggagt acgccggcaa cggtgaaact    360
caaaggaatt gacggggggcc cgcacaagcg gaggaacatg tggtttaatt cgatgatacg    420
cgaggaacct tacccgggct aaattgcaa cagaatatat tggaaacagt atagccgtaa    480
ggctgttgtg aaggtgctgc atggttgtcg tcagctcgtg ccgtgaggtg tcggcttaag    540
tgccataacg agcgcaaccc ttatctttag ttactaacag gtkatgctga ggactctaga    600
gagactgccg tcgtaagatg tgaggaaggt ggggatgacg tcaaatcagc acggccctta    660
```

```
cgtccggggc tacacacgtg ttacaatggg gggtacagaa ggcsgctacc tggtgacagg    720
atgctaatcc caaaaacctc tctcagttcg gatcgaagtc tgcaacccga cttcgtgaag    780
ctggattcgc tagtaatcgc gcatcagcca tggcgcggtg aatacgttcc cgggccttgt    840
acacaccgcc cgtcaagcca tgaaagccgg gggtacctga agtacgtaac cgcaaggagc    900
gtcctagggg taaaactggt aattggggc                                      929
```

```
<210> SEQ ID NO 46
<211> LENGTH: 873
<212> TYPE: DNA
<213> ORGANISM: Bacteroides thetaiotaomicron
<220> FEATURE:
<221> NAME/KEY: misc_feature
<222> LOCATION: (287)..(287)
<223> OTHER INFORMATION: w is a or t
<220> FEATURE:
<221> NAME/KEY: misc_feature
<222> LOCATION: (429)..(430)
<223> OTHER INFORMATION: w is a or t
<220> FEATURE:
<221> NAME/KEY: misc_feature
<222> LOCATION: (437)..(438)
<223> OTHER INFORMATION: w is a or t
<220> FEATURE:
<221> NAME/KEY: misc_feature
<222> LOCATION: (439)..(439)
<223> OTHER INFORMATION: y is c or t
<220> FEATURE:
<221> NAME/KEY: misc_feature
<222> LOCATION: (449)..(449)
<223> OTHER INFORMATION: k is g or t
<220> FEATURE:
<221> NAME/KEY: misc_feature
<222> LOCATION: (450)..(450)
<223> OTHER INFORMATION: w is a or t
<220> FEATURE:
<221> NAME/KEY: misc_feature
<222> LOCATION: (454)..(454)
<223> OTHER INFORMATION: y is c or t
<220> FEATURE:
<221> NAME/KEY: misc_feature
<222> LOCATION: (457)..(457)
<223> OTHER INFORMATION: y is c or t
<220> FEATURE:
<221> NAME/KEY: misc_feature
<222> LOCATION: (461)..(461)
<223> OTHER INFORMATION: r is a or g
<220> FEATURE:
<221> NAME/KEY: misc_feature
<222> LOCATION: (464)..(465)
<223> OTHER INFORMATION: w is a or t

<400> SEQUENCE: 46
tttaagggag cgtaggtgga cagttaagtc agttgtgaaa gtttgcggct caaccgtaaa     60
attgcagttg atactggctg tcttgagtac agtagaggtg ggcggaattc gtggtgtagc    120
ggtgaaatgc ttagatatca cgaagaactc cgattgcgaa ggcagctcac tggactgcaa    180
ctgacactga tgctcgaaag tgtgggtatc aaacaggatt agataccctg gtagtccaca    240
cagtaaacga tgaatactcg ctgtttgcga tatacagtaa gcggccwagc gaaagcatta    300
agtattccac ctggggagta cgccggcaac ggtgaaactc aaaggaattg acggggcccc    360
gcacaagcgg aggaacatgt ggtttaattc gatgatacgc gaggaacctt acccgggctt    420
aaattgcaww tgaatawwyt ggaaacagkw tagycgyaag rcawtgtga aggtgctgca    480 tggttgtcgt cagctcgtgc cgtgaggtgt cggcttaagt gccataacga gcgcaaccct    540
tatctttagt tactaacagg tcatgctgag gactctagag agactgccgt cgtaagatgt    600
gaggaaggtg gggatgacgt caaatcagca cggcccttac gtccggggct acacacgtgt    660
```

| | |
|---|---|
| tacaatgggg ggtacagaag gcagctacct ggtgacagga tgctaatccc aaaagcctct | 720 |
| ctcagttcgg atcgaagtct gcaacccgac ttcgtgaagc tggattcgct agtaatcgcg | 780 |
| catcagccat ggcgcggtga atacgttccc gggccttgta cacaccgccc gtcaagccat | 840 |
| gaaagccggg ggtacctgaa gtacgtaacc gca | 873 |

<210> SEQ ID NO 47
<211> LENGTH: 1474
<212> TYPE: DNA
<213> ORGANISM: Bacteroides uniformis

<400> SEQUENCE: 47

| | |
|---|---|
| ctggctcagg atgaacgcta gctacaggct taacacatgc aagtcgaggg gcagcatgaa | 60 |
| cttagcttgc taagtttgat ggcgaccggc gcacgggtga gtaacacgta tccaacctgc | 120 |
| cgatgactcg gggatagcct ttcgaaagaa agattaatac ccgatggcat agttcttccg | 180 |
| catggtagaa ctattaaaga atttcggtca tcgatgggga tgcgttccat taggttgttg | 240 |
| gcggggtaac ggcccaccaa gccttcgatg gatagggggtt ctgagaggaa ggtcccccac | 300 |
| attggaactg agacacggtc caaactccta cgggaggcag cagtgaggaa tattggtcaa | 360 |
| tggacgagag tctgaaccag ccaagtagcg tgaaggatga ctgccctatg ggttgtaaac | 420 |
| ttcttttata cggaataaag tgaggcacg tgtgcctttt tgtatgtacc gtatgaataa | 480 |
| ggatcggcta actccgtgcc agcagccgcg gtaatacgga ggatccgagc gttatccgga | 540 |
| tttattgggt ttaaagggag cgtaggcgga cgcttaagtc agttgtgaaa gtttgcggct | 600 |
| caaccgtaaa attgcagttg atactgggtg tcttgagtac agtagaggca ggcggaattc | 660 |
| gtggtgtagc ggtgaaatgc ttagatatca cgaagaactc cgattgcgaa ggcagcttgc | 720 |
| tggactgtaa ctgacgctga tgctcgaaag tgtgggtatc aaacaggatt agataccctg | 780 |
| gtagtccaca cagtaaacga tgaatactcg ctgtttgcga tatacagtaa gcggccaagc | 840 |
| gaaagcgtta agtattccac ctggggagta cgccggcaac ggtgaaactc aaaggaattg | 900 |
| acgggggccc gcacaagcgg aggaacatgt ggtttaattc gatgatacgc gaggaaccct | 960 |
| acccgggctt gaattgcaac tgaatgatgt ggagacatgt cagccgcaag gcagttgtga | 1020 |
| aggtgctgca tggttgtcgt cagctcgtgc cgtgaggtgt cggcttaagt gccataacga | 1080 |
| gcgcaaccct tatcgatagt taccatcagg ttatgctggg gactctgtcg agactgccgt | 1140 |
| cgtaagatgt gaggaaggtg gggatgacgt caaatcagca cggcccttac gtccggggct | 1200 |
| acacacgtgt tacaatgggg ggtacagaag gcagctacac ggcgacgtga tgctaatccc | 1260 |
| taaagcctct ctcagttcgg attggagtct gcaacccgac tccatgaagc tggattcgct | 1320 |
| agtaatcgcg catcagccac ggcgcggtga atacgttccc gggccttgta cacaccgccc | 1380 |
| gtcaagccat gaaagccggg ggtacctgaa gtgcgtaacc gcgaggagcg ccctagggta | 1440 |
| aaactggtga ttggggctaa gtcgtaacaa ggta | 1474 |

<210> SEQ ID NO 48
<211> LENGTH: 1503
<212> TYPE: DNA
<213> ORGANISM: Bacteroides vulgatus

<400> SEQUENCE: 48

| | |
|---|---|
| atgaagagtt tgatcctggc tcaggatgaa cgctagctac aggcttaaca catgcaagtc | 60 |
| gaggggcagc atggtcttag cttgctaagg ccgatggcga ccggcgcacg ggtgagtaac | 120 |

| | |
|---|---|
| acgtatccaa cctgccgtct actcttggac agccttctga aaggaagatt aatacaagat | 180 |
| ggcatcatga gttcacatgt tcacatgatt aaaggtattc cggtagacga tggggatgcg | 240 |
| ttccattaga tagtaggcgg ggtaacggcc cacctagtct tcgatggata ggggttctga | 300 |
| gaggaaggtc ccccacattg gaactgagac acggtccaaa ctcctacggg aggcagcagt | 360 |
| gaggaatatt ggtcaatggg cgagagcctg aaccagccaa gtagcgtgaa ggatgactgc | 420 |
| cctatgggtt gtaaacttct tttataaagg aataaagtcg ggtatgcata cccgtttgca | 480 |
| tgtactttat gaataaggat cggctaactc cgtgccagca gccgcggtaa tacgaggat | 540 |
| ccgagcgtta tccggattta ttgggtttaa agggagcgta gatggatgtt taagtcagtt | 600 |
| gtgaaagttt gcggctcaac cgtaaaattg cagttgatac tggatatctt gagtgcagtt | 660 |
| gaggcaggcg gaattcgtgg tgtagcggtg aaatgcttag atatcacgaa gaactccgat | 720 |
| tgcgaaggca gcctgctaag ctgcaactga cattgaggct cgaaagtgtg ggtatcaaac | 780 |
| aggattagat accctggtag tccacacggt aaacgatgaa tactcgctgt ttgcgatata | 840 |
| cggcaagcgg ccaagcgaaa gcgttaagta ttccacctgg ggagtacgcc ggcaacggtg | 900 |
| aaactcaaag gaattgacgg gggcccgcac aagcggagga acatgtggtt taattcgatg | 960 |
| atacgcgagg aaccttaccc gggcttaaat tgcagatgaa ttacggtgaa agccgtaagc | 1020 |
| cgcaaggcat ctgtgaaggt gctgcatggt tgtcgtcagc tcgtgccgtg aggtgtcggc | 1080 |
| ttaagtgcca taacgagcgc aaccttgtt gtcagttact aacaggttcc gctgaggact | 1140 |
| ctgacaagac tgccatcgta agatgtgagg aaggtgggga tgacgtcaaa tcagcacggc | 1200 |
| ccttacgtcc ggggctacac acgtgttaca atggggggta cagagggccg ctaccacgcg | 1260 |
| agtggatgcc aatcccaaaa acctctctca gttcggactg gagtctgcaa cccgactcca | 1320 |
| cgaagctgga ttcgctagta atcgcgcatc agccacggcg cggtgaatac gttcccgggc | 1380 |
| cttgtacaca ccgcccgtca agccatggga gccggggta cctgaagtgc gtaaccgcga | 1440 |
| ggagcgccct agggtaaaac tggtgactgg ggctaagtcg taacaaggta gccgtaccgg | 1500 |
| aag | 1503 |

<210> SEQ ID NO 49
<211> LENGTH: 887
<212> TYPE: DNA
<213> ORGANISM: Bifidobacterium adolescentis
<220> FEATURE:
<221> NAME/KEY: misc_feature
<222> LOCATION: (11)..(11)
<223> OTHER INFORMATION: k is g or t
<220> FEATURE:
<221> NAME/KEY: misc_feature
<222> LOCATION: (40)..(40)
<223> OTHER INFORMATION: y is c or t

<400> SEQUENCE: 49

| | |
|---|---|
| gggctcgtag kcggttcgtc gcgtccggtg tgaaagtcca ycgcttaacg gtggatccgc | 60 |
| gccgggtacg ggcgggcttg agtgcggtag gggagactgg aattcccggt gtaacggtgg | 120 |
| aatgtgtaga tatcgggaag aacaccaatg gcgaaggcag gtctctgggc cgtcactgac | 180 |
| gctgaggagc gaaagcgtgg ggagcgaaca ggattagata ccctggtagt ccacgccgta | 240 |
| aacggtggat gctggatgtg gggaccattc cacggtctcc gtgtcggagc caacgcgtta | 300 |
| agcatcccgc ctggggagta cggccgcaag gctaaaactc aaagaaattg acggggggccc | 360 |
| gcacaagcgc ggagcatgc ggattaattc gatgcaacgc gaagaacctt acctgggctt | 420 |
| gacatgttcc cgacagcccc agagatgggg cctcccttcg ggcgggttc acaggtggtg | 480 |

```
catggtcgtc gtcagctcgt gtcgtgagat gttgggttaa gtcccgcaac gagcgcaacc    540
ctcgccctgt gttgccagca cgtcgtggtg ggaactcacg ggggaccgcc ggggtcaact    600
cggaggaagg tggggatgac gtcagatcat catgcccctt acgtccaggg cttcacgcat    660
gctacaatgg ccggtacaac gggatgcgac actgtgaggt ggagcggatc ccttaaaacc    720
ggtctcagtt cggattggag tctgcaaccc gactccatga aggcggagtc gctagtaatc    780
gcggatcagc aacgccgcgg tgaatgcgtt cccgggcctt gtacacaccg cccgtcaagt    840
catgaaagtg ggtagcaccc gaagccggtg gcccatcctt tttgggg                  887
```

<210> SEQ ID NO 50
<211> LENGTH: 1495
<212> TYPE: DNA
<213> ORGANISM: Bifidobacterium longum

<400> SEQUENCE: 50

```
tggctcagga tgaacgctgg cggcgtgctt aacacatgca agtcgaacgg gatccatcag     60
gctttgcttg gtggtgagag tggcgaacgg gtgagtaatg cgtgaccgac ctgccccata    120
caccggaata gctcctggaa acgggtggta atgccggatg ctccagttga tcgcatggtc    180
ttctgggaaa gctttcgcgg tatgggatgg ggtcgcgtcc tatcagcttg acggcgggt     240 aacggcccac cgtggcttcg acgggtagcc ggcctgagag ggcgaccggc cacattggga    300
ctgagatacg gcccagactc ctacgggagg cagcagtggg gaatattgca caatgggcgc    360
aagcctgatg cagcgacgcc gcgtgaggga tggaggcctt cgggttgtaa acctctttta    420
tcggggagca agcgagagtg agtttacccg ttgaataagc accggctaac tacgtgccag    480
cagccgcggt aatacgtagg gtgcaagcgt tatccggaat tattgggcgt aaagggctcg    540
taggcggttc gtcgcgtccg gtgtgaaagt ccatcgctta acggtggatc cgcgccgggt    600
acgggcgggc ttgagtgcgg tagggagac tggaattccc ggtgtaacgg tggaatgtgt     660
agatatcggg aagaacacca atggcgaagg caggtctctg ggccgttact gacgctgagg    720
agcgaaagcg tggggagcga acaggattag ataccctggt agtccacgcc gtaaacggtg    780
gatgctggat gtgggcccg ttccacgggt tccgtgtcgg agctaacgcg ttaagcatcc      840
cgcctgggga gtacggccgc aaggctaaaa ctcaaagaaa ttgacggggg cccgcacaag    900
cggcggagca tgcggattaa ttcgatgcaa cgcgaagaac cttacctggg cttgacatgt    960
tcccgacggt cgtagagata cggcttccct tcggggcggg ttcacaggtg gtgcatggtc   1020
gtcgtcagct cgtgtcgtga gatgttgggt taagtcccgc aacgagcgca accctcgccc   1080
cgtgttgcca gcggattatg ccgggaactc acggggggacc gccggggtta actcggagga   1140
aggtggggat gacgtcagat catcatgccc cttacgtcca gggcttcacg catgctacaa   1200
tggccggtac aacgggatgc gacgcggcga cgcggagcgg atccctgaaa accggtctca   1260
gttcggatcg cagtctgcaa ctcgactgcg tgaaggcgga gtcgctagta atcgcgaatc   1320
agcaacgtcg cggtgaatgc gttcccgggc cttgtacaca ccgcccgtca agtcatgaaa   1380
gtgggcagca cccgaagccg gtggcctaac cccttgtggg atggagccgt ctaaggtgag   1440
gctcgtgatt gggactaagt cgtaacaagg tagccgtacc ggaaggtgcg gctgg         1495
```

<210> SEQ ID NO 51
<211> LENGTH: 689
<212> TYPE: DNA
<213> ORGANISM: Bifidobacterium pseudocatenulatum
<220> FEATURE:

```
<221> NAME/KEY: misc_feature
<222> LOCATION: (272)..(272)
<223> OTHER INFORMATION: w is a or t
<220> FEATURE:
<221> NAME/KEY: misc_feature
<222> LOCATION: (327)..(327)
<223> OTHER INFORMATION: w is a or t
<220> FEATURE:
<221> NAME/KEY: misc_feature
<222> LOCATION: (328)..(328)
<223> OTHER INFORMATION: m is a or c
<220> FEATURE:
<221> NAME/KEY: misc_feature
<222> LOCATION: (332)..(332)
<223> OTHER INFORMATION: k is g or t

<400> SEQUENCE: 51
ggttcgtcgc gtccggtgtg aaagtccatc gtttaacggt ggatctgcgc cgggtacggg      60
cgggctggag tgcggtaggg gagactggaa ttcccggtgt aacggtggaa tgtgtagata     120
tcgggaagaa caccaatggc gaaggcaggt ctctgggccg ttactgacgc tgaggagcga     180
aagcgtgggg agcgaacagg attagatacc ctggtagtcc acgccgtaaa cggtggatgc     240
tggatgtggg gcccgttcca cgggttccgt gwcggagcta acgcgttaag catcccgcct     300
ggggagtacg gccgcaaggc taaaacwmaa akaaattgac gggggcccgc acaagcggcg     360
gagcatgcgg attaattcga tgcaacgcga agaaccttac ctgggcttga catgttcccg     420
acagccgtag agatatggcc tcccttcggg gcgggttcac aggtggtgca tggtcgtcgt     480
cagctcgtgt cgtgagatgt tgggttaagt cccgcaacga gcgcaaccct cgccctgtgt     540
tgccagcacg tcatggtggg aactcacggg ggaccgccgg ggtcaactcg gaggaaggtg     600
gggatgacgt cagatcatca tgccccttac gttcagggct tcacgcatgc tacaatggcc     660
ggtacaacgg gatgcgacac ggcgacgtg                                       689

<210> SEQ ID NO 52
<211> LENGTH: 1394
<212> TYPE: DNA
<213> ORGANISM: Blautia coccoides

<400> SEQUENCE: 52
tgtgactgag cggcggacgg gtgagtaacg cgtgggtaac ctgcctcata caggggata      60
acagttagaa atgactgcta ataccgcata agcgcacagg accgcatggt ctggtgtgaa    120
aaactccggt ggtatgagat ggacccgcgt ctgattagct agttggaggg gtaacggccc    180
accaaggcga cgatcagtag ccggcctgag agggtgaacg gccacattgg gactgagaca    240
cggcccagac tcctacggga ggcagcagtg gggaatattg cacaatgggg gaaaccctga    300
tgcagcgacg ccgcgtgaag gaagaagtat ctcggtatgt aaacttctat cagcagggaa    360
gaaaatgacg gtacctgact aagaagcccc ggctaactac gtgccagcag ccgcggtaat    420
acgtagggg caagcgttat ccggatttac tgggtgtaaa gggagcgtag acggaagagc    480
aagtctgatg tgaaaggctg gggcttaacc ccaggactgc attggaaact gttgttctag    540
agtgccggag aggtaagcgg aattcctagt gtagcggtga aatgcgtaga tattaggagg    600
aacaccagtg gcgaaggcgg cttactggac ggtaactgac gttgaggctc gaaagcgtgg    660
ggagcaaaca ggattagata ccctggtagt ccacgccgta acgatgaat actaggtgtc    720
gggtggcaaa gccattcggt gccgcagcaa acgcaataag tattccacct ggggagtacg    780
ttcgcaagaa tgaaactcaa aggaattgac ggggacccgc acaagcggtg gagcatgtgg    840
tttaattcga agcaacgcga agaaccttac caagtcttga catccctctg accgtcccgt    900
```

```
aacgggggct tcccttcggg gcagaggaga caggtggtgc atggttgtcg tcagctcgtg 960
tcgtgagatg ttgggttaag tcccgcaacg agcgcaaccc ttatccttag tagccagcac 1020
atgatggtgg gcactctagg gagactgccg gggataaccc ggaggaaggc ggggacgacg 1080
tcaaatcatc atgcccctta tgatttgggc tacacacgtg ctacaatggc gtaaacaaag 1140
ggaagcgaga cagcgatgtt gagcgaatcc caaaaataac gtcccagttc ggactgcagt 1200
ctgcaactcg actgcacgaa gctggaatcg ctagtaatcg cggatcagaa tgccgcggtg 1260
aatacgttcc cgggtcttgt acacaccgcc cgtcacacca tgggagtcag taacgcccga 1320
agtcagtgac ctaaccgaaa ggaaggagct gccgaaggcg ggaccgataa ctggggtgaa 1380
gtcgtaacaa ggta 1394
```

<210> SEQ ID NO 53
<211> LENGTH: 918
<212> TYPE: DNA
<213> ORGANISM: Clostridium citroniae

<400> SEQUENCE: 53

```
tccggattta ctggagtagt aagggagcgt agacggcgaa gcaagtctgg agtgaaaacc 60
cagggctcaa ccctgggact gctttggaaa ctgttttgct agagtgtcgg agaggtaagt 120
ggaattccta gtgtagcggt gaaatgcgta gatattagga ggaacaccag tggcgaaggc 180
ggcttactgg acgataactg acgttgaggc tcgaaagcgt ggggagcaaa caggattaga 240
taccctggta gtccacgccg taaacgatga atgctaggtg ttgggggggca aagcccttcg 300
gtgccgtcgc aaacgcaata agcattccac ctggggagta cgttcgcaag aatgaaactc 360
aaaggaattg acggggaccc gcacaagcgg tggagcatgt ggtttaattc gaagcaacgc 420
gaagaacctt accaagtctt gacatccccc tgaccggtca gtaaagtgac ctttccttcg 480
ggacagggga gacaggtggt gcatggttgt cgtcagctcg tgtcgtgaga tgttgggtta 540
agtcccgcaa cgagcgcaac ccttatcctt agtagccagc aggtaaagct gggcactcta 600
gggagactgc cagggataac ctggaggaag gtggggatga cgtcaaatca tcatgcccct 660
tatgatttgg gctacacacg tgctacaatg gcgtaaacaa agggaagcga ccctgcgaag 720
gcaagcaaat cccaaaaata acgtcccagt tcggactgta gtctgcaacc cgactacacg 780
aagctggaat cgctagtaat cgcgaatcag aatgtcgcgg tgaatacgtt cccgggtctt 840
gtacacaccg cccgtcacac catgggagtc agcaacgccc gaagtcagtg acccaaccga 900
aaggagggag ctgccgaa 918

<210> SEQ ID NO 54
<211> LENGTH: 1307
<212> TYPE: DNA
<213> ORGANISM: Clostridium clostridioforme
<400> SEQUENCE: 54
taataccgca taagcgcaca gtgccgcatg gcagtgtgtg aaaaactccg gtggtgtgag 60
atggatccgc gtctgattag ccagttggcg gggtaacggc ccaccaaagc gacgatcagt 120
agccgacctg agagggtgac cggccacatt gggactgaga cacggcccaa actcctacgg 180
gaggcagcag tggggaatat tgcacaatgg gcgaaagcct gatgcagcga cgccgcgtga 240
gtgaagaagt atttcggtat gtaaagctct atcagcaggg aagaaaatga cggtacctga 300
ctaagaagcc ccggctaact acgtgccagc agccgcggta atacgtaggg ggcaagcgtt 360
```

| | |
|---|---|
| atccggattt actgggtgta aagggagcgt agacggcgaa gcaagtctga agtgaaaacc | 420 |
| cggggctcaa ccctgggact gctttggaaa ctgttttgct agagtgtcgg agaggtaagt | 480 |
| ggaattccta gtgtagcggt gaaatgcgta gatattagga ggaacaccag tggcgaaggc | 540 |
| ggcttactgg acgataactg acgttgaggc tcgaaagcgt ggggagcaaa caggattaga | 600 |
| taccctggta gtccacgccg taaacgatga atgctaggtg ttggggggca aagcccttcg | 660 |
| gtgccgccgc aaacgcagta agcattccac ctggggagta cgttcgcaag aatgaaactc | 720 |
| aaaggaattg acggggaccc gcacaagcgg tggagcatgt ggtttaattc gaagcaacgc | 780 |
| gaagaacctt accaagtctt gacatccccc tgacgggccg gtaacgcggc ctttccttcg | 840 |
| ggacagggga gacaggtggt gcatggttgt cgtcagctcg tgtcgtgaga tgttgggtta | 900 |
| agtcccgcaa cgagcgcaac ccttatcctt agtagccagc aggtagagcc gggcactcta | 960 |
| gggagactgc cagggataac ctggaggaag gtggggatga cgtcaaatca tcatgcccct | 1020 |
| tatgatttgg gctacacacg tgctacaatg gcgtaaacaa agggaagcga gacagtgatg | 1080 |
| tggagcaaat cccaaaaata acgtcccagt tcggactgta gtctgcaacc cgactacacg | 1140 |
| aagctggaat cgctagtaat cgcgaatcag aatgtcgcgg tgaatacgtt cccgggtctt | 1200 |
| gtacacaccg cccgtcacac catgggagtc agcaacgccc gaagtcagtg acccaaccga | 1260 |
| aaggagggag ctgccgaagg cggggcaggt aactggggtg aagtcgt | 1307 |

<210> SEQ ID NO 55
<211> LENGTH: 1475
<212> TYPE: DNA
<213> ORGANISM: Clostridium innocuum

<400> SEQUENCE: 55

| | |
|---|---|
| atggagagtt tgatcctggc tcaggatgaa cgctggcggc atgcctaata catgcaagtc | 60 |
| gaacgaagtt tcgaggaagc ttgcttccaa agagacttag tggcgaacgg gtgagtaaca | 120 |
| cgtaggtaac ctgcccatgt gtccgggata actgctggaa acggtagcta aaaccggata | 180 |
| ggtatacaga gcgcatgctc agtatattaa agcgcccatc aaggcgtgaa catggatgga | 240 |
| cctgcggcgc attagctagt tggtgaggta acggcccacc aaggcgatga tgcgtagccg | 300 |
| gcctgagagg gtaaacggcc acattgggac tgagacacgg cccaaactcc tacgggaggc | 360 |
| agcagtaggg aattttcgtc aatggggaa accctgaacg agcaatgccg cgtgagtgaa | 420 |
| gaaggtcttc ggatcgtaaa gctctgttgt aagtgaagaa cggctcatag aggaaatgct | 480 |
| atgggagtga cggtagctta ccagaaagcc acggctaact acgtgccagc agccgcggta | 540 |
| atacgtaggt ggcaagcgtt atccggaatc attgggcgta aagggtgcgt aggtggcgta | 600 |
| ctaagtctgt agtaaaaggc aatggctcaa ccattgtaag ctatggaaac tggtatgctg | 660 |
| gagtgcagaa gagggcgatg gaattccatg tgtagcggta aaatgcgtag atatatggag | 720 |
| gaacaccagt ggcgaaggcg tcgcctggt ctgtaactga cactgaggca cgaaagcgtg | 780 |
| gggagcaaat aggattagat accctagtag tccacgccgt aaacgatgag aactaagtgt | 840 |
| tggaggaatt cagtgctgca gttaacgcaa taagttctcc gcctggggag tatgcacgca | 900 |
| agtgtgaaac tcaaaggaat tgacggggc cgcacaagc ggtggagtat gtggtttaat | 960 |
| tcgaagcaac gcgaagaacc ttaccaggcc ttgacatgga acaaatacc ctagagatag | 1020 |
| gggataatt atggatcaca caggtggtgc atggttgtcg tcagctcgtg tcgtgagatg | 1080 |
| ttgggttaag tcccgcaacg agcgcaaccc ttgtcgcatg ttaccagcat caagttgggg | 1140 |
| actcatgcga gactgccggt gacaaaccgg aggaaggtgg ggatgacgtc aaatcatcat | 1200 |

```
gcccttatg gcctgggcta cacacgtact acaatggcgg ccacaaagag cagcgacaca   1260
gtgatgtgaa gcgaatctca taaaggtcgt ctcagttcgg attgaagtct gcaactcgac   1320
ttcatgaagt cggaatcgct agtaatcgca gatcagcatg ctgcggtgaa tacgttctcg   1380
ggccttgtac acaccgcccg tcaaaccatg ggagtcagta atacccgaag ccggtggcat   1440
aaccgtaagg agtgagccgt cgaaggtagg accga                              1475
```

```
<210> SEQ ID NO 56
<211> LENGTH: 1475
<212> TYPE: DNA
<213> ORGANISM: Clostridium innocuum

<400> SEQUENCE: 56
atggagagtt tgatcctggc tcaggatgaa cgctggcggc atgcctaata catgcaagtc     60
gaacgaagtt tcgaggaagc ttgcttccaa agagacttag tggcgaacgg gtgagtaaca   120
cgtaggtaac ctgcccatgt gtccgggata actgctggaa acggtagcta aaaccggata   180
ggtatacaga gcgcatgctc agtatattaa agcgcccatc aaggcgtgaa catggatgga   240
cctgcggcgc attagctagt tggtgaggta acggcccacc aaggcgatga tgcgtagccg   300
gcctgagagg gtaaacggcc acattgggac tgagacacgg cccaaactcc tacgggaggc   360
agcagtaggg aattttcgtc aatgggggaa accctgaacg agcaatgccg cgtgagtgaa   420
gaaggtcttc ggatcgtaaa gctctgttgt aagtgaagaa cggctcatag aggaaatgct   480
atgggagtga cggtagctta ccagaaagcc acggctaact acgtgccagc agccgcggta   540
atacgtaggt ggcaagcgtt atccggaatc attgggcgta aagggtgcgt aggtggcgta   600
ctaagtctgt agtaaaaggc aatggctcaa ccattgtaag ctatggaaac tggtatgctg   660
gagtgcagaa gagggcgatg gaattccatg tgtagcggta aaatgcgtag atatatggag   720
gaacaccagt ggcgaaggcg gtcgcctggt ctgtaactga cactgaggca cgaaagcgtg   780
gggagcaaat aggattagat accctagtag tccacgccgt aaacgatgag aactaagtgt   840
tggaggaatt cagtgctgca gttaacgcaa taagttctcc gcctggggag tatgcacgca   900
agtgtgaaac tcaaaggaat tgacgggggc ccgcacaagc ggtggagtat gtggtttaat   960
tcgaagcaac gcgaagaacc ttaccaggcc ttgacatgga acaaatacc ctagagatag  1020 ggggataatt atggatcaca caggtggtgc atggttgtcg tcagctcgtg tcgtgagatg  1080
ttgggttaag tcccgcaacg agcgcaaccc ttgtcgcatg ttaccagcat caagttgggg  1140
actcatgcga gactgccggt gacaaaccgg aggaaggtgg ggatgacgtc aaatcatcat  1200 gcccttatg gcctgggcta cacacgtact acaatggcga ccacaaagag cagcgacaca   1260
gtgatgtgaa gcgaatctca taaaggtcgt ctcagttcgg attgaagtct gcaactcgac   1320
ttcatgaagt cggaatcgct agtaatcgca gatcagcatg ctgcggtgaa tacgttctcg   1380
ggccttgtac acaccgcccg tcaaaccatg ggagtcagta atacccgaag ccggtggcat   1440
aaccgtaagg agtgagccgt cgaaggtagg accga                              1475
```

```
<210> SEQ ID NO 57
<211> LENGTH: 906
<212> TYPE: DNA
<213> ORGANISM: Clostridium sordellii
<220> FEATURE:
<221> NAME/KEY: misc_feature
<222> LOCATION: (114)..(114)
<223> OTHER INFORMATION: r is a or g
<220> FEATURE:
```

```
<221> NAME/KEY: misc_feature
<222> LOCATION: (116)..(116)
<223> OTHER INFORMATION: y is c or t
<220> FEATURE:
<221> NAME/KEY: misc_feature
<222> LOCATION: (277)..(277)
<223> OTHER INFORMATION: m is a or c
<220> FEATURE:
<221> NAME/KEY: misc_feature
<222> LOCATION: (897)..(897)
<223> OTHER INFORMATION: r is a or g

<400> SEQUENCE: 57
acacatgcaa gtcgagcgaa cccttcgggg tgagcggcgg acgggtgagt aacgcgtggg      60
taacctgccc tgtacacacg gataacatac cgaaaggtat gctaatacgg gatrayatat    120
gagagtcgca tggcttttgt atcaaagctc cggcggtaca ggatggaccc gcgtctgatt    180
agctagttgg taaggtaacg gcttaccaag gcaacgatca gtagccgacc tgagagggtg    240
atcggccaca ttggaactga gacacggtcc aaactcmtac gggaggcagc agtggggaat    300
attgcacaat gggcgaaagc ctgatgcagc aacgccgcgt gagcgatgaa ggccttcggg    360
tcgtaaagct ctgtcctcaa ggaagataat gacggtactt gaggaggaag ccccggctaa    420
ctacgtgcca gcagccgcgg taatacgtag ggggctagcg ttatccggaa ttactgggcg    480
taaagggtgc gtaggcggtc tttcaagcca gaagtgaaag gctacggctc aaccgtagta    540
agcttttgga actgtaggac ttgagtgcag gagaggagag tggaattcct agtgtagcgg    600
tgaaatgcgt agatattagg aggaacacca gtagcgaagg cggctctctg gactgtaact    660
gacgctgagg cacgaaagcg tggggagcaa acaggattag ataccctggt agtccacgcc    720
gtaaacgatg agtactaggt gtcgggggtt acccccctcg gtgccgcagc taacgcatta    780
agtactccgc ctgggaagta cgctcgcaag agtgaaactc aaaggaattg acggggaccc    840
gcacaagtag cggagcatgt ggtttaattc gaagcaacgc gaagaacctt atctaarctt    900
gacatc                                                              906

<210> SEQ ID NO 58
<211> LENGTH: 380
<212> TYPE: DNA
<213> ORGANISM: Coprococcus comes
<220> FEATURE:
<221> NAME/KEY: misc_feature
<222> LOCATION: (59)..(59)
<223> OTHER INFORMATION: r is a or g
<220> FEATURE:
<221> NAME/KEY: misc_feature
<222> LOCATION: (78)..(78)
<223> OTHER INFORMATION: k is g or t
<220> FEATURE:
<221> NAME/KEY: misc_feature
<222> LOCATION: (355)..(355)
<223> OTHER INFORMATION: k is g or t
<220> FEATURE:
<221> NAME/KEY: misc_feature
<222> LOCATION: (367)..(367)
<223> OTHER INFORMATION: s is g or c
<220> FEATURE:
<221> NAME/KEY: misc_feature
<222> LOCATION: (378)..(378)
<223> OTHER INFORMATION: r is a or g

<400> SEQUENCE: 58
acrggaggca gcagtgggga atattgcaca atgggggaaa ccctgatgca gcgacgccrc     60
gtgagcgaag aagtattkcg gtatgtaaag ctctatcagc agggaagaaa atgacggtac    120
ctgactaaga agcaccggct aaatacgtgc cagcagccgc ggtaatacgt atggtgcaag    180
```

```
cgttatccgg atttactggg tgtaaaggga gcgtagacgg ctgtgtaagt ctgaagtgaa      240 aggcggggc tccccccgg ggactgcttt ggaaactatg cagctagact gtcggacagg       300
taagtggaat tcccagtgta gcggtgaaat gcgtagatat tgggaggaac agcaktgggt    360
aaggctsctt acaggacrat                                                  380

<210> SEQ ID NO 59
<211> LENGTH: 1317
<212> TYPE: DNA
<213> ORGANISM: Dorea longicatena

<400> SEQUENCE: 59
taacgcgtgg gtaacctgcc tcatacaggg ggataacagt tagaaatgac tgctaatacc      60
gcataagacc acggtaccgc atggtacagt ggtaaaaact ccggtggtat gagatggacc     120
cgcgtctgat taggtagttg gtggggtaac ggcctaccaa gccgacgatc agtagccgac    180
ctgagagggt gaccggccac attgggactg agacacggcc cagactccta cgggaggcag    240
cagtggggaa tattgcacaa tggaggaaac tctgatgcag cgacgccgcg tgaaggatga    300
agtatttcgg tatgtaaact tctatcagca gggaagaaaa tgacggtacc tgactaagaa    360
gccccggcta actacgtgcc agcagccgcg gtaatacgta gggggcaagc gttatccgga    420
tttactgggt gtaaagggag cgtagacggc acggcaagcc agatgtgaaa gcccggggct    480
caaccccggg actgcatttg aactgctga gctagagtgt cggagaggca agtggaattc     540
ctagtgtagc ggtgaaatgc gtagatatta ggaggaacac cagtggcgaa ggcggcttgc    600
tggacgatga ctgacgttga ggctcgaaag cgtggggagc aaacaggatt agataccctg    660
gtagtccacg ccgtaaacga tgactgctag gtgtcgggtg gcaaagccat tcggtgccgc    720
agctaacgca ataagcagtc cacctgggga gtacgttcgc aagaatgaaa ctcaaaggaa    780
ttgacgggga cccgcacaag cggtggagca tgtggtttaa ttcgaagcaa cgcgaagaac    840
cttacctgat cttgacatcc cgatgaccgc ttcgtaatgg aagctttcct tcggaacatc    900
ggtgacaggt ggtgcatggt tgtcgtcagc tcgtgtcgtg agatgttggg ttaagtcccg    960
caacgagcgc aaccctatc ttcagtagcc agcaggttaa gctgggcact ctggagagac    1020
tgccagggat aacctggagg aaggtgggga tgacgtcaaa tcatcatgcc ccttatgacc    1080
agggctacac acgtgctaca atggcgtaaa caaagagaag cgaactcgcg agggtaagca    1140
aatctcaaaa ataacgtctc agttcggatt gtagtctgca actcgactac atgaagctgg    1200
aatcgctagt aatcgcagat cagaatgctg cggtgaatac gttcccgggt cttgtacaca    1260
ccgcccgtca caccatggga gtcagtaacg cccgaagtca gtgacccaac cgtaagg       1317

<210> SEQ ID NO 60
<211> LENGTH: 808
<212> TYPE: DNA
<213> ORGANISM: Erysipelatoclostridium ramosum
<220> FEATURE:
<221> NAME/KEY: misc_feature
<222> LOCATION: (94)..(94)
<223> OTHER INFORMATION: k is g or t
<220> FEATURE:
<221> NAME/KEY: misc_feature
<222> LOCATION: (253)..(253)
<223> OTHER INFORMATION: r is a or g
<220> FEATURE:
<221> NAME/KEY: misc_feature
<222> LOCATION: (598)..(598)
<223> OTHER INFORMATION: r is a or g
<220> FEATURE:
```

-continued

```
<221> NAME/KEY: misc_feature
<222> LOCATION: (736)..(736)
<223> OTHER INFORMATION: r is a or g
<220> FEATURE:
<221> NAME/KEY: misc_feature
<222> LOCATION: (778)..(778)
<223> OTHER INFORMATION: r is a or g
<220> FEATURE:
<221> NAME/KEY: misc_feature
<222> LOCATION: (795)..(795)
<223> OTHER INFORMATION: m is a or c

<400> SEQUENCE: 60
gagggagcag gcggcagcaa gggtctgtgg tgaaagcctg aagttaaact tcagtaagcc      60
atagaaacca ggcagctaga gtgcaggaga ggakcgtgga attccatgtg tagcggtgaa     120
atgcgtagat atatggagga acaccagtgg cgaaggcgac gatctggcct gcaactgacg     180
ctcagtcccg aaagcgtggg gagcaaatag gattagatac cctagtagtc cacgccgtaa     240
acgatgagta ctragtgttg gatgtcaaag ttcagtgctg cagttaacgc aataagtact     300
ccgcctgagt agtacgttcg caagaatgaa actcaaagga attgacgggg gcccgcacaa     360
gcggtggagc atgtggttta attcgaagca acgcgaagaa ccttaccagg tcttgacata     420
ctcataaagg ctccagagat ggagagatag ctatatgaga tacaggtggt gcatggttgt     480
cgtcagctcg tgtcgtgaga tgttgggtta agtcccgcaa cgagcgcaac ccttatcgtt     540
agttaccatc attaagttgg ggactctagc gagactgcca gtgacaagct ggaggaargc     600
ggggatgacg tcaaatcatc atgcccctta tgacctgggc tacacacgtg ctacaatgga     660
tggtgcagag ggaagcgaag ccgcgaggtg aagcaaaacc cataaaacca ttctcagttc     720
ggattgtagt ctgcarctcg actacatgaa gttggaatcg ctagtaatcg cgaatcarca     780
tgtcgcgatg aatamgttct cgggcctt                                         808

<210> SEQ ID NO 61
<211> LENGTH: 1521
<212> TYPE: DNA
<213> ORGANISM: Eubacterium rectale

<400> SEQUENCE: 61
agagtttgat cctggctcag gatgaacgct ggcggcgtgc ttaacacatg caagtcgaac      60
gaagcacttt atttgatttc cttcgggact gattattttg tgactgagtg gcggacgggt     120
gagtaacgcg tgggtaacct gccttgtaca gggggataac agttggaaac ggctgctaat     180
accgcataag cgcacggcat cgcatgatgc agtgtgaaaa actccggtgg tataagatgg     240
acccgcgttg gattagctag ttggtgaggt aacggcccac caaggcgacg atccatagcc     300
gacctgagag ggtgaccggc cacattggga ctgagacacg gcccaaactc ctacgggagg     360
cagcagtggg gaatattgca caatgggcga aagcctgatg cagcgacgcc gcgtgagcga     420
agaagtattt cggtatgtaa agctctatca gcagggaaga taatgacggt acctgactaa     480
gaagcaccgg ctaaatacgt gccagcagcc gcggtaatac gtatggtgca agcgttatcc     540
ggatttactg ggtgtaaagg gagcgcaggc ggtgcggcaa gtctgatgtg aaagcccggg     600
gctcaacccc ggtactgcat tggaaactgt cgtactagag tgtcggaggg gtaagcggaa     660
ttcctagtgt agcggtgaaa tgcgtagata ttaggaggaa caccagtggc gaaggcggct     720
tactggacga taactgacgc tgaggctcga aagcgtgggg agcaaacagg attagatacc     780
ctggtagtcc acgccgtaaa cgatgaatac taggtgttgg gaagcattgc ttctcggtgc     840
cgtcgcaaac gcagtaagta ttccacctgg ggagtacgtt cgcaagaatg aaactcaaag     900
```

```
gaattgacgg ggacccgcac aagcggtgga gcatgtggtt taattcgaag caacgcgaag      960
aaccttacca agtcttgaca tccttctgac cggtacttaa ccgtaccttc tcttcggagc     1020
aggagtgaca ggtggtgcat ggttgtcgtc agctcgtgtc gtgagatgtt gggttaagtc     1080
ccgcaacgag cgcaacccct tatctttagta gccagcggtt cggccgggca ctctagagag     1140
actgccaggg ataacctgga ggaaggcggg gatgacgtca atcatcatg ccccttatga      1200 cttgggctac acacgtgcta caatggcgta acaaaggga agcaaagctg tgaagccgag      1260
caaatctcaa aaataacgtc tcagttcgga ctgtagtctg caacccgact acacgaagct     1320
ggaatcgcta gtaatcgcag atcagaatgc tgcggtgaat acgttcccgg gtcttgtaca     1380
caccgcccgt cacaccatgg gagttgggaa tgcccgaagc cagtgaccta accgaaagga     1440
aggagctgtc gaaggcaggc tcgataactg gggtgaagtc gtaacaaggt agccgtatcg     1500
gaaggtgcgg ctggatcacc t                                               1521

<210> SEQ ID NO 62
<211> LENGTH: 1482
<212> TYPE: DNA
<213> ORGANISM: Odoribacter splanchnicus

<400> SEQUENCE: 62
agagtttgat cctggctcag gatgaacgct agcgacaggc ttaacacatg caagtcgagg       60
ggcatcatga ggtagcaata ccttgatggc gaccggcgca cgggtgagta acgcgtatgc      120
aacctgcccg ataccggggt atagccatg gaaacgtgga ttaacacccc atagtacttt       180
tatcctgcat gggatgtgag ttaaatgttt aaggtatcgg atgggcatgc gtcctattag      240
ttagttggcg gggtaacagc ccaccaagac gatgataggt aggggttctg agaggaaggt      300
cccccacatt ggaactgaga cacggtccaa actcctacgg gaggcagcag tgaggaatat      360
tggtcaatgg acgagagtct gaaccagcca agtcgcgtga gggaagactg ccctatgggt      420
tgtaaacctc ttttataagg gaagaataag ttctacgtgt agaatgatgc ctgtaccttg      480
tgaataagca tcggctaact ccgtgccagc agccgcggta atacggagga tgcgagcgtt      540
atccggattt attgggttta aagggtgcgt aggcggttta ttaagttagt ggttaaatat      600
ttgagctaaa ctcaattgtg ccattaatac tggtaaactg gagtacagac gaggtaggcg      660
gaataagtta agtagcggtg aaatgcatag atataactta gaactccgat agcgaaggca      720
gcttaccaga ctgtaactga cgctgatgca cgagagcgtg ggtagcgaac aggattagat      780
accctggtag tccacgccgt aaacgatgct cactggttct gtgcgatata ttgtacggga      840
ttaagcgaaa gtattaagtg agccacctgg ggagtacgtc ggcaacgatg aaactcaaag      900
gaattgacgg gggcccgcac aagcggagga acatgtggtt taattcgatg atacgcgagg      960
aaccttacct gggtttaaat gggaaatgtc gtatttggaa acagatattc tcttcggagc     1020 gttttttcaag gtgctgcatg gttgtcgtca gctcgtgccg tgaggtgtcg ggttaagtcc     1080
cataacgagc gcaaccctta ccgttagttg ctagcatgta atgatgagca ctctaacggg     1140
actgccaccg taaggtgaga ggaaggcggg gatgacgtca atcagcacg gcccttacac      1200 ccagggctac acacgtgtta caatggccgg tacagagggc gctaccagg tgactggatg      1260 ccaatctcaa agccggtcg tagttcggat tggagtctgt aacccgactc catgaagttg      1320
gattcgctag taatcgcgca tcagccatgg cgcggtgaat acgttcccgg gccttgtaca     1380
caccgcccgt caagccatgg aagccggggg tgcctgaagt ccgtaaccgc gaggatcggc     1440
```
ctagggcaaa actggtaact ggggctaagt cgtaacaagg ta                1482

<210> SEQ ID NO 63
<211> LENGTH: 738
<212> TYPE: DNA
<213> ORGANISM: Parabacteroides distasonis
<220> FEATURE:
<221> NAME/KEY: misc_feature
<222> LOCATION: (12)..(12)
<223> OTHER INFORMATION: r is a or g
<220> FEATURE:
<221> NAME/KEY: misc_feature
<222> LOCATION: (30)..(30)
<223> OTHER INFORMATION: s is g or c
<220> FEATURE:
<221> NAME/KEY: misc_feature
<222> LOCATION: (72)..(72)
<223> OTHER INFORMATION: r is a or g
<220> FEATURE:
<221> NAME/KEY: misc_feature
<222> LOCATION: (130)..(130)
<223> OTHER INFORMATION: y is c or t
<220> FEATURE:
<221> NAME/KEY: misc_feature
<222> LOCATION: (140)..(140)
<223> OTHER INFORMATION: r is a or g
<220> FEATURE:
<221> NAME/KEY: misc_feature
<222> LOCATION: (206)..(306)
<223> OTHER INFORMATION: r is a or g
<220> FEATURE:
<221> NAME/KEY: misc_feature
<222> LOCATION: (319)..(319)
<223> OTHER INFORMATION: s is g or c
<220> FEATURE:
<221> NAME/KEY: misc_feature
<222> LOCATION: (322)..(322)
<223> OTHER INFORMATION: w is a or t
<220> FEATURE:
<221> NAME/KEY: misc_feature
<222> LOCATION: (323)..(323)
<223> OTHER INFORMATION: r is a or g
<220> FEATURE:
<221> NAME/KEY: misc_feature
<222> LOCATION: (411)..(411)
<223> OTHER INFORMATION: y is c or t
<220> FEATURE:
<221> NAME/KEY: misc_feature
<222> LOCATION: (412)..(412)
<223> OTHER INFORMATION: r is a or g
<220> FEATURE:
<221> NAME/KEY: misc_feature
<222> LOCATION: (658)..(658)
<223> OTHER INFORMATION: w is a or t

<400> SEQUENCE: 63 cgagggcag crcaggagtt agcaataccs ggtggcgacc ggcgcacggg tgagtaacgc    60
gtatgcaact trcctatcag aggggataa cccggcgaaa gtcggactaa taccgcatga   120
agcagggaty ccgcatgggr atatttgcta aagattcatc gctgatagat aggcatgcgt   180
tccattaggc agttggcggg gtaacrgccc accaaaccga cgatggatag gggttctgag   240
aggaaggtcc cccacattgg tactgagaca cggaccaaac tcctacggga ggcagcagtg   300
aggaatattg gtcaatggsc gwragsctga accagccaag tcgcgtgagg gatgaaggtt   360
ctatggatcg taaacctctt ttataaggga ataaagtgcg ggacgtgtcc yrttttgtat   420
gtaccttatg aataaggatc ggctaactcc gtgccagcag ccgcggtaat acggaggatc   480
cgagcgttat ccggatttat tgggtttaaa gggtgcgtag gcggccttt aagtcagcgg   540 tgaaagtctg tggctcaacc atagaattgc cgttgaaact gggggcttg agtatgtttg   600 aggcaggcgg aatgcgtggt gtagcggtga aatgcataga tatcacgcag aaccccgwtt   660

```
gcgaaggcag cctgccaagc cgtaactgac gcggatgcac gaaagcgtgg ggatcaaaca    720
ggattagata ccctggta                                                 738
```

<210> SEQ ID NO 64
<211> LENGTH: 521
<212> TYPE: DNA
<213> ORGANISM: Parabacteroides merdae
<220> FEATURE:
<221> NAME/KEY: misc_feature
<222> LOCATION: (249)..(249)
<223> OTHER INFORMATION: k is g or t
<220> FEATURE:
<221> NAME/KEY: misc_feature
<222> LOCATION: (466)..(466)
<223> OTHER INFORMATION: m is a or c
<220> FEATURE:
<221> NAME/KEY: misc_feature
<222> LOCATION: (466)..(466)
<223> OTHER INFORMATION: m is a or c
<220> FEATURE:
<221> NAME/KEY: misc_feature
<222> LOCATION: (467)..(467)
<223> OTHER INFORMATION: s is g or c
<220> FEATURE:
<221> NAME/KEY: misc_feature
<222> LOCATION: (469)..(469)
<223> OTHER INFORMATION: r is a or g
<220> FEATURE:
<221> NAME/KEY: misc_feature
<222> LOCATION: (510)..(510)
<223> OTHER INFORMATION: w is a or t

<400> SEQUENCE: 64

```
catgcaagtc gagggcagc atgatttgta gcaatacaga ttgatggcga ccggcgcacg    60
ggtgagtaac gcgtatgcaa cttacctatc agagggggat agcccggcga aagtcggatt    120 aatacccat aaaacagggg tcccgcatgg gaatatttgt taaagattca tcgctgatag    180
ataggcatgc gttccattag gcagttggcg gggtaacggc ccaccaaacc gacgatggat    240 agggggttckg agaggaaggt cccccacatt ggtactgaga cacggaccaa actcctacgg    300
gaggcagcag tgaggaatat tggtcaatgg ccgagaggct gaaccagcca agtcgcgtga    360
aggaagaagg atctatggtt tgtaaacttc ttttatatggg gaataaagtg gaggacgtgt    420 cctttttttgt atgtacccta tgaataagca tcggctaact ccgtgmsarc mgccgcggga    480
atacggaaga tgcagagcgt tatccggatw tattgggtt a                        521
```

<210> SEQ ID NO 65
<211> LENGTH: 1368
<212> TYPE: DNA
<213> ORGANISM: Bacteroides xylanisolvens

<400> SEQUENCE: 65

```
catgcaagtc gagggcagc attttagttt gcttgcaaac taaagatggc gaccggcgca    60
cgggtgagta acacgtatcc aacctgccga taactcgggg atagcctttc gaaagaaaga    120
ttaatatccg atagtatatt aaaaccgcat ggttttacta ttaaagaatt tcggttatcg    180
atggggatgc gttccattag tttgttggcg gggtaacggc ccaccaagac tacgatggat    240 agggggttctg agaggaaggt cccccacatt ggaactgaga cacggtccaa actcctacgg    300
gaggcagcag tgaggaatat tggtcaatgg acgagagtct gaaccagcca agtagcgtga    360
aggatgactg ccctatgggt tgtaaacttc ttttatatgg gaataaagta ttccacgtgt    420
gggattttgt atgtaccata tgaataagga tcggctaact ccgtgccagc agccgcggta    480
```

-continued

| | |
|---|---|
| atacggagga tccgagcgtt atccggattt attgggttta aagggagcgt aggtggattg | 540 |
| ttaagtcagt tgtgaaagtt tgcggctcaa ccgtaaaatt gcagttgaaa ctggcagtct | 600 |
| tgagtacagt agaggtgggc ggaattcgtg gtgtagcggt gaaatgctta gatatcacga | 660 |
| agaactccga ttgcgaaggc agctcactag actgcaactg acactgatgc tcgaaagtgt | 720 |
| gggtatcaaa caggattaga taccctggta gtccacacag taaacgatga atactcgctg | 780 |
| tttgcgatat acagtaagcg gccaagcgaa agcattaagt attccacctg ggagtacgc | 840 |
| cggcaacggt gaaactcaaa ggaattgacg ggggcccgca caagcggagg aacatgtggt | 900 |
| ttaattcgat gatacgcgag gaaccttacc cgggcttaaa ttgcatttga ataatctgga | 960 |
| aacaggttag ccgcaaggca aatgtgaagg tgctgcatgg ttgtcgtcag ctcgtgccgt | 1020 |
| gaggtgtcgg cttaagtgcc ataacgagcg caacccttat ctttagttac taacaggtta | 1080 |
| tgctgaggac tctagagaga ctgccgtcgt aagatgtgag gaaggtgggg atgacgtcaa | 1140 |
| atcagcacgg cccttacgtc cggggctaca cacgtgttac aatgggggt acagaaggca | 1200 |
| gctacctggc gacaggatgc taatcccaaa aacctctctc agttcggatc gaagtctgca | 1260 |
| acccgacttc gtgaagctgg attcgctagt aatcgcgcat cagccatggc gcggtgaata | 1320 |
| cgttcccggg ccttgtacac accgcccgtc aagccatgaa agccgggg | 1368 |

<210> SEQ ID NO 66
<211> LENGTH: 1399
<212> TYPE: DNA
<213> ORGANISM: Blautia obeum

<400> SEQUENCE: 66

| | |
|---|---|
| ggcgtgctta acacatgcaa gtcgaacggg aaaccttta ttgaagcttc ggcagattta | 60 |
| gctggtttct agtggcggac gggtgagtaa cgcgtgggta acctgcctta tacagggga | 120 |
| taacaaccag aaatggttgc taataccgca taagcgcaca ggaccgcatg gtccggtgtg | 180 |
| aaaaactccg gtggtataag atggacccgc gttggattag ctagttggca gggtaacggc | 240 |
| ctaccaaggc gacgatccat agccggcctg agagggtgaa cggccacatt gggactgaga | 300 |
| cacggcccag actcctacgg gaggcagcag tggggaatat tgcacaatgg gggaaaccct | 360 |
| gatgcagcga cgccgcgtga aggaagaagt atctcggtat gtaaacttct atcagcaggg | 420 |
| aagatagtga cggtacctga ctaagaagcc ccggctaact acgtgccagc agccgcggta | 480 |
| atacgtaggg ggcaagcgtt atccggattt actgggtgta aagggagcgt agacggactg | 540 |
| gcaagtctga tgtgaaaggc gggggctcaa cccctggact gcattggaaa ctgttagtct | 600 |
| tgagtgccgg agaggtaagc ggaattccta gtgtagcggt gaaatgcgta gatattagga | 660 |
| ggaacaccag tggcgaaggc ggcttactgg acgtaactg acgttgaggc tcgaaagcgt | 720 |
| ggggagcaaa caggattaga taccctggta gtccacgccg taaacgatga atactaggtg | 780 |
| ttggggagca agctcttcg gtgccgccgc aaacgcatta agtattccac ctggggagta | 840 |
| cgttcgcaag aatgaaactc aaaggaattg acggggaccc gcacaagcgg tggagcatgt | 900 |
| ggtttaattc gaagcaacgc gaagaacctt accaagtctt gacatccctc tgaccgttcc | 960 |
| ttaaccggaa ctttccttcg gacaggggga gacaggtggt gcatggttgt cgtcagctcg | 1020 |
| tgtcgtgaga tgttgggtta agtcccgcaa cgagcgcaac ccctatcccc agtagccagc | 1080 |
| agtccggctg ggcactctga ggagactgcc aggataacc tggaggaagg cggggatgac | 1140 |
| gtcaaatcat catgccccctt atgatttggg ctacacacgt gctacaatgg cgtaaacaaa | 1200 |
| gggaagcaag cctgcgaagg taagcaaatc ccaaaaataa cgtcccagtt cggactgcag | 1260 |

```
tctgcaactc gactgcacga agctggaatc gctagtaatc gcggatcaga atgccgcggt    1320
gaatacgttc ccgggtcttg tacacaccgc ccgtcacacc atgggagtca gtaacgcccg    1380
aagtcagtga cctaactgc                                                 1399
```

<210> SEQ ID NO 67
<211> LENGTH: 1485
<212> TYPE: DNA
<213> ORGANISM: Alistipes putredinis

<400> SEQUENCE: 67

```
agagtttgat cctggctcag gatgaacgct agcggcaggc ttaacacatg caagtcgagg     60
ggcagcataa tggatagcaa tatctatggt ggcgaccggc gcacgggtgc gtaacgcgta    120
tgcaacctac ctttaacagg gggataacac tgagaaattg gtactaatac ccataatat    180 catagaaggc atcttttatg gttgaaaatt ccgatggtta gagatgggca tgcgttgtat    240
tagctagttg gtggggtaac ggctcaccaa ggcgacgata cataggggga ctgagaggtt    300
aaccccccac actggtactg agacacggac cagactccta cgggaggcag cagtgaggaa    360
tattggtcaa tggacgcaag tctgaaccag ccatgccgcg tgcaggatga cggctctatg    420
agttgtaaac tgcttttgta cgagggtaaa cgcagatacg tgtatctgtc tgaaagtatc    480
gtacgaataa ggatcggcta actccgtgcc agcagccgcg gtaatacgga ggattcaagc    540
gttatccgga tttattgggt ttaaagggtg cgtaggcggt ttgataagtt agaggtgaaa    600
tttcggggct caaccctgaa cgtgcctcta atactgttga gctagagagt agttgcggta    660
ggcggaatgt atggtgtagc ggtgaaatgc ttagagatca tacagaacac cgattgcgaa    720
ggcagcttac caaactatat ctgacgttga ggcacgaaag cgtggggagc aaacaggatt    780
agataccctg gtagtccacg cagtaaacga tgataactcg ttgtcggcga tacacagtcg    840
gtgactaagc gaaagcgata agttatccac ctggggagta cgttcgcaag aatgaaactc    900
aaaggaattg acggggcccc gcacaagcgg aggaacatgt ggtttaattc gatgatacgc    960
gaggaacctt acccgggctt gaaagttagc gacgattctt gaaagaggat tcccttcgg    1020 ggcgcgaaac taggtgctgc atggttgtcg tcagctcgtg ccgtgaggtg tcgggttaag    1080
tcccataacg agcgcaaccc ctaccgttag ttgccatcag gtgaagctgg gcactctggc    1140
gggactgccg gtgtaagccg agaggaaggt ggggatgacg tcaaatcagc acggccctta    1200
cgtccggggc tacacacgtg ttacaatggt aggtacagag ggcagctacc cagcgatggg    1260
atgcgaatct cgaaagccta tctcagttcg gattggagct gaaacccgc ctccatgaag    1320 ttggattcgc tagtaatcgc gcatcagcca tggcgcggtg aatacgttcc cgggccttgt    1380
acacaccgcc cgtcaagcca tgggagccgg gggtgcctga agttcgtgac gcaaggagc    1440 gacctagggc aaaactggtg actggggcta agtcgtaaca aggta                   1485
```

<210> SEQ ID NO 68
<211> LENGTH: 1464
<212> TYPE: DNA
<213> ORGANISM: Collinsella aerofaciens

<400> SEQUENCE: 68

```
agagttcgat cctggctcag gatgaacgct ggcggcgcgc ctaacacatg caagtcgaac     60
ggcacctatc ttcggataga agcgagtggc gaacggctga gtaacacgtg agaacctgc    120 cccctccccc gggatagccg cccgaaagga cgggtaatac cggataccccc ggggtgccgc    180
```

| | |
|---|---|
| atggcacccc ggctaaagcc ccgacgggag gggatggctc cgcggcccat caggtagacg | 240 |
| gcggggtgac ggcccaccgt gccgacaacg ggtagccggg ttgagagacc gaccggccag | 300 |
| attgggactg agacacggcc cagactccta cgggaggcag cagtggggaa tcttgcgcaa | 360 |
| tgggggggaac cctgacgcag cgacgccgcg tgcgggacgg aggccttcgg gtcgtaaacc | 420 |
| gctttcagca gggaagagtc aagactgtac ctgcagaaga agccccggct aactacgtgc | 480 |
| cagcagccgc ggtaatacgt aggggcgag cgttatccgg attcattggg cgtaaagcgc | 540 |
| gcgtaggcgg cccggcaggc cggggtcga agcgggggc tcaaccccc gaagcccccg | 600 |
| gaacctccgc ggcttgggtc cggtagggga gggtggaaca cccggtgtag cggtggaatg | 660 |
| cgcagatatc gggtggaaca ccggtggcga aggcggccct ctgggccgag accgacgctg | 720 |
| aggcgcgaaa gctgggggag cgaacaggat tagataccct ggtagtccca gccgtaaacg | 780 |
| atggacgcta ggtgtggggg gacgatcccc ccgtgccgca gccaacgcat taagcgtccc | 840 |
| gcctggggag tacggccgca aggctaaaac tcaaaggaat tgacggggc ccgcacaagc | 900 |
| agcggagcat gtggcttaat tcgaagcaac gcgaagaacc ttaccagggc ttgacatatg | 960 |
| ggtgaagcgg gggagacccc gtggccgaga ggagcccata caggtggtgc atggctgtcg | 1020 |
| tcagctcgtg tcgtgagatg ttgggttaag tcccgcaacg agcgcaaccc ccgccgcgtg | 1080 |
| ttgccatcgg gtgatgccgg gaacccacgc gggaccgccg ccgtcaaggc ggaggagggc | 1140 |
| ggggacgacg tcaagtcatc atgccccta tgccctgggc tgcacacgtg ctacaatggc | 1200 |
| cggtacagag ggatgccacc ccgcgagggg gagcggatcc cggaaagccg gccccagttc | 1260 |
| ggattggggg ctgcaacccg cccccatgaa gtcggagttg ctagtaatcg cggatcagca | 1320 |
| tgccgcggtg aatgcgttcc cgggccttgt acacaccgcc cgtcacacca cccgagtcgt | 1380 |
| ctgcacccga gtcgccggc ccaaccgaga gggggaggc gccgaaggtg tggagggtga | 1440 |
| gggggggtgaa gtcgtaacaa ggta | 1464 |

<210> SEQ ID NO 69
<211> LENGTH: 1472
<212> TYPE: DNA
<213> ORGANISM: Bacteroides faecis

<400> SEQUENCE: 69

| | |
|---|---|
| ctcaggatga acgctagcta caggcttaac acatgcaagt cgaggggcag cattccagtt | 60 |
| tgcttgcaaa ctggagatgg cgaccggcgc acgggtgagt aacacgtatc caacctgccg | 120 |
| ataactcggg gatagccttt cgaaagaaag attaataccc gatggcataa tagaaccgca | 180 |
| tggtttgatt attaaagaat ttcggttatc gatggggatg cgttccatta ggcagttggt | 240 |
| ggggtaacgg cccaccaaac cttcgatgga taggggttct gagaggaagg tcccccacat | 300 |
| tggaactgag acacggtcca aactcctacg ggaggcagca gtgaggaata ttggtcaatg | 360 |
| gacgagagtc tgaaccagcc aagtagcgtg aaggatgact gccctatggg ttgtaaactt | 420 |
| cttttatatg ggaataaagt ggtccacgtg tggatttttg tatgtaccat atgaataagg | 480 |
| atcggctaac tccgtgccag cagccgcggt aatacggagg atccgagcgt tatccggatt | 540 |
| tattgggttt aaagggagcg taggtggaca gttaagtcag ttgtgaaagt ttgcggctca | 600 |
| accgtaaaat tgcagttgat actggctgtc ttgagtacag tagaggcggg cggaattcgt | 660 |
| ggtgtagcgg tgaaatgctt agatatcacg aagaactccg attgcgaagg cagctcactg | 720 |
| gactgcaact gacactgatg ctcgaaagtg tgggtatcaa acaggattag ataccctggt | 780 |
| agtccacaca gtaaacgatg aatactcgct gtttgcgata tacagtaagc ggccaagcga | 840 |

-continued

```
aagcattaag tattccacct ggggagtacg ccggcaacgg tgaaactcaa aggaattgac    900
gggggcccgc acaagcggag gaacatgtgg tttaattcga tgatacgcga ggaaccttac    960
ccgggcttaa attgcatttg aatatattgg aaacagtata gtcgtaagac aaatgtgaag   1020
gtgctgcatg gttgtcgtca gctcgtgccg tgaggtgtcg gcttaagtgc cataacgagc   1080 gcaacccta tctttagtta ctaacaggtc atgctgagga ctctggagag actgccgtcg   1140
taagatgtga ggaaggtggg gatgacgtca aatcagcacg gcccttacgt ccggggctac   1200
acacgtgtta caatgggggg tacagaaggc cgctacctgg tgacaggatg ctaatcccaa   1260
aagcctctct cagttcggat cgaagtctgc aacccgactt cgtgaagctg gattcgctag   1320
taatcgcgca tcagccatgg cgcggtgaat acgttcccgg gccttgtaca caccgcccgt   1380
caagccatga agccgggggg tacctgaagt acgtaaccgc aaggagcgtc ctagggtaaa   1440
actggtaatt ggggctaagt cgtaacaagg ta                                 1472
```

<210> SEQ ID NO 70
<211> LENGTH: 317
<212> TYPE: DNA
<213> ORGANISM: Alistipes shahii
<220> FEATURE:
<221> NAME/KEY: misc_feature
<222> LOCATION: (11)..(11)
<223> OTHER INFORMATION: w is a or t
<220> FEATURE:
<221> NAME/KEY: misc_feature
<222> LOCATION: (12)..(12)
<223> OTHER INFORMATION: s is g or c
<220> FEATURE:
<221> NAME/KEY: misc_feature
<222> LOCATION: (15)..(15)
<223> OTHER INFORMATION: w is a or t
<220> FEATURE:
<221> NAME/KEY: misc_feature
<222> LOCATION: (16)..(16)
<223> OTHER INFORMATION: w is g or t
<220> FEATURE:
<221> NAME/KEY: misc_feature
<222> LOCATION: (22)..(22)
<223> OTHER INFORMATION: w is g or t
<220> FEATURE:
<221> NAME/KEY: misc_feature
<222> LOCATION: (23)..(23)
<223> OTHER INFORMATION: r is a or g
<220> FEATURE:
<221> NAME/KEY: misc_feature
<222> LOCATION: (26)..(26)
<223> OTHER INFORMATION: s is g or c
<220> FEATURE:
<221> NAME/KEY: misc_feature
<222> LOCATION: (27)..(27)
<223> OTHER INFORMATION: r is a or g
<220> FEATURE:
<221> NAME/KEY: misc_feature
<222> LOCATION: (35)..(35)
<223> OTHER INFORMATION: s is g or c
<220> FEATURE:
<221> NAME/KEY: misc_feature
<222> LOCATION: (36)..(36)
<223> OTHER INFORMATION: r is a or g
<220> FEATURE:
<221> NAME/KEY: misc_feature
<222> LOCATION: (44)..(44)
<223> OTHER INFORMATION: m is a or c
<220> FEATURE:
<221> NAME/KEY: misc_feature
<222> LOCATION: (50)..(50)
<223> OTHER INFORMATION: w is a or t
<220> FEATURE:
<221> NAME/KEY: misc_feature
<222> LOCATION: (52)..(52)

```
<223> OTHER INFORMATION: m is a or c
<220> FEATURE:
<221> NAME/KEY: misc_feature
<222> LOCATION: (59)..(59)
<223> OTHER INFORMATION: m is a or c
<220> FEATURE:
<221> NAME/KEY: misc_feature
<222> LOCATION: (67)..(67)
<223> OTHER INFORMATION: r is a or g
<220> FEATURE:
<221> NAME/KEY: misc_feature
<222> LOCATION: (90)..(91)
<223> OTHER INFORMATION: r is a or g
<220> FEATURE:
<221> NAME/KEY: misc_feature
<222> LOCATION: (120)..(120)
<223> OTHER INFORMATION: s is g or c
<220> FEATURE:
<221> NAME/KEY: misc_feature
<222> LOCATION: (125)..(125)
<223> OTHER INFORMATION: r is a or g
<220> FEATURE:
<221> NAME/KEY: misc_feature
<222> LOCATION: (138)..(138)
<223> OTHER INFORMATION: k is g or t
<220> FEATURE:
<221> NAME/KEY: misc_feature
<222> LOCATION: (145)..(145)
<223> OTHER INFORMATION: k is g or t
<220> FEATURE:
<221> NAME/KEY: misc_feature
<222> LOCATION: (147)..(147)
<223> OTHER INFORMATION: k is g or t
<220> FEATURE:
<221> NAME/KEY: misc_feature
<222> LOCATION: (163)..(163)
<223> OTHER INFORMATION: r is a or g
<220> FEATURE:
<221> NAME/KEY: misc_feature
<222> LOCATION: (165)..(166)
<223> OTHER INFORMATION: r is a or g
<220> FEATURE:
<221> NAME/KEY: misc_feature
<222> LOCATION: (201)..(201)
<223> OTHER INFORMATION: s is g or c
<220> FEATURE:
<221> NAME/KEY: misc_feature
<222> LOCATION: (206)..(206)
<223> OTHER INFORMATION: r is a or g
<220> FEATURE:
<221> NAME/KEY: misc_feature
<222> LOCATION: (315)..(315)
<223> OTHER INFORMATION: r is a or g

<400> SEQUENCE: 70
acataggggg wstgwkaggt twrccsccca cattsrtact gagmcatgaw cmaactctmt      60
acgggargsa gsagtgagga atattggtcr rtggacgcaa gtctgaacca gccatgccgs     120
gtgcrggaag acggctckat gagtkgkaaa ctgcttttgt acrarrgtaa acgctcttac     180
gtgtaagagc ctgaaagtat sgtacraatg aggatcggct aactccgtgc cagcagccgc     240
ggtaatacgg aggatccaag cgttatccgg atttattggg tttaaagggt gcgtaggcgg     300
gttgataaag ttagrgg                                                   317

<210> SEQ ID NO 71
<211> LENGTH: 811
<212> TYPE: DNA
<213> ORGANISM: Anaerostipes caccae
<220> FEATURE:
<221> NAME/KEY: misc_feature
<222> LOCATION: (32)..(32)
<223> OTHER INFORMATION: r is a or g

<400> SEQUENCE: 71
```

```
gcttacacat gcaagtcgaa cgaagcattt argattgaag ttttcggatg gatttcctat      60
atgactgagt ggcggacggg tgagtaacgc gtggggaacc tgccctatac aggggggataa    120 cagctggaaa cggctgctaa taccgcataa gcgcacagaa tcgcatgatt cagtgtgaaa    180
agccctggca gtataggatg gtcccgcgtc tgattagctg gttggtgagg taacggctca    240
ccaaggcgac gatcagtagc cggcttgaga gagtgaacgg ccacattggg actgagacac    300
ggcccaaact cctacgggag gcagcagtgg ggaatattgc acaatggggg aaaccctgat    360
gcagcgacgc cgcgtgagtg aagaagtatt tcggtatgta aagctctatc agcagggaag    420
aaaacagacg gtacctgact aagaagcccc ggctaactac gtgccagcag ccgcggtaat    480 acgtagggggg caagcgttat ccggaattac tgggtgtaaa gggtgcgtag gtggcatggt    540
aagtcagaag tgaaagcccg ggcttaaccc cgggactgc ttttgaaact gtcatgctgg    600
agtgcaggag aggtaagcgg aattcctagt gtagcggtga aatgcgtaga tattaggagg    660
aacaccagtg gcgaaggcgg cttactggac tgtcactgac actgatgcac gaaagcgtgg    720
ggagcaaaca ggattagata ccctggtagt ccacgccgta acgatgaat actaggtgtc    780 ggggccgtag aggcttcggt gccgcagcaa a                                   811

<210> SEQ ID NO 72
<211> LENGTH: 728
<212> TYPE: DNA
<213> ORGANISM: Phascolarctobacterium faecium

<400> SEQUENCE: 72
cggagaattt tcatttcggt agaattctta gtggcgaacg ggtgagtaac gcgtaggcaa      60
cctgcccttt agacggggac aacattccga aaggagtgct aataccggat gtgatcatcg    120
tgccgcatgg caggatgaag aaagatggcc tctacaagta agctatcgct aaaggatggg    180
cctgcgtctg attagctagt tggtagtgta acggactacc aaggcgatga tcagtagccg    240
gtctgagagg atgaacggcc acattgggac tgagacacgg cccaaactcc tacgggaggc    300
agcagtgggg aatcttccgc aatggacgaa agtctgacag caacgccg cgtgagtgat    360 gaaggatttc ggtctgtaaa gctctgttgt ttatgacgaa cgtgcagtgt gtgaacaatg    420
cattgcaatg acggtagtaa acgaggaagc cacggctaac tacgtgccag cagccgcggt    480
aatacgtagg tggcgagcgt tgtccggaat tattgggcgt aaagagcatg taggcggctt    540
aataagtcga gcgtgaaaaa tgcggggctc aaccccgtat ggcgctggaa actgttaggc    600
ttgagtgcag gagaggaaag gggaattccc agtgtagcgg tgaaatgcgt agatattggg    660
aggaacacca gtggcgaagg cgcctttctg gactgtgttt gacgctgaga tgcgaaagcc    720
agggtagc                                                             728

<210> SEQ ID NO 73
<211> LENGTH: 707
<212> TYPE: DNA
<213> ORGANISM: Agathobaculum butyriciproducens
<220> FEATURE:
<221> NAME/KEY: misc_feature
<222> LOCATION: (287)..(287)
<223> OTHER INFORMATION: r is a or g
<220> FEATURE:
<221> NAME/KEY: misc_feature
<222> LOCATION: (360)..(360)
<223> OTHER INFORMATION: m is a or c

<400> SEQUENCE: 73
```

```
tagtggcgga cgggtgagta acgcgtgagc aatctgcctt taagaggggg ataacagtcg    60
gaaacggctg ctaataccgc ataaagcatt gaattcgcat gttttcgatg ccaaaggagc   120
aatccgcttt tagatgagct cgcgtctgat tagctagttg gcggggtaac ggcccaccaa   180
ggcgacgatc agtagccgga ctgagaggtt gaacggccac attgggactg agacacggcc   240
cagactccta cgggaggcag cagtggggaa tattgcgcaa tgggggraac cctgacgcag   300
caacgccgcg tgattgaaga aggccttcgg gttgtaaaga tctttaatca gggacgaaam   360
atgacggtac ctgaagaata agctccggct aactacgtgc cagcagccgc ggtaatacgt   420
agggagcaag cgttatccgg atttactggg tgtaaagggc gcgcaggcgg ccggcaagt    480 tggaagtgaa atccgggggc ttaaccccga aactgctttc aaaactgctg gtcttgagtg   540
atggagaggc aggcggaatt ccgtgtgtag cggtgaaatg cgtagatata cggaggaaca   600
ccagtggcga aggcggcctg ctggacatta actgacgctg aggcgcgaaa gcgtggggag   660
caaacaggat tagatacccct ggtagtccac gccgtaaacg atggata             707

<210> SEQ ID NO 74
<211> LENGTH: 1525
<212> TYPE: DNA
<213> ORGANISM: Bacteroides fragilis

<400> SEQUENCE: 74
atgaagagtt tgatcctggc tcaggatgaa cgctagctac aggcttaaca catgcaagtc    60
gaggggcatc aggaagaaag cttgctttct ttgctggcga ccggcgcacg ggtgagtaac   120
acgtatccaa cctgcccttt actcggggat agcctttcga agaaagatt ataccccgat    180 ggcataatga ttccgcatgg tttcattatt aaaggattcc ggtaaaggat ggggatgcgt   240
tccattaggt tgttggtgag gtaacggctc accaagcctt cgatggatag ggttctgag    300 aggaaggtcc cccacattgg aactgagaca cggtccaaac tcctacggga ggcagcagtg   360
aggaatattg gtcaatgggc gctagcctga accagccaag tagcgtgaag gatgaaggct   420
ctatgggtcg taaacttctt ttatataaga ataaagtgca gtatgtatac tgttttgtat   480
gtattatatg aataaggatc ggctaactcc gtgccagcag ccgcggtaat acggaggatc   540
cgagcgttat ccggatttat tgggtttaaa gggagcgtag gtggactggt aagtcagttg   600
tgaaagtttg cggctcaacc gtaaaattgc agttgatact gtcagtcttg agtacagtag   660
aggtgggcgg aattcgtggt gtagcggtga atgcttaga tatcacgaag aactccgatt   720
gcgaaggcag ctcactggac tgcaactgac actgatgctc gaaagtgtgg gtatcaaaca   780
ggattagata ccctggtagt ccacacagta aacgatgaat actcgctgtt tgcgatatac   840
agtaagcggc caagcgaaag cattaagtat tccacctggg gagtacgccg gcaacggtga   900
aactcaaagg aattgacggg ggcccgcaca agcggaggaa catgtggttt aattcgatga   960
tacgcgagga accttacccg ggcttaaatt gcagtggaat gatgtggaaa catgtcagtg  1020
agcaatcacc gctgtgaagg tgctgcatgg ttgtcgtcag ctcgtgccgt gaggtgtcgg  1080
cttaagtgcc ataacgagcg caaccccttat ctttagttac taacaggtta tgctgaggac  1140
tctagagaga ctgccgtcgt aagatgtgag gaaggtgggg atgacgtcaa atcagcacgg  1200
cccttacgtc cggggctaca cacgtgttac aatgggggt acagaaggca gctagcgggt  1260
gaccgtatgc taatcccaaa agcctctctc agttcggatc gaagtctgca acccgacttc  1320
gtgaagctgg attcgctagt aatcgcgcat cagccacggc gcggtgaata cgttcccggg  1380
ccttgtacac accgcccgtc aagccatggg agccggggt acctgaagta cgtaaccgca  1440
```

```
aggatcgtcc tagggtaaaa ctggtgactg gggctaagtc gtaacaaggt agccgtaccg    1500
gaaggtgcgg ctggaacacc tcctt                                          1525

<210> SEQ ID NO 75
<211> LENGTH: 1022
<212> TYPE: DNA
<213> ORGANISM: Fusobacterium mortiferum

<400> SEQUENCE: 75
tggctcagga tgaacgctga cagaatgctt aacacatgca agtctacttg atccttcggg      60
tgatggtggc ggacgggtga gtaacgcgta aagaacttgc cctgcagtct gggacaacat     120
ttggaaacga atgctaatac cggatattat gtatttctcg catgagtttt acatgaaagc     180
tatatgcgct gcaggagagc tttgcgtcct attagctagt tggtgaggta acggctcacc     240
aaggccatga taggtagccg gcctgagagg gtgaacggcc acaaggggac tgagacacgg     300
cccttactcc tacgggaggc agcagtgggg aatattggac aatggaccaa agtctgatc     360 cagcaattct gtgtgcacga tgaagttttt cggaatgtaa agtgctttca gttgggacga     420
agtaagtgac ggtaccaaca gaagaagcga cggctaaata cgtgccagca gccgcggtaa     480
tacgtatgtc gcaagcgtta ccggattta ttgggcgtaa agcgcgtcta ggcggtttgg     540
taagtctgat gtgaaaatgc ggggctcaac tccgtattgc gttggaaact gctaaactag     600
agtactggag aggtgggcgg aactacaagt gtagaggtga aattcgtaga tatttgtagg     660
aatgccgatg gggaagccag cccactggac agatactgac gctaaagcgc gaaagcgtgg     720
gtagcaaaca ggattagata ccctggtagt ccacgccgta acgatgatt actaggtgtt     780 gggggtcgaa cctcagcgcc caagctaacg cgataagtaa tccgcctggg gagtacgtac     840
gcaagtatga aactcaaagg aattgacggg acccgcaca agcggtggag catgtggttt     900
aattcgacgc aacgcgagga accttaccag cgtttgacat cctaagaaat tagcagagat     960
gcttttgtgc cccttcgggg gaacttagtg acaggtggtg catggctgtc gtcagctcgt    1020
gt                                                                 1022

<210> SEQ ID NO 76
<211> LENGTH: 1490
<212> TYPE: DNA
<213> ORGANISM: Paraclostridium benzoelyticum

<400> SEQUENCE: 76
agagtttgat cctggctcag gatgaacgct ggcggcgtgc ctaacacatg caagtcgagc      60
gatctcttcg gagagagcgg cggacgggtg agtaacgcgt gggtaacctg ccctgtacac     120
acggataaca taccgaaagg tatactaata cgggataaca tacgaaagtc gcatggcttt     180
tgtatcaaag ctccggcggt acaggatgga cccgcgtctg attagctagt tggtaaggta     240
atggcttacc aaggcaacga tcagtagccg acctgagagg gtgatcggcc acactggaac     300
tgagacacgg tccagactcc tacgggaggc agcagtgggg aatattgcac aatgggcgaa     360
agcctgatgc agcaacgccg cgtgagcgat gaaggccttc gggtcgtaaa gctctgtcct     420
caaggaagat aatgacggta cttgaggagg aagcccggc taactacgtg ccagcagccg     480
cggtaatacg taggggcta gcgttatccg gaattactgg gcgtaaaggg tgcgtaggtg     540 gtttttttaag tcagaagtga aaggctacgg ctcaaccgta gtaagctttt gaactagag     600 aacttgagtg caggagagga gagtagaatt cctagtgtag cggtgaaatg cgtagatatt     660
```

| | |
|---|---:|
| aggaggaata ccagtagcga aggcggctct ctggactgta actgacactg aggcacgaaa | 720 |
| gcgtggggag caaacaggat tagataccct ggtagtccac gccgtaaacg atgagtacta | 780 |
| ggtgtcgggg gttacccccc tcggtgccgc agctaacgca ttaagtactc cgcctgggaa | 840 |
| gtacgctcgc aagagtgaaa ctcaaaggaa ttgacgggga cccgcacaag tagcggagca | 900 |
| tgtggtttaa ttcgaagcaa cgcgaagaac cttacctaag cttgacatcc cactgacctc | 960 |
| tccctaatcg agatttccc ttcggggaca gtggtgacag gtggtgcatg gttgtcgtca | 1020 |
| gctcgtgtcg tgagatgttg ggttaagtcc cgcaacgagc gcaacccttg cctttagttg | 1080 |
| ccagcattaa gttgggcact ctagagggac tgccgaggat aactcggagg aaggtgggga | 1140 |
| tgacgtcaaa tcatcatgcc ccttatgctt agggctacac acgtgctaca atgggtggta | 1200 |
| cagagggttg ccaagccgcg aggtggagct aatcccttaa agccattctc agttcggatt | 1260 |
| gtaggctgaa actcgcctac atgaagctgg agttactagt aatcgcagat cagaatgctg | 1320 |
| cggtgaatgc gttcccgggt cttgtacaca ccgcccgtca caccatggaa gttggggcg | 1380 |
| cccgaagccg gttagctaac cttttaggaa gcggccgtcg aaggtgaaac caatgactgg | 1440 |
| ggtgaagtcg taacaaggta gccgtatcgg aaggtgcggc tggatcacct | 1490 |

<210> SEQ ID NO 77
<211> LENGTH: 1538
<212> TYPE: DNA
<213> ORGANISM: Escherichia fergusonii

<400> SEQUENCE: 77

| | |
|---|---:|
| ttgaagagtt tgatcatggc tcagattgaa cgctggcggc aggcctaaca catgcaagtc | 60 |
| gaacggtaac aggaagcagc ttgctgcttt gctgacgagt ggcggacggg tgagtaatgt | 120 |
| ctgggaaact gcctgatgga gggggataac tactggaaac ggtagctaat accgcataac | 180 |
| gtcgcaagac caaagagggg gaccttcggg cctcttgcca tcggatgtgc ccagatggga | 240 |
| ttagctagta ggtggggtaa cggctcacct aggcgacgat ccctagctgg tctgagagga | 300 |
| tgaccagcca cactggaact gagacacggt ccagactcct acgggaggca gcagtgggga | 360 |
| atattgcaca atgggcgcaa gcctgatgca gccatgccgc gtgtatgaag aaggccttcg | 420 |
| ggttgtaaag tactttcagc ggggaggaag ggagtaaagt taatacccttt gctcattgac | 480 |
| gttacccgca gaagaagcac cggctaactc cgtgccagca gccgcggtaa tacgagggt | 540 |
| gcaagcgtta atcggaatta ctgggcgtaa agcgcacgca ggcggtttgt taagtcagat | 600 |
| gtgaaatccc cgggctcaac ctgggaactg catctgatac tggcaagctt gagtctcgta | 660 |
| gaggggggta gaattccagg tgtagcggtg aaatgcgtag agatctggag gaataccggt | 720 |
| ggcgaaggcg gccccctgga cgaagactga cgctcaggtg cgaaagcgtg gggagcaaac | 780 |
| aggattagat accctggtag tccacgccgt aaacgatgtc gacttggagg ttgtgccctt | 840 |
| gaggcgtggc ttccggagct aacgcgttaa gtcgaccgcc tggggagtac ggccgcaagg | 900 |
| ttaaaactca aatgaattga cggggcccg cacaagcggt ggagcatgtg gtttaattcg | 960 |
| atgcaacgcg aagaacctta cctggtcttg acatccacgg aagttttcag agatgagaat | 1020 |
| gtgccttcgg gaaccgtgag acaggtgctg catggctgtc gtcagctcgt gttgtgaaat | 1080 |
| gttgggttaa gtcccgcaac gagcgcaacc cttatccttt gttgccagcg gtccggccgg | 1140 |
| gaactcaaag gagactgcca gtgataaact ggaggaaggt ggggatgacg tcaagtcatc | 1200 |
| atggccctta cgaccagggc tacacacgtg ctacaatggc gcatacaaag agaagcgacc | 1260 |
| tcgcgagagc aagcggacct cataaagtgc gtcgtagtcc ggattggagt ctgcaactcg | 1320 |

```
actccatgaa gtcggaatcg ctagtaatcg tggatcagaa tgccacggtg aatacgttcc    1380
cgggccttgt acacaccgcc cgtcacacca tgggagtggg ttgcaaaaga agtaggtagc    1440
ttaaccttcg ggagggcgct taccactttg tgattcatga ctggggtgaa gtcgtaacaa    1500
ggtaaccgta ggggaacctg cggttggatc acctcctt                            1538
```